US007714189B2

(12) United States Patent
Manjunath et al.

(10) Patent No.: US 7,714,189 B2
(45) Date of Patent: May 11, 2010

(54) HIGH TRYPTOPHAN MAIZE

(75) Inventors: Siva Manjunath, Chesterfield, MO (US); Jiexin Peng, St. Louis, MO (US); Marguerite J. Varagona, Ballwin, MO (US)

(73) Assignee: Monsanto Technology LLC, St. Louis, MO (US)

(*) Notice: Subject to any disclaimer, the term of this patent is extended or adjusted under 35 U.S.C. 154(b) by 505 days.

(21) Appl. No.: 11/503,532

(22) Filed: Aug. 11, 2006

(65) Prior Publication Data

US 2007/0028321 A1 Feb. 1, 2007

Related U.S. Application Data

(63) Continuation-in-part of application No. 10/430,011, filed on May 5, 2003.

(60) Provisional application No. 60/377,727, filed on May 3, 2002.

(51) Int. Cl.
*C12N 15/00* (2006.01)
*C12N 15/82* (2006.01)
*C12N 15/11* (2006.01)
*C12N 15/31* (2006.01)
*A01H 5/00* (2006.01)
*A01H 5/10* (2006.01)
*A01H 5/04* (2006.01)

(52) U.S. Cl. .................. 800/288; 800/278; 800/295; 800/298; 435/320.1; 435/468; 536/23.1; 536/23.7; 536/23.2

(58) Field of Classification Search .................. None
See application file for complete search history.

(56) References Cited

U.S. PATENT DOCUMENTS

| 4,581,847 | A |   | 4/1986  | Hibberd et al.    | 800/268  |
| 6,118,047 | A | * | 9/2000  | Anderson et al.   | 800/278  |
| 6,329,574 | B1| * | 12/2001 | Lundquist et al.  | 800/300.1|
| 7,217,865 | B2|   | 5/2007  | Weaver et al.     | 800/300  |
| 2003/0213010 | A1 | | 11/2003 | Weaver et al.  | 800/278  |
| 2005/0005327 | A1 | | 1/2005  | Ravanello et al. | 800/281 |

FOREIGN PATENT DOCUMENTS

WO    WO 02/090497    11/2002

OTHER PUBLICATIONS

Wood et al 2001 Science 294:2317-2323.*
Sequence alignment from Wood et al.*
Bae et al., "Rhizobium meliloti anthranilate synthase gene: cloning, sequence, and expression in *escherichia coli*," *J. of Bacteriol.*, 171(6):3471-3478, 1989.
Bohlmann et al., "Anthranilate synthase from ruta graveolens[1]," *Plant Physiol.*, 111:507-514, 1996.
Caligiuri, "Identification of amino acid residues involved in feedback regulation of the anthranilate synthase complex from *salmonella typhimurium*," *J. Biol. Chem.*, 13:8328-8335, 1991.
De Troch et al., "Isolation and characterization of the azospirillum brasilense trpE(G) gene, encoding anthranilate synthase," *Curr. Microbiol.*, 34:27-32, 1997.
GenBank Accession No. GI 1004323, 2005.
GenBank Accession No. GI 1004324, 2005.
GenBank Accession No. GI 1174156, 2000.
GenBank Accession No. GI 13472468, 2000.
GenBank Accession No. GI 152445, 1993.
GenBank Accession No. GI 15889565, 2001.
GenBank Accession No. GI 15966140, 2001.
GenBank Accession No. GI 1717765, 1997.
GenBank Accession No. GI 17227910, 2001.
GenBank Accession No. Gi 17230725, 2001.
GenBank Accession No. GI 17982357, 2001.
GenBank Accession No. GI 95177, 1989.
GenBank Accession No. GI 960291, 1995.
GenBank Accession No. P15395, 1990.
Goodner et al., "Genome sequence of the plant pathogen and biotechnology agent *agrobacterium tumefaciens* C58," *Science*, 294:2323-2328, 2001.
Knochel et al., "The crystal structure of anthranilate synthase from sulfolobus solfataricus: functional implications," *Proc. Natl. Acad. Sci. USA*, 96:9479-9489, 1999.
Niyogi et al., "Two anthranilate synthase genes in arabidopsis: defense-related regulation of the tryptophan pathway," *The Plant Cell*, 4:721-733, 1992.
Niyogi, "Suppressors of trp 1 fluorescence identify a new arabidopsis gene, TRP4, encoding the anthranilate synthase β subunit," *The Plant Cell*, 5:1011-1027, 1993.
Stark et al., "Regulation of the amount of starch in plant tissues by ADP glucose pyrophosphorylase," *Science*, 258:287-292, 1992.

* cited by examiner

*Primary Examiner*—Anne Marie Grunberg
*Assistant Examiner*—Brent Page
(74) *Attorney, Agent, or Firm*—Chunping Li, Esq.; Sonnenschein Nath & Rosenthal LLP

(57) ABSTRACT

The present invention provides a method for altering the tryptophan content of a plant by introducing and expressing an artificial polynucleotide sequence encoding an anthranilate synthase in the cells of the plant. Transgenic plants transformed with an artificial polynucleotide sequence encoding an anthranilate synthase, as well as human or animal food, seeds, and progeny derived from these plants, are also provided.

34 Claims, 53 Drawing Sheets

```
  1 MVTIIQDDGAETYETKGGIQVSRKRRPTDYANAIDNYIEKLDSHRGAVFS    50
    | :| :||||.| ||||| |.|:||   |..||  |:::||  ||||||
  1 MAAVILEDGAESYTTKGGIVVTRRRREASYSDAIAGYVDRLDERRGAVFS    50

51 SNYEYPGRYTRWDTAIVDPPLGISCFGRKMWIEAYNGRGEVLLDFITEKL   100
    ||||||||||||||||:|||||  || |||  :||||||  ||||||   | | |
 51 SNYEYPGRYTRWDTAVVDPPLAISSFGRSLWIEAYNERGEVLLALIAEDL   100

101 KATPDLTLGASSTRRLDLTVNEPDRVFTEEERSKIPTVFTALRAIVDLFY   150
    |. |:|||.. ||||||:|||||||||||||||.||||| |||: .||:
101 KSVADITLGSLAARRLDLTINEPDRVFTEEERSKMPTVFTVLRAVTNLFH   150

151 SSADSAIGLFGAFGYDLAFQFDAIKLSLARPEDQRDMVLFLPDEILVVDH   200
    |   || :||:|||||||||||||||.| |.||:||||||||||||||||
151 SEEDSNLGLYGAFGYDLAFQFDAIELKLSRPDDQRDMVLFLPDEILVVDH   200

201 YSAKAWIDRYDFEKDGMTTDGKSSDITPDPFKTTDTIPPKGDHRPGEYSE   250
    |.|||||||||| :: :.|:||..|| |:||:. |.||| ||||||||.|
201 YAAKAWIDRYDFARENLSTEGKAADIAPEPFRSVDSIPPHGDHRPGEYAE   250

251 LVVKAKESFRRGDLFEVVPGQKFMERCESNPSAISRRLKAINPSPYSFFI   300
    ||||||||||||||||||||||| ||||| || || ||||||||||||||
251 LVVKAKESFRRGDLFEVVPGQKFYERCESRPSEISNRLKAINPSPYSFFI   300

301 NLGDQEYLVGASPEMFVRVSGRRIETCPISGTIKRGDDPIADSEQILKLL   350
    |||.||||||||||||||||||||||||||||||||||||||||||||||
301 NLGNQEYLVGASPEMFVRVSGRRIETCPISGTIKRGDDPIADSEQILKLL   350

351 NSKKDESELTMCSDVDRNDKSRVCEPGSVKVIGRRQIEMYSRLIHTVDHI   400
    ||||||||||||||||||||||||| |||||||||||||||||||||||
351 NSKKDESELTMCSDVDRNDKSRVCVPGSVKVIGRRQIEMYSRLIHTVDHI   400

401 EGRLRDDMDAFDGFLSHAWAVTVTGAPKLWAMRFIEGHEKSPRAWYGGAI   450
    |||||||||||||||||||||||||||||||||||| |||||||||||||
401 EGRLRDDMDAFDGFLSHAWAVTVTGAPKLWAMRFIESHEKSPRAWYGGAI   450

451 GMVGFNGDMNTGLTLRTIRIKDGIAEVRAGATLLNDSNPQEEEAETELKA   500
    ||||||||||||||||||||||||||||||||||| ||||:|||||||||
451 GMVGFNGDMNTGLTLRTIRIKDGIAEVRAGATLLYDSNPEEEEAETELKA   500

501 SAMISAIRDAKGTNSAATKRDAAKVGTGVKILLVDHEDSFVHTLANYFRQ   550
    ||||.||||||   ||| . ||  || || |||||||||||||||||||||
501 SAMIAAIRDAKSANSAKSARDVAAVGAGVSILLVDHEDSFVHTLANYFRQ   550

551 TGATVSTVRSPVAADVFDRFQPDLVVLSPGPGSPTDFDCKATIKAARARD   600
    |||.|.|||:||| ::|||  .|||||||||.| |||||||||| |||||
551 TGASVTTVRTPVAEEIFDRVKPDLVVLSPGPGTPKDFDCKATIKKARARD   600

601 LPIFGVCLGLQALAEAYGGELRQLAVPMHGKPSRIRVLEPGLVFSGLGKE   650
    ||||||||||||||||||:|||||:|||||||||||||||:||||||||
601 LPIFGVCLGLQALAEAYGGDLRQLAIPMHGKPSRIRVLEPGIVFSGLGKE   650

651 VTVGRYHSIFADPATLPRDFIITAESEDGTIMGIEHAKEPVAAVQFHPES   700
    ||||||||||||||. |||:|:||||||||||||||.||||||||||||||
651 VTVGRYHSIFADPSNLPREFVITAESEDGTIMGIEHSKEPVAAVQFHPES   700

701 IMTLGQDAGMRMIENVVVHLTRKAKTKAA        729
    ||||| ||||||||||| ||::|||||||
701 IMTLGGDAGMRMIENVVAHLAKRAKTKAA        729
```

Fig. 1

| | |
|---|---|
| Agrobacterium_TrpEG<br>Sulfolobus_TrpE | MVTIIQDDGAETYETKGGIQVSRKRRPTDYANAIDNYIEKLDSHRGAVFSSNYEYPGRYT<br>------------------------------------------MEVHPISEFASPFEVFKCIE |
| Agrobacterium_TrpEG<br>Sulfolobus_TrpE | R-WDTAIVDPPLGISCFGRKMWIEAYNGRGEVLLDFITEKLKATPDLTLGASSTRRLDLT<br>RDFKVAGLLESIGGPQYKARYSVIAWSTNG-----------------YLKIHDDP |
| Agrobacterium_TrpEG<br>Sulfolobus_TrpE | VNEPDRVFTEEERSKIPTVFTALRAIVDLFYSSADSAIGLFGAFGYDLAFQFDAIKLSLA<br>VNILNGYLKDLKLADIPGLFKG-----------------GMIGYISYDAVRFWEKIRDLKP |
| Agrobacterium_TrpEG<br>Sulfolobus_TrpE | RPEDQRDMVLFLPDEILVVDHYSAKAWIDRYDFEKDGMTTDGKSSDITPDFKTTDTIPP<br>AAEDWPYAEFFTPDNIIIYDHNEGKVYVN------ADLSSVGGCGDIGEFKVSFYDESLN |
| Agrobacterium_TrpEG<br>Sulfolobus_TrpE | KGDHRPGEYSELVVKAKESFRRGDLFEVVPGQKFMERCESNPSAISRRLKAINPSYSFF<br>KN------SYERIVSESLEYIRSGYIFQVVLSRFYRYIFSGDPLRIYYNLRRINPSPYMFY |
| Agrobacterium_TrpEG<br>Sulfolobus_TrpE | INLGDQEYLVGASPEMFVRVSGRRIETCPISGTIKRGDDPIADSEQILKLLNSKKDESEL<br>LKF-DEKYLIGSSPELLFRVQDNIVETYPIAGTRPRGADQEEDLKLELELMNSEKDKAEH |
| Agrobacterium_TrpEG<br>Sulfolobus_TrpE | TMCSDVDRNDKSRVCEPGSVKVIGRRQIEMYSRLIHTVDHIEGRLRDDMDAFDGFLSHAW<br>LMLVDLARNDLGKVCVPGTVKVPELMYVEKYSHVQHIVSKVIGTLKKYNALNVLSATFP |

Fig. 3A

```
Agrobacterium_TrpEG    AVTVTGAPKLWAMRFIEGHEKSPRAWYGGAIGMVGFNGDMNTGLTLRTIRIKDGIAEVRA
Sulfolobus_TrpE        AGTVSGRPKPMAMNIIETLEEYKRGPYAGAVGFISADGNAEFAIAIRTAFLNKELLRIHA Agrobacterium_TrpEG    GATLLNDSNPQEEEAETELKASAMISAIRDAKGTNSAATKRDAAKVGTGVKILLVDHEDS
Sulfolobus_TrpE        GAGIVYDSNPESEYFETEHKLKALKTAIGVR-----------------------------

Agrobacterium_TrpEG    FVHTLANYFRQTGATVSTVRSPVAADVFDRFQPDLVVLSPGPGSPTDFDCKATIKAARAR
Sulfolobus_TrpE        ------------------------------------------------------------

Agrobacterium_TrpEG    DLPIFGVCLGLQALAEAYGGELRQLAVPMHGKPSRIRVLEPGLVFSGLGKEVTVGRYHSI
Sulfolobus_TrpE        ------------------------------------------------------------

Agrobacterium_TrpEG    FADPATLPRDFIITAESEDGTIMGIEHAKEPVAAVQFHPESIMTLGQDAGMRMIENVVH
Sulfolobus_TrpE        ------------------------------------------------------------

Agrobacterium_TrpEG    LTRKAKTKAA
Sulfolobus_TrpE        ----------
```

*Fig. 3B*

| | | |
|---|---|---|
| V48F-F: | CCATCGGGCGCGGTtTTTTTCGTCCAACTATG | (SEQ ID NO: 9) |
| V48F-R: | CATAGTTGGACGAAAAAAaCGCGCCGCGATGG | (SEQ ID NO: 10) |
| V48Y-F: | CCATCGGGCGCGCGtaTTTTTCGTCCAACTATGAATATCC | (SEQ ID NO: 11) |
| V48Y-R: | GGATATTCATAGTTGGACGAAAAAtaCGCGCCCGCGATGG | (SEQ ID NO: 12) |
| V48W-F: | CCATCGGGCGCGTgGTTTTCGTCCAACTATGAATATCC | (SEQ ID NO: 13) |
| V48W-R: | GGATATTCATAGTTGGACGAAAACcaCGCGCCCGCGATGG | (SEQ ID NO: 14) |
| V50K-F: | CCATCGGGCGCGGTTTTaaGTCCAACTATGAATATCCGGG | (SEQ ID NO: 15) |
| V50K-R: | GGATATTCATAGTTGGACttAAAAAACCGGCCGCGATGG | (SEQ ID NO: 16) |
| S51C-F: | GCGCGGTTTTTCGTgCAACTATGAATATCCGGG | (SEQ ID NO: 17) |
| S51C-R: | CCCGGATATTCATAGTTGcACGAAAAAACCGCGC | (SEQ ID NO: 18) |
| S51F-F: | CGCGGTTTTTCGTtCAACTATGAATATCCGGGC | (SEQ ID NO: 19) |
| S51F-R: | GCCCGGATATTCATAGTTGaACGAAAAAACCGCG | (SEQ ID NO: 20) |
| S51I-F: | CGGCGGTTTTTTCGatCAACTATGAATATCCGGGC | (SEQ ID NO: 21) |
| S51I-R: | GCCCGGATATTCATAGTTGatCGAAAAAACCGCGCCG | (SEQ ID NO: 22) |
| S51L-F: | GGGCGGTTTTTTCGctCAACTATGAATATCCGGGC | (SEQ ID NO: 23) |
| S51L-R: | GCCCGGATATTCATAGTTGagCGAAAAAACCGCGCC | (SEQ ID NO: 24) |
| S51M-F: | CGGCGCGGTTTTTCGAtgAACTATGAATATCCGGGCCG | (SEQ ID NO: 25) |
| S51M-R: | CGGCCCGGATATTCATAGTTcaTCGAAAAAACCGCGCCG | (SEQ ID NO: 26) |

*Fig. 4A*

| | | |
|---|---|---|
| S51T-F: | CGCGGTTTTTCGaCCAACTATGAATATCCGGGC | (SEQ ID NO: 27) |
| S51T-R: | GCCCGGATATTCATAGTTGGtCGAAAAAACCGCG | (SEQ ID NO: 28) |
| S51V-F: | GGCGCGGTTTTTCGgtCAACTATGAATATCCGGGC | (SEQ ID NO: 29) |
| S51V-R: | GCCCGGATATTCATAGTTGacCGAAAAAACCGCGCC | (SEQ ID NO: 30) |
| S51Y-F: | GCGCGGTTTTTCGTaCAACTATGAATATCCGGGC | (SEQ ID NO: 31) |
| S51Y-R: | GCCCGGATATTCATAGTTGtaCGAAAAAACCGCGC | (SEQ ID NO: 32) |
| N52F-F: | CGGCGCGGTTTTTCGTCCttCTATGAATATCCGGG | (SEQ ID NO: 33) |
| N52F-R: | CCCGGATATTCATAGaaGGACGAAAAAACCGCGCCG | (SEQ ID NO: 34) |
| P293A-F: | CTGAAGGCGATCAACgCGTCGCCCTATTC | (SEQ ID NO: 35) |
| P293A-R: | GAATAGGGCGACGCGTTGATCGCCTTCAG | (SEQ ID NO: 36) |
| F293G-F: | CCTGAAGGCGATCAACggGTCGCCCTATTCC | (SEQ ID NO: 37) |
| F293G-R: | GGAATAGGGCGACCCGTTGATCGCCTTCAGG | (SEQ ID NO: 38) |
| F298A-F: | CGTCGCCCTATTCCgcCTTCATCAATCTCGGCG | (SEQ ID NO: 39) |
| F298A-R: | CGCCGAGATTGATGAAGgCGGAATAGGGCGACG | (SEQ ID NO: 40) |
| F298W-F: | CGTCGCCCTATTCCTggTTCATCAATCTCGGCG | (SEQ ID NO: 41) |
| F298W-R: | CGCCGAGATTGATGAAccAGGAATAGGGCGACG | (SEQ ID NO: 42) |

Fig. 4B

```
TRPEG_AGRTU_MONSANTO   MVTIIQDDGAETYETKGGIQVSRKRRP--------------------------     27
TRPEG_RHIME_A30904     MAAVILEDGAESYTTKGGIVVTRRRRE--------------------------     27
TRPE_SULSO_Q06128      MEVHPISEFASPFEVFKCIER--------------------------------     21
TRPE_ARATH_S27752      MSAVSISAVKSDFFTVEAIAVTHHRTPHPHFPSLRFPLSLKSPPATSLN         50
                       *     .          .               .

TRPEG_AGRTU_MONSANTO   TDYANAIDNYIEKLDSHRGAVFSSNYEYPGRYTRWDTAIVDPPLGISCFG         77
TRPEG_RHIME_A30904     ASYSDAIAGYVDRLDERRGAVFSSNYEYPGRYTRWDTAVVDPPLAISSFG         77
TRPE_SULSO_Q06128      ---------------------------------DFKVAG-----------      27
TRPE_ARATH_S27752      LVAGSKLLHFSRRLPSIKCSYTPSLDLSEEQFTKFKKASEKGNLVPLFRC        100
                                   .   :                *

TRPEG_AGRTU_MONSANTO   ----------RKMWIEAYNGRGEVLLDFITEKLKATPDLTLGASSTRR---       115
TRPEG_RHIME_A30904     ----------RSLWIEAYNERGEVLLALIAEDLKSVADITLGSLAARR---       115
TRPE_SULSO_Q06128      ----------LLESIG-GPQ-YKARYSVIAWST-----------------        48
TRPE_ARATH_S27752      VFSDHLTPILAYRCLVKEDDRDAPSFLFESVEPGSQSSNIGRYSVVGAQP        150
                                *  :     :    .    :

TRPEG_AGRTU_MONSANTO   LDLTVNEPDRVFTE-------------EERSKIPTVFTALRAIVDLFYSSA      153
TRPEG_RHIME_A30904     LDLTINEPDRVFTE-------------EERSKMPTVFTVLRAVTNLFHSEE      153
TRPE_SULSO_Q06128      NGYLKIH--------------------DDPVNILNGYLKD---LKLADIPG       76
TRPE_ARATH_S27752      TIEIVAKGNVVTVMDHGASLRTEEEVDDPMMVPQKIMEEWNPQGIDELPE       200
                           :                        :              .

TRPEG_AGRTU_MONSANTO   DSAIGLFGAFGYDLAFGYDLAFQFDAIKLSLARPEDQ-----RDMVLFLPDEILVVD      199
TRPEG_RHIME_A30904     DSNLGLYGAFGYDLAFGYDLAFQFDAIELKLSRPDDQ-----RDMVLFLPDEILVVD      199
TRPE_SULSO_Q06128      LFKGGMIGYISYDAVRFWEKIR-DLKPAAED------WPYAEFFTPDNIIIYD      122
TRPE_ARATH_S27752      AFCGGWVGYFSYDTVRYVEKKKLPFSNAPEDDRSLPDVNLGLYDDVIVFD        250
                        *              .          .         *           *    *::.:

Fig. 7A
```

```
TRPEG_AGRTU_MONSANTO_    HYSAKAWIDRYDFEKDGMTTDG----KSSDITP--------------------------    228
TRPEG_RHIME_A30904_      HYAAKAWIDRYDFARENLSTEG----KAADIAP--------------------------    228
TRPE_SULSO_Q06128_       HNEGKVYVN------ADLSSVG----GCGDIG---------------------------    144
TRPE_ARATH_S27752_       HVEKKAYVIHWVRIDKDRSVEENFREGMNRLESLTSRIQDQKPPKMPTGF           300
                          *  *  : :

TRPEG_AGRTU_MONSANTO_    --DPFKTTDTIPPKGDHRPGEYSELVVKAKESFRRGDLFEVVPGQKFMER           276
TRPEG_RHIME_A30904_      --EPFRSVDSIPPHGDHRPGEYAELVVKAKESFRRGDLFEVVPGQKFYER           276
TRPE_SULSO_Q06128_       -EFKVSFYDESLNK-----NSYERIVSESLEYIRSGYIFQVVLSRFYRYI           188
TRPE_ARATH_S27752_       IKLRTQLFGPKLEKSTMTSEAYKEAVVEAKEHILAGDIFQIVLSQRFERR           350
                                    *     *   *   ::   *   * :::   *   :  ::

TRPEG_AGRTU_MONSANTO_    CESNPSAISRRLKAINPSYSFFINLGDQEYLVGASPEMFVRVSGRRIET            326
TRPEG_RHIME_A30904_      CESRPSEISNRLKAINPSYSFFINLGNQEYLVGASPEMFVRVSGRRIET            326
TRPE_SULSO_Q06128_       FSGDPLRIYNLRRINPSPYMFYLKF-DEKYLIGSSPELLFRVQDNIVET            237
TRPE_ARATH_S27752_       TFADPFEIYRALRIVNPSPYMAYLQVR-GCILVASSPEILLRSKNRKITN           399
                           :   *::******    :  *   ::  *   : :* :**:* ::  :

TRPEG_AGRTU_MONSANTO_    CPISGTIKRGDDPIADSEQILKLLNSKKDESELTMCSDVDRNDKSRVCEP            376
TRPEG_RHIME_A30904_      CPISGTIKRGDDPIADSEQILKLLNSKKDESELTMCSDVDRNDKSRVCVP            376
TRPE_SULSO_Q06128_       YPIAGTRPRGADQEEDLKLELELMNSEKDKAEHLMLVDLARNDLGKVCVP            287
TRPE_ARATH_S27752_       RPLAGTVRRGKTPKEDLMLEKELLSDEKQCAEHIMLVDLGRNDVGKVSKP            449
                          * :** *  *   : :*:    :*:  ::  :   ** .:  ***

TRPEG_AGRTU_MONSANTO_    GSVKVIGRRQIEMYSRLIHTVDHIEGRLRDDMDAFDGFLSHAWAVTVTGA            426
TRPEG_RHIME_A30904_      GSVKVIGRRQIEMYSRLIHTVDHIEGRLRDDMDAFDGFLSHAWAVTVTGA            426
TRPE_SULSO_Q06128_       GTVKVPELMYVEKYSHVQHIVSKVIGTLKKYNALNVLSATFPAGTVSGR            337
TRPE_ARATH_S27752_       GSVEVKKLKDIEWFSHVMHISSTVVGELLDHLTSWDALRAVLPVGTVSGA            499
                          *:: *          .  .:   :      :     *   : .  *
```

*Fig. 7B*

```
TRPEG_AGRTU_MONSANTO    PKLWAMRFIEGHEKSPRAWYGGAIGMVGFNGDMNTGLTLRTIRIKDG---- 473
TRPEG_RHIME_A30904      PKLWAMRFIESHEKSPRAWYGGAIGMVGFNGDMNTGLTLRTIRIKDG---- 473
TRPE_SULSO_Q06128       PKPMAMNIIETLEEYKRGPYAGAVGFISADGNAEFAIAIRTAFLN------ 382
TRPE_ARATH_S27752       PKVKAMELIDELEVTRRGPYSGGFGGISFNGDMDIALALRTMVFPTNTRY  549
                        **  **  *:  *    :*.     * :   *::* .: ::::**

TRPEG_AGRTU_MONSANTO    ----------IAEVRAGATLLNDSNPQEEEAETELKASAMISAIR 508
TRPEG_RHIME_A30904      ----------IAEVRAGATLLYDSNPEEEEAETELKASAMIAAIR 508
TRPE_SULSO_Q06128       ----KELLR-------IHAGAGIVYDSNPESEYFETEHKLKALKTAIG 419
TRPE_ARATH_S27752       DTLYSYKHPQRRREWIAHIQAGAGIVADSNPDDEHRECENKAAALARAID 599
                                          :: *****:.. *    *   *

TRPEG_AGRTU_MONSANTO    DAKGTNSAATKRDAAKVGTGVKILLVDHEDSFVHTLANYFRQTGATVSTV 558
TRPEG_RHIME_A30904      DAKSANSAKSARDVAAVGAGVSILLVDHEDSFVHTLANYFRQTGASVTTV 558
TRPE_SULSO_Q06128       VR------------------------------------------------ 421
TRPE_ARATH_S27752       LAESSFLEAPFTTITPHINNI----------------------------- 621

TRPEG_AGRTU_MONSANTO    GMVGFNGDMNTGLTLRTIRIKDGIAEVRAGATLLNDSNPQEEEAETELKA 500
TRPEG_RHIME_A30904      GMVGFNGDMNTGLTLRTIRIKDGIAEVRAGATLLYDSNPEEEEAETELKA 500
TRPG_SULSO_B40635       -------------------------------------------------- 
TRPG_ARATH_AAA32742     -------MAASTLYKSCLLQPKSGSTTRRLNPSLVNPLTNPTRVSVLGKSR 44

TRPEG_AGRTU_MONSANTO    SAMISAIRDAKGTNSAATKRDAAKVGTGVKILLVDHEDSFVHTLANYFRQ 550
TRPEG_RHIME_A30904      SAMIAAIRDAKSANSAKSARDVAAVGAGVSILLVDHEDSFVHTLANYFRQ 550
TRPG_SULSO_B40635       ---- MDLT------------LIIDNYDSFVYNIAQIVGE           23
TRPG_ARATH_AAA32742     RDVFAKASIEMAESNSIPSVVVNSSKQHGPIIVIDNYDSFTYNLCQYMGE 94
                                                 .::*.::  *.**.:* .    .
```

Fig. 7C

```
TRPEG_AGRTU_MONSANTO_  TGATVSTVRSP-VAADVFDRFQPDLVVLSPGPGSPT---DFDCKATIKAA  596
TRPEG_RHIME_A30904_    TGASVTTVRTP-VAEEIFDRVKPDLVVLSPGPGTPK---DFDCKATIKKA  596
TRPG_SULSO_B40635_     LGSYPIVIRNDEISIKGIERIDPDRLIISPGPGTPEKREDIGVSLDVIKY   73
TRPG_ARATH_AAA32742_   LGCHFFEVYRNDELTVEELKKKNPRGVLISPGPGTPQ---DSGISLQTVLE  141
                        *      .         . :: :::******.*  *    .

TRPEG_AGRTU_MONSANTO_  RARDLPIFGVCLGLQALAEAYGGELR-QLAVPMHGKPSRIRVLEPG---LV  643
TRPEG_RHIME_A30904_    RARDLPIFGVCLGLQALAEAYGGDLR-QLAIPMHGKPSRIRVLEPG---IV  643
TRPG_SULSO_B40635_     LGKRTPILGVCLGHQAIGYAFGAKIRRARK-VFHGKISNIILVNNSPLSL  122
TRPG_ARATH_AAA32742_   LGPLVPLFGVCMGLQCIGEAFGGKIVRSPFGVMHGKSSMVHYDEKGEEGL  191
                        *  :::****:*:** *  *:.*  **  *. : **..  . .

TRPEG_AGRTU_MONSANTO_  FSGLGKEVTVGRYHSIFADPATLPR-DFIITAES-EDGTIMGIEHAKEP-  690
TRPEG_RHIME_A30904_    FSGLGKEVTVGRYHSIFADPSNLPR-EFVITAES-EDGTIMGIEHSKEP-  690
TRPG_SULSO_B40635_     YYGIAKEFKATRYHSLVVDEVHRP---LIVDAISAEDNEIMAIHHEEYP-  168
TRPG_ARATH_AAA32742_   FSGLSNPFIVGRYHSLVIEKDTFPSDELEVTAWT-EDGLVMAARHRKYKH  240
                         * :  ::  ****   ..  *       ::  .:  .:  *  .

TRPEG_AGRTU_MONSANTO_  VAAVQFHPESIMTLGQDAGMRMIENVVVHLTRKAKTKAA       729  (SEQ ID NO:4)
TRPEG_RHIME_A30904_    VAAVQFHPESIMTLGGDAGMRMIENVVAHLAKRAKTKAA       729  (SEQ ID NO:43)
TRPG_SULSO_B40635_     IYGVQFHPESVGTS---LGYKILYNFLNRV--------          195  (SEQ ID NO:44)
TRPG_ARATH_AAA32742_   IQGVQFHPESIITT---EGKTIVRNFIKIVEKKESEKLT       276  (SEQ ID NO:45)
                        *:.******  :      :  :  *:: :
```

*Fig. 7D*

```
atgcaaacacaaaaaccgactctcgaactggaattcctggtggaaaacggtatcgccaccgt
gcaagcgggtgctggtgtagtccttgattctgttccgcagtcggaagccgacgaaacccgta
acaaagcccgcgctgtactgcgcgctattgccaccgcgcatcatgcacaggagactttctga
tggctgacattctgctgctcgataatatcgactcttttacgtacaacctggcagatcagttg
cgca
```

*Fig. 10*

```
  1 - ATGGTAACGATCATTCAGGATGACGGAGCGGAGACCTACGAGACGAAAGGCGGCATCCAG -  60
    - M  V  T  I  I  Q  D  D  G  A  E  T  Y  E  T  K  G  G  I  Q
 61 - GTCAGCCGAAAGCGCCGGCCCACCGATTATGCCAACGCCATCGATAATTACATCGAAAAG - 120
    - V  S  R  K  R  R  P  T  D  Y  A  N  A  I  D  N  Y  I  E  K
121 - CTTGATTCCCATCGCGGCGCGGTTTTTTCGTCCAACTATGAATATCCGGGCCGTTACACC - 180
    - L  D  S  H  R  G  A  V  F  S  S  N  Y  E  Y  P  G  R  Y  T
181 - CGCTGGGATACGGCCATCGTCGATCCGCCGCTCGGCATTTCCTGTTTTGGCCGCAAGATG - 240
    - R  W  D  T  A  I  V  D  P  P  L  G  I  S  C  F  G  R  K  M
241 - TGGATCGAAGCCTATAATGGCCGCGGCGAAGTGCTGCTCGATTTCATTACGGAAAAGCTG - 300
    - W  I  E  A  Y  N  G  R  G  E  V  L  L  D  F  I  T  E  K  L
301 - AAGGCGACACCCGATCTCACCCTCGGCGCTTCCTCGACCCGCCGGCTCGATCTTACCGTC - 360
    - K  A  T  P  D  L  T  L  G  A  S  S  T  R  R  L  D  L  T  V
361 - AACGAACCGGACCGTGTCTTCACCGAAGAAGAACGCTCGAAAATCCCGACGGTCTTCACC - 420
    - N  E  P  D  R  V  F  T  E  E  E  R  S  K  I  P  T  V  F  T
421 - GCTCTCAGAGCCATCGTCGACCTCTTCTATTCGAGCGCGGATTCGGCCATCGGCCTGTTC - 480
    - A  L  R  A  I  V  D  L  F  Y  S  S  A  D  S  A  I  G  L  F
481 - GGTGCCTTCGGTTACGATCTCGCCTTCCAGTTCGACGCGATCAAGCTTTCGCTGGCGCGT - 540
    - G  A  F  G  Y  D  L  A  F  Q  F  D  A  I  K  L  S  L  A  R
541 - CCGGAAGACCAGCGTGACATGGTGCTGTTTCTGCCCGATGAAATCCTCGTCGTTGATCAC - 600
    - P  E  D  Q  R  D  M  V  L  F  L  P  D  E  I  L  V  V  D  H
601 - TATTCCGCCAAGGCCTGGATCGACCGTTACGATTTCGAGAAGGACGGCATGACGACGGAC - 660
    - Y  S  A  K  A  W  I  D  R  Y  D  F  E  K  D  G  M  T  T  D
661 - GGCAAATCCTCCGACATTACCCCCGATCCCTTCAAGACCACCGATACCATCCCGCCCAAG - 720
    - G  K  S  S  D  I  T  P  D  P  F  K  T  T  D  T  I  P  P  K
721 - GGCGATCACCGTCCCGGCGAATATTCCGAGCTTGTGGTGAAGGCCAAGGAAAGCTTCCGC - 780
    - G  D  H  R  P  G  E  Y  S  E  L  V  V  K  A  K  E  S  F  R
781 - CGCGGCGACCTGTTCGAGGTCGTTCCCGGCCAGAAATTCATGGAGCGTTGCGAAAGCAAT - 840
    - R  G  D  L  F  E  V  V  P  G  Q  K  F  M  E  R  C  E  S  N
```

Fig. 12A

```
 841 - CCGTCGGCGATTTCCCGCCGCCTGAAGGCGATCAACCCGTCGCCCTATTCCTTCTTCATC -  900
     -  P  S  A  I  S  R  R  L  K  A  I  N  P  S  P  Y  S  F  F  I
 901 - AATCTCGGCGATCAGGAATATCTGGTCGGCGCCTCGCCGGAAATGTTCGTGCGCGTCTCC -  960
     -  N  L  G  D  Q  E  Y  L  V  G  A  S  P  E  M  F  V  R  V  S
 961 - GGCCGTCGCATCGAGACCTGCCCGATATCAGGCACCATCAAGCGCGGCGACGATCCGATT - 1020
     -  G  R  R  I  E  T  C  P  I  S  G  T  I  K  R  G  D  D  P  I
1021 - GCCGACAGCGAGCAGATTTTGAAACTGCTCAACTCGAAAAAGGACGAATCCGAACTGACC - 1080
     -  A  D  S  E  Q  I  L  K  L  L  N  S  K  K  D  E  S  E  L  T
1081 - ATGTGCTCGGACGTGGACCGCAACGACAAGAGCCGCGTCTGCGAGCCGGGTTCGGTGAAG - 1140
     -  M  C  S  D  V  D  R  N  D  K  S  R  V  C  E  P  G  S  V  K
1141 - GTCATTGGCCGCCGCCAGATCGAGATGTATTCACGCCTCATCCACACCGTCGATCACATC - 1200
     -  V  I  G  R  R  Q  I  E  M  Y  S  R  L  I  H  T  V  D  H  I
1201 - GAAGGCCGCCTGCGCGACGATATGGACGCCTTTGACGGTTTCCTCAGCCACGCCTGGGCC - 1260
     -  E  G  R  L  R  D  D  M  D  A  F  D  G  F  L  S  H  A  W  A
1261 - GTCACCGTCACCGGTGCACCAAAGCTGTGGGCCATGCGCTTCATCGAAGGTCATGAAAAG - 1320
     -  V  T  V  T  G  A  P  K  L  W  A  M  R  F  I  E  G  H  E  K
1321 - AGCCCGCGCGCCTGGTATGGCGGTGCGATCGGCATGGTCGGCTTCAACGGCGACATGAAT - 1380
     -  S  P  R  A  W  Y  G  G  A  I  G  M  V  G  F  N  G  D  M  N
1381 - ACCGGCCTGACGCTGCGCACCATCCGGATCAAGGACGGTATTGCCGAAGTGCGCGCCGGC - 1440
     -  T  G  L  T  L  R  T  I  R  I  K  D  G  I  A  E  V  R  A  G
1441 - GCGACCCTGCTCAATGATTCCAACCCGCAGGAAGAAGAAGCCGAAACCGAACTGAAGGCC - 1500
     -  A  T  L  L  N  D  S  N  P  Q  E  E  E  A  E  T  E  L  K  A
1501 - TCCGCCATGATATCAGCCATTCGTGACGCAAAAGGCACCAACTCTGCCGCCACCAAGCGT - 1560
     -  S  A  M  I  S  A  I  R  D  A  K  G  T  N  S  A  A  T  K  R
1561 - GATGCCGCCAAAGTCGGCACCGGCGTCAAGATCCTGCTCGTCGACCACGAAGACAGCTTC - 1620
     -  D  A  A  K  V  G  T  G  V  K  I  L  L  V  D  H  E  D  S  F
1621 - GTGCACACGCTGGCGAATTATTTCCGCCAGACGGGCGCGACGGTCTCGACCGTCAGATCA - 1680
     -  V  H  T  L  A  N  Y  F  R  Q  T  G  A  T  V  S  T  V  R  S
```

*Fig. 12B*

1681 - CCGGTCGCAGCCGACGTGTTCGATCGCTTCCAGCCGGACCTCGTTGTCCTGTCGCCCGGA - 1740
     -  P  V  A  A  D  V  F  D  R  F  Q  P  D  L  V  V  L  S  P  G
1741 - CCCGGCAGCCCGACGGATTTCGACTGCAAGGCAACGATCAAGGCCGCCCGCGCCCGCGAT - 1800
     -  P  G  S  P  T  D  F  D  C  K  A  T  I  K  A  A  R  A  R  D
1801 - CTGCCGATCTTCGGCGTTTGCCTCGGTCTGCAGGCATTGGCAGAAGCCTATGGCGGCGAG - 1860
     -  L  P  I  F  G  V  C  L  G  L  Q  A  L  A  E  A  Y  G  G  E
1861 - CTGCGCCAGCTTGCTGTGCCCATGCACGGCAAGCCTTCGCGCATCCGCGTGCTGGAACCC - 1920
     -  L  R  Q  L  A  V  P  M  H  G  K  P  S  R  I  R  V  L  E  P
1921 - GGCCTCGTCTTCTCCGGTCTCGGCAAGGAAGTCACGGTCGGTCGTTACCATTCGATCTTC - 1980
     -  G  L  V  F  S  G  L  G  K  E  V  T  V  G  R  Y  H  S  I  F
1981 - GCCGATCCCGCCACCCTGCCGCGTGATTTCATCATCACCGCAGAAAGCGAGGACGGCACG - 2040
     -  A  D  P  A  T  L  P  R  D  F  I  I  T  A  E  S  E  D  G  T
2041 - ATCATGGGCATCGAACACGCCAAGGAACCGGTGGCCGCCGTTCAGTTCCACCCGGAATCG - 2100
     -  I  M  G  I  E  H  A  K  E  P  V  A  A  V  Q  F  H  P  E  S
2101 - ATCATGACGCTCGGACAGGACGCGGGCATGCGGATGATCGAGAATGTCGTGGTGCATCTG - 2160
     -  I  M  T  L  G  Q  D  A  G  M  R  M  I  E  N  V  V  V  H  L
2161 - ACCCGCAAGGCGAAGACCAAGGCCGCGTGA - 2190
     -  T  R  K  A  K  T  K  A  A  *

*Fig. 12C*

```
  1 ATGGAATCCC TAGCCGCCAC CTCCGTGTTC GCGCCCTCCC GCGTCGCCGT
 51 CCCGGCGGCG CGGGCCCTGG TTAGGGCGGG GACGGTGGTA CCAACCAGGC
101 GGACGAGCAG CCGGAGCGGA ACCAGCGGGG TGAAATGCTC TGCTGCCGTG
151 ACGCCGCAGG CGAGCCCAGT GATTAGCAGG AGCGCTGCGG CGGCGAAGGC
201 GGCGGAGGAG GACAAGAGGC GGTTCTTCGA GGCGGCGGCG CGGGGGAGCG
251 GGAAGGGGAA CCTGGTGCCC ATGTGGGAGT GCATCGTGTC GGACCATCTC
301 ACCCCCGTGC TCGCCTACCG CTGCCTCGTC CCCGAGGACA ACGTCGACGC
351 CCCCAGCTTC CTCTTCGAGT CCGTCGAGCA GGGGCCCCAG GGCACCACCA
401 ACGTCGGCCG CTATAGCATG GTGGGAGCCC ACCCAGTGAT GGAGATTGTG
451 GCCAAAGACC ACAAGGTTAC GATCATGGAC CACGAGAAGA GCCAAGTGAC
501 AGAGCAGGTA GTGGACGACC CGATGCAGAT CCCGAGGACC ATGATGGAGG
551 GATGGCACCC ACAGCAGATC GACGAGCTCC CTGAATCCTT CTCCGGTGGA
601 TGGGTTGGGT CTTTTCCTA TGATACGGTT AGGTATGTTG AGAAGAAGAA
```

*Fig. 13A*

```
 651 GCTACCGTTC TCCAGTGCTC CTCAGGACGA TAGGAACCTT CCTGATGTGC
 701 ACTTGGGACT CTATGATGAT GTTCTAGTCT TCGATAATGT TGAGAAGAAA
 751 GTATATGTTA TCCATTGGGT CAATGTGGAC CGGCATGCAT CTGTTGAGGA
 801 AGCATACCAA GATGGCAGGT CCCGACTAAA CATGTTGCTA TCTAAAGTGC
 851 ACAATTCCAA TGTCCCCACA CTCTCTCCTG GATTTGTGAA GCTGCACACA
 901 CGCAAGTTTG GTACACCTTT GAACAAGTCG ACCATGACAA GTGATGAGTA
 951 TAAGAATGCT GTTCTGCAGG CTAAGGAACA TATTATGGCT GGGGATATCT
1001 TCCAGATTGT TTTAAGCCAG AGGTTCGAGA GACGAACATA TGCCAACCCA
1051 TTTGAGGTTT ATCGAGCATT ACGGATTGTG AATCCTAGCC CATACATGGC
1101 GTATGTACAG GCAAGAGGCT GTGTATTGGT TGCGTCTAGT CCTGAAATTC
1151 TTACACGAGT CAGTAAGGGG AAGATTATTA ATCGACCACT TGCTGGAACT
1201 GTTCGAAGGG GCAAGACAGA GAAGGAAGAT CAAATGCAAG AGCAGCAACT
1251 GTTAAGTGAT GAAAAACAGT GTGCCGAGCA CATAATGCTT GTGGACTTGG
```

*Fig. 13B*

```
1301 GAAGGAATGA TGTTGGCAAG GTATCCAAAC CAGGATCAGT GAAGGTGGAG

1351 AAGTTGATGA ACATTGAGAG ATACTCCCAT GTTATGCACA TCAGCTCAAC

1401 GGTTAGTGGA CAGTTGGATG ATCATCTCCA GAGTTGGGAT GCCTTGAGAG

1451 CTGCCTTGCC CGTTGGAACA GTCAGTGGTG CACCAAAGGT GAAGGCCATG

1501 GAGTTGATTG ATAAGTTGGA AGTTACGAGG CGAGGACCAT ATAGTGGTGG

1551 TCTAGGAGGA ATATCGTTTG ATGGTGACAT GCAAATTGCA CTTTCTCTCC

1601 GCACCATCGT ATTCTCAACA GCGCCGAGCC ACAACACGAT GTACTCATAC

1651 AAAGACGCAG ATAGGCGTCG GGAGTGGGTC GCTCATCTTC AGGCTGGTGC

1701 AGGCATTGTT GCCGACAGTA GCCCAGATGA CGAACAACGT GAATGCGAGA

1751 ATAAGGCTGC TGCACTAGCT CGGGCCATCG ATCTTGCAGA GTCAGCTTTT

1801 GTAGACAAAG AATAG
```

*Fig. 13C*

```
  1 MESLAATSVF APSRVAVPAA RALVRAGTVV PTRRTSSRSG TSGVKCSAAV
 51 TPQASPVISR SAAAAKAAEE DKRRFFEAAA RGSGKGNLVP MWECIVSDHL
101 TPVLAYRCLV PEDNVDAPSF LFESVEQGPQ GTTNVGRYSM VGAHPVMEIV
151 AKDHKVTIMD HEKSQVTEQV VDDPMQIPRT MMEGWHPQQI DELPESFSGG
201 WVGFFSYDTV RYVEKKKLPF SSAPQDDRNL PDVHLGLYDD VLVFDNVEKK
251 VYVIHWVNVD RHASVEEAYQ DGRSRLNMLL SKVHNSNVPT LSPGFVKLHT
301 RKFGTPLNKS TMTSDEYKNA VLQAKEHIMA GDIFQIVLSQ RFERRTYANP
351 FEVYRALRIV NPSPYMAYVQ ARGCVLVASS PEILTRVSKG KIINRPLAGT
401 VRRGKTEKED QMQEQQLLSD EKQCAEHIML VDLGRNDVGK VSKPGSVKVE
451 KLMNIERYSH VMHISSTVSG QLDDHLQSWD ALRAALPVGT VSGAPKVKAM
501 ELIDKLEVTR RGPYSGGLGG ISFDGDMQIA LSLRTIVFST APSHNTMYSY
551 KDADRRREWV AHLQAGAGIV ADSSPDDEQR ECENKAAALA RAIDLAESAF
601 VDKE*
```

Fig. 13D

```
AgrTu_15889565  -----MVTIIQDDGAETYETKGGIQVSRKRRPTDYANAIDNYIEKLDSHRGAVFSSNYEY   55
RhiMe_136328    -----MAAVILEDGAESYTTKGIVTRRRREASYSDAIAGYVDRLDERRGAVFSSNYEY    55
MesLo_13472468  -METAMTMKVLENGAESFVTAGGITITRERHDRPYAGAIDAYVDGLNSRRGAVFSSNYEY  59
AzoBr_1717765   MYPADLLASPDLLEPLRFQTRGGVTVTRRATALDPRTALDPVIDALDRRRGLLLSSGVEA  60
BruMe_17986732  -----MNAKTADSEIFQHETAGGIIVERVRHLTAYKGAIESYIDVLNEWRGAVFSSNYEY  55
Nostoc_17227910 ----------MIADSHSYRTNGNVRVSRSITQVKMETALEEILFYLNSQRGGLLTSSYEY  50
Nostoc_17230725 --------------MRVSRSTTEVKMDTALDEILFHLNQVRGGLLTSSYEY          37
RhoPa_TrpEG     -----MNRTVFSLPATSDYKTAAGLAVTRSAQPFAGGQALDELIDLLDHRRGVMLSSGTTV 56
                         :    :      * :    .    .      .       :.   :   *:.  ..*:

AgrTu_15889565  PGRYTRWDTAIVDPPLGISCFGRKMWIEAYNGRGEVLLDFITEKLKATPDLTLGASSTRR 115
RhiMe_136328    PGRYTRWDTAVVDPPLAISSFGRSLWIEAYNERGEVLLALIAEDLKSVADITLGSLAARR 115
MesLo_13472468  PGRYTRWDTAIIDPPLVISARGRAMRIEALNRRGEALLPVIGKTLGGLADITIAETTKTL 119
AzoBr_1717765   PGRYRRHALGFTDPAVALTARGRTLRIDALNGRGQVLLPAVAEALRGLEALAGLEEAPSR 120
BruMe_17986732  PGRYTRWDTAIVDPPVVITSRARTMRIEALNARGVILLRPILDTVKALSEVKIDQSGENR 115
Nostoc_17227910 PGRYKRWAIGFVNPPVELSTSGNTFTLTALNERGYVLLPVIFECLSKSEQLQKLTEHHHK 110
Nostoc_17230725 PGRYKRWAIGFINPPLQLTTRENAFTISSLNPRGQVLLPTLFQHLSAQSLQQISLNHDY   97
RhoPa_TrpEG     PGRYESFDLGFADPPLALTTRAEKFTIEALNPRGRVLIAFLSDKLEEPCVVVEQACATKI 116
                ***           .             ::    *   *    :       .

AgrTu_15889565  LDLTVNEPDRVFTEEERSKIPTVFTALRAIVDLFYSSADSAIGLFGAFGYDLAFQFDAIK 175
RhiMe_136328    LDLTINEPDRVFTEEERSKMPTVFTVLRAVTNLFHSEEDSNLGLYGAFGYDLAFQFDAIE 175
MesLo_13472468  IRLDVAKPGRVFTEEERSRVPSVFTVLRAITALFKTDEDANLGLYGAFGYDLSFQFDPVD 179
AzoBr_1717765   VTASSASPAPL-PGEERSRQPSVFSVLRAVLDLFAAPDDPLLGLYGAFAYDLGAFQFDPIQ 179
BruMe_17986732  IDLTIVEPVGTFTEEERSRMPSVFTVLRAIVGLFFSEEDANLGLYGAFGYDLGAFQFDPIQ 175
Nostoc_17227910 ITGLVKSTPEFFAEEERSKQPSTFTVIREILHIFSSQEDEHLGLYGAFGYDLVFQFEQIT 170
Nostoc_17230725 ITGEIRPTKQLFTEEQRSKQPSAFTVIREILQIFASDEDEHLGLYGAFGYDLVFQFEPIP 157
RhoPa_TrpEG     RGHIVRGEAPV-DEEQRTRRASASLVRAVIAAFASPADPMLGLYGAFAYDLVFQFEDLK  175
                   :        :**. ::   : ::   :  .*     .  **:*** :**. **:  .
```

Fig. 15A

```
AgrTu_15889565    LSLARPEDQRDMVLFLPDEILVVDHYSAKAWIDRYDFEKDGMTTDGKSSDITPDPFKTTD  235
RhiMe_136328      LKLSRPDDQRDMVLFLPDEILVVDHYAAKAWIDRYDFARENLSTEGKAADIAPEPFRSVD  235
MesLo_13472468    YKLERKPSQRDLVLFLPDEILVVDHYSAKAWTDRYDYSGEGFSTEGLPRDAIAEPFKTAD  239
AzoBr_1717765     QRLERPDDQRDLLLYLPDRLVALDPIAGLARLVAYEFITAAGSTEGLECGGRDHPYRPDT  239
BruMe_17986732    YKLKRPDDQRDLVLFIPDEIFVADHYAARAWVDRYEFRCGGSSTHGLDRATPVVPFKPSE  235
Nostoc_17227910   QCLERPQDQRDLVLYLPDELIVVDYYQQQAFRLEYDFITAHGSTYDLPRTGESVDYRGQC  230
Nostoc_17230725   QKIARPADQRDLVLYLPDELIVVDYYLQKAYRHQYEFATEHGNTEHLPRTGQSIDYQGKH  217
RhoPa_TrpEG       QKRAREADQRDIVLYVPDRLLAYDRATGRGVDISYEFAWKGQSTAGLPNETAESVYT-QT  234
                   *  : :*** ::* *:: **..:.   .        .    *            :

AgrTu_15889565    TIPPK-GDHRPGEYSELVVKAKESFRRGDLFEVVPGQKFMERCESNPSAISRRLKAINPS  294
RhiMe_136328      SIPPH-GDHRPGEYAELVVKAKESFRRGDLFEVVPGQKFYERCESRPSEISNRLKAINPS  294
MesLo_13472468    RIPPR-GDHEPGEYANLVRRAMDSFKRGDLFEVVPGQMFYERCETQPSDISRKLKSINPS  298
AzoBr_1717765     NAEAG-CDHAPGDYQRVVESAKAAFRRGDLFEVVPGQTFAEPCADAPSSVFRRLRAANPA  298
BruMe_17986732    RKLAR-GDHNPGEYARLVERAKESFKRGDLFEVVPGQTFYERCHTAPSEIFRRLKSINPS  294
Nostoc_17227910   LTPPQNADHKIGEYAKLVEFALDYFRRGDLFEVVPSQNFFTACEAPPSQLFETLKQINPS  290
Nostoc_17230725   LLPNQTADHQPGEYANLVEQALDYFRRGDLFEVVPSQNFFTACEQSPSQLFQTLRQINPS  277
RhoPa_TrpEG       GRQGF-ADHAPGDYPKVVEKARAAFARGDLFEAVPGQLFGEPCERSPAEVFKRLCRINPS  293
                   .     .** .*:*  :*.   * *****:**.*::.  *   *. :*: *  **:

AgrTu_15889565    PYSFFINLGDQEYLVGASPEMFVRVSGRRIETCPISGTIKRGDDPIADSEQILKLLNSKK  354
RhiMe_136328      PYSFFINLGNQEYLVGASPEMFVRVSGRRIETCPISGTIKRGDDPIADSEQILKLLNSKK  354
MesLo_13472468    PYSFFINLGENEYLIGASPEMFVRVNGRRVETCPISGTIKRGDDAISDSEQILKLLNSKK  358
AzoBr_1717765     PYEAFVNLGRGEFLVAASPEMYRVRVAGGRVETCPISGTVARGADALGDAAQVLRLLTSAK  358
BruMe_17986732    PYSFFINLGESEYLVGASPEMFVRVNGRRIETCPISGTIKRGEDAISDSEQILKLLNSKK  354
Nostoc_17227910   PYGFIFNLG-GEYIIGASPEMFVREGRRVETCPISGTITRGHDAIDDAVQIRQLLNSHK  349
Nostoc_17230725   PYGFLLNLG-GEYLIGASPEMFVRVDGRRVETCPISGTIRRGEDALGDAVQIRQLLNSHK  336
RhoPa_TrpEG       PYGGLLNLGDGEFLVSASPEMFVRSDGRRIETCPISGTIARGVDAISDAEQIQKLLNSEK  353
                   *:   :**   *::.*****::  .***:************  *.  .*::: ****.:
```

Fig. 15B

```
AgrTu_15889565    DESELTMCSDVDRNDKSRVCEPGSVKVIGRRQIEMYSRLIHTVDHIEGRLRDDMDAFDGF  414
RhiMe_136328      DESELTMCSDVDRNDKSRVCVPGSVKVIGRRQIEMYSRLIHTVDHIEGRLRDDMDAFDGF  414
MesLo_13472468    DESELTMCSDVDRNDKSRVCEPGSVKVIGRRQIEMYSRLIHTVDHIEGRLREGMDAFDAF  418
AzoBr_1717765     DAAELTMCTDVDRNDKARVCEPGSVRVIGRRMIELYSRLIHTVDHVEGRLRSGMDALDAF  418
BruMe_17986732    DESELTMCSDVDRNDKSRVCEPGSVRVIGRRQIEMYSRLIHTVDHIEGRLRDGMDAFDGF  414
Nostoc_17227910   DEAELTMCTDVDRNDKSRICEPGSVRVIGRRQIELYSHLIHTVDHVEGILRPEFDALDAF  409
Nostoc_17230725   DEAELTMCTDVDRNDKSRICEPGSVRVIGRRQIELYSHLIHTVDHVEGILRPEFDALDAF  396
RhoPa_TrpEG       DEFELNMCTDVDRNDKARVCVPGTIKVLARRQIETYSKLFHTVDHVEGMLRPGFDALDAF  413
                   * :*.***:******:.:.: *.**::.:* ** :**::******;.** :.**:.*.*

AgrTu_15889565    LSHAWAVTVTGAPKLWAMRFIEGHEKSPRAWYGGAIGMVGFNGDMNTGLTLRTIRIKDGI  474
RhiMe_136328      LSHAWAVTVTGAPKLWAMRFIESHEKSPRAWYGGAIGMVGFNGDMNTGLTLRTIRIKDGI  474
MesLo_13472468    LSHAWAVTVTGAPKLWAMRFIEQNEKSPRAWYGGAIGMVGFNGDMNTGLTLRTIRIKDGI  478
AzoBr_1717765     LTHSWAVTVTGAPKRWAMQFLEDTEQSPRRWYGGAFGRLGFDGGMDTGLTLRTIRMAEGV  478
BruMe_17986732    LSHAWAVTVTGAPKLWAMRFLEENERSPRAWYGGAIGMMHFNGDMNTGLTLRTIRIKDGV  474
Nostoc_17227910   LSHTWAVTVTGAPKRAAIQFIEKNERSVRRWYGGAVGYLNFNGNLNTGLILRTIRLQDSI  469
Nostoc_17230725   LSHTWAVTVTGAPKRAAMQFIEQHERSARRWYGGAVGYLGFNGNLNTGLTLRTIRLQDSI  456
RhoPa_TrpEG       LTHAWAVTVTGAPKLWAMQFVEDHERSPRRWYAGAFGVVGFDGSINTGLTIRTIRMKDGL  473
                  *:*.********** .*::*:* *::* *.*:* *: . .::. :*** ::*****..:.

AgrTu_15889565    AEVRAGATLLNDSNPQEEEAETELKASAMISAIRDAKGTNSAATKRDAAK-------VGT  527
RhiMe_136328      AEVRAGATLLYDSNPEEEEAETELKASAMIAAIRDAKSANSAKSARDVAA-------VGA  527
MesLo_13472468    AEVRAGATLLFDSIPEEEEAETELKASAMLSAIRDAKTGNSASTERTTAR-------VGD  531
AzoBr_1717765     AYVRAGATLLSDSDPDAEDAECRLKAAAFRDAIRGTAAGAAPTLPAAPRG-------GE   530
BruMe_17986732    AEIRAGATLLFDSNPDEEEAETELKASAMIAAVRDAQKSNQIAEESVAAK-------VGE  527
Nostoc_17227910   AEVRVGATLLYDSIPQAEEQETITKAAAAFETIRRAKQIDPQIEESSTRKLSKYLPDGQS  529
Nostoc_17230725   AEVRVGATVLYDSIPSAEEEETITKATALFETIRRHTANKTQGNDSHRP-----GDIAH  511
RhoPa_TrpEG       AEVRVGATCLFDSNPVAEDKECQVKAAALFQALRGDPAKPLSAV-APDAT-------GS   524
                  * :* .***.*.****. *:* ** * *: :::        *:            .*
```

*Fig. 15C*

```
AgrTu_15889565    GVKILLVDHEDSFVHTLANYFRQTGATVSTVRSPVAADVFDRFQPDLVVLSPGPGSPTDF  587
RhiMe_136328      GVSILLVDHEDSFVHTLANYFRQTGASVTTVRTPVAEEIFDRVKPDLVVLSPGPGTPKDF  587
MesLo_13472468    GVNILLVDHEDSFVHTLANYFRQTGANVSTVRTPVDEVFERLKPDLVVLSPGPGTPKDF   591
AzoBr_1717765     GRRVLLVDHDDSFVHTLADYLRQTGASVTTLRHSHARAALAERRPDLVVLSPGPGRPADF  590
BruMe_17986732    GVSILLVDHEDSFVHTLANYFRQTGAKVSTVRSPVAEEIFDRVNPDLVVLSPGPGSPQDF  587
Nostoc_17227910   GKHILLIDHEDSFVHTLANYIRSTGATVTTLRHGFSESLFDTERPDLVVLSPGPGRPSEF  589
Nostoc_17230725   NKRILLIDYEDSFVHTLANYIRTTGATVTTLRHGFAESYFDAERPDLVVLSPGPGRPSDF  571
RhoPa_TrpEG       GKKVLLVDHDDSFVHMLADYFRQVGAQVTVVRYVHGLKMLAENSYDLLVLSPGPGRPEDF  584
                      :**.*::.*******..**:**:*.  ***..***..*  :  **:*********.*:*

AgrTu_15889565    DCKATIKAARARDLPIFGVCLGLQALAEAYGGELRQLAVPMHGKPSRIRVLEP-GLVFSG  646
RhiMe_136328      DCKATIKKARARDLPIFGVCLGLQALAEAYGGDLRQLAIPMHGKPSRIRVLEP-GIVFSG  646
MesLo_13472468    DCAATIRRARARDLPIFGVCLGLQALAEAYGGELRQLHIPMHGKPSRIRVSKP-GIIFSG  650
AzoBr_1717765     DVAGTIDAALALGLPVFGVCLGLPVFGVCLGLQGMVERFGGALDVLPEPVHGKATEVRVLGG--ALFAG  648
BruMe_17986732    DCKATIDKARKRQLPIFGVCLPLFGVCLGLQALAEAYGGALRQLRVPVHGKPSRIRVSKP-ERIFSG  646
Nostoc_17227910   KVQETVAACVRRQIPLFGVCLGLQGIVEAFGGELGVLNYPQHGKSSRIFVTAPDSVMFQD  649
Nostoc_17230725   RVPQTVAALVGREIPIFGVCLGLQGIVEAFGGELGVLDYPQHGKPARISVTAPDSVLFQN  631
RhoPa_TrpEG       KIKDTIDAALAKKLPIFGVCLGVQAMGEYFGGTLGQLAQPAHGRPSRIQVRGG--ALMRG  642
                   .  *:   .   :  *:******..:.. : ..*  ::..        .     *

AgrTu_15889565    LGKEVTVGRYHSIFADPATLPRDFIITAESEDGTIMGIEHAKEPVAAVQFHPESIMTLGQ  706
RhiMe_136328      LGKEVTVGRYHSIFADPSNLPREFVITAESEDGTIMGIEHSKEPVAAVQFHPESIMTLGG  706
MesLo_13472468    LPKEVTVGRYHSIFADPVRLPDDFIVTAETEDGIIMAFEHRKEPIAAVQFHPESIMTLGH  710
AzoBr_1717765     LPERLTVGRYHSLVARRDRLPADLTVTAETADGLVMAVEHRRLPLAAVQFHPESILSLDG  708
BruMe_17986732    LPEEVTVGRYHSIFADPERLPDDFLVTAETEDGIIMAFEHKHEPVAAVQFHPESIMTLGH  706
Nostoc_17227910   LPESFTVGRYHSLFALSQRLPKELKVTAISDDEVIMAIEHQTLPIAAVQFHPESIMTLAG  709
Nostoc_17230725   LPASFIVGRYHSLFAQPQTIPGELKVTAISEDNVIMAIEHQTLPIAAVQFHPESIMTLAG  691
RhoPa_TrpEG       LPNEVTIGRYHSLYVDMRDMPKELTVTASTDDGIAMAIEHKTLPVGGVQFHPESLMSLGG  702
                  *    :*****:   .   * : : :* : :. : .*:  *:..********:: : 
```

*Fig. 15D*

```
AgrTu_15889565    DAGMRMIENVVVHLTRKAKTKAA------  729
RhiMe_136328      DAGMRMIENVVAHLAKRAKTKAA------  729
MesLo_13472468    NAGMRIIENIVAHLPRKAKEKAA------  733
AzoBr_1717765     GAGLALLGNVMDRLAAGALTDAAA-----  732
BruMe_17986732    NAGMRMIENIVTHLAGKHKARRTNY----  731
Nostoc_17227910   EVGLMMIKNVVQKYTQSQQSTVPIYD   735
Nostoc_17230725   EVGQTIIKNVVQTYTQTLETSIYS-----  715
RhoPa_TrpEG       EVGLRIVENAFRLGQAA------------  719
                   .*   ::  *    .
```

Fig. 15E

```
   1 ATGGTGACCA TCATTCAGGA TGACGGTGCC GAGACCTACG AGACCAAGGG CGGCATCCAG
  61 GTGAGCCGCA AGCGCCGCCC CACCGATTAC GCCAACGCCA TCGATAACTA CATCGAAAAG
 121 CTTGATTCCC ATCGCGGTGC CGTGTTCTCC TCCAACTACG AATACCCAGG CCGCTACACC
 181 CGCTGGGATA CCGCCATCGT CGATCCACCA CTCGGCATTT CCTGCTTCGG CCGCAAGATG
 241 TGGATCGAAG CCTACAACGG CCGCGGCGAA GTGCTGCTCG ATTTCATTAC CGAAAAGCTG
 301 AAGGCCACAC CCGATCTCAC CCTCGGCGCT TCCTCCACCC GCCGCCTCGA TCTTACCGTC
 361 AACGAACCAG ACCGCGTCTT CACCGAAGAA GAACGCTCCA AAATCCCAAC CGTCTTCACC
 421 GCTCTCAGGG CCATCGTCGA CCTCTTTCTA TCCAGCGCCG ATTCCGCCAT CGGCCTGTTC
 481 GGTGCCTTCG GTTACGATCT CGCCTTCCAG TTCGACGCCA TCAAGCTTTC CCTGGCCCGC
 541 CCAGAAGACC AGCCGCACAT GGTGCTGTTC CTGCCCGATG AAATCCTCGT CGTTGATCAC
 601 TACTCCGCCA AGGCCTGGAT CGACCGCTAC GATTTCGAGA AGGACGGCAT GACCACCGAC
 661 GGCAAATCCT CCGACATTAC CCCCGATCCC TTCAAGACCA CCGATACCAT CCCACCCAAG
 721 GGCGATCACC GCCCCGGCGA ATACTCCGAG CTTGTGGTGA AGGCCAAGGA AAGCTTCCGC
 781 CGCGGCGACC TGTTCGAGGT CGTTCCCGGC CAGAAATTCA TGGAGCGCTG CGAAAGCAAC
 841 CCATCCGCCA TTTCCCGCCG CCTGGAAGGC CTCCCCCAG  AAATGTTCGT CTTCTTCATC
 901 AACCTCGGCG ATCAGGAATA CCTGGTCGGC GCCTCCCCAG AGCGCGGGCA CGATCCAATT
 961 GGCCGCCGCA TCGAGACCTG CCCAATCTCA GGCACCATCA AGCGCGGGGA CGAACTGACC
1021 GCCGACAGCG AGCAGATTTT GAAACTGCTC AACTCCAAAA AGGACGAATC CGAACTGACC
1081 ATGTGCTCCG ACGTGGACCG CAACGACAAG AGCCGCGTCT GCGAGCCAGG TTCCGTGAAG
1141 GTCATTGGCC GCCGCCAGAT CGAGATGTAC TCACGCCTCA TCCACACCGT CGATCACATC
1201 GAAGGCCGCC TGCGCGACGA TATGGACGCC TTCGACGGTT TCCTCAGCCA CGCCTGGGCC
1261 GTCACCGTCA CCGGTGCACC AAAGCTGTGG GCCATGCGCT TCATCGAAGG TCATGAAAAG
1321 AGCCCACGCG CCTGGTACGG GCCATGGTCG GCTTCAACGG CGACATGAAC
1381 ACCGGCCTGA CCCTGCGCAC CATCCGCATC AAGGACGGTA TTGCCGAAGT GCGCGCCGGC
1441 GCCACCCTGC TCAACGATTC CAACCCACAG CGAAACCGA ACTCTGCCGC ACTGAAGGCC
1501 TCCGCCATGA TCTCAGCCAT TCGCGACGCA AAAGGCACCA AAAGGCACCA ACTCTGCCGC CACCAAGCGC
1561 GATGCCGCCA AAGTCGGCAC CGGCGTCAAG ATCCTGCTCG TCGACCACGA AGACAGCTTC
```

*Fig. 16A*

```
1621  GTGCACACCC  TGGCCAACTA  CTTCCGCCAG  ACCGGCGCCA  CCGTCTCCAC  CGTCAGGTCA
1681  CCAGTCGCAG  CCGACGTGTT  CGATCGCTTC  CAGCCAGACC  TCGTTGTCCT  GTCCCCGGT
1741  CCCGGCAGCC  CAACCGATTT  CGACTGCAAG  GCAACCATCA  AGGCCGCCCG  CGCCGCGAT
1801  CTGCCAATCT  TCGGCGTTTG  CCTCGGTCTG  CAGGCATTGG  CAGAAGCCTA  CGGCGGCGAG
1861  CTGCGCCAGC  TTGCTGTGCC  CATGCACGGC  AAGCCTTCCC  GCATCCGCGT  GCTGGAACCC
1921  GGCCTCGTCT  TCTCCGGTCT  CGGCAAGGAA  GTCACCGTCG  GTCGCTACCA  TTCCATCTTC
1981  GCCGATCCCG  CCACCCTGCC  ACGCGATTTC  ATCATCACCG  CAGAAAGCGA  GGACGGCACC
2041  ATCATGGGCA  TCGAACACGC  CAAGGAACCA  GTGGCCGCCG  TTCAGTTCCA  CCCAGAATCC
2101  ATCATGACCC  TCGGTCAGGA  CGCCGGCATG  CGCATGATCG  AGAACGTCGT  GGTGCATCTG
2161  ACCCGCAAGG  CCAAGACCAA  GGCCGCCTGA
```

```
           |1550       |1560       |1570       |1580       |1590       |1600       |1610       |1620       |1630       |1640       |1650
ACTCTGCCGCCACCAAGCGTGATGCCGCCAAAGTCGGCACCGGCCACCGGCCAAGATCCTGCTCGTCGTGCAGATCCTGCTGGCGGCGCTTCGTGCACACCGTTCCGCCAG
ACTCTGCCGCCACCAAGCG GATGCCGCCAAAGTCGGCACCGGCCACCGGCCAAGATCCTGCTCGTCGTGCAGATCCTGCTGGCGGCGCTTCGTGCAGATCCTGCTGGCGGCGCTTCGTGCACACC CTGGC AA TA TTCCGCCAG
ACTCTGCCGCCACCAAGCGCGATGCCGCCAAAGTCGGCACCGGCCACCGGCCAAGATCCTGCTCGTCGTGCAGATCCTGCTGGCGGCGCTTCGTGCACACCGTTCCGCCAG
           °1550       °1560       °1570       °1580       °1590       °1600       °1610       °1620       °1630       °1640       °1650

|1660       |1670       |1680       |1690       |1700       |1710       |1720       |1730       |1740       |1750       |1760
ACGGGGCGACGGTCTCAGATCAGATCCAGCCGTCGACCGTTCAGCCGACGTGTTCGATCGTTCAGCCGACCTCGTTGTCCTGTCGCCCGGACCTCGCCCCGGACCCGACGATTT
AC GGCGC AC GTCTC ACCGTCAG TCACC GTCCGCAGCCGACGTGTTCGATCGTTCAGCCG GACCTCGTTGTCCTGTC CCCGG CCCGGCAGCCC AC GATTT
ACCGGGCCACCGTCTCCACCGTCTCAGTCCACCAGTCCGAGCCGACGTGTCCAGCCAGACGTTCGATCGTTCCAGCCGCCAGCAGCCTCGTTGTCCTGTCCCCGGTCCCGGCAGCCCAACGATTT
           °1660       °1670       °1680       °1690       °1700       °1710       °1720       °1730       °1740       °1750       °1760

|1770       |1780       |1790       |1800       |1810       |1820       |1830       |1840       |1850       |1860       |1870
CGACTCGAAGGCAACGATCAAGGCCCGCCCCGCCCCGCGATCTGCCGATCTGCCGGTTTGCCTCGGTCTGCAGGCATTGGCAGAAGCCTATGGCGGCGAGCTGCGCCAGC
CGACTCGAAGGCAAC ATCAAGGCCCGCCCCGCCCCGCGATCTGCC ATCTTCGGCGTTTGCCTCGGTCTGCAGGCATTGGCAGAAGCCTATGGCGGCGAGCTGCGCCAGC
CGACTCGAAGGCAACCATCAAGGCCCGCCCCGCCCCGCCCCGCGATCTGCCAATCTTCGGCGTTTGCCAATCTTCGGCGTTTGCCTCGGTCTGCAGGCATTGGCAGGCATTGGCAGAAGCCTACGGCGGCTACGGCGGCGAGCTGCGCCAGC
           °1770       °1780       °1790       °1800       °1810       °1820       °1830       °1840       °1850       °1860       °1870

|1880       |1890       |1900       |1910       |1920       |1930       |1940       |1950       |1960       |1970       |1980
TTGCTGTGCCCATGCCAAGCCTTCGCGATCCGCGTGCTGGAACCCGGCCTCGTCTTCTCCGGTCTCGGCAAGGAAGTCACGGTCGGTCGTCGTTACCATTCGATCTTC
TTGCTGTGCCCATGCCAAGCCTTC CGCATCCGCGTGCTGGAACCCGGCCTCGTCTTCTCCGGTCTCGGCAAGGAAGTCACGGTCGGTCG TACCATTC ATCTTC
TTGCTGTGCCCATGCCAAGCCTTCCCCGCATCCGCGTGCTGGAACCCGGCCTCGTCTTCTCCGGTCTCGGCAAGGAAGTCACGGTCGGTCGCTACCATTCGCTACCATTCCATTCTTC
           °1880       °1890       °1900       °1910       °1920       °1930       °1940       °1950       °1960       °1970       °1980

|1990       |2000       |2010       |2020       |2030       |2040       |2050       |2060       |2070       |2080       |2090
GCCGATCCCGCCACCCTGCCGCGTGATTTCATCATCACCGCAGAAAGCGAGGACGGCACGATCATGGGCACGCACCACGACGACGCACCGAAGGAACCGGTGGCCGCCGTTCAGTTCCA
GCCGATCCCGCCACCCTGCC CG GATTTCATCATCACCGCAGAAGCGAGGACGGCACG ATCATGGGCACG ATCATGGGCACCACGACGACGCAC CGAACCCGAAGGACCC GTGGCCGCCGTTCAGTTCCA
GCCGATCCCGCCACCCTGCCGCCGCGATTTCATCATCACCGCAGAAAGCGAGGACGGCACCGAAGAACACGCAAAGCGAGGACGGCACCGAAGAACACGCCAAGGAACCGGTGGCCGCCGTTCAGTTCCA
           °1990       °2000       °2010       °2020       °2030       °2040       °2050       °2060       °2070       °2080       °2090

|2100       |2110       |2120       |2130       |2140       |2150       |2160       |2170       |2180       |2190
CCCGGAATCGATCATGATGACCTCGGACAGGACGGGCATGCGGGATGATCGGGATGCATGCGGCATGTCGATGAATGTCGAGAATCTCGTGGTGCATCGACCCGCAAGGCGAAGACCAAGGCCGCGTGA
CCC GAATC ATCATGAC CTCGG CAGGACGC ATCATGCG GGCATGCG ATGATCGAGAA GTCGTGGTGCATCGACCCGAAGGC AAGACCAAGGCCGC TGA
CCCAGAATCCATCATGACCTCGGACAGGACGGGCATGCGGTCGGTCGCATGCGATGATCGAGAACGTCGAGAACGTCGAGAATCTCGTGGTGCATCGACCCGAAGGCCAAGGACCAAGGCCGCCTGA
           °2100       °2110       °2120       °2130       °2140       °2150       °2160       °2170       °2180       °2190
```

*Fig. 17C*

| | | | | | |
|---|---|---|---|---|---|
| ATGGTGACCA | TCATTCAGGA | CGACGGCGCT | GAGACCTACG | AGACTAAGGG | CGGTATCCAA | 60 |
| GTGAGCCGTA | AGCGTAGGCC | CACTGACTAC | GCTAACGCCA | TCGACAACTA | CATCGAGAAG | 120 |
| CTAGACTCCC | ATCGCGGCGC | TGTGTTCTCC | TTCAACTACG | AATACCCTGG | GCGCTACACG | 180 |
| AGGTGGGATA | CCGCCATCGT | cGATCCTCCA | TTGGGCATCT | CCTGTTTTGG | GCGTAAGATG | 240 |
| TGGATCGAGG | CGTACAACGG | CCGtGGCGAA | GTCTTGCTGG | AcTTcATCAC | GGAGAAGCTC | 300 |
| AAGGCCACAC | CgGACCTcAC | cCTCGGcGCT | TCCTCGACcC | GCCGCCTcGA | CCTTACGGTC | 360 |
| AACGAGCCGG | ACCGCGTGTT | cACCGAGGAA | GAGCGTAGCA | AGATCCCgAC | TGTcTTCACC | 420 |
| GCGCTCAGAG | CcATCGTGGA | cCTATTCTAC | TCTTCtGCGG | ACAGCGCCAT | cGGGTTGTTC | 480 |
| GGTGCcTTcG | GTTACGACCT | cGCGTTCCAG | TTCGACGCCA | TCAAGCTCTC | GCTCGCGCGG | 540 |
| CCGGAGGACC | AGCGAGAcAT | GGTGCTCTTC | CTcCCTGACG | AGATcCTGGT | cGTCGATCAC | 600 |
| TATTCCGCgA | AGGCgTGGAT | CGACCGGTAC | GACTTcGAGA | AGGATGGCAT | GACCACgGAT | 660 |
| GGCAAGAGCA | GCGACATCAC | TCCCGACCCA | TTCAAGACCA | CcGACACcAT | CCCTCCAAAG | 720 |
| GGCGATCACC | GCCCTGGCGA | GTATTCcGAA | CTCGTGGTGA | AGGCCAAGGA | ATCCTTCcGG | 780 |
| CGCGGCGAtC | TGTTTGAGGT | GGTTCCcGGC | CAAAAGTTCA | TGGAgAGGTG | cGAGTCGAAT | 840 |
| CCgTCTGCgA | TCAGTCGCCG | ACTGAAaGCG | ATCAACCCGA | GCCCGTATTC | CTTCTTcATC | 900 |
| AACCTcGGCG | ATCAGGAATA | TCTGGTCGGA | GCcTCACCCG | AgATGTTcGT | CAGGGTCTCc | 960 |
| GGCCGCCGGA | TCGAGACgTG | CCCAATTTCC | GGAACCATCA | GCGCGGAGA | TGACCCGATA | 1020 |
| GCCGACTCTG | AGCAGATCCT | GAAACTCTTG | AAcAGCAAGA | AgGACGAGTC | cGAGCTGACT | 1080 |
| ATGTGCTCAG | ATGTGGACcG | AAACGACAAG | TCACGTGTCT | GCGAGCCCGG | TAGCGTCAAG | 1140 |
| GTcATTGGCC | GCCGTCAGAT | CGAGATGTAC | TCCAGGCTGA | TTCACACGGT | CGATCATATc | 1200 |
| GAAGGGCGGC | TGCGCGACGA | TATGGACGCA | TTCGACGGGT | TCCTcAGTCA | CGCCTGGGCC | 1260 |
| GTTACTGTCA | CCGGAGCGCC | TAAGCTCTGG | GCTATGAGgT | TCATCGAGGG | CCACGAGAAG | 1320 |
| AGCCCTAGGG | CTTGGTATGG | TGGtGCCATc | GGCATGGTTG | GGTTcAACGG | CGACATGAAC | 1380 |
| ACCGGGCTGA | CGCTCCGGAC | CATcAGGATC | AAAGACGGCA | TTGCCGAGGT | GAGGGCcGGT | 1440 |
| GCCACGCTTC | TCAACGATAG | CAAcCCTCAG | GAGGAAGAGG | CGGAGACCGA | GCTGAAaGCc | 1500 |
| tctGCGATGA | TCTCCGCGAT | TAGAGATGCA | AAGGGTACgA | AcAGTGCTGC | CACCAAGcGG | 1560 |
| GACGCAGCCA | AGGTGGGCAC | CGGCGTCAAG | ATtTACTTG | TCGAtCACGA | GGACTCcTTC | 1620 |

*Fig. 22A*

```
GTGCAcACTC TGGCgAACTA CTTCCGCCAG ACAGGCGCGA CgGTCTCCAC CGTTAGGTCA 1680

CCGGTGGCCG CTGACGTGTT CGATAGGTTc CAGCCCGACC TTGTGGTGCT CTCTCCCGGt 1740

CCCGGcTCGC CCACGGACTT CGAcTGCAAG GCCACCATTA AGGCCGCcAG GGCCAGGGAT 1800

CTgCCAATCT TCGGcGTTTG CCTCGGGCTt CAGGCATTGG CCGAGGCATA CGGTGGAGAG 1860

CTGAGgCAGC TCGCCGTCCC GATGCACGGG AAgCCATCCC GCATcAGAGT CCTgGAGCCC 1920

GGCCTCGTcT TCTCCGGTCT cGGGAAGGAG GTCACGGTCG GTCGGTAtCA TTCGATCTTC 1980

GCCGATCCGG CAACcCTCCC GCGCGACTTC ATCATAACCG CCGAGTCGGA GGAcGGAACg 2040

ATCATGGGAA TcGAACACGC cAAGGAGCCC GTAGCTGCGG TTCAGTTCCA CCCTGAGTCC 2100

ATcATGACCC TcGGTCAAGA TGCGGGTATG CGgATGATcG AGAATGTGGT gGTTCACCTc 2160

ACCCGcAAGG CcAAGACcAA GGCAGCATGA tag  2193
```

Fig. 22B

```
  1 A T G G T A A C G A T C A T T C A G G A T G A C G G A G C G   AS-S51F
  1 . . . . . . G . . . C . . . . . . . . . . . C . . . . . C . . T   AS(S51F) Codon_Opt 31 G A G A C C T A C G A G A C G A A A G G C G G C A T C C A G   AS-S51F
 31 . . . . . . . . . . . . . . . T . . G . . . . . T . . . . . A   AS(S51F) Codon_Opt 61 G T C A G C C G A A A G C G C C G G C C C A C C G A T T A T   AS-S51F
 61 . . G . . . . . T . . . . . T A . . . . . . . T . . C . . C   AS(S51F) Codon_Opt 91 G C C A A C G C C A T C G A T A A T T A C A T C G A A A A G   AS-S51F
 91 . . T . . . . . . . . . . . C . . C . . . . . . . . G . . .   AS(S51F) Codon_Opt 121 C T T G A T T C C C A T C G C G G C G C G G T T T T T T C G   AS-S51F
121 . . A . . C . . . . . . . . . . . . . T . G . . C . . C     AS(S51F) Codon_Opt 151 T T C A A C T A T G A A T A T C C G G G C C G T T A C A C C   AS-S51F
151 . . . . . . . . . . C . . . . . C . . T . . G . . C . . . . . G   AS(S51F) Codon_Opt 181 C G C T G G G A T A C G G C C A T C G T C G A T C C G C C G   AS-S51F
181 A . G . . . . . . . . C . . . . . . . . . . . . . . T . . A   AS(S51F) Codon_Opt 211 C T C G G C A T T T C C T G T T T T G G C C G C A A G A T G   AS-S51F
211 T . G . . . . . C . . . . . . . . . . . G . . T . . . . . .   AS(S51F) Codon_Opt 241 T G G A T C G A A G C C T A T A A T G G C C G C G G C G A A   AS-S51F
241 . . . . . . . . G . . G . . C . . . C . . . . . T . . . . . .   AS(S51F) Codon_Opt 271 G T G C T G C T C G A T T T C A T T A C G G A A A A G C T G   AS-S51F
271 . . C T . . . . G . . C . . . . . . . C . . . . . G . . . . . C   AS(S51F) Codon_Opt 301 A A G G C G A C A C C C G A T C T C A C C C T C G G C G C T   AS-S51F
301 . . . . . C . . . . . G . . C . . . . . . . . . . . . .     AS(S51F) Codon_Opt 331 T C C T C G A C C C G C C G G C T C G A T C T T A C C G T C   AS-S51F
331 . . . . . . . . . . . . C . . . . . C . . . . . G . . .     AS(S51F) Codon_Opt 361 A A C G A A C C G G A C C G T G T C T T C A C C G A A G A A   AS-S51F
361 . . . . . G . . . . . . . . C . . G . . . . . . . . G . . .   AS(S51F) Codon_Opt 391 G A A C G C T C G A A A A T C C C G A C G G T C T T C A C C   AS-S51F
391 . . G . . T A G C . . . G . . . . . . . . . . T . . . . . .   AS(S51F) Codon_Opt 421 G C T C T C A G A G C C A T C G T C G A C C T C T T C T A T   AS-S51F
421 . . G . . . . . . . . . . . . . . . G . . . . A . . . . . C   AS(S51F) Codon_Opt 451 T C G A G C G C G G A T T C G G C C A T C G G C C T G T T C   AS-S51F
451 . . T T C T . . . . . C A G C . . . . . . . . G T . . . . .   AS(S51F) Codon_Opt 481 G G T G C C T T C G G T T A C G A T C T C G C C T T C C A G   AS-S51F
481 . . . . . . . . . . . . . . . . . . . . . C . . . . . . G . . . . . .   AS(S51F) Codon_Opt 511 T T C G A C G C G A T C A A G C T T T T C G C T G G C G C G T   AS-S51F
511 . . . . . . . . C . . . . . . . C . . . . . . . C . . . . . G   AS(S51F) Codon_Opt 541 C C G G A A G A C C A G C G T G A C A T G G T G C T G T T T   AS-S51F
541 . . . . . G . . . . . . . . . A . . . . . . . . . . C . . C   AS(S51F) Codon_Opt 571 C T G C C C G A T G A A A T C C T C G T C G T T G A T C A C   AS-S51F
571 . . C . . . T . . C . . . G . . . . . . G . . . . . C . . . . . .   AS(S51F) Codon_Opt 601 T A T T C C G C C A A G G C C T G G A T C G A C C G T T A C   AS-S51F
601 . . . . . . . . G . . . . . G . . . . . . . . . . . G . . .   AS(S51F) Codon_Opt 631 G A T T T C G A G A A G G A C G G C A T G A C G A C G G A C   AS-S51F
631 . . C . . . . . . . . . . . . . . T . . . . . . . . C . . . . . T   AS(S51F) Codon_Opt 661 G G C A A A T C C T C C G A C A T T A C C C C C G A T C C C   AS-S51F
661 . . . . . . G A G . A G . . . . . . C . . T . . . . . C . . . A   AS(S51F) Codon_Opt 691 T T C A A G A C C A C C G A T A C C A T C C C G C C C A A G   AS-S51F
691 . . . . . . . . . . . . . . . . . . C . . . . . . . T . . A . . .   AS(S51F) Codon_Opt
```

*Fig. 23A*

```
721  G G C G A T C A C C G T C C C G G C G A A T A T T C C G A G  AS-S51F
721  . . . . . . . . . . . C . . . T . . . . . G . . . . . . . . . A  AS(S51F) Codon_Opt 751  C T T G T G G T G A A G G C C A A G G A A A G C T T C C G C  AS-S51F
751  . . C . . . . . . . . . . . . . . . . T C . . . . . . G . . .  AS(S51F) Codon_Opt 781  C G C G G C G A C C T G T T C G A G G T C G T T C C C G G C  AS-S51F
781  . . . . . . . . T . . . . . T . . . . . G . . . . . . . . . .  AS(S51F) Codon_Opt 811  C A G A A A T T C A T G G A G C G T T G C G A A A G C A A T  AS-S51F
811  . . A . . . G . . . . . . . . . A . G . . . . . . G T C G . . .  AS(S51F) Codon_Opt 841  C C G T C G G C G A T T T C C C G C C G C C T G A A G G C G  AS-S51F
841  . . . . . T . . . . . . C A G T . . . . . A . . . . . A . . . .  AS(S51F) Codon_Opt 871  A T C A A C C C G T C G C C C T A T T C C T T C T T C A T C  AS-S51F
871  . . . . . . . . . A G C . . G . . . . . . . . . . . . . . . .  AS(S51F) Codon_Opt 901  A A T C T C G G C G A T C A G G A A T A T C T G G T C G G C  AS-S51F
901  . . C . . . . . . . . . . . . . . . . . . . . . . . . . . . A  AS(S51F) Codon_Opt 931  G C C T C G C C G G A A A T G T T C G T G C G C G T C T C C  AS-S51F
931  . . . . . A . . C . . G . . . . . . . . C A . G . . . . . . .  AS(S51F) Codon_Opt 961  G G C C G T C G C A T C G A G A C C T G C C C G A T A T C A  AS-S51F
961  . . . . . C . . G . . . . . . . . G . . . . . A . . . T . . C  AS(S51F) Codon_Opt 991  G G C A C C A T C A A G C G C G G C G A C G A T C C G A T T  AS-S51F
991  . . A . . . . . . . . . . . . . A . . . T . . C . . . . . A  AS(S51F) Codon_Opt 1021 G C C G A C A G C G A G C A G A T T T T G A A A C T G C T C  AS-S51F
1021 . . . . . . T C T . . . . . . . . . C C . . . . . . C T . G  AS(S51F) Codon_Opt 1051 A A C T C G A A A A A G G A C G A A T C C G A A C T G A C C  AS-S51F
1051 . . . A G C . . G . . . . . . . . G . . . . . . G . . . . . T  AS(S51F) Codon_Opt 1081 A T G T G C T C G G A C G T G G A C C G C A A C G A C A A G  AS-S51F
1081 . . . . . . . . . A . . T . . . . . . . . A . . . . . . . . .  AS(S51F) Codon_Opt 1111 A G C C G C G T C T G C G A G C C G G G T T C G G T G A A G  AS-S51F
1111 T C A . . T . . . . . . . . . . . C . . . A G C . . C . . .  AS(S51F) Codon_Opt 1141 G T C A T T G G C C G C C G C C A G A T C G A G A T G T A T  AS-S51F
1141 . . . . . . . . . . . . . . T . . . . . . . . . . . . . . C  AS(S51F) Codon_Opt 1171 T C A C G C C T C A T C C A C A C C G T C G A T C A C A T C  AS-S51F
1171 . . C A . G . . . G . . . T . . . . . . G . . . . . . . T . . .  AS(S51F) Codon_Opt 1201 G A A G G C C G C C T G C G C G A C G A T A T G G A C G C C  AS-S51F
1201 . . . . . G . . G . . . . . . . . . . . . . . . . . . . . . A  AS(S51F) Codon_Opt 1231 T T T G A C G G T T T C C T C A G C C A C G C C T G G G C C  AS-S51F
1231 . . C . . . . . G . . . . . . . T . . . . . . . . . . . . . .  AS(S51F) Codon_Opt 1261 G T C A C C G T C A C C G G T G C A C C A A A G C T G T G G  AS-S51F
1261 . . T . . T . . . . . . . . . . A . . G . . T . . . . C . . .  AS(S51F) Codon_Opt 1291 G C C A T G C G C T T C A T C G A A G G T C A T G A A A A G  AS-S51F
1291 . . T . . . A . G . . . . . . . . . G . . C . . C . . G . . .  AS(S51F) Codon_Opt 1321 A G C C C G C G C G C C T G G T A T G G C G G T G C G A T C  AS-S51F
1321 . . . . . T A . G . . T . . . . . . . . . T . . . . . C . . .  AS(S51F) Codon_Opt 1351 G G C A T G G T C G G C T T C A A C G G C G A C A T G A A T  AS-S51F
1351 . . . . . . . . . T . G . . . . . . . . . . . . . . . . . C  AS(S51F) Codon_Opt 1381 A C C G G C C T G A C G C T G C G C A C C A T C C G G A T C  AS-S51F
1381 . . . . . G . . . . . . . . C . . G . . . . . . A . . . . . .  AS(S51F) Codon_Opt 1411 A A G G A C G G T A T T G C C G A A G T G C G C G C C G G C  AS-S51F
1411 . . A . . . . . . C . . . . . . . . . G . . . A . G . . . . T  AS(S51F) Codon_Opt 1441 G C G A C C C T G C T C A A T G A T T C C A A C C C G C A G  AS-S51F
1441 . . C . . G . . T . . . . . C . . . A G . . . . . . T . . .  AS(S51F) Codon_Opt
```

*Fig. 23B*

```
1471  G A A G A A G A A G C C G A A A C C G A A C T G A A G G C C   AS-S51F
1471  . . G . . . . . . G . . G . . G . . . . . G . . . . . A . . .   AS(S51F) Codon_Opt 1501  T C C G C C A T G A T A T C A G C C A T T C G T G A C G C A   AS-S51F
1501  . . T . . G . . . . . C . . C . . G . . . A . A . . T . . .   AS(S51F) Codon_Opt 1531  A A A G G C A C C A A C T C T G C C G C C A C C A A G C G T   AS-S51F
1531  . . G . . T . . G . . . A G . . . T . . . . . . . . . . . G   AS(S51F) Codon_Opt 1561  G A T G C C G C C A A A G T C G G C A C C G G C G T C A A G   AS-S51F
1561  . . C . . . A . . . . . G . . G . . . . . . . . . . . . . .   AS(S51F) Codon_Opt 1591  A T C C T G C T C G T C G A C C A C G A A G A C A G C T T C   AS-S51F
1591  . . T T . A . . T . . . . . T . . . . . G . . . T C . . . .   AS(S51F) Codon_Opt 1621  G T G C A C A C G C T G G C G A A T T A T T T C C G C C A G   AS-S51F
1621  . . . . . . . . T . . . . . . . . . C . . C . . . . . . . .   AS(S51F) Codon_Opt 1651  A C G G G C G C G A C G G T C T C G A C C G T C A G A T C A   AS-S51F
1651  . . A . . . . . . . . . . . . . C . . . . . T . . G . . .   AS(S51F) Codon_Opt 1681  C C G G T C G C A G C C G A C G T G T T C G A T C G C T T C   AS-S51F
1681  . . . . . G . . C . . T . . . . . . . . . . A . G . . .   AS(S51F) Codon_Opt 1711  C A G C C G G A C C T C G T T G T C C T G T C G C C C G G A   AS-S51F
1711  . . . . . C . . . . . T . . G . . G . . C . . T . . . . . T   AS(S51F) Codon_Opt 1741  C C C G G C A G C C C G A C G G A T T T C G A C T G C A A G   AS-S51F
1741  . . . . . . T C G . . C . . . . . C . . . . . . . . . . . .   AS(S51F) Codon_Opt 1771  G C A A C G A T C A A G G C C G C C C G C G C C C G C G A T   AS-S51F
1771  . . C . . . C . . T . . . . . . . . A . G . . . A . G . . .   AS(S51F) Codon_Opt 1801  C T G C C G A T C T T C G G C G T T T G C C T C G G T C T G   AS-S51F
1801  . . . . . A . . . . . . . . . . . . . . . . . G . . T   AS(S51F) Codon_Opt 1831  C A G G C A T T G G C A G A A G C C T A T G G C G G C G A G   AS-S51F
1831  . . . . . . . . . . . . C . . G . . A . . C . . . T . . A . . .   AS(S51F) Codon_Opt 1861  C T G C G C C A G C T T G C T G T G C C C A T G C A C G G C   AS-S51F
1861  . . . A . G . . . . . C . . C . . C . . G . . . . . . . . G   AS(S51F) Codon_Opt 1891  A A G C C T T C G C G C A T C C G C G T G C T G G A A C C C   AS-S51F
1891  . . . . . A . . . C . . . . . . A . A . . C . . . . . G . . .   AS(S51F) Codon_Opt 1921  G G C C T C G T C T T C T C C G G T C T C G G C A A G G A A   AS-S51F
1921  . . . . . . . . . . . . . . . . . . . . . . . G . . . . . G   AS(S51F) Codon_Opt 1951  G T C A C G G T C G G T C G T T A C C A T T C G A T C T T C   AS-S51F
1951  . . . . . . . . . . . . . G . . T . . . . . . . . . . . .   AS(S51F) Codon_Opt 1981  G C C G A T C C C G C C A C C C T G C C G C G T G A T T T C   AS-S51F
1981  . . . . . . . . G . . . A . . . . . C . . . . . . C . . C . . .   AS(S51F) Codon_Opt 2011  A T C A T C A C C G C A G A A A G C G A G G A C G G C A C G   AS-S51F
2011  . . . . . A . . . . . . C . . G T C G . . . . . . . . A . . .   AS(S51F) Codon_Opt 2041  A T C A T G G G C A T C G A A C A C G C C A A G G A A C C G   AS-S51F
2041  . . . . . . . . . A . . . . . . . . . . . . . . . . G . . C   AS(S51F) Codon_Opt 2071  G T G G C C G C C G T T C A G T T C C A C C C G G A A T C G   AS-S51F
2071  . . A . . T . . G . . . . . . . . . . . . . . T . . G . . C   AS(S51F) Codon_Opt 2101  A T C A T G A C G C T C G G A C A G G A C G C G G G C A T G   AS-S51F
2101  . . . . . . . . . C . . . . . . T . A . . T . . . . . T . . .   AS(S51F) Codon_Opt 2131  C G G A T G A T C G A G A A T G T C G T G G T G C A T C T G   AS-S51F
2131  . . . . . . . . . . . . . . . . . G . . . . . T . . C . . C   AS(S51F) Codon_Opt 2161  A C C C G C A A G G C G A A G A C C A A G G C C G C G T G A   AS-S51F
2161  . . . . . . . . . C . . . . . . . . . . . . . A . . A . . .   AS(S51F) Codon_Opt 2191  T G G   AS-S51F
2191  . A .   AS(S51F) Codon_Opt
```

*Fig. 23C*

```
  1  M V T I I Q D D G A E T Y E T K G G I Q    AgroAS-S51F
  1  . . . . . . . . . . . . . . . . . . . .    AS(S51F) Codon_Opt-Final 21  V S R K R R P T D Y A N A I D N Y I E K    AgroAS-S51F
 21  . . . . . . . . . . . . . . . . . . . .    AS(S51F) Codon_Opt-Final 41  L D S H R G A V F S C N Y E Y P G R Y T    AgroAS-S51F
 41  . . . . . . . . . . . . . . . . . . . .    AS(S51F) Codon_Opt-Final 61  R W D T A I V D P P L G I S C F G R K M    AgroAS-S51F
 61  . . . . . . . . . . . . . . . . . . . .    AS(S51F) Codon_Opt-Final 81  W I E A Y N G R G E V L L D F I T E K L    AgroAS-S51F
 81  . . . . . . . . . . . . . . . . . . . .    AS(S51F) Codon_Opt-Final 101  K A T P D L T L G A S S T R R L D L T V    AgroAS-S51F
101  . . . . . . . . . . . . . . . . . . . .    AS(S51F) Codon_Opt-Final 121  N E P D R V F T E E E R S K I P T V F T    AgroAS-S51F
121  . . . . . . . . . . . . . . . . . . . .    AS(S51F) Codon_Opt-Final 141  A L R A I V D L F Y S S A D S A I G L F    AgroAS-S51F
141  . . . . . . . . . . . . . . . . . . . .    AS(S51F) Codon_Opt-Final 161  G A F G Y D L A F Q F D A I K L S L A R    AgroAS-S51F
161  . . . . . . . . . . . . . . . . . . . .    AS(S51F) Codon_Opt-Final 181  P E D Q R D M V L F L P D E I L V V D H    AgroAS-S51F
181  . . . . . . . . . . . . . . . . . . . .    AS(S51F) Codon_Opt-Final 201  Y S A K A W I D R Y D F E K D G M T T D    AgroAS-S51F
201  . . . . . . . . . . . . . . . . . . . .    AS(S51F) Codon_Opt-Final 221  G K S S D I T P D P F K T T D T I P P K    AgroAS-S51F
221  . . . . . . . . . . . . . . . . . . . .    AS(S51F) Codon_Opt-Final 241  G D H R P G E Y S E L V V K A K E S F R    AgroAS-S51F
241  . . . . . . . . . . . . . . . . . . . .    AS(S51F) Codon_Opt-Final 261  R G D L F E V V P G Q K F M E R C E S N    AgroAS-S51F
261  . . . . . . . . . . . . . . . . . . . .    AS(S51F) Codon_Opt-Final 281  P S A I S R R L K A I N P S P Y S F F I    AgroAS-S51F
281  . . . . . . . . . . . . . . . . . . . .    AS(S51F) Codon_Opt-Final 301  N L G D Q E Y L V G A S P E M F V R V S    AgroAS-S51F
301  . . . . . . . . . . . . . . . . . . . .    AS(S51F) Codon_Opt-Final 321  G R R I E T C P I S G T I K R G D D P I    AgroAS-S51F
321  . . . . . . . . . . . . . . . . . . . .    AS(S51F) Codon_Opt-Final 341  A D S E Q I L K L L N S K K D E S E L T    AgroAS-S51F
341  . . . . . . . . . . . . . . . . . . . .    AS(S51F) Codon_Opt-Final 361  M C S D V D R N D K S R V C E P G S V K    AgroAS-S51F
361  . . . . . . . . . . . . . . . . . . . .    AS(S51F) Codon_Opt-Final 381  V I G R R Q I E M Y S R L I H T V D H I    AgroAS-S51F
381  . . . . . . . . . . . . . . . . . . . .    AS(S51F) Codon_Opt-Final 401  E G R L R D D M D A F D G F L S H A W A    AgroAS-S51F
401  . . . . . . . . . . . . . . . . . . . .    AS(S51F) Codon_Opt-Final 421  V T V T G A P K L W A M R F I E G H E K    AgroAS-S51F
421  . . . . . . . . . . . . . . . . . . . .    AS(S51F) Codon_Opt-Final 441  S P R A W Y G G A I G M V G F N G D M N    AgroAS-S51F
441  . . . . . . . . . . . . . . . . . . . .    AS(S51F) Codon_Opt-Final 461  T G L T L R T I R I K D G I A E V R A G    AgroAS-S51F
461  . . . . . . . . . . . . . . . . . . . .    AS(S51F) Codon_Opt-Final
```

*Fig. 24A*

```
481  A T L L N D S N P Q E E E A E T E L K A    AgroAS-S51F
481  . . . . . . . . . . . . . . . . . . . .    AS(S51F) Codon_Opt-Final 501  S A M I S A I R D A K G T N S A A T K R    AgroAS-S51F
501  . . . . . . . . . . . . . . . . . . . .    AS(S51F) Codon_Opt-Final 521  D A A K V G T G V K I L L V D H E D S F    AgroAS-S51F
521  . . . . . . . . . . . . . . . . . . . .    AS(S51F) Codon_Opt-Final 541  V H T L A N Y F R Q T G A T V S T V R S    AgroAS-S51F
541  . . . . . . . . . . . . . . . . . . . .    AS(S51F) Codon_Opt-Final 561  P V A A D V F D R F Q P D L V V L S P G    AgroAS-S51F
561  . . . . . . . . . . . . . . . . . . . .    AS(S51F) Codon_Opt-Final 581  P G S P T D F D C K A T I K A A R A R D    AgroAS-S51F
581  . . . . . . . . . . . . . . . . . . . .    AS(S51F) Codon_Opt-Final 601  L P I F G V C L G L Q A L A E A Y G G E    AgroAS-S51F
601  . . . . . . . . . . . . . . . . . . . .    AS(S51F) Codon_Opt-Final 621  L R Q L A V P M H G K P S R I R V L E P    AgroAS-S51F
621  . . . . . . . . . . . . . . . . . . . .    AS(S51F) Codon_Opt-Final 641  G L V F S G L G K E V T V G R Y H S I F    AgroAS-S51F
641  . . . . . . . . . . . . . . . . . . . .    AS(S51F) Codon_Opt-Final 661  A D P A T L P R D F I I T A E S E D G T    AgroAS-S51F
661  . . . . . . . . . . . . . . . . . . . .    AS(S51F) Codon_Opt-Final 681  I M G I E H A K E P V A A V Q F H P E S    AgroAS-S51F
681  . . . . . . . . . . . . . . . . . . . .    AS(S51F) Codon_Opt-Final 701  I M T L G Q D A G M R M I E N V V V H L    AgroAS-S51F
701  . . . . . . . . . . . . . . . . . . . .    AS(S51F) Codon_Opt-Final 721  T R K A K T K A A .                        AgroAS-S51F
721  . . . . . . . . .                          AS(S51F) Codon_Opt-Final
```

Fig. 24B

```
ATGGTGACCA TCATTCAGGA CGACGGCGCT GAGACCTACG AGACTAAGGG CGGTATCCAA    60
GTGAGCCGTA AGCGTAGGCC CACTGACTAC GCTAACGCCA TCGACAACTA CATCGAGAAG   120
CTAGACTCCC ATCGCGGCGC TGTGTTCTCC TGCAACTACG AATACCCTGG GCGCTACACG   180
AGGTGGGATA CCGCCATCGT cGATCCTCCA TTGGGCATCT CCTGTTTTGG GCGTAAGATG   240
TGGATCGAGG CGTACAACGG CCGtGGCGAA GTCTTGCTGG AcTTcATCAC GGAGAAGCTC   300
AAGGCCACAC CgGACCTcAC cCTCGGcGCT TCCTCGACcC GCCGCCTcGA CCTTACGGTC   360
AACGAGCCGG ACCGCGTGTT cACCGAGGAA GAGCGTAGCA AGATCCCgAC TGTcTTCACC   420
GCGCTCAGAG CcATCGTGGA cCTATTCTAC TCTTCtGCGG ACAGCGCCAT cGGGTTGTTC   480
GGTGCcTTCG GTTACGACCT cGCGTTCCAG TTCGACGCCA TCAAGCTCTC GCTCGCGCGG   540
CCGGAGGACC AGCGAGAcAT GGTGCTCTTC CTcCCTGACG AGATcCTGGT cGTCGATCAC   600
TATTCCGCgA AGGCgTGGAT CGACCGGTAC GACTTcGAGA AGGATGGCAT GACCACgGAT   660
GGCAAGAGCA GCGACATCAC TCCCGACCCA TTCAAGACCA CcGACACcAT CCCTCCAAAG   720
GGCGATCACC GCCCTGGCGA GTATTCcGAA CTCGTGGTGA AGGCCAAGGA ATCCTTCcGG   780
CGCGGCGAtC TGTTTGAGGT GGTTCCcGGC CAAAAGTTCA TGGAgAGGTG cGAGTCGAAT   840
CCgTCTGCgA TCAGTCGCCG ACTGAAaGCG ATCAACCCGA GCCCGTATTC CTTCTTcATC   900
AACCTcGGCG ATCAGGAATA TCTGGTCGGA GCcTCACCCG AgATGTTcGT CAGGGTCTCc   960
GGCCGCCGGA TCGAGACgTG CCCAATTTCC GGAACCATCA AGCGCGGAGA TGACCCGATA  1020
GCCGACTCTG AGCAGATCCT GAAACTCTTG AAcAGCAAGA AgGACGAGTC cGAGCTGACT  1080
ATGTGCTCAG ATGTGGACCg AAACGACAAG TCACGTGTCT GCGAGCCCGG TAGCGTCAAG  1140
GTcATTGGCC GCCGTCAGAT CGAGATGTAC TCCAGGCTGA TTCACACGGT CGATCATATc  1200
GAAGGGCGGC TGCGCGACGA TATGGACGCA TTCGACGGGT TCCTcAGTCA CGCCTGGGCC  1260
GTTACTGTCA CCGGAGCGCC TAAGCTCTGG GCTATGAGgT TCATCGAGGG CCACGAGAAG  1320
AGCCCTAGGG CTTGGTATGG TGGtGCCATc GGCATGGTTG GGTTcAACGG CGACATGAAC  1380
ACCGGGCTGA CGCTCCGGAC CATcAGGATC AAAGACGGCA TTGCCGAGGT GAGGGCcGGT  1440
GCCACGCTTC TCAACGATAG CAAcCCTCAG GAGGAAGAGG CGGAGACCGA GCTGAAaGCc  1500
tctGCGATGA TCTCCGCGAT TAGAGATGCA AAGGGTACgA AcAGTGCTGC CACCAAGcGG  1560
GACGCAGCCA AGGTGGGCAC CGGCGTCAAG AtTTACTTG TCGAtCACGA GGACTCcTTC  1620
GTGCAcACTC TGGCgAACTA CTTCCGCCAG ACAGGCGCGA CgTCTCCAC CGTTAGGTCA  1680
```

*Fig. 25A*

```
CCGGTGGCCG CTGACGTGTT CGATAGGTTc CAGCCCGACC TTGTGGTGCT CTCTCCCGGt    1740
CCCGGcTCGC CCACGGACTT CGAcTGCAAG GCCACCATTA AGGCCGCcAG GGCCAGGGAT    1800
CTgCCAATCT TCGGcGTTTG CCTCGGGCTt CAGGCATTGG CCGAGGCATA CGGTGGAGAG    1860
CTGAGgCAGC TCGCCGTCCC GATGCACGGG AAgCCATCCC GCATcAGAGT CCTgGAGCCC    1920
GGCCTCGTcT TCTCCGGTCT cGGGAAGGAG GTCACGGTCG GTCGGTAtCA TTCGATCTTC    1980
GCCGATCCGG CAACcCTCCC GCGCGACTTC ATCATAACCG CCGAGTCGGA GGAcGGAACg    2040
ATCATGGGAA TcGAACACGC cAAGGAGCCC GTAGCTGCGG TTCAGTTCCA CCCTGAGTCC    2100
ATcATGACCC TcGGTCAAGA TGCGGGTATG CGgATGATcG AGAATGTGGT gGTTCACCTc    2160
ACCCGcAAGG CcAAGACcAA GGCAGCATGA tag    2193
```

Fig. 25B

| | | | | | | |
|---|---|---|---|---|---|---|
| MVTIIQDDGA | ETYETKGGIQ | VSRKRRPTDY | ANAIDNYIEK | LDSHRGAVFS | FNYEYPGRYT | 60 |
| RWDTAIVDPP | LGISCFGRKM | WIEAYNGRGE | VLLDFITEKL | KATPDLTLGA | SSTRRLDLTV | 120 |
| NEPDRVFTEE | ERSKIPTVFT | ALRAIVDLFY | SSADSAIGLF | GAFGYDLAFQ | FDAIKLSLAR | 180 |
| PEDQRDMVLF | LPDEILVVDH | YSAKAWIDRY | DFEKDGMTTD | GKSSDITPDP | FKTTDTIPPK | 240 |
| GDHRPGEYSE | LVVKAKESFR | RGDLFEVVPG | QKFMERCESN | PSAISRRLKA | INPSPYSFFI | 300 |
| NLGDQEYLVG | ASPEMFVRVS | GRRIETCPIS | GTIKRGDDPI | ADSEQILKLL | NSKKDESELT | 360 |
| MCSDVDRNDK | SRVCEPGSVK | VIGRRQIEMY | SRLIHTVDHI | EGRLRDDMDA | FDGFLSHAWA | 420 |
| VTVTGAPKLW | AMRFIEGHEK | SPRAWYGGAI | GMVGFNGDMN | TGLTLRTIRI | KDGIAEVRAG | 480 |
| ATLLNDSNPQ | EEEAETELKA | SAMISAIRDA | KGTNSAATKR | DAAKVGTGVK | ILLVDHEDSF | 540 |
| VHTLANYFRQ | TGATVSTVRS | PVAADVFDRF | QPDLVVLSPG | PGSPTDFDCK | ATIKAARARD | 600 |
| LPIFGVCLGL | QALAEAYGGE | LRQLAVPMHG | KPSRIRVLEP | GLVFSGLGKE | VTVGRYHSIF | 660 |
| ADPATLPRDF | IITAESEDGT | IMGIEHAKEP | VAAVQFHPES | IMTLGQDAGM | RMIENVVVHL | 720 |
| TRKAKTKAA* | | | | | | |

*Fig. 26*

SEQUENCE LISTING

<160> NUMBER OF SEQ ID NOS: 151

<210> SEQ ID NO 1
<211> LENGTH: 2190
<212> TYPE: DNA
<213> ORGANISM: Agrobacterium tumefaciens

<400> SEQUENCE: 1

| | | | | | | |
|---|---|---|---|---|---|---|
| atggtaacga | tcattcagga | tgacggagcg | gagacctacg | agacgaaagg | cggcatccag | 60 |
| gtcagccgaa | agcgccggcc | caccgattat | gccaacgcca | tcgataatta | catcgaaaag | 120 |
| cttgattccc | atcgcggcgc | ggttttttcg | tccaactatg | aatatccggg | ccgttacacc | 180 |
| cgctgggata | cggccatcgt | cgatccgccg | ctcggcattt | cctgttttgg | ccgcaagatg | 240 |
| tggatcgaag | cctataatgg | ccgcggcgaa | gtgctgctcg | atttcattac | ggaaaagctg | 300 |
| aaggcgacac | ccgatctcac | cctcggcgct | tcctcgaccc | gccggctcga | tcttaccgtc | 360 |
| aacgaaccgg | accgtgtctt | caccgaagaa | gaacgctcga | aaatcccgac | ggtcttcacc | 420 |
| gctctcagag | ccatcgtcga | cctcttctat | tcgagcgcgg | attcggccat | cggcctgttc | 480 |
| ggtgccttcg | gttacgatct | cgccttccag | ttcgacgcga | tcaagctttc | gctggcgcgt | 540 |
| ccggaagacc | agcgtgacat | ggtgctgttt | ctgcccgatg | aaatcctcgt | cgttgatcac | 600 |
| tattccgcca | aggcctggat | cgaccgttac | gatttcgaga | aggacggcat | gacgacggac | 660 |
| ggcaaatcct | ccgacattac | ccccgatccc | ttcaagacca | ccgataccat | cccgcccaag | 720 |
| ggcgatcacc | gtcccggcga | atattccgag | cttgtggtga | aggccaagga | aagcttccgc | 780 |
| cgcggcgacc | tgttcgaggt | cgttcccggc | cagaaattca | tggagcgttg | cgaaagcaat | 840 |
| ccgtcggcga | tttccgccg | cctgaaggcg | atcaacccgt | cgccctattc | cttcttcatc | 900 |
| aatctcggcg | atcaggaata | tctggtcggc | gcctcgccgg | aaatgttcgt | gcgcgtctcc | 960 |
| ggccgtcgca | tcgagacctg | cccgatatca | ggcaccatca | agcgcggcga | cgatccgatt | 1020 |
| gccgacagcg | agcagatttt | gaaactgctc | aactcgaaaa | aggacgaatc | cgaactgacc | 1080 |
| atgtgctcgg | acgtggaccg | caacgacaag | agccgcgtct | gcgagccggg | ttcggtgaag | 1140 |
| gtcattggcc | gccgcagat | cgagatgtat | tcacgcctca | tccacaccgt | cgatcacatc | 1200 |
| gaaggccgcc | tgcgcgacga | tatggacgcc | tttgacggtt | tcctcagcca | cgcctgggcc | 1260 |
| gtcaccgtca | ccggtgcacc | aaagctgtgg | gccatgcgct | tcatcgaagg | tcatgaaaag | 1320 |
| agcccgcgcg | cctggtatgg | cggtgcgatc | ggcatggtcg | gcttcaacgg | cgacatgaat | 1380 |
| accggcctga | cgctgcgcac | catccggatc | aaggacggta | ttgccgaagt | gcgcgccggc | 1440 |
| gcgaccctgc | tcaatgattc | caacccgcag | gaagaagaag | ccgaaaccga | actgaaggcc | 1500 |
| tccgccatga | tatcagccat | tcgtgacgca | aaaggcacca | actctgccgc | caccaagcgt | 1560 |
| gatgccgcca | aagtcggcac | cggcgtcaag | atcctgctcg | tcgaccacga | agacagcttc | 1620 |
| gtgcacacgc | tggcgaatta | tttccgccag | acgggcgcga | cggtctcgac | cgtcagatca | 1680 |
| ccggtcgcag | ccgacgtgtt | cgatcgcttc | cagccggacc | tcgttgtcct | gtcgcccgga | 1740 |
| cccggcagcc | cgacggattt | cgactgcaag | gcaacgatca | aggccgcccg | cgcccgcgat | 1800 |
| ctgccgatct | tcggcgtttg | cctcggtctg | caggcattgg | cagaagccta | tggcggcgag | 1860 |
| ctgcgccagc | ttgctgtgcc | catgcacggc | aagccttcgc | gcatccgcgt | gctggaaccc | 1920 |
| ggcctcgtct | tctccggtct | cggcaaggaa | gtcacggtcg | tcgttacca | ttcgatcttc | 1980 |
| gccgatcccg | ccaccctgcc | gcgtgatttc | atcatcaccg | cagaaagcga | ggacggcacg | 2040 |

```
atcatgggca tcgaacacgc caaggaaccg gtggccgccg ttcagttcca cccggaatcg    2100
atcatgacgc tcggacagga cgcgggcatg cggatgatcg agaatgtcgt ggtgcatctg    2160
acccgcaagg cgaagaccaa ggccgcgtga                                     2190

<210> SEQ ID NO 2
<211> LENGTH: 1815
<212> TYPE: DNA
<213> ORGANISM: Zea mays

<400> SEQUENCE: 2
atggaatccc tagccgccac ctccgtgttc gcgccctccc gcgtcgccgt cccggcggcg      60
cgggccctgg ttagggcggg gacggtggta ccaaccaggc ggacgagcag ccggagcgga    120
accagcgggg tgaaatgctc tgctgccgtg acgccgcagg cgagcccagt gattagcagg    180
agcgctgcgg cggcgaaggc ggcggaggag gacaagaggc ggttcttcga ggcggcggcg    240
cgggggagcg ggaagggga cctggtgccc atgtgggagt gcatcgtgtc ggaccatctc    300 accccgtgc tcgcctaccg ctgcctcgtc cccgaggaca cgtcgacgc cccagcttc      360 ctcttcgagt ccgtcgagca ggggcccag ggcaccacca acgtcggccg ctatagcatg     420
gtgggagccc acccagtgat ggagattgtg gccaaagacc acaaggttac gatcatggac    480
cacgagaaga gccaagtgac agagcaggta gtggacgacc cgatgcagat cccgaggacc    540
atgatggagg gatggcaccc acagcagatc gacgagctcc ctgaatcctt ctccggtgga    600
tgggttgggt tcttttccta tgatacggtt aggtatgttg agaagaagaa gctaccgttc    660
tccagtgctc ctcaggacga taggaacctt cctgatgtgc acttgggact ctatgatgat    720
gttctagtct tcgataatgt tgagaagaaa gtatatgtta tccattgggt caatgtggac    780
cggcatgcat ctgttgagga agcataccaa gatggcaggt cccgactaaa catgttgcta    840
tctaaagtgc acaattccaa tgtccccaca ctctctcctg gatttgtgaa gctgcacaca    900
cgcaagtttg gtacaccttt gaacaagtcg accatgacaa gtgatgagta taagaatgct    960
gttctgcagg ctaaggaaca tattatggct ggggatatct tccagattgt tttaagccag   1020
aggttcgaga acgaacata tgccaaccca tttgaggttt atcgagcatt acggattgtg   1080
aatcctagcc catacatggc gtatgtacag gcaagaggct gtgtattggt tgcgtctagt    1140
cctgaaattc ttacacgagt cagtaagggg aagattatta atcgaccact tgctggaact   1200
gttcgaaggg gcaagacaga gaaggaagat caaatgcaag agcagcaact gttaagtgat   1260
gaaaaacagt gtgccgagca cataatgctt gtggacttgg aaggaatga tgttggcaag    1320 gtatccaaac caggatcagt gaaggtggag aagttgatga acattgagag atactcccat    1380
gttatgcaca tcagctcaac ggttagtgga cagttggatg atcatctcca gagttgggat   1440
gccttgagag ctgccttgcc cgttggaaca gtcagtggtg caccaaaggt gaaggccatg   1500
gagttgattg ataagttgga agttacgagg cgaggaccat atagtggtgg tctaggagga   1560
atatcgtttg atggtgacat gcaaattgca ctttctctcc gcaccatcgt attctcaaca   1620
gcgccgagcc acaacacgat gtactcatac aaagacgcag ataggcgtcg ggagtgggtc   1680
gctcatcttc aggctggtgc aggcattgtt gccgacagta gcccagatga cgaacaacgt   1740
gaatgcgaga ataaggctgc tgcactagct cgggccatcg atcttgcaga gtcagctttt   1800
gtagacaaag aatag                                                    1815

<210> SEQ ID NO 3
```

-continued

```
<211> LENGTH: 1993
<212> TYPE: DNA
<213> ORGANISM: Ruta graveolens

<400> SEQUENCE: 3
aaaaaatctg tctgtttttc gtgtttggac atttcagcgg cactgggtgc catcagttga       60
ttcgactcat ttgatttatt ttgtttgttg gccatgagtg cagcggcaac gtcgatgcaa      120
tcccttaaat tctccaaccg tctggtccca cccagtcgcc gtctgtctcc ggttccgaac      180
aatgtcacct gcaataacct ccccaagtct gcagctcccg tccggacagt caaatgctgc      240
gcttcttcct ggaacagtac catcaacggc gcggccgcca cgaccaacgg tgcgtccgcc      300
gccagtaacg gcgcatccac gaccaccact acatatgtta gtgatgcaac cagatttatc      360
gactcttcta aaagggcaaa tctagtgcca ttataccgtt gcatattcgc ggatcatctc      420
acgccggtgc ttgcctatag atgtttggtt caagaagacg ataaagagac tccaagtttt      480
ttattcgaat cagtagagcc gggtcggatt tctactgttg ggaggtatag tgtggttgga      540
gctcatcccg tgatggaagt tatagctaaa gataatatgg ttacggtgat ggatcatgag      600
aaagggagct tagttgagga ggtggtcgat gatcccatgg agattcctag aagaatttcc      660
gaggattgga agcctcaaat aatcgatgat cttcctgaag cttttgcgg tggttgggtt       720 ggtttcttct catacgatac agttcgatat gtggagaaga aaaagttacc attctcaaag      780
gcacctcagg atgataggaa tcttgcagat atgcatctag gtctctataa cgatgttatt      840
gtgtttgatc atgtggaaaa gaaagtatat gttattcatt gggtgaggct aaatcaacag      900
tcttctgaag aaaaagcata tgccgagggt ctggaacact ggagagact agtatccaga       960 gtacaggatg agaacacgcc aaggctcgcc ccaggttcca tagacttaca cactggtcat     1020
tttggacctc cattaaaaaa gtcaaacatg acatgtgaag aatacaaaat ggctgtacta     1080
gcggcaaaag aacatattca ggctggggat atttttcaaa tcgtactaag ccaacgtttt     1140
gaacgtcgaa catttgctga tccatttgaa gtttataggg cactgagagt tgttaatccg     1200
agtccctata tgacgtatat gcaggcaaga gggtgtgttc tggtagcttc aagtccagaa     1260
attcttactc gagtaaagaa gaataagatt gtgaatcgac ctttggctgg aacagcccga     1320
agagggagga ctactgaaga agatgagatg ttggaaacac agttgctaaa agacgcaaag     1380
caatgtgctg agcatgttat gctggtcgat ttgggacgga atgatgttgg caaggtttca     1440
aaatctggtt ctgtgaaagt ggaaaagctg atgaatgttg aacgatattc acatgttatg     1500
cacataagct ctacggtcac aggtgagttg caagataatc tcagttgctg ggatgccctg     1560
cgtgctgcac tgcctgtcgg gactgttagt ggagcaccaa aggtgaaggc aatggagtta     1620
atcgatgaat tggaggtaaa tagacgtggc ccctacagtg gtgggtttgg cggtatctcc     1680
ttcaccggag atatggacat tgccctggct ctaaggacca ttgttttcca aaccggtaca     1740
cgctatgaca caatgtactc gtacaagaat gctaccaaac gccggcagtg gtggcatac      1800 cttcaagccg gggctggcat tgttgctgat agtgatccag acgacgagca tcgtgagtgc     1860
cagaacaaag ccgccggact ggcccgtgcc atcgacctag ctgagtctgc tttttgtgaac    1920 aaatcaagta gctaaagttt tggatttgga agtggagttg agtctcggat aggatttaga     1980 gtaaaaaag agg                                                         1993

<210> SEQ ID NO 4
<211> LENGTH: 729
<212> TYPE: PRT
<213> ORGANISM: Agrobacterium tumefaciens
```

```
<400> SEQUENCE: 4

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
```

-continued

```
                405                 410                 415
His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
            485                 490                 495

Glu Leu Lys Ala Ser Ala Met Ile Ser Ala Ile Arg Asp Ala Lys Gly
        500                 505                 510

Thr Asn Ser Ala Ala Thr Lys Arg Asp Ala Ala Lys Val Gly Thr Gly
    515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
            565                 570                 575

Leu Ser Pro Gly Pro Gly Ser Pro Thr Asp Phe Asp Cys Lys Ala Thr
        580                 585                 590

Ile Lys Ala Ala Arg Ala Arg Asp Leu Pro Ile Phe Gly Val Cys Leu
    595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
            645                 650                 655

His Ser Ile Phe Ala Asp Pro Ala Thr Leu Pro Arg Asp Phe Ile Ile
        660                 665                 670

Thr Ala Glu Ser Glu Asp Gly Thr Ile Met Gly Ile Glu His Ala Lys
    675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
            725

<210> SEQ ID NO 5
<211> LENGTH: 604
<212> TYPE: PRT
<213> ORGANISM: Zea mays

<400> SEQUENCE: 5

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45
```

-continued

```
Ala Val Thr Pro Gln Ala Ser Pro Val Ile Ser Arg Ser Ala Ala
 50                  55                  60

Ala Lys Ala Ala Glu Glu Asp Lys Arg Arg Phe Glu Ala Ala Ala
 65                  70                  75                  80

Arg Gly Ser Gly Lys Gly Asn Leu Val Pro Met Trp Glu Cys Ile Val
                 85                  90                  95

Ser Asp His Leu Thr Pro Val Leu Ala Tyr Arg Cys Leu Val Pro Glu
                100                 105                 110

Asp Asn Val Asp Ala Pro Ser Phe Leu Phe Glu Ser Val Glu Gln Gly
                115                 120                 125

Pro Gln Gly Thr Thr Asn Val Gly Arg Tyr Ser Met Val Gly Ala His
                130                 135                 140

Pro Val Met Glu Ile Val Ala Lys Asp His Lys Val Thr Ile Met Asp
145                 150                 155                 160

His Glu Lys Ser Gln Val Thr Glu Gln Val Val Asp Asp Pro Met Gln
                165                 170                 175

Ile Pro Arg Thr Met Met Glu Gly Trp His Pro Gln Gln Ile Asp Glu
                180                 185                 190

Leu Pro Glu Ser Phe Ser Gly Gly Trp Val Gly Phe Phe Ser Tyr Asp
                195                 200                 205

Thr Val Arg Tyr Val Glu Lys Lys Lys Leu Pro Phe Ser Ser Ala Pro
                210                 215                 220

Gln Asp Asp Arg Asn Leu Pro Asp Val His Leu Gly Leu Tyr Asp Asp
225                 230                 235                 240

Val Leu Val Phe Asp Asn Val Glu Lys Lys Val Tyr Val Ile His Trp
                245                 250                 255

Val Asn Val Asp Arg His Ala Ser Val Glu Glu Ala Tyr Gln Asp Gly
                260                 265                 270

Arg Ser Arg Leu Asn Met Leu Leu Ser Lys Val His Asn Ser Asn Val
                275                 280                 285

Pro Thr Leu Ser Pro Gly Phe Val Lys Leu His Thr Arg Lys Phe Gly
                290                 295                 300

Thr Pro Leu Asn Lys Ser Thr Met Thr Ser Asp Glu Tyr Lys Asn Ala
305                 310                 315                 320

Val Leu Gln Ala Lys Glu His Ile Met Ala Gly Asp Ile Phe Gln Ile
                325                 330                 335

Val Leu Ser Gln Arg Phe Glu Arg Arg Thr Tyr Ala Asn Pro Phe Glu
                340                 345                 350

Val Tyr Arg Ala Leu Arg Ile Val Asn Pro Ser Pro Tyr Met Ala Tyr
                355                 360                 365

Val Gln Ala Arg Gly Cys Val Leu Val Ala Ser Ser Pro Glu Ile Leu
                370                 375                 380

Thr Arg Val Ser Lys Gly Lys Ile Ile Asn Arg Pro Leu Ala Gly Thr
385                 390                 395                 400

Val Arg Arg Gly Lys Thr Glu Lys Glu Asp Gln Met Gln Glu Gln Gln
                405                 410                 415

Leu Leu Ser Asp Glu Lys Gln Cys Ala Glu His Ile Met Leu Val Asp
                420                 425                 430

Leu Gly Arg Asn Asp Val Gly Lys Val Ser Lys Pro Gly Ser Val Lys
                435                 440                 445

Val Glu Lys Leu Met Asn Ile Glu Arg Tyr Ser His Val Met His Ile
                450                 455                 460

Ser Ser Thr Val Ser Gly Gln Leu Asp Asp His Leu Gln Ser Trp Asp
```

```
                                        465                 470                 475                 480
Ala Leu Arg Ala Ala Leu Pro Val Gly Thr Val Ser Gly Ala Pro Lys
                485                 490                 495

Val Lys Ala Met Glu Leu Ile Asp Lys Leu Glu Val Thr Arg Arg Gly
                500                 505                 510

Pro Tyr Ser Gly Gly Leu Gly Gly Ile Ser Phe Asp Gly Asp Met Gln
                515                 520                 525

Ile Ala Leu Ser Leu Arg Thr Ile Val Phe Ser Thr Ala Pro Ser His
                530                 535                 540

Asn Thr Met Tyr Ser Tyr Lys Asp Ala Asp Arg Arg Glu Trp Val
545                 550                 555                 560

Ala His Leu Gln Ala Gly Ala Gly Ile Val Ala Asp Ser Ser Pro Asp
                565                 570                 575

Asp Glu Gln Arg Glu Cys Glu Asn Lys Ala Ala Ala Leu Ala Arg Ala
                580                 585                 590

Ile Asp Leu Ala Glu Ser Ala Phe Val Asp Lys Glu
                595                 600

<210> SEQ ID NO 6
<211> LENGTH: 613
<212> TYPE: PRT
<213> ORGANISM: Ruta graveolens

<400> SEQUENCE: 6

Met Ser Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
                20                  25                  30

Cys Asn Asn Leu Pro Lys Ser Ala Ala Pro Val Arg Thr Val Lys Cys
            35                  40                  45

Cys Ala Ser Ser Trp Asn Ser Thr Ile Asn Gly Ala Ala Ala Thr Thr
        50                  55                  60

Asn Gly Ala Ser Ala Ser Asn Gly Ala Ser Thr Thr Thr Thr Thr
65                  70                  75                  80

Tyr Val Ser Asp Ala Thr Arg Phe Ile Asp Ser Ser Lys Arg Ala Asn
                85                  90                  95

Leu Val Pro Leu Tyr Arg Cys Ile Phe Ala Asp His Leu Thr Pro Val
                100                 105                 110

Leu Ala Tyr Arg Cys Leu Val Gln Glu Asp Asp Lys Glu Thr Pro Ser
                115                 120                 125

Phe Leu Phe Glu Ser Val Glu Pro Gly Arg Ile Ser Thr Val Gly Arg
                130                 135                 140

Tyr Ser Val Val Gly Ala His Pro Val Met Glu Val Ile Ala Lys Asp
145                 150                 155                 160

Asn Met Val Thr Val Met Asp His Glu Lys Gly Ser Leu Val Glu Glu
                165                 170                 175

Val Val Asp Asp Pro Met Glu Ile Pro Arg Arg Ile Ser Glu Asp Trp
                180                 185                 190

Lys Pro Gln Ile Ile Asp Asp Leu Pro Glu Ala Phe Cys Gly Gly Trp
                195                 200                 205

Val Gly Phe Phe Ser Tyr Asp Thr Val Arg Tyr Val Glu Lys Lys Lys
                210                 215                 220

Leu Pro Phe Ser Lys Ala Pro Gln Asp Asp Arg Asn Leu Ala Asp Met
225                 230                 235                 240
```

```
His Leu Gly Leu Tyr Asn Asp Val Ile Val Phe Asp His Val Glu Lys
                245                 250                 255

Lys Val Tyr Val Ile His Trp Val Arg Leu Asn Gln Gln Ser Ser Glu
            260                 265                 270

Glu Lys Ala Tyr Ala Glu Gly Leu Glu His Leu Glu Arg Leu Val Ser
        275                 280                 285

Arg Val Gln Asp Glu Asn Thr Pro Arg Leu Ala Pro Gly Ser Ile Asp
    290                 295                 300

Leu His Thr Gly His Phe Gly Pro Pro Leu Lys Lys Ser Asn Met Thr
305                 310                 315                 320

Cys Glu Glu Tyr Lys Met Ala Val Leu Ala Ala Lys Glu His Ile Gln
                325                 330                 335

Ala Gly Asp Ile Phe Gln Ile Val Leu Ser Gln Arg Phe Glu Arg Arg
            340                 345                 350

Thr Phe Ala Asp Pro Phe Glu Val Tyr Arg Ala Leu Arg Val Val Asn
        355                 360                 365

Pro Ser Pro Tyr Met Thr Tyr Met Gln Ala Arg Gly Cys Val Leu Val
    370                 375                 380

Ala Ser Ser Pro Glu Ile Leu Thr Arg Val Lys Lys Asn Lys Ile Val
385                 390                 395                 400

Asn Arg Pro Leu Ala Gly Thr Ala Arg Arg Gly Arg Thr Thr Glu Glu
                405                 410                 415

Asp Glu Met Leu Glu Thr Gln Leu Leu Lys Asp Ala Lys Gln Cys Ala
            420                 425                 430

Glu His Val Met Leu Val Asp Leu Gly Arg Asn Asp Val Gly Lys Val
        435                 440                 445

Ser Lys Ser Gly Ser Val Lys Val Glu Lys Leu Met Asn Val Glu Arg
    450                 455                 460

Tyr Ser His Val Met His Ile Ser Ser Thr Val Thr Gly Glu Leu Gln
465                 470                 475                 480

Asp Asn Leu Ser Cys Trp Asp Ala Leu Arg Ala Ala Leu Pro Val Gly
                485                 490                 495

Thr Val Ser Gly Ala Pro Lys Val Lys Ala Met Glu Leu Ile Asp Glu
            500                 505                 510

Leu Glu Val Asn Arg Arg Gly Pro Tyr Ser Gly Gly Phe Gly Gly Ile
        515                 520                 525

Ser Phe Thr Gly Asp Met Asp Ile Ala Leu Ala Leu Arg Thr Ile Val
    530                 535                 540

Phe Gln Thr Gly Thr Arg Tyr Asp Thr Met Tyr Ser Tyr Lys Asn Ala
545                 550                 555                 560

Thr Lys Arg Arg Gln Trp Val Ala Tyr Leu Gln Ala Gly Ala Gly Ile
                565                 570                 575

Val Ala Asp Ser Asp Pro Asp Glu His Arg Glu Cys Gln Asn Lys
            580                 585                 590

Ala Ala Gly Leu Ala Arg Ala Ile Asp Leu Ala Glu Ser Ala Phe Val
        595                 600                 605

Asn Lys Ser Ser Ser
    610

<210> SEQ ID NO 7
<211> LENGTH: 729
<212> TYPE: PRT
<213> ORGANISM: Rhizobium meliloti

<400> SEQUENCE: 7
```

-continued

```
Met Ala Ala Val Ile Leu Glu Asp Gly Ala Glu Ser Tyr Thr Thr Lys
1               5                   10                  15

Gly Gly Ile Val Val Thr Arg Arg Arg Glu Ala Ser Tyr Ser Asp
            20                  25                  30

Ala Ile Ala Gly Tyr Val Asp Arg Leu Asp Glu Arg Arg Gly Ala Val
            35                  40                  45

Phe Ser Ser Asn Tyr Glu Tyr Pro Gly Arg Tyr Thr Arg Trp Asp Thr
            50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
            115                 120                 125

Glu Glu Glu Arg Ser Lys Met Pro Thr Val Phe Thr Val Leu Arg Ala
            130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
            195                 200                 205

Arg Tyr Asp Phe Ala Arg Glu Asn Leu Ser Thr Glu Gly Lys Ala Ala
            210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Val Lys Ala Lys
                245                 250                 255

Glu Ser Phe Arg Arg Gly Asp Leu Phe Glu Val Val Pro Gly Gln Lys
            260                 265                 270

Phe Tyr Glu Arg Cys Glu Ser Arg Pro Ser Glu Ile Ser Asn Arg Leu
            275                 280                 285

Lys Ala Ile Asn Pro Ser Pro Tyr Ser Phe Phe Ile Asn Leu Gly Asn
            290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
            355                 360                 365

Asp Lys Ser Arg Val Cys Val Pro Gly Ser Val Lys Val Ile Gly Arg
            370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415
```

His Ala Trp Ala Val Thr Val Thr Gly Ala Pro Lys Leu Trp Ala Met
            420                 425                 430

Arg Phe Ile Glu Ser His Glu Lys Ser Pro Arg Ala Trp Tyr Gly Gly
            435                 440                 445

Ala Ile Gly Met Val Gly Phe Asn Gly Asp Met Asn Thr Gly Leu Thr
        450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Ala Glu Thr
                485                 490                 495

Glu Leu Lys Ala Ser Ala Met Ile Ala Ala Ile Arg Asp Ala Lys Ser
            500                 505                 510

Ala Asn Ser Ala Lys Ser Ala Arg Asp Val Ala Val Gly Ala Gly
        515                 520                 525

Val Ser Ile Leu Leu Val Asp His Glu Asp Ser Phe Val His Thr Leu
530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
        610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
            660                 665                 670

Thr Ala Glu Ser Glu Asp Gly Thr Ile Met Gly Ile Glu His Ser Lys
        675                 680                 685

Glu Pro Val Ala Ala Val Gln Phe His Pro Glu Ser Ile Met Thr Leu
        690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725

<210> SEQ ID NO 8
<211> LENGTH: 421
<212> TYPE: PRT
<213> ORGANISM: Sulfolobus solfataricus

<400> SEQUENCE: 8

Met Glu Val His Pro Ile Ser Glu Phe Ala Ser Pro Phe Glu Val Phe
1               5                   10                  15

Lys Cys Ile Glu Arg Asp Phe Lys Val Ala Gly Leu Leu Glu Ser Ile
            20                  25                  30

Gly Gly Pro Gln Tyr Lys Ala Arg Tyr Ser Val Ile Ala Trp Ser Thr
        35                  40                  45

Asn Gly Tyr Leu Lys Ile His Asp Asp Pro Val Asn Ile Leu Asn Gly
    50                  55                  60

Tyr Leu Lys Asp Leu Lys Leu Ala Asp Ile Pro Gly Leu Phe Lys Gly
65                  70                  75                  80

Gly Met Ile Gly Tyr Ile Ser Tyr Asp Ala Val Arg Phe Trp Glu Lys
                85                  90                  95

Ile Arg Asp Leu Lys Pro Ala Ala Glu Asp Trp Pro Tyr Ala Glu Phe
            100                 105                 110

Phe Thr Pro Asp Asn Ile Ile Tyr Asp His Asn Glu Gly Lys Val
        115                 120                 125

Tyr Val Asn Ala Asp Leu Ser Ser Val Gly Gly Cys Gly Asp Ile Gly
    130                 135                 140

Glu Phe Lys Val Ser Phe Tyr Asp Glu Ser Leu Asn Lys Asn Ser Tyr
145                 150                 155                 160

Glu Arg Ile Val Ser Glu Ser Leu Glu Tyr Ile Arg Ser Gly Tyr Ile
                165                 170                 175

Phe Gln Val Val Leu Ser Arg Phe Tyr Arg Tyr Ile Phe Ser Gly Asp
            180                 185                 190

Pro Leu Arg Ile Tyr Tyr Asn Leu Arg Arg Ile Asn Pro Ser Pro Tyr
        195                 200                 205

Met Phe Tyr Leu Lys Phe Asp Glu Lys Tyr Leu Ile Gly Ser Ser Pro
    210                 215                 220

Glu Leu Leu Phe Arg Val Gln Asp Asn Ile Val Glu Thr Tyr Pro Ile
225                 230                 235                 240

Ala Gly Thr Arg Pro Arg Gly Ala Asp Gln Glu Glu Asp Leu Lys Leu
                245                 250                 255

Glu Leu Glu Leu Met Asn Ser Glu Lys Asp Lys Ala Glu His Leu Met
            260                 265                 270

Leu Val Asp Leu Ala Arg Asn Asp Leu Gly Lys Val Cys Val Pro Gly
        275                 280                 285

Thr Val Lys Val Pro Glu Leu Met Tyr Val Glu Lys Tyr Ser His Val
    290                 295                 300

Gln His Ile Val Ser Lys Val Ile Gly Thr Leu Lys Lys Lys Tyr Asn
305                 310                 315                 320

Ala Leu Asn Val Leu Ser Ala Thr Phe Pro Ala Gly Thr Val Ser Gly
                325                 330                 335

Arg Pro Lys Pro Met Ala Met Asn Ile Ile Glu Thr Leu Glu Glu Tyr
            340                 345                 350

Lys Arg Gly Pro Tyr Ala Gly Ala Val Gly Phe Ile Ser Ala Asp Gly
        355                 360                 365

Asn Ala Glu Phe Ala Ile Ala Ile Arg Thr Ala Phe Leu Asn Lys Glu
    370                 375                 380

Leu Leu Arg Ile His Ala Gly Ala Gly Ile Val Tyr Asp Ser Asn Pro
385                 390                 395                 400

Glu Ser Glu Tyr Phe Glu Thr Glu His Lys Leu Lys Ala Leu Lys Thr
                405                 410                 415

Ala Ile Gly Val Arg
            420

<210> SEQ ID NO 9
<211> LENGTH: 32
<212> TYPE: DNA
<213> ORGANISM: Artificial Sequence
<220> FEATURE:
<223> OTHER INFORMATION: A primer

<400> SEQUENCE: 9

```
ccatcgcggc gcgttttttt cgtccaacta tg                              32

<210> SEQ ID NO 10
<211> LENGTH: 32
<212> TYPE: DNA
<213> ORGANISM: Artificial Sequence
<220> FEATURE:
<223> OTHER INFORMATION: A primer

<400> SEQUENCE: 10
catagttgga cgaaaaaaac gcgccgcgat gg                              32

<210> SEQ ID NO 11
<211> LENGTH: 39
<212> TYPE: DNA
<213> ORGANISM: Artificial Sequence
<220> FEATURE:
<223> OTHER INFORMATION: A primer

<400> SEQUENCE: 11
ccatcgcggc gcgtattttt cgtccaacta tgaatatcc                       39

<210> SEQ ID NO 12
<211> LENGTH: 39
<212> TYPE: DNA
<213> ORGANISM: Artificial Sequence
<220> FEATURE:
<223> OTHER INFORMATION: A primer

<400> SEQUENCE: 12
ggatattcat agttggacga aaaatacgcg ccgcgatgg                       39

<210> SEQ ID NO 13
<211> LENGTH: 39
<212> TYPE: DNA
<213> ORGANISM: Artificial Sequence
<220> FEATURE:
<223> OTHER INFORMATION: A primer

<400> SEQUENCE: 13
ccatcgcggc gcgtggtttt cgtccaacta tgaatatcc                       39

<210> SEQ ID NO 14
<211> LENGTH: 39
<212> TYPE: DNA
<213> ORGANISM: Artificial Sequence
<220> FEATURE:
<223> OTHER INFORMATION: A primer

<400> SEQUENCE: 14
ggatattcat agttggacga aaaccacgcg ccgcgatgg                       39

<210> SEQ ID NO 15
<211> LENGTH: 39
<212> TYPE: DNA
<213> ORGANISM: Artificial Sequence
<220> FEATURE:
<223> OTHER INFORMATION: A primer

<400> SEQUENCE: 15
ccatcgcggc gcggttttta agtccaacta tgaatatcc                       39

<210> SEQ ID NO 16
<211> LENGTH: 39
<212> TYPE: DNA
```

-continued

<213> ORGANISM: Artificial Sequence
<220> FEATURE:
<223> OTHER INFORMATION: A primer

<400> SEQUENCE: 16
ggatattcat agttggactt aaaaaccgcg ccgcgatgg                39

<210> SEQ ID NO 17
<211> LENGTH: 34
<212> TYPE: DNA
<213> ORGANISM: Artificial Sequence
<220> FEATURE:
<223> OTHER INFORMATION: A primer

<400> SEQUENCE: 17
gcgcggtttt ttcgtgcaac tatgaatatc cggg                34

<210> SEQ ID NO 18
<211> LENGTH: 34
<212> TYPE: DNA
<213> ORGANISM: Artificial Sequence
<220> FEATURE:
<223> OTHER INFORMATION: A primer

<400> SEQUENCE: 18
cccggatatt catagttgca cgaaaaaacc gcgc                34

<210> SEQ ID NO 19
<211> LENGTH: 34
<212> TYPE: DNA
<213> ORGANISM: Artificial Sequence
<220> FEATURE:
<223> OTHER INFORMATION: A primer

<400> SEQUENCE: 19
cgcggttttt tcgttcaact atgaatatcc gggc                34

<210> SEQ ID NO 20
<211> LENGTH: 34
<212> TYPE: DNA
<213> ORGANISM: Artificial Sequence
<220> FEATURE:
<223> OTHER INFORMATION: A primer

<400> SEQUENCE: 20
gcccggatat tcatagttga acgaaaaaac cgcg                34

<210> SEQ ID NO 21
<211> LENGTH: 37
<212> TYPE: DNA
<213> ORGANISM: Artificial Sequence
<220> FEATURE:
<223> OTHER INFORMATION: A primer

<400> SEQUENCE: 21
cggcgcggtt tttcgatca actatgaata tccgggc                37

<210> SEQ ID NO 22
<211> LENGTH: 37
<212> TYPE: DNA
<213> ORGANISM: Artificial Sequence
<220> FEATURE:
<223> OTHER INFORMATION: A primer

<400> SEQUENCE: 22
gcccggatat tcatagttga tcgaaaaaac cgcgccg                37

<210> SEQ ID NO 23
<211> LENGTH: 36
<212> TYPE: DNA
<213> ORGANISM: Artificial Sequence
<220> FEATURE:
<223> OTHER INFORMATION: A primer

<400> SEQUENCE: 23
ggcgcggttt tttcgctcaa ctatgaatat ccgggc                        36

<210> SEQ ID NO 24
<211> LENGTH: 36
<212> TYPE: DNA
<213> ORGANISM: Artificial Sequence
<220> FEATURE:
<223> OTHER INFORMATION: A primer

<400> SEQUENCE: 24
gcccggatat tcatagttga gcgaaaaaac cgcgcc                        36

<210> SEQ ID NO 25
<211> LENGTH: 39
<212> TYPE: DNA
<213> ORGANISM: Artificial Sequence
<220> FEATURE:
<223> OTHER INFORMATION: A primer

<400> SEQUENCE: 25
cggcgcggtt tttcgatga actatgaata tccgggccg                      39

<210> SEQ ID NO 26
<211> LENGTH: 39
<212> TYPE: DNA
<213> ORGANISM: Artificial Sequence
<220> FEATURE:
<223> OTHER INFORMATION: A primer

<400> SEQUENCE: 26
cggcccggat attcatagtt catcgaaaaa accgcgccg                     39

<210> SEQ ID NO 27
<211> LENGTH: 34
<212> TYPE: DNA
<213> ORGANISM: Artificial Sequence
<220> FEATURE:
<223> OTHER INFORMATION: A primer

<400> SEQUENCE: 27
cgcggttttt tcgaccaact atgaatatcc gggc                          34

<210> SEQ ID NO 28
<211> LENGTH: 34
<212> TYPE: DNA
<213> ORGANISM: Artificial Sequence
<220> FEATURE:
<223> OTHER INFORMATION: A primer

<400> SEQUENCE: 28
gcccggatat tcatagttgg tcgaaaaaac cgcg                          34

<210> SEQ ID NO 29
<211> LENGTH: 36
<212> TYPE: DNA
<213> ORGANISM: Artificial Sequence
<220> FEATURE:

<223> OTHER INFORMATION: A primer

<400> SEQUENCE: 29
ggcgcggttt tttcggtcaa ctatgaatat ccgggc    36

<210> SEQ ID NO 30
<211> LENGTH: 36
<212> TYPE: DNA
<213> ORGANISM: Artificial Sequence
<220> FEATURE:
<223> OTHER INFORMATION: A primer

<400> SEQUENCE: 30
gcccggatat tcatagttga ccgaaaaaac cgcgcc    36

<210> SEQ ID NO 31
<211> LENGTH: 35
<212> TYPE: DNA
<213> ORGANISM: Artificial Sequence
<220> FEATURE:
<223> OTHER INFORMATION: A primer

<400> SEQUENCE: 31
gcgcggtttt tcgtacaac tatgaatatc cgggc    35

<210> SEQ ID NO 32
<211> LENGTH: 35
<212> TYPE: DNA
<213> ORGANISM: Artificial Sequence
<220> FEATURE:
<223> OTHER INFORMATION: A primer

<400> SEQUENCE: 32
gcccggatat tcatagttgt acgaaaaaac cgcgc    35

<210> SEQ ID NO 33
<211> LENGTH: 36
<212> TYPE: DNA
<213> ORGANISM: Artificial Sequence
<220> FEATURE:
<223> OTHER INFORMATION: A primer

<400> SEQUENCE: 33
cggcgcggtt ttttcgtcct tctatgaata tccggg    36

<210> SEQ ID NO 34
<211> LENGTH: 36
<212> TYPE: DNA
<213> ORGANISM: Artificial Sequence
<220> FEATURE:
<223> OTHER INFORMATION: A primer

<400> SEQUENCE: 34
cccggatatt catagaagga cgaaaaaacc gcgccg    36

<210> SEQ ID NO 35
<211> LENGTH: 29
<212> TYPE: DNA
<213> ORGANISM: Artificial Sequence
<220> FEATURE:
<223> OTHER INFORMATION: A primer

<400> SEQUENCE: 35
ctgaaggcga tcaacgcgtc gccctattc    29

```
<210> SEQ ID NO 36
<211> LENGTH: 29
<212> TYPE: DNA
<213> ORGANISM: Artificial Sequence
<220> FEATURE:
<223> OTHER INFORMATION: A primer

<400> SEQUENCE: 36
gaatagggcg acgcgttgat cgccttcag                              29

<210> SEQ ID NO 37
<211> LENGTH: 31
<212> TYPE: DNA
<213> ORGANISM: Artificial Sequence
<220> FEATURE:
<223> OTHER INFORMATION: A primer

<400> SEQUENCE: 37
cctgaaggcg atcaacgggt cgccctattc c                           31

<210> SEQ ID NO 38
<211> LENGTH: 31
<212> TYPE: DNA
<213> ORGANISM: Artificial Sequence
<220> FEATURE:
<223> OTHER INFORMATION: A primer

<400> SEQUENCE: 38
ggaatagggc gacccgttga tcgccttcag g                           31

<210> SEQ ID NO 39
<211> LENGTH: 33
<212> TYPE: DNA
<213> ORGANISM: Artificial Sequence
<220> FEATURE:
<223> OTHER INFORMATION: A primer

<400> SEQUENCE: 39
cgtcgcccta ttccgccttc atcaatctcg gcg                         33

<210> SEQ ID NO 40
<211> LENGTH: 33
<212> TYPE: DNA
<213> ORGANISM: Artificial Sequence
<220> FEATURE:
<223> OTHER INFORMATION: A primer

<400> SEQUENCE: 40
cgccgagatt gatgaaggcg gaatagggcg acg                         33

<210> SEQ ID NO 41
<211> LENGTH: 33
<212> TYPE: DNA
<213> ORGANISM: Artificial Sequence
<220> FEATURE:
<223> OTHER INFORMATION: A primer

<400> SEQUENCE: 41
cgtcgcccta ttcctggttc atcaatctcg gcg                         33

<210> SEQ ID NO 42
<211> LENGTH: 33
<212> TYPE: DNA
<213> ORGANISM: Artificial Sequence
<220> FEATURE:
<223> OTHER INFORMATION: A primer
```

```
<400> SEQUENCE: 42
cgccgagatt gatgaaccag gaatagggcg acg                                      33

<210> SEQ ID NO 43
<211> LENGTH: 729
<212> TYPE: PRT
<213> ORGANISM: Rhizobium meliloti

<400> SEQUENCE: 43
```

| Met | Ala | Ala | Val | Ile | Leu | Glu | Asp | Gly | Ala | Glu | Ser | Tyr | Thr | Thr | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Gly Ile Val Val Thr Arg Arg Arg Glu Ala Ser Tyr Ser Asp
            20                  25                  30

Ala Ile Ala Gly Tyr Val Asp Arg Leu Asp Glu Arg Arg Gly Ala Val
            35                  40                  45

Phe Ser Ser Asn Tyr Glu Tyr Pro Gly Arg Tyr Thr Arg Trp Asp Thr
 50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
        115                 120                 125

Glu Glu Glu Arg Ser Lys Met Pro Thr Val Phe Thr Val Leu Arg Ala
130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
        195                 200                 205

Arg Tyr Asp Phe Ala Arg Glu Asn Leu Ser Thr Glu Gly Lys Ala Ala
210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Val Lys Ala Lys
                245                 250                 255

Glu Ser Phe Arg Arg Gly Asp Leu Phe Glu Val Val Pro Gly Gln Lys
            260                 265                 270

Phe Tyr Glu Arg Cys Glu Ser Arg Pro Ser Glu Ile Ser Asn Arg Leu
        275                 280                 285

Lys Ala Ile Asn Pro Ser Pro Tyr Ser Phe Phe Ile Asn Leu Gly Asn
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn

```
                355                 360                 365
Asp Lys Ser Arg Val Cys Val Pro Gly Ser Val Lys Val Ile Gly Arg
            370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Ser His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Ala Glu Thr
                485                 490                 495

Glu Leu Lys Ala Ser Ala Met Ile Ala Ala Ile Arg Asp Ala Lys Ser
            500                 505                 510

Ala Asn Ser Ala Lys Ser Ala Arg Asp Val Ala Val Gly Ala Gly
        515                 520                 525

Val Ser Ile Leu Leu Val Asp His Glu Asp Ser Phe Val His Thr Leu
530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
            660                 665                 670

Thr Ala Glu Ser Glu Asp Gly Thr Ile Met Gly Ile Glu His Ser Lys
        675                 680                 685

Glu Pro Val Ala Ala Val Gln Phe His Pro Glu Ser Ile Met Thr Leu
690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725

<210> SEQ ID NO 44
<211> LENGTH: 616
<212> TYPE: PRT
<213> ORGANISM: Sulfolobus solfataricus

<400> SEQUENCE: 44
```

-continued

```
Met Glu Val His Pro Ile Ser Glu Phe Ala Ser Pro Phe Glu Val Phe
1               5                   10                  15

Lys Cys Ile Glu Arg Asp Phe Lys Val Ala Gly Leu Leu Glu Ser Ile
            20                  25                  30

Gly Gly Pro Gln Tyr Lys Ala Arg Tyr Ser Val Ile Ala Trp Ser Thr
                35                  40                  45

Asn Gly Tyr Leu Lys Ile His Asp Asp Pro Val Asn Ile Leu Asn Gly
    50                  55                  60

Tyr Leu Lys Asp Leu Lys Leu Ala Asp Ile Pro Gly Leu Phe Lys Gly
65                  70                  75                  80

Gly Met Ile Gly Tyr Ile Ser Tyr Asp Ala Val Arg Phe Trp Glu Lys
                85                  90                  95

Ile Arg Asp Leu Lys Pro Ala Ala Glu Asp Trp Pro Tyr Ala Glu Phe
            100                 105                 110

Phe Thr Pro Asp Asn Ile Ile Ile Tyr Asp His Asn Glu Gly Lys Val
            115                 120                 125

Tyr Val Asn Ala Asp Leu Ser Ser Val Gly Gly Cys Gly Asp Ile Gly
    130                 135                 140

Glu Phe Lys Val Ser Phe Tyr Asp Glu Ser Leu Asn Lys Asn Ser Tyr
145                 150                 155                 160

Glu Arg Ile Val Ser Glu Ser Leu Glu Tyr Ile Arg Ser Gly Tyr Ile
                165                 170                 175

Phe Gln Val Val Leu Ser Arg Phe Tyr Arg Tyr Ile Phe Ser Gly Asp
            180                 185                 190

Pro Leu Arg Ile Tyr Tyr Asn Leu Arg Arg Ile Asn Pro Ser Pro Tyr
            195                 200                 205

Met Phe Tyr Leu Lys Phe Asp Glu Lys Tyr Leu Ile Gly Ser Ser Pro
    210                 215                 220

Glu Leu Leu Phe Arg Val Gln Asp Asn Ile Val Glu Thr Tyr Pro Ile
225                 230                 235                 240

Ala Gly Thr Arg Pro Arg Gly Ala Asp Gln Glu Glu Asp Leu Lys Leu
                245                 250                 255

Glu Leu Glu Leu Met Asn Ser Glu Lys Asp Lys Ala Glu His Leu Met
            260                 265                 270

Leu Val Asp Leu Ala Arg Asn Asp Leu Gly Lys Val Cys Val Pro Gly
            275                 280                 285

Thr Val Lys Val Pro Glu Leu Met Tyr Val Glu Lys Tyr Ser His Val
    290                 295                 300

Gln His Ile Val Ser Lys Val Ile Gly Thr Leu Lys Lys Lys Tyr Asn
305                 310                 315                 320

Ala Leu Asn Val Leu Ser Ala Thr Phe Pro Ala Gly Thr Val Ser Gly
                325                 330                 335

Arg Pro Lys Pro Met Ala Met Asn Ile Ile Glu Thr Leu Glu Glu Tyr
            340                 345                 350

Lys Arg Gly Pro Tyr Ala Gly Ala Val Gly Phe Ile Ser Ala Asp Gly
            355                 360                 365

Asn Ala Glu Phe Ala Ile Ala Ile Arg Thr Ala Phe Leu Asn Lys Glu
    370                 375                 380

Leu Leu Arg Ile His Ala Gly Ala Gly Ile Val Tyr Asp Ser Asn Pro
385                 390                 395                 400

Glu Ser Glu Tyr Phe Glu Thr Glu His Lys Leu Lys Ala Leu Lys Thr
                405                 410                 415

Ala Ile Gly Val Arg Met Asp Leu Thr Leu Ile Ile Asp Asn Tyr Asp
```

```
                    420                 425                 430
Ser Phe Val Tyr Asn Ile Ala Gln Ile Val Gly Glu Leu Gly Ser Tyr
            435                 440                 445

Pro Ile Val Ile Arg Asn Asp Glu Ile Ser Ile Lys Gly Ile Glu Arg
        450                 455                 460

Ile Asp Pro Asp Arg Leu Ile Ile Ser Pro Gly Pro Gly Thr Pro Glu
465                 470                 475                 480

Lys Arg Glu Asp Ile Gly Val Ser Leu Asp Val Ile Lys Tyr Leu Gly
                485                 490                 495

Lys Arg Thr Pro Ile Leu Gly Val Cys Leu Gly His Gln Ala Ile Gly
            500                 505                 510

Tyr Ala Phe Gly Ala Lys Ile Arg Arg Ala Arg Lys Val Phe His Gly
            515                 520                 525

Lys Ile Ser Asn Ile Ile Leu Val Asn Asn Ser Pro Leu Ser Leu Tyr
        530                 535                 540

Tyr Gly Ile Ala Lys Glu Phe Lys Ala Thr Arg Tyr His Ser Leu Val
545                 550                 555                 560

Val Asp Glu Val His Arg Pro Leu Ile Val Asp Ala Ile Ser Ala Glu
                565                 570                 575

Asp Asn Glu Ile Met Ala Ile His His Glu Glu Tyr Pro Ile Tyr Gly
            580                 585                 590

Val Gln Phe His Pro Glu Ser Val Gly Thr Ser Leu Gly Tyr Lys Ile
            595                 600                 605

Leu Tyr Asn Phe Leu Asn Arg Val
        610                 615

<210> SEQ ID NO 45
<211> LENGTH: 897
<212> TYPE: PRT
<213> ORGANISM: Arabidopsis thaliana

<400> SEQUENCE: 45

Met Ser Ala Val Ser Ile Ser Ala Val Lys Ser Asp Phe Phe Thr Val
1               5                   10                  15

Glu Ala Ile Ala Val Thr His His Arg Thr Pro His Pro Pro His Phe
            20                  25                  30

Pro Ser Leu Arg Phe Pro Leu Ser Leu Lys Ser Pro Ala Thr Ser
        35                  40                  45

Leu Asn Leu Val Ala Gly Ser Lys Leu Leu His Phe Ser Arg Arg Leu
    50                  55                  60

Pro Ser Ile Lys Cys Ser Tyr Thr Pro Ser Leu Asp Leu Ser Glu Glu
65                  70                  75                  80

Gln Phe Thr Lys Phe Lys Lys Ala Ser Glu Lys Gly Asn Leu Val Pro
                85                  90                  95

Leu Phe Arg Cys Val Phe Ser Asp His Leu Thr Pro Ile Leu Ala Tyr
            100                 105                 110

Arg Cys Leu Val Lys Glu Asp Asp Arg Asp Ala Pro Ser Phe Leu Phe
        115                 120                 125

Glu Ser Val Glu Pro Gly Ser Gln Ser Ser Asn Ile Gly Arg Tyr Ser
    130                 135                 140

Val Val Gly Ala Gln Pro Thr Ile Glu Ile Val Ala Lys Gly Asn Val
145                 150                 155                 160

Val Thr Val Met Asp His Gly Ala Ser Leu Arg Thr Glu Glu Glu Val
                165                 170                 175
```

```
Asp Asp Pro Met Met Val Pro Gln Lys Ile Met Glu Glu Trp Asn Pro
            180                 185                 190

Gln Gly Ile Asp Glu Leu Pro Glu Ala Phe Cys Gly Trp Val Gly
        195                 200                 205

Tyr Phe Ser Tyr Asp Thr Val Arg Tyr Val Lys Lys Lys Leu Pro
    210                 215                 220

Phe Ser Asn Ala Pro Glu Asp Arg Ser Leu Pro Asp Val Asn Leu
225                 230                 235                 240

Gly Leu Tyr Asp Asp Val Ile Val Phe Asp His Val Glu Lys Ala
                245                 250                 255

Tyr Val Ile His Trp Val Arg Ile Asp Lys Asp Arg Ser Val Glu Glu
                260                 265                 270

Asn Phe Arg Glu Gly Met Asn Arg Leu Glu Ser Leu Thr Ser Arg Ile
            275                 280                 285

Gln Asp Gln Lys Pro Pro Lys Met Pro Thr Gly Phe Ile Lys Leu Arg
290                 295                 300

Thr Gln Leu Phe Gly Pro Lys Leu Glu Lys Ser Thr Met Thr Ser Glu
305                 310                 315                 320

Ala Tyr Lys Glu Ala Val Val Glu Ala Lys Glu His Ile Leu Ala Gly
                325                 330                 335

Asp Ile Phe Gln Ile Val Leu Ser Gln Arg Phe Glu Arg Arg Thr Phe
                340                 345                 350

Ala Asp Pro Phe Glu Ile Tyr Arg Ala Leu Arg Ile Val Asn Pro Ser
                355                 360                 365

Pro Tyr Met Ala Tyr Leu Gln Val Arg Gly Cys Ile Leu Val Ala Ser
            370                 375                 380

Ser Pro Glu Ile Leu Leu Arg Ser Lys Asn Arg Lys Ile Thr Asn Arg
385                 390                 395                 400

Pro Leu Ala Gly Thr Val Arg Arg Gly Lys Thr Pro Lys Glu Asp Leu
                405                 410                 415

Met Leu Glu Lys Glu Leu Leu Ser Asp Glu Lys Gln Cys Ala Glu His
                420                 425                 430

Ile Met Leu Val Asp Leu Gly Arg Asn Asp Val Gly Lys Val Ser Lys
            435                 440                 445

Pro Gly Ser Val Glu Val Lys Lys Leu Lys Asp Ile Glu Trp Phe Ser
450                 455                 460

His Val Met His Ile Ser Ser Thr Val Val Gly Glu Leu Leu Asp His
465                 470                 475                 480

Leu Thr Ser Trp Asp Ala Leu Arg Ala Val Leu Pro Val Gly Thr Val
                485                 490                 495

Ser Gly Ala Pro Lys Val Lys Ala Met Glu Leu Ile Asp Glu Leu Glu
                500                 505                 510

Val Thr Arg Arg Gly Pro Tyr Ser Gly Gly Phe Gly Gly Ile Ser Phe
            515                 520                 525

Asn Gly Asp Met Asp Ile Ala Leu Ala Leu Arg Thr Met Val Phe Pro
530                 535                 540

Thr Asn Thr Arg Tyr Asp Thr Leu Tyr Ser Tyr Lys His Pro Gln Arg
545                 550                 555                 560

Arg Arg Glu Trp Ile Ala His Ile Gln Ala Gly Ala Gly Ile Val Ala
                565                 570                 575

Asp Ser Asn Pro Asp Asp Glu His Arg Glu Cys Glu Asn Lys Ala Ala
                580                 585                 590

Ala Leu Ala Arg Ala Ile Asp Leu Ala Glu Ser Ser Phe Leu Glu Ala
```

-continued

```
                  595                 600                 605
Pro Glu Phe Thr Thr Ile Thr Pro His Ile Asn Asn Ile Met Ala Ala
    610                 615                 620

Ser Thr Leu Tyr Lys Ser Cys Leu Leu Gln Pro Lys Ser Gly Ser Thr
625                 630                 635                 640

Thr Arg Arg Leu Asn Pro Ser Leu Val Asn Pro Leu Thr Asn Pro Thr
                645                 650                 655

Arg Val Ser Val Leu Gly Lys Ser Arg Arg Asp Val Phe Ala Lys Ala
            660                 665                 670

Ser Ile Glu Met Ala Glu Ser Asn Ser Ile Pro Ser Val Val Val Asn
        675                 680                 685

Ser Ser Lys Gln His Gly Pro Ile Ile Val Ile Asp Asn Tyr Asp Ser
690                 695                 700

Phe Thr Tyr Asn Leu Cys Gln Tyr Met Gly Glu Leu Gly Cys His Phe
705                 710                 715                 720

Glu Val Tyr Arg Asn Asp Glu Leu Thr Val Glu Leu Lys Lys Lys
                725                 730                 735

Asn Pro Arg Gly Val Leu Ile Ser Pro Gly Pro Gly Thr Pro Gln Asp
            740                 745                 750

Ser Gly Ile Ser Leu Gln Thr Val Leu Glu Leu Gly Pro Leu Val Pro
        755                 760                 765

Leu Phe Gly Val Cys Met Gly Leu Gln Cys Ile Gly Glu Ala Phe Gly
770                 775                 780

Gly Lys Ile Val Arg Ser Pro Phe Gly Val Met His Gly Lys Ser Ser
785                 790                 795                 800

Met Val His Tyr Asp Glu Lys Gly Glu Glu Gly Leu Phe Ser Gly Leu
                805                 810                 815

Ser Asn Pro Phe Ile Val Gly Arg Tyr His Ser Leu Val Ile Glu Lys
            820                 825                 830

Asp Thr Phe Pro Ser Asp Glu Leu Glu Val Thr Ala Trp Thr Glu Asp
        835                 840                 845

Gly Leu Val Met Ala Ala Arg His Arg Lys Tyr Lys His Ile Gln Gly
850                 855                 860

Val Gln Phe His Pro Glu Ser Ile Ile Thr Thr Glu Gly Lys Thr Ile
865                 870                 875                 880

Val Arg Asn Phe Ile Lys Ile Val Glu Lys Glu Ser Glu Lys Leu
                885                 890                 895
Thr
```

<210> SEQ ID NO 46
<211> LENGTH: 252
<212> TYPE: DNA
<213> ORGANISM: Artificial Sequence
<220> FEATURE:
<223> OTHER INFORMATION: A truncated gene

<400> SEQUENCE: 46

```
atgcaaacac aaaaaccgac tctcgaactg gaattcctgg tggaaaacgg tatcgccacc      60
gtgcaagcgg gtgctggtgt agtccttgat tctgttccgc agtcggaagc cgacgaaacc     120
cgtaacaaag cccgcgctgt actgcgcgct attgccaccg cgcatcatgc acaggagact     180
ttctgatggc tgacattctg ctgctcgata atatcgactc ttttacgtac aacctggcag     240
atcagttgcg ca                                                         252
```

```
<210> SEQ ID NO 47
<211> LENGTH: 18
<212> TYPE: DNA
<213> ORGANISM: Artificial Sequence
<220> FEATURE:
<223> OTHER INFORMATION: A primer

<400> SEQUENCE: 47
ttatgccgcc tgtcatcg                                                 18

<210> SEQ ID NO 48
<211> LENGTH: 19
<212> TYPE: DNA
<213> ORGANISM: Artificial Sequence
<220> FEATURE:
<223> OTHER INFORMATION: A primer

<400> SEQUENCE: 48
ataggcttaa tggtaaccg                                                19

<210> SEQ ID NO 49
<211> LENGTH: 18
<212> TYPE: DNA
<213> ORGANISM: Artificial Sequence
<220> FEATURE:
<223> OTHER INFORMATION: A primer

<400> SEQUENCE: 49
ctgaacaaca gaagtacg                                                 18

<210> SEQ ID NO 50
<211> LENGTH: 18
<212> TYPE: DNA
<213> ORGANISM: Artificial Sequence
<220> FEATURE:
<223> OTHER INFORMATION: A primer

<400> SEQUENCE: 50
taaccgtgtc atcgagcg                                                 18

<210> SEQ ID NO 51
<211> LENGTH: 31
<212> TYPE: DNA
<213> ORGANISM: Artificial Sequence
<220> FEATURE:
<223> OTHER INFORMATION: A primer

<400> SEQUENCE: 51
aaaaagatct ccatggtaac gatcattcag g                                  31

<210> SEQ ID NO 52
<211> LENGTH: 35
<212> TYPE: DNA
<213> ORGANISM: Artificial Sequence
<220> FEATURE:
<223> OTHER INFORMATION: A primer

<400> SEQUENCE: 52 aaagaattc ttatcacgcg gccttggtct tcgcc                               35

<210> SEQ ID NO 53
<211> LENGTH: 19
<212> TYPE: DNA
<213> ORGANISM: Artificial Sequence
<220> FEATURE:
<223> OTHER INFORMATION: A primer
```

<210> SEQ ID NO 54
<211> LENGTH: 23
<212> TYPE: DNA
<213> ORGANISM: Artificial Sequence
<220> FEATURE:
<223> OTHER INFORMATION: A primer

<400> SEQUENCE: 54
cctatccgag atctctcaac tcc                                           23

<210> SEQ ID NO 55
<211> LENGTH: 31
<212> TYPE: DNA
<213> ORGANISM: Artificial Sequence
<220> FEATURE:
<223> OTHER INFORMATION: A primer

<400> SEQUENCE: 55
catcccatgg atggtaacga tcattcagga t                                  31

<210> SEQ ID NO 56
<211> LENGTH: 31
<212> TYPE: DNA
<213> ORGANISM: Artificial Sequence
<220> FEATURE:
<223> OTHER INFORMATION: A primer

<400> SEQUENCE: 56
gatgtctaga gacactatag aatactcaag c                                  31

<210> SEQ ID NO 57
<211> LENGTH: 719
<212> TYPE: PRT
<213> ORGANISM: Rhodopseudomonas palustris

<400> SEQUENCE: 57

```
Met Asn Arg Thr Val Phe Ser Leu Pro Ala Thr Ser Asp Tyr Lys Thr
1               5                   10                  15

Ala Ala Gly Leu Ala Val Thr Arg Ser Ala Gln Pro Phe Ala Gly Gly
            20                  25                  30

Gln Ala Leu Asp Glu Leu Ile Asp Leu Leu Asp His Arg Arg Gly Val
        35                  40                  45

Met Leu Ser Ser Gly Thr Thr Val Pro Gly Arg Tyr Glu Ser Phe Asp
    50                  55                  60

Leu Gly Phe Ala Asp Pro Pro Leu Ala Leu Thr Thr Arg Ala Glu Lys
65                  70                  75                  80

Phe Thr Ile Glu Ala Leu Asn Pro Arg Gly Arg Val Leu Ile Ala Phe
                85                  90                  95

Leu Ser Asp Lys Leu Glu Glu Pro Cys Val Val Glu Gln Ala Cys
            100                 105                 110

Ala Thr Lys Ile Arg Gly His Ile Val Arg Gly Glu Ala Pro Val Asp
        115                 120                 125

Glu Glu Gln Arg Thr Arg Arg Ala Ser Ala Ile Ser Leu Val Arg Ala
    130                 135                 140

Val Ile Ala Ala Phe Ala Ser Pro Ala Asp Pro Met Leu Gly Leu Tyr
145                 150                 155                 160

Gly Ala Phe Ala Tyr Asp Leu Val Phe Gln Phe Glu Asp Leu Lys Gln
```

-continued

```
                165                 170                 175
Lys Arg Ala Arg Glu Ala Asp Gln Arg Asp Ile Val Leu Tyr Val Pro
            180                 185                 190
Asp Arg Leu Leu Ala Tyr Asp Arg Ala Thr Gly Arg Gly Val Asp Ile
        195                 200                 205
Ser Tyr Glu Phe Ala Trp Lys Gly Gln Ser Thr Ala Gly Leu Pro Asn
    210                 215                 220
Glu Thr Ala Glu Ser Val Tyr Thr Gln Thr Gly Arg Gln Gly Phe Ala
225                 230                 235                 240
Asp His Ala Pro Gly Asp Tyr Pro Lys Val Val Glu Lys Ala Arg Ala
                245                 250                 255
Ala Phe Ala Arg Gly Asp Leu Phe Glu Ala Val Pro Gly Gln Leu Phe
            260                 265                 270
Gly Glu Pro Cys Glu Arg Ser Pro Ala Glu Val Phe Lys Arg Leu Cys
        275                 280                 285
Arg Ile Asn Pro Ser Pro Tyr Gly Gly Leu Leu Asn Leu Gly Asp Gly
    290                 295                 300
Glu Phe Leu Val Ser Ala Ser Pro Glu Met Phe Val Arg Ser Asp Gly
305                 310                 315                 320
Arg Arg Ile Glu Thr Cys Pro Ile Ser Gly Thr Ile Ala Arg Gly Val
                325                 330                 335
Asp Ala Ile Ser Asp Ala Glu Gln Ile Gln Lys Leu Leu Asn Ser Glu
            340                 345                 350
Lys Asp Glu Phe Glu Leu Asn Met Cys Thr Asp Val Asp Arg Asn Asp
        355                 360                 365
Lys Ala Arg Val Cys Val Pro Gly Thr Ile Lys Val Leu Ala Arg Arg
    370                 375                 380
Gln Ile Glu Thr Tyr Ser Lys Leu Phe His Thr Val Asp His Val Glu
385                 390                 395                 400
Gly Met Leu Arg Pro Gly Phe Asp Ala Leu Asp Ala Phe Leu Thr His
                405                 410                 415
Ala Trp Ala Val Thr Val Thr Gly Ala Pro Lys Leu Trp Ala Met Gln
            420                 425                 430
Phe Val Glu Asp His Glu Arg Ser Pro Arg Arg Trp Tyr Ala Gly Ala
        435                 440                 445
Phe Gly Val Val Gly Phe Asp Gly Ser Ile Asn Thr Gly Leu Thr Ile
    450                 455                 460
Arg Thr Ile Arg Met Lys Asp Gly Leu Ala Glu Val Arg Val Gly Ala
465                 470                 475                 480
Thr Cys Leu Phe Asp Ser Asn Pro Val Ala Glu Asp Lys Glu Cys Gln
                485                 490                 495
Val Lys Ala Ala Ala Leu Phe Gln Ala Leu Arg Gly Asp Pro Ala Lys
            500                 505                 510
Pro Leu Ser Ala Val Ala Pro Ala Thr Gly Ser Gly Lys Lys Val
        515                 520                 525
Leu Leu Val Asp His Asp Ser Phe Val His Met Leu Ala Asp Tyr
    530                 535                 540
Phe Arg Gln Val Gly Ala Gln Val Thr Val Val Arg Tyr Val His Gly
545                 550                 555                 560
Leu Lys Met Leu Ala Glu Asn Ser Tyr Asp Leu Leu Val Leu Ser Pro
                565                 570                 575
Gly Pro Gly Arg Pro Glu Asp Phe Lys Ile Lys Asp Thr Ile Asp Ala
            580                 585                 590
```

```
Ala Leu Ala Lys Lys Leu Pro Ile Phe Gly Val Cys Leu Gly Val Gln
            595                 600                 605

Ala Met Gly Glu Tyr Phe Gly Gly Thr Leu Gly Gln Leu Ala Gln Pro
            610                 615                 620

Ala His Gly Arg Pro Ser Arg Ile Gln Val Arg Gly Ala Leu Met
625                 630                 635                 640

Arg Gly Leu Pro Asn Glu Val Thr Ile Gly Arg Tyr His Ser Leu Tyr
                    645                 650                 655

Val Asp Met Arg Asp Met Pro Lys Glu Leu Thr Val Thr Ala Ser Thr
            660                 665                 670

Asp Asp Gly Ile Ala Met Ala Ile Glu His Lys Thr Leu Pro Val Gly
            675                 680                 685

Gly Val Gln Phe His Pro Glu Ser Leu Met Ser Leu Gly Gly Glu Val
            690                 695                 700

Gly Leu Arg Ile Val Glu Asn Ala Phe Arg Leu Gly Gln Ala Ala
705                 710                 715

<210> SEQ ID NO 58
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 58

Met Val Thr Ile Ile Gln Asp Asp Gly Ala Glu Thr Tyr Glu Thr Lys
1               5                   10                  15

Gly Gly Ile Gln Val Ser Arg Lys Arg Pro Thr Asp Tyr Ala Asn
            20                  25                  30

Ala Ile Asp Asn Tyr Ile Glu Lys Leu Asp Ser His Arg Gly Ala Phe
            35                  40                  45

Phe Ser Ser Asn Tyr Glu Tyr Pro Gly Arg Tyr Thr Arg Trp Asp Thr
50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
            115                 120                 125

Glu Glu Glu Arg Ser Lys Ile Pro Thr Val Phe Thr Ala Leu Arg Ala
            130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
            195                 200                 205

Arg Tyr Asp Phe Glu Lys Asp Gly Met Thr Thr Asp Gly Lys Ser Ser
            210                 215                 220

Asp Ile Thr Pro Asp Pro Phe Lys Thr Thr Asp Thr Ile Pro Pro Lys
225                 230                 235                 240
```

-continued

```
Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655
```

```
His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
            675                 680                 685

Glu Pro Val Ala Ala Val Gln Phe His Pro Glu Ser Ile Met Thr Leu
        690                 695                 700

Gly Gln Asp Ala Gly Met Arg Met Ile Glu Asn Val Val His Leu
705                 710                 715                 720

Thr Arg Lys Ala Lys Thr Lys Ala Ala
                725

<210> SEQ ID NO 59
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 59

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Tyr
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285
```

```
Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
```

```
                705                 710                 715                 720
Thr Arg Lys Ala Lys Thr Lys Ala Ala
                725

<210> SEQ ID NO 60
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 60

Met Val Thr Ile Ile Gln Asp Asp Gly Ala Glu Tyr Glu Thr Lys
1               5                   10                  15

Gly Gly Ile Gln Val Ser Arg Lys Arg Pro Thr Asp Tyr Ala Asn
                20                  25                  30

Ala Ile Asp Asn Tyr Ile Glu Lys Leu Asp Ser His Arg Gly Ala Val
                35                  40                  45

Phe Ser Phe Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
                100                 105                 110

Thr Arg Arg Leu Asp Leu Thr Val Asn Glu Pro Asp Arg Val Phe Thr
            115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
```

```
                340                 345                 350
Lys Lys Asp Glu Ser Glu Leu Thr Met Cys Ser Asp Val Asp Arg Asn
            355                 360                 365

Asp Lys Ser Arg Val Cys Glu Pro Gly Ser Val Lys Val Ile Gly Arg
        370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
        450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Lys Val Gly Thr Gly
        515                 520                 525

Val Lys Ile Leu Leu Val Asp His Glu Asp Ser Phe Val His Thr Leu
        530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
        610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
        690                 695                 700

Gly Gln Asp Ala Gly Met Arg Met Ile Glu Asn Val Val His Leu
705                 710                 715                 720

Thr Arg Lys Ala Lys Thr Lys Ala Ala
                725

<210> SEQ ID NO 61
<211> LENGTH: 729
<212> TYPE: PRT
<213> ORGANISM: Artificial Sequence
```

```
<220> FEATURE:
<223> OTHER INFORMATION: An A. tumefaciens mutant

<400> SEQUENCE: 61

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Cys Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400
```

```
Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
            485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
            515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val His Leu
705                 710                 715                 720

Thr Arg Lys Ala Lys Thr Lys Ala Ala
            725

<210> SEQ ID NO 62
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 62

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30
```

-continued

```
Ala Ile Asp Asn Tyr Ile Glu Lys Leu Asp Ser His Arg Gly Ala Val
         35                  40                  45

Phe Ser Ser Phe Tyr Glu Tyr Pro Gly Arg Tyr Thr Arg Trp Asp Thr
         50                  55                  60

Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
                100                 105                 110

Thr Arg Arg Leu Asp Leu Thr Val Asn Glu Pro Asp Arg Val Phe Thr
            115                 120                 125

Glu Glu Glu Arg Ser Lys Ile Pro Thr Val Phe Thr Ala Leu Arg Ala
        130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
                180                 185                 190

Asp Glu Ile Leu Val Val Asp His Tyr Ser Ala Lys Ala Trp Ile Asp
            195                 200                 205

Arg Tyr Asp Phe Glu Lys Asp Gly Met Thr Thr Asp Gly Lys Ser Ser
        210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
                260                 265                 270

Phe Met Glu Arg Cys Glu Ser Asn Pro Ser Ala Ile Ser Arg Arg Leu
            275                 280                 285

Lys Ala Ile Asn Pro Ser Pro Tyr Ser Phe Phe Ile Asn Leu Gly Asp
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445
```

```
Ala Ile Gly Met Val Gly Phe Asn Gly Asp Met Asn Thr Gly Leu Thr
    450                 455                 460
Leu Arg Thr Ile Arg Ile Lys Asp Gly Ile Ala Glu Val Arg Ala Gly
465                 470                 475                 480
Ala Thr Leu Leu Asn Asp Ser Asn Pro Gln Glu Glu Ala Glu Thr
                485                 490                 495
Glu Leu Lys Ala Ser Ala Met Ile Ser Ala Ile Arg Asp Ala Lys Gly
            500                 505                 510
Thr Asn Ser Ala Ala Thr Lys Arg Asp Ala Ala Lys Val Gly Thr Gly
                515                 520                 525
Val Lys Ile Leu Leu Val Asp His Glu Asp Ser Phe Val His Thr Leu
    530                 535                 540
Ala Asn Tyr Phe Arg Gln Thr Gly Ala Thr Val Ser Thr Val Arg Ser
545                 550                 555                 560
Pro Val Ala Ala Asp Val Phe Asp Arg Phe Gln Pro Asp Leu Val Val
                565                 570                 575
Leu Ser Pro Gly Pro Gly Ser Pro Thr Asp Phe Asp Cys Lys Ala Thr
            580                 585                 590
Ile Lys Ala Ala Arg Ala Arg Asp Leu Pro Ile Phe Gly Val Cys Leu
        595                 600                 605
Gly Leu Gln Ala Leu Ala Glu Ala Tyr Gly Gly Glu Leu Arg Gln Leu
    610                 615                 620
Ala Val Pro Met His Gly Lys Pro Ser Arg Ile Arg Val Leu Glu Pro
625                 630                 635                 640
Gly Leu Val Phe Ser Gly Leu Gly Lys Glu Val Thr Val Gly Arg Tyr
                645                 650                 655
His Ser Ile Phe Ala Asp Pro Ala Thr Leu Pro Arg Asp Phe Ile Ile
            660                 665                 670
Thr Ala Glu Ser Glu Asp Gly Thr Ile Met Gly Ile Glu His Ala Lys
        675                 680                 685
Glu Pro Val Ala Ala Val Gln Phe His Pro Glu Ser Ile Met Thr Leu
    690                 695                 700
Gly Gln Asp Ala Gly Met Arg Met Ile Glu Asn Val Val Val His Leu
705                 710                 715                 720
Thr Arg Lys Ala Lys Thr Lys Ala Ala
                725

<210> SEQ ID NO 63
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 63

Met Val Thr Ile Ile Gln Asp Asp Gly Ala Glu Thr Tyr Glu Thr Lys
1               5                   10                  15
Gly Gly Ile Gln Val Ser Arg Lys Arg Pro Thr Asp Tyr Ala Asn
            20                  25                  30
Ala Ile Asp Asn Tyr Ile Glu Lys Leu Asp Ser His Arg Gly Ala Val
        35                  40                  45
Phe Ser Ser Asn Tyr Glu Tyr Pro Gly Arg Tyr Thr Arg Trp Asp Thr
    50                  55                  60
Ala Ile Val Asp Pro Pro Leu Gly Ile Ser Cys Phe Gly Arg Lys Met
65                  70                  75                  80
```

-continued

```
Trp Ile Glu Ala Tyr Asn Gly Arg Gly Glu Val Leu Leu Asp Phe Ile
             85                  90                  95
Thr Glu Lys Leu Lys Ala Thr Pro Asp Leu Thr Leu Gly Ala Ser Ser
            100                 105                 110
Thr Arg Arg Leu Asp Leu Thr Val Asn Glu Pro Asp Arg Val Phe Thr
            115                 120                 125
Glu Glu Glu Arg Ser Lys Ile Pro Thr Val Phe Thr Ala Leu Arg Ala
        130                 135                 140
Ile Val Asp Leu Phe Tyr Ser Ser Ala Asp Ser Ala Ile Gly Leu Phe
145                 150                 155                 160
Gly Ala Phe Gly Tyr Asp Leu Ala Phe Gln Phe Asp Ala Ile Lys Leu
                165                 170                 175
Ser Leu Ala Arg Pro Glu Asp Gln Arg Asp Met Val Leu Phe Leu Pro
            180                 185                 190
Asp Glu Ile Leu Val Val Asp His Tyr Ser Ala Lys Ala Trp Ile Asp
            195                 200                 205
Arg Tyr Asp Phe Glu Lys Asp Gly Met Thr Thr Asp Gly Lys Ser Ser
        210                 215                 220
Asp Ile Thr Pro Asp Pro Phe Lys Thr Thr Asp Thr Ile Pro Pro Lys
225                 230                 235                 240
Gly Asp His Arg Pro Gly Glu Tyr Ser Glu Leu Val Val Lys Ala Lys
                245                 250                 255
Glu Ser Phe Arg Arg Gly Asp Leu Phe Glu Val Val Pro Gly Gln Lys
            260                 265                 270
Phe Met Glu Arg Cys Glu Ser Asn Pro Ser Ala Ile Ser Arg Arg Leu
            275                 280                 285
Lys Ala Ile Asn Ala Ser Pro Tyr Ser Phe Phe Ile Asn Leu Gly Asp
        290                 295                 300
Gln Glu Tyr Leu Val Gly Ala Ser Pro Glu Met Phe Val Arg Val Ser
305                 310                 315                 320
Gly Arg Arg Ile Glu Thr Cys Pro Ile Ser Gly Thr Ile Lys Arg Gly
                325                 330                 335
Asp Asp Pro Ile Ala Asp Ser Glu Gln Ile Leu Lys Leu Leu Asn Ser
            340                 345                 350
Lys Lys Asp Glu Ser Glu Leu Thr Met Cys Ser Asp Val Asp Arg Asn
        355                 360                 365
Asp Lys Ser Arg Val Cys Glu Pro Gly Ser Val Lys Val Ile Gly Arg
    370                 375                 380
Arg Gln Ile Glu Met Tyr Ser Arg Leu Ile His Thr Val Asp His Ile
385                 390                 395                 400
Glu Gly Arg Leu Arg Asp Asp Met Asp Ala Phe Asp Gly Phe Leu Ser
                405                 410                 415
His Ala Trp Ala Val Thr Val Thr Gly Ala Pro Lys Leu Trp Ala Met
            420                 425                 430
Arg Phe Ile Glu Gly His Glu Lys Ser Pro Arg Ala Trp Tyr Gly Gly
            435                 440                 445
Ala Ile Gly Met Val Gly Phe Asn Gly Asp Met Asn Thr Gly Leu Thr
        450                 455                 460
Leu Arg Thr Ile Arg Ile Lys Asp Gly Ile Ala Glu Val Arg Ala Gly
465                 470                 475                 480
Ala Thr Leu Leu Asn Asp Ser Asn Pro Gln Glu Glu Ala Glu Thr
                485                 490                 495
Glu Leu Lys Ala Ser Ala Met Ile Ser Ala Ile Arg Asp Ala Lys Gly
```

```
                500             505             510
Thr Asn Ser Ala Ala Thr Lys Arg Asp Ala Ala Lys Val Gly Thr Gly
            515                 520                 525

Val Lys Ile Leu Leu Val Asp His Glu Asp Ser Phe Val His Thr Leu
        530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val His Leu
705                 710                 715                 720

Thr Arg Lys Ala Lys Thr Lys Ala Ala
                725

<210> SEQ ID NO 64
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 64

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
```

```
                130                 135                 140
Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
                180                 185                 190

Asp Glu Ile Leu Val Val Asp His Tyr Ser Ala Lys Ala Trp Ile Asp
                195                 200                 205

Arg Tyr Asp Phe Glu Lys Asp Gly Met Thr Thr Asp Gly Lys Ser Ser
210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
                260                 265                 270

Phe Met Glu Arg Cys Glu Ser Asn Pro Ser Ala Ile Ser Arg Arg Leu
                275                 280                 285

Lys Ala Ile Asn Gly Ser Pro Tyr Ser Phe Phe Ile Asn Leu Gly Asp
                290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
                340                 345                 350

Lys Lys Asp Glu Ser Glu Leu Thr Met Cys Ser Asp Val Asp Arg Asn
                355                 360                 365

Asp Lys Ser Arg Val Cys Glu Pro Gly Ser Val Lys Val Ile Gly Arg
                370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Ile Glu Gly His Glu Lys Ser Pro Arg Ala Trp Tyr Gly Gly
                435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
                500                 505                 510

Thr Asn Ser Ala Ala Thr Lys Arg Asp Ala Ala Lys Val Gly Thr Gly
                515                 520                 525

Val Lys Ile Leu Leu Val Asp His Glu Asp Ser Phe Val His Thr Leu
                530                 535                 540

Ala Asn Tyr Phe Arg Gln Thr Gly Ala Thr Val Ser Thr Val Arg Ser
545                 550                 555                 560
```

```
Pro Val Ala Ala Asp Val Phe Asp Arg Phe Gln Pro Asp Leu Val Val
                565                 570                 575
Leu Ser Pro Gly Pro Gly Ser Pro Thr Asp Phe Asp Cys Lys Ala Thr
            580                 585                 590
Ile Lys Ala Ala Arg Ala Arg Asp Leu Pro Ile Phe Gly Val Cys Leu
        595                 600                 605
Gly Leu Gln Ala Leu Ala Glu Ala Tyr Gly Glu Leu Arg Gln Leu
    610                 615                 620
Ala Val Pro Met His Gly Lys Pro Ser Arg Ile Arg Val Leu Glu Pro
625                 630                 635                 640
Gly Leu Val Phe Ser Gly Leu Gly Lys Glu Val Thr Val Gly Arg Tyr
                645                 650                 655
His Ser Ile Phe Ala Asp Pro Ala Thr Leu Pro Arg Asp Phe Ile Ile
            660                 665                 670
Thr Ala Glu Ser Glu Asp Gly Thr Ile Met Gly Ile Glu His Ala Lys
        675                 680                 685
Glu Pro Val Ala Ala Val Gln Phe His Pro Glu Ser Ile Met Thr Leu
    690                 695                 700
Gly Gln Asp Ala Gly Met Arg Met Ile Glu Asn Val Val His Leu
705                 710                 715                 720
Thr Arg Lys Ala Lys Thr Lys Ala Ala
                725

<210> SEQ ID NO 65
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 65

Met Val Thr Ile Ile Gln Asp Asp Gly Ala Glu Thr Tyr Glu Thr Lys
1               5                   10                  15
Gly Gly Ile Gln Val Ser Arg Lys Arg Arg Pro Thr Asp Tyr Ala Asn
            20                  25                  30
Ala Ile Asp Asn Tyr Ile Glu Lys Leu Asp Ser His Arg Gly Ala Val
        35                  40                  45
Phe Ser Ser Asn Tyr Glu Tyr Pro Gly Arg Tyr Thr Arg Trp Asp Thr
    50                  55                  60
Ala Ile Val Asp Pro Pro Leu Gly Ile Ser Cys Phe Gly Arg Lys Met
65                  70                  75                  80
Trp Ile Glu Ala Tyr Asn Gly Arg Gly Glu Val Leu Leu Asp Phe Ile
                85                  90                  95
Thr Glu Lys Leu Lys Ala Thr Pro Asp Leu Thr Leu Gly Ala Ser Ser
            100                 105                 110
Thr Arg Arg Leu Asp Leu Thr Val Asn Glu Pro Asp Arg Val Phe Thr
        115                 120                 125
Glu Glu Glu Arg Ser Lys Ile Pro Thr Val Phe Thr Ala Leu Arg Ala
    130                 135                 140
Ile Val Asp Leu Phe Tyr Ser Ser Ala Asp Ser Ala Ile Gly Leu Phe
145                 150                 155                 160
Gly Ala Phe Gly Tyr Asp Leu Ala Phe Gln Phe Asp Ala Ile Lys Leu
                165                 170                 175
Ser Leu Ala Arg Pro Glu Asp Gln Arg Asp Met Val Leu Phe Leu Pro
            180                 185                 190
```

```
Asp Glu Ile Leu Val Val Asp His Tyr Ser Ala Lys Ala Trp Ile Asp
            195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
                260                 265                 270

Phe Met Glu Arg Cys Glu Ser Asn Pro Ser Ala Ile Ser Arg Arg Leu
            275                 280                 285

Lys Ala Ile Asn Pro Ser Pro Tyr Ser Trp Phe Ile Asn Leu Gly Asp
            290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
                340                 345                 350

Lys Lys Asp Glu Ser Glu Leu Thr Met Cys Ser Asp Val Asp Arg Asn
            355                 360                 365

Asp Lys Ser Arg Val Cys Glu Pro Gly Ser Val Lys Val Ile Gly Arg
            370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
            435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Lys Val Gly Thr Gly
            515                 520                 525

Val Lys Ile Leu Leu Val Asp His Glu Asp Ser Phe Val His Thr Leu
            530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
            595                 600                 605
```

-continued

```
Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Val Gln Phe His Pro Glu Ser Ile Met Thr Leu
    690                 695                 700

Gly Gln Asp Ala Gly Met Arg Met Ile Glu Asn Val Val His Leu
705                 710                 715                 720

Thr Arg Lys Ala Lys Thr Lys Ala Ala
                725

<210> SEQ ID NO 66
<211> LENGTH: 604
<212> TYPE: PRT
<213> ORGANISM: Artificial Sequence
<220> FEATURE:
<223> OTHER INFORMATION: A Zea mays mutant

<400> SEQUENCE: 66

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala Lys Ala Ala Glu Glu Asp Lys Arg Arg Phe Phe Glu Ala Ala Ala
65                  70                  75                  80

Arg Gly Ser Gly Lys Gly Asn Leu Val Pro Met Trp Glu Cys Ile Val
                85                  90                  95

Ser Asp His Leu Thr Pro Val Leu Ala Tyr Arg Cys Leu Val Pro Glu
            100                 105                 110

Asp Asn Val Asp Ala Pro Ser Phe Leu Phe Glu Ser Val Glu Gln Gly
        115                 120                 125

Pro Gln Gly Thr Thr Asn Val Gly Arg Tyr Ser Met Val Gly Ala His
    130                 135                 140

Pro Val Met Glu Ile Val Ala Lys Asp His Lys Val Thr Ile Met Asp
145                 150                 155                 160

His Glu Lys Ser Gln Val Thr Glu Gln Val Val Asp Asp Pro Met Gln
                165                 170                 175

Ile Pro Arg Thr Met Met Glu Gly Trp His Pro Gln Gln Ile Asp Glu
            180                 185                 190

Leu Pro Glu Ser Phe Ser Gly Gly Trp Val Gly Phe Phe Ser Tyr Asp
        195                 200                 205

Thr Val Arg Tyr Val Glu Lys Lys Lys Leu Pro Phe Ser Ser Ala Pro
    210                 215                 220

Gln Asp Asp Arg Asn Leu Pro Asp Val His Leu Gly Leu Tyr Asp Asp
225                 230                 235                 240
```

-continued

Val Leu Val Phe Asp Asn Val Glu Lys Lys Val Tyr Val Ile His Trp
            245                 250                 255

Val Asn Val Asp Arg His Ala Ser Val Glu Glu Ala Tyr Gln Asp Gly
        260                 265                 270

Arg Ser Arg Leu Asn Met Leu Leu Ser Lys Val His Asn Ser Asn Val
    275                 280                 285

Pro Thr Leu Ser Pro Gly Phe Val Lys Leu His Thr Arg Lys Phe Gly
290                 295                 300

Thr Pro Leu Asn Lys Ser Thr Met Thr Ser Asp Glu Tyr Lys Asn Ala
305                 310                 315                 320

Val Leu Gln Ala Lys Glu His Ile Met Ala Gly Asp Ile Phe Gln Ile
                325                 330                 335

Val Leu Ser Gln Arg Phe Glu Arg Arg Thr Tyr Ala Asn Pro Phe Glu
            340                 345                 350

Val Tyr Arg Ala Leu Arg Ile Val Asn Pro Ser Pro Tyr Lys Ala Tyr
        355                 360                 365

Val Gln Ala Arg Gly Cys Val Leu Val Ala Ser Ser Pro Glu Ile Leu
    370                 375                 380

Thr Arg Val Ser Lys Gly Lys Ile Ile Asn Arg Pro Leu Ala Gly Thr
385                 390                 395                 400

Val Arg Arg Gly Lys Thr Glu Lys Glu Asp Gln Met Gln Glu Gln Gln
                405                 410                 415

Leu Leu Ser Asp Glu Lys Gln Cys Ala Glu His Ile Met Leu Val Asp
            420                 425                 430

Leu Gly Arg Asn Asp Val Gly Lys Val Ser Lys Pro Gly Ser Val Lys
        435                 440                 445

Val Glu Lys Leu Met Asn Ile Glu Arg Tyr Ser His Val Met His Ile
    450                 455                 460

Ser Ser Thr Val Ser Gly Gln Leu Asp Asp His Leu Gln Ser Trp Asp
465                 470                 475                 480

Ala Leu Arg Ala Ala Leu Pro Val Gly Thr Val Ser Gly Ala Pro Lys
                485                 490                 495

Val Lys Ala Met Glu Leu Ile Asp Lys Leu Glu Val Thr Arg Arg Gly
            500                 505                 510

Pro Tyr Ser Gly Gly Leu Gly Gly Ile Ser Phe Asp Gly Asp Met Gln
        515                 520                 525

Ile Ala Leu Ser Leu Arg Thr Ile Val Phe Ser Thr Ala Pro Ser His
    530                 535                 540

Asn Thr Met Tyr Ser Tyr Lys Asp Ala Asp Arg Arg Glu Trp Val
545                 550                 555                 560

Ala His Leu Gln Ala Gly Ala Gly Ile Val Ala Asp Ser Ser Pro Asp
                565                 570                 575

Asp Glu Gln Arg Glu Cys Glu Asn Lys Ala Ala Ala Leu Ala Arg Ala
            580                 585                 590

Ile Asp Leu Ala Glu Ser Ala Phe Val Asp Lys Glu
        595                 600

<210> SEQ ID NO 67
<211> LENGTH: 1815
<212> TYPE: DNA
<213> ORGANISM: Artificial Sequence
<220> FEATURE:
<223> OTHER INFORMATION: A Zea mays mutant

<400> SEQUENCE: 67

-continued

```
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc tgctgccgtg acgccgcagg cgagcccagt gattagcagg     180
agcgctgcgg cggcgaaggc ggcggaggag gacaagaggc ggttcttcga ggcggcggcg     240
cgggggagcg ggaagggaa cctggtgccc atgtgggagt gcatcgtgtc ggaccatctc     300
acccccgtgc tcgcctaccg ctgcctcgtc ccgaggaca cgtcgacgc ccccagcttc      360
ctcttcgagt ccgtcgagca ggggccccag ggcaccacca acgtcggccg ctatagcatg     420
gtgggagccc acccagtgat ggagattgtg gccaaagacc acaaggttac gatcatggac     480
cacgagaaga gccaagtgac agagcaggta gtggacgacc cgatgcagat cccgaggacc     540
atgatggagg gatggcaccc acagcagatc gacgagctcc ctgaatcctt ctccggtgga     600
tgggttgggt tctttttccta tgatacggtt aggtatgttg agaagaagaa gctaccgttc     660
tccagtgctc ctcaggacga taggaaccctt cctgatgtgc acttgggact ctatgatgat     720
gttctagtct tcgataatgt tgagaagaaa gtatatgtta tccattgggt caatgtggac     780
cggcatgcat ctgttgagga agcataccaa gatggcaggt cccgactaaa catgttgcta     840
tctaaagtgc acaattccaa tgtccccaca ctctctcctg gatttgtgaa gctgcacaca     900
cgcaagtttg gtacaccttt gaacaagtcg accatgacaa gtgatgagta taagaatgct     960
gttctgcagg ctaaggaaca tattatggct ggggatatct tccagattgt tttaagccag    1020
aggttcgaga gacgaacata tgccaaccca tttgaggttt atcgagcatt acggattgtg    1080
aatcctagcc catacaaggc gtatgtacag gcaagaggct gtgtattggt tgcgtctagt    1140
cctgaaattc ttacacgagt cagtaagggg aagattatta atcgaccact tgctggaact    1200
gttcgaaggg gcaagacaga gaaggaagat caaatgcaag agcagcaact gttaagtgat    1260
gaaaaacagt gtgccgagca cataatgctt gtggacttgg gaaggaatga tgttggcaag    1320
gtatccaaac caggatcagt gaaggtggag aagttgatga acattgagag atactcccat    1380
gttatgcaca tcagctcaac ggttagtgga cagttggatg atcatctcca gagttgggat    1440
gccttgagag ctgccttgcc cgttggaaca gtcagtggtg caccaaaggt gaaggccatg    1500
gagttgattg ataagttgga agttacgagg cgaggaccat atagtggtgg tctaggagga    1560
atatcgtttg atggtgacat gcaaattgca ctttctctcc gcaccatcgt attctcaaca    1620
gcgccgagcc acaacacgat gtactcatac aaagacgcag ataggcgtcg ggagtgggtc    1680
gctcatcttc aggctggtgc aggcattgtt gccgacagta gcccagatga cgaacaacgt    1740
gaatgcgaga ataaggctgc tgcactagct cgggccatcg atcttgcaga gtcagctttt    1800
gtagacaaag aatag                                                     1815
```

<210> SEQ ID NO 68
<211> LENGTH: 2204
<212> TYPE: DNA
<213> ORGANISM: Artificial Sequence
<220> FEATURE:
<223> OTHER INFORMATION: A Zea mays mutant

<400> SEQUENCE: 68

```
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc tgctgccgtg acgccgcagg cgagcccagt gattagcagg     180
agcgctgcgg cggcgaaggc ggcggaggag gacaagaggc ggttcttcga ggcggcggcg     240
```

-continued

```
cgggggagcg ggaaggggaa cctggtgccc atgtgggagt gcatcgtgtc ggaccatctc      300
acccccgtgc tcgcctaccg ctgcctcgtc cccgaggaca acgtcgacgc ccccagcttc      360
ctcttcgagt ccgtcgagca ggggccccag ggcaccacca acgtcggccg ctatagcatg      420
gtgggagccc acccagtgat ggagattgtg gccaagacc acaaggttac gatcatggac       480
cacgagaaga gccaagtgac agagcaggta gtggacgacc cgatgcagat cccgaggacc      540
atgatggagg gatggcaccc acagcagatc gacgagctcc ctgaatcctt ctccggtgga      600
tgggttgggt tcttttccta tgatacggtt aggtatgttg agaagaagaa gctaccgttc      660
tccagtgctc ctcaggacga taggaacctt cctgatgtgc acttgggact ctatgatgat      720
gttctagtct tcgataatgt tgagaagaaa gtatatgtta tccattgggt caatgtggac      780
cggcatgcat ctgttgagga agcataccaa gatggcaggt cccgactaaa catgttgcta      840
tctaaagtgc acaattccaa tgtccccaca ctctctcctg gatttgtgaa gctgcacaca      900
cgcaagtttg gtacaccttt gaacaagtcg accatgacaa gtgatgagta taagaatgct      960
gttctgcagg ctaaggaaca tattatggct ggggatatct tccagattgt tttaagccag     1020
aggttcgaga cgaacata tgccaaccca tttgaggttt atcgagcatt acggattgtg        1080
aatcctagcc catacaaggc gtatgtacag gcaagaggct gtgtattggt tgcgtctagt     1140
cctgaaattc ttacacgagt cagtaagggg aagattatta atcgaccact tgctggaact     1200
gttcgaaggg gcaagacaga gaaggaagat caaatgcaag agcagcaact gttaagtgat     1260
gaaaaacagt gtgccgagca cataatgctt gtggacttgg gaaggaatga tgttggcaag     1320
gtatccaaac caggatcagt gaaggtggag aagttgatga acattgagag atactcccat     1380
gttatgcaca tcagctcaac ggttagtgga cagttggatg atcatctcca gagttgggat     1440
gccttgagag ctgccttgcc cgttggaaca gtcagtggtg caccaaaggt gaaggccatg     1500
gagttgattg ataagttgga agttacgagg cgaggaccat atagtggtgg tctaggagga     1560
atatcgtttg atggtgacat gcaaattgca ctttctctcc gcaccatcgt attctcaaca     1620
gcgccgagcc acaacacgat gtactcatac aaagacgcag ataggcgtcg ggagtgggtc     1680
gctcatcttc aggctggtgc aggcattgtt gccgacagta gcccagatga cgaacaacgt     1740
gaatgcgaga ataaggctgc tgcactagct cgggccatcg atcttgcaga gtcagctttt     1800
gtagacaaag aatagtgtgc tatggttatc gtttagttct tgttcatgtt tcttttaccc     1860
actttccgtt aaaaaagat gtcattagtg ggtggagaaa agcaataaga ctgttctcta     1920
gaattcgagc tcggtaccgg atccaattcc cgatcgttca aacatttggc aataaagttt     1980
cttaagattg aatcctgttg ccggtcttgc gatgattatc atataatttc tgttgaatta     2040
cgttaagcat gtaataatta acatgtaatg catgacgtta tttatgagat gggtttttat     2100
gattagagtc ccgcaattat acatttaata cgcgatagaa aacaaaatat agcgcgcaaa     2160
ctaggataaa ttatcgcgcg cggtgtcatc tatgttacta gatc                       2204
```

<210> SEQ ID NO 69
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 69

```
Met Val Thr Ile Ile Gln Asp Asp Gly Ala Glu Thr Tyr Glu Thr Lys
1               5                   10                  15
```

-continued

Gly Gly Ile Gln Val Ser Arg Lys Arg Pro Thr Asp Tyr Ala Asn
            20                  25                  30

Ala Ile Asp Asn Tyr Ile Glu Lys Leu Asp Ser His Arg Gly Ala Val
 35                  40                  45

Phe Lys Ser Asn Tyr Glu Tyr Pro Gly Arg Tyr Thr Arg Trp Asp Thr
 50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
                100                 105                 110

Thr Arg Arg Leu Asp Leu Thr Val Asn Glu Pro Asp Arg Val Phe Thr
                115                 120                 125

Glu Glu Glu Arg Ser Lys Ile Pro Thr Val Phe Thr Ala Leu Arg Ala
            130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
                180                 185                 190

Asp Glu Ile Leu Val Val Asp His Tyr Ser Ala Lys Ala Trp Ile Asp
            195                 200                 205

Arg Tyr Asp Phe Glu Lys Asp Gly Met Thr Thr Asp Gly Lys Ser Ser
210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
                260                 265                 270

Phe Met Glu Arg Cys Glu Ser Asn Pro Ser Ala Ile Ser Arg Arg Leu
            275                 280                 285

Lys Ala Ile Asn Pro Ser Pro Tyr Ser Phe Phe Ile Asn Leu Gly Asp
            290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
            355                 360                 365

Asp Lys Ser Arg Val Cys Glu Pro Gly Ser Val Lys Val Ile Gly Arg
            370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

```
Arg Phe Ile Glu Gly His Glu Lys Ser Pro Arg Ala Trp Tyr Gly Gly
            435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
                500                 505                 510

Thr Asn Ser Ala Ala Thr Lys Arg Asp Ala Ala Lys Val Gly Thr Gly
            515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
                580                 585                 590

Ile Lys Ala Ala Arg Ala Arg Asp Leu Pro Ile Phe Gly Val Cys Leu
            595                 600                 605

Gly Leu Gln Ala Leu Ala Glu Ala Tyr Gly Gly Glu Leu Arg Gln Leu
            610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
            675                 680                 685

Glu Pro Val Ala Ala Val Gln Phe His Pro Glu Ser Ile Met Thr Leu
            690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725
```

<210> SEQ ID NO 70
<211> LENGTH: 729
<212> TYPE: PRT
<213> ORGANISM: Artificial Sequence
<220> FEATURE:
<223> OTHER INFORMATION: An A. tumefaciens mutant

<400> SEQUENCE: 70

```
Met Val Thr Ile Ile Gln Asp Asp Gly Ala Glu Thr Tyr Glu Thr Lys
1               5                   10                  15

Gly Gly Ile Gln Val Ser Arg Lys Arg Pro Thr Asp Tyr Ala Asn
            20                  25                  30

Ala Ile Asp Asn Tyr Ile Glu Lys Leu Asp Ser His Arg Gly Ala Val
                35                  40                  45

Phe Ser Ser Asn Tyr Glu Tyr Pro Gly Arg Tyr Thr Arg Trp Asp Thr
            50                  55                  60
```

-continued

```
Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Ala Phe Ile Asn Leu Gly Asp
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Glu Ala Glu Thr
```

```
                    485                 490                 495
Glu Leu Lys Ala Ser Ala Met Ile Ser Ala Ile Arg Asp Ala Lys Gly
                500                 505                 510
Thr Asn Ser Ala Ala Thr Lys Arg Asp Ala Ala Lys Val Gly Thr Gly
            515                 520                 525
Val Lys Ile Leu Leu Val Asp His Glu Asp Ser Phe Val His Thr Leu
        530                 535                 540
Ala Asn Tyr Phe Arg Gln Thr Gly Ala Thr Val Ser Thr Val Arg Ser
545                 550                 555                 560
Pro Val Ala Ala Asp Val Phe Asp Arg Phe Gln Pro Asp Leu Val Val
                565                 570                 575
Leu Ser Pro Gly Pro Gly Ser Pro Thr Asp Phe Asp Cys Lys Ala Thr
                580                 585                 590
Ile Lys Ala Ala Arg Ala Arg Asp Leu Pro Ile Phe Gly Val Cys Leu
            595                 600                 605
Gly Leu Gln Ala Leu Ala Glu Ala Tyr Gly Gly Glu Leu Arg Gln Leu
        610                 615                 620
Ala Val Pro Met His Gly Lys Pro Ser Arg Ile Arg Val Leu Glu Pro
625                 630                 635                 640
Gly Leu Val Phe Ser Gly Leu Gly Lys Glu Val Thr Val Gly Arg Tyr
                645                 650                 655
His Ser Ile Phe Ala Asp Pro Ala Thr Leu Pro Arg Asp Phe Ile Ile
                660                 665                 670
Thr Ala Glu Ser Glu Asp Gly Thr Ile Met Gly Ile Glu His Ala Lys
            675                 680                 685
Glu Pro Val Ala Val Gln Phe His Pro Glu Ser Ile Met Thr Leu
        690                 695                 700
Gly Gln Asp Ala Gly Met Arg Met Ile Glu Asn Val Val His Leu
705                 710                 715                 720
Thr Arg Lys Ala Lys Thr Lys Ala Ala
                725

<210> SEQ ID NO 71
<211> LENGTH: 264
<212> TYPE: DNA
<213> ORGANISM: Artificial Sequence
<220> FEATURE:
<223> OTHER INFORMATION: The sequence of a CTP

<400> SEQUENCE: 71
atggcttcct ctatgctctc ttccgctact atggttgcct ctccggctca ggccactatg      60
gtcgctcctt tcaacggact taagtcctcc gctgccttcc cagccacccg caaggctaac     120
aacgacatta cttccatcac aagcaacggc ggaagagtta actgcatgca ggtgtggcct     180
ccgattggaa agaagaagtt tgagactctc tcttaccttc ctgaccttac cgattccggt     240
ggtcgcgtca actgcatgca ggcc                                            264

<210> SEQ ID NO 72
<211> LENGTH: 88
<212> TYPE: PRT
<213> ORGANISM: Artificial Sequence
<220> FEATURE:
<223> OTHER INFORMATION: The sequence of a CTP

<400> SEQUENCE: 72

Met Ala Ser Ser Met Leu Ser Ser Ala Thr Met Val Ala Ser Pro Ala
1               5                   10                  15
```

```
Gln Ala Thr Met Val Ala Pro Phe Asn Gly Leu Lys Ser Ser Ala Ala
             20                  25                  30

Phe Pro Ala Thr Arg Lys Ala Asn Asn Asp Ile Thr Ser Ile Thr Ser
         35                  40                  45

Asn Gly Gly Arg Val Asn Cys Met Gln Val Trp Pro Pro Ile Gly Lys
     50                  55                  60

Lys Lys Phe Glu Thr Leu Ser Tyr Leu Pro Asp Leu Thr Asp Ser Gly
 65                  70                  75                  80

Gly Arg Val Asn Cys Met Gln Ala
                 85

<210> SEQ ID NO 73
<211> LENGTH: 264
<212> TYPE: DNA
<213> ORGANISM: Artificial Sequence
<220> FEATURE:
<223> OTHER INFORMATION: The sequence of a CTP

<400> SEQUENCE: 73
atggcttcct ctatgctctc ttccgctact atggttgcct ctccggctca ggccactatg      60
gtcgctcctt tcaacggact taagtcctcc gctgccttcc agccacccg caaggctaac      120 aacgacatta cttccatcac aagcaacggc ggaagagtta actgcatgca ggtgtggcct      180
ccgattgaaa agaagaagtt tgagactctc tcttaccttc ctgaccttac cgattccggt      240
ggtcgcgtca actgcatgca ggcc                                             264

<210> SEQ ID NO 74
<211> LENGTH: 88
<212> TYPE: PRT
<213> ORGANISM: Artificial Sequence
<220> FEATURE:
<223> OTHER INFORMATION: The sequence of a CTP

<400> SEQUENCE: 74

Met Ala Ser Ser Met Leu Ser Ser Ala Thr Met Val Ala Ser Pro Ala
  1               5                  10                  15

Gln Ala Thr Met Val Ala Pro Phe Asn Gly Leu Lys Ser Ser Ala Ala
             20                  25                  30

Phe Pro Ala Thr Arg Lys Ala Asn Asn Asp Ile Thr Ser Ile Thr Ser
         35                  40                  45

Asn Gly Gly Arg Val Asn Cys Met Gln Val Trp Pro Pro Ile Glu Lys
     50                  55                  60

Lys Lys Phe Glu Thr Leu Ser Tyr Leu Pro Asp Leu Thr Asp Ser Gly
 65                  70                  75                  80

Gly Arg Val Asn Cys Met Gln Ala
                 85

<210> SEQ ID NO 75
<211> LENGTH: 2190
<212> TYPE: DNA
<213> ORGANISM: Artificial Sequence
<220> FEATURE:
<223> OTHER INFORMATION: An optimized A. tumefaciens

<400> SEQUENCE: 75
atggtgacca tcattcagga tgacggtgcc gagacctacg agaccaaggg cggcatccag      60
gtgagccgca agcgccgccc caccgattac gccaacgcca tcgataacta catcgaaaag     120
cttgattccc atcgcggtgc cgtgttctcc tccaactacg aatacccagg ccgctacacc     180
```

```
cgctgggata ccgccatcgt cgatccacca ctcggcattt cctgcttcgg ccgcaagatg        240
tggatcgaag cctacaacgg ccgcggcgaa gtgctgctcg atttcattac cgaaaagctg        300
aaggccacac ccgatctcac cctcggcgct cctccaccc gccgcctcga tcttaccgtc         360
aacgaaccag accgcgtctt caccgaagaa gaacgctcca aaatcccaac cgtcttcacc        420
gctctcaggg ccatcgtcga cctcttctac tccagcgccg attccgccat cggcctgttc        480
ggtgccttcg gttacgatct cgccttccag ttcgacgcca tcaagctttc cctggcccgc       540
ccagaagacc agcgcgacat ggtgctgttc ctgcccgatg aaatcctcgt cgttgatcac       600
tactccgcca aggcctggat cgaccgctac gatttcgaga aggacggcat gaccaccgac       660
ggcaaatcct ccgacattac ccccgatccc ttcaagacca ccgataccat cccacccaag       720
ggcgatcacc gccccggcga atactccgag cttgtggtga aggccaagga aagcttccgc       780
cgcggcgacc tgttcgaggt cgttcccggc cagaaattca tggagcgctg cgaaagcaac       840
ccatccgcca tttccgccg cctgaaggcc atcaacccat ccccctactc cttcttcatc        900
aacctcggcg atcaggaata cctggtcggc gcctccccag aaatgttcgt gcgcgtctcc      960
ggccgccgca tcgagacctg cccaatctca ggcaccatca agcgcggcga cgatccaatt     1020
gccgacagcg agcagatttt gaaactgctc aactccaaaa aggacgaatc cgaactgacc     1080
atgtgctccg acgtggaccg caacgacaag agccgcgtct gcgagccagg ttccgtgaag     1140
gtcattggcc gccgcagat cgagatgtac tcacgcctca tccacaccgt cgatcacatc       1200
gaaggccgcc tgcgcgacga tatggacgcc ttcgacggtt cctcagcca cgcctgggcc       1260 gtcaccgtca ccggtgcacc aaagctgtgg gccatgcgct tcatcgaagg tcatgaaaag     1320
agcccacgcg cctggtacgg cggtgccatc ggcatggtcg gcttcaacgg cgacatgaac     1380
accggcctga ccctgcgcac catccgcatc aaggacggta ttgccgaagt gcgcgccggc     1440
gccaccctgc tcaacgattc caacccacag gaagaagaag ccgaaaccga actgaaggcc     1500
tccgccatga tctcagccat cgcgacgca aaaggcacca actctgccgc caccaagcgc      1560
gatgccgcca aagtcggcac cggcgtcaag atcctgctcg tcgaccacga agacagcttc     1620
gtgcacaccc tggccaacta cttccgccag accggcgcca ccgtctccac cgtcaggtca     1680
ccagtcgcag ccgacgtgtt cgatcgcttc cagccagacc tcgttgtcct gtccccgggt     1740
cccggcagcc caaccgattt cgactgcaag gcaaccatca aggccgcccg cgcccgcgat     1800
ctgccaatct tcggcgtttg cctcggtctg caggcattgg cagaagccta cggcggcgag     1860
ctgcgccagc ttgctgtgcc catgcacggc aagccttccc gcatccgcgt gctggaaccc      1920
ggcctcgtct tctccggtct cggcaaggaa gtcaccgtcg gtcgctacca ttccatcttc     1980
gccgatcccg ccaccctgcc acgcgatttc atcatcaccg cagaaagcga ggacggcacc     2040
atcatgggca tcaacacgcc caaggaacca gtggccgccg ttcagttcca cccagaatcc     2100
atcatgaccc tcggtcagga cgccggcatg cgcatgatcg agaacgtcgt ggtgcatctg     2160
acccgcaagg ccaagaccaa ggccgcctga                                      2190
```

<210> SEQ ID NO 76
<211> LENGTH: 2160
<212> TYPE: DNA
<213> ORGANISM: Rhodopseudomonas palustris

<400> SEQUENCE: 76

```
atgaacagga ccgtttttctc gcttcccgcg accagcgact ataagaccgc cgcgggcctc        60
```

-continued

```
gcggtgacgc gcagcgccca gccttttgcc ggcggccagg cgctcgacga gctgatcgat    120
ctgctcgacc accgccgcgg cgtgatgctg tcgtccggca caaccgtgcc gggccgctac    180
gagagcttcg acctcggctt tgccgatccg ccgctggcgc tcaccactag gccgaaaaaa    240
ttcaccatcg aggcgctcaa tccgcgcggc cgggtgctga tcgcgttcct gtccgacaag    300
cttgaagagc cctgcgtggt ggtggagcag gcctgcgcca ccaagatcag gggccacatc    360
gtccgcggcg aggccccggt cgacgaagaa caacgcaccc gccgcgccag cgcgatctcc    420
ctggtgcgcg cggtgattgc tgccttcgcc tcgccggccg atccgatgct cgggctgtac    480
ggcgccttcg cctacgacct tgtgttccag ttcgaggatc tgaagcagaa gcgtgccccgc   540
gaagccgacc agcgcgacat cgtgctgtac gtgccggatc gcctgctggc ctacgatcgc    600
gccaccggcc gcggcgtcga catttcctac gaattcgcct ggaagggcca gtccaccgcc    660
ggcctgccga acgagaccgc cgagagcgtc tacacccaga ccggccggca gggtttcgcc    720
gaccacgccc cggcgactac tcccaaggtg gtcgagaagg cccgcgcggc gttcgccccgc   780
ggcgacctgt tcgaggcggt gccgggccag ctgttcggcg agccatgcga gcggtcgccg    840
gccgaagtgt tcaagcggtt gtgccggatc aacccgtcgc cctatggcgg cctgctcaat    900
ctcggcgacg gcgaattcct ggtgtcggcc tcgccggaaa tgttcgtccg ctcggacggc    960
cgccggatcg agacctgccc gatctccggc actatcgccc gcggcgtcga tgcgatcagc   1020
gatgctgagc agatccagaa gctcttgaac tccgagaagg acgagttcga gctgaatatg   1080
tgcaccgacg tcgaccgcaa cgacaaggcg cgggtctgcg tgccgggcac gatcaaagtt   1140
ctcgcgcgcc gccagatcga gacctattcg aagctgttcc acaccgtcga tcacgtcgag   1200
ggcatgctgc gaccgggttt cgacgcgctc gacgccttcc tcacccacgc ctgggcggtc   1260
accgtcaccg gcgcgccgaa gctgtgggcg atgcagttcg tcgaggatca cgagcgtagc   1320
ccgcggcgct ggtatgccgg cgcgttcggc gtggtcggct cgatggctc gatcaacacc    1380
ggcctcacca tccgcaccat ccggatgaag gacggcctcg ccgaagttcg cgtcggcgcc   1440
acctgcctgt cgacagcaa tccggtcgcc gaggacaagg aatgccaggt caaggccgcg    1500
gcactgttcc aggcgctgcg cggcgatccc gccaagccgc tgtcggcggt ggcgccggac    1560
gccactggct cgggcaagaa ggtgctgctg tcgaccacg acgacagctt cgtgcacatg     1620
ctggcggact atttcaggca ggtcggcgcc caggtcaccg tggtgcgcta cgttcacggc    1680
ctgaagatgc tggccgaaaa cagctatgat cttctggtgc tgtcgcccgg tccggccgg    1740
ccggaggact tcaagatcaa ggatacgatc gacgccgcgc tcgccaagaa gctgccgatc    1800
ttcggcgtct gcctcggcgt ccaggcgatg ggcgaatatt ttggcggtac gctcggccag    1860
ctcgcgcagc cggctcacgg ccgcccgtcg cggattcagg tgcgcggcgg cgcgctgatg    1920
cgcggtctcc cgaacgaggt caccatcggc cgctaccact cgctctatgt cgacatgcgc    1980
gacatgccga aggagctgac cgtcaccgcc tccaccgatg acggcatcgc gatggcgatc    2040
gagcacaaga ccctgccggt cggcggcgtg cagttccacc ccgagtcgct gatgtcgctc    2100
ggcggcgagg tcgggctgcg gatcgtcgaa aacgccttcc ggctcggcca ggcggcctaa    2160
```

<210> SEQ ID NO 77
<211> LENGTH: 733
<212> TYPE: PRT
<213> ORGANISM: Mesorhizobium loti

<400> SEQUENCE: 77

Met Glu Thr Ala Met Thr Met Lys Val Leu Glu Asn Gly Ala Glu Ser

-continued

```
1               5                   10                  15
Phe Val Thr Ala Gly Gly Ile Thr Ile Thr Arg Glu Arg His Asp Arg
            20                  25                  30
Pro Tyr Ala Gly Ala Ile Asp Ala Tyr Val Asp Gly Leu Asn Ser Arg
            35                  40                  45
Arg Gly Ala Val Phe Ser Ser Asn Tyr Glu Tyr Pro Gly Arg Tyr Thr
            50                  55                  60
Arg Trp Asp Thr Ala Ile Ile Asp Pro Pro Leu Val Ile Ser Ala Arg
65                          70                  75                  80
Gly Arg Ala Met Arg Ile Glu Ala Leu Asn Arg Arg Gly Glu Ala Leu
                    85                  90                  95
Leu Pro Val Ile Gly Lys Thr Leu Gly Gly Leu Ala Asp Ile Thr Ile
                    100                 105                 110
Ala Glu Thr Thr Lys Thr Leu Ile Arg Leu Asp Val Ala Lys Pro Gly
                    115                 120                 125
Arg Val Phe Thr Glu Glu Arg Ser Arg Val Pro Ser Val Phe Thr
            130                 135                 140
Val Leu Arg Ala Ile Thr Ala Leu Phe Lys Thr Asp Glu Asp Ala Asn
145                         150                 155                 160
Leu Gly Leu Tyr Gly Ala Phe Gly Tyr Asp Leu Ser Phe Gln Phe Asp
                    165                 170                 175
Pro Val Asp Tyr Lys Leu Glu Arg Lys Pro Ser Gln Arg Asp Leu Val
                    180                 185                 190
Leu Phe Leu Pro Asp Glu Ile Leu Val Val Asp His Tyr Ser Ala Lys
                    195                 200                 205
Ala Trp Thr Asp Arg Tyr Asp Tyr Ser Gly Glu Gly Phe Ser Thr Glu
                    210                 215                 220
Gly Leu Pro Arg Asp Ala Ile Ala Glu Pro Phe Lys Thr Ala Asp Arg
225                         230                 235                 240
Ile Pro Pro Arg Gly Asp His Glu Pro Gly Glu Tyr Ala Asn Leu Val
                    245                 250                 255
Arg Arg Ala Met Asp Ser Phe Lys Arg Gly Asp Leu Phe Glu Val Val
                    260                 265                 270
Pro Gly Gln Met Phe Tyr Glu Arg Cys Glu Thr Gln Pro Ser Asp Ile
                    275                 280                 285
Ser Arg Lys Leu Lys Ser Ile Asn Pro Ser Pro Tyr Ser Phe Phe Ile
                    290                 295                 300
Asn Leu Gly Glu Asn Glu Tyr Leu Ile Gly Ala Ser Pro Glu Met Phe
305                         310                 315                 320
Val Arg Val Asn Gly Arg Val Glu Thr Cys Pro Ile Ser Gly Thr
                    325                 330                 335
Ile Lys Arg Gly Asp Ala Ile Ser Asp Ser Glu Gln Ile Leu Lys
                    340                 345                 350
Leu Leu Asn Ser Lys Lys Asp Glu Ser Glu Leu Thr Met Cys Ser Asp
                    355                 360                 365
Val Asp Arg Asn Asp Lys Ser Arg Val Cys Glu Pro Gly Ser Val Arg
                    370                 375                 380
Val Ile Gly Arg Arg Gln Ile Glu Met Tyr Ser Arg Leu Ile His Thr
385                         390                 395                 400
Val Asp His Ile Glu Gly Arg Leu Arg Glu Gly Met Asp Ala Phe Asp
                    405                 410                 415
Ala Phe Leu Ser His Ala Trp Ala Val Thr Val Thr Gly Ala Pro Lys
                    420                 425                 430
```

-continued

Leu Trp Ala Met Arg Phe Ile Glu Gln Asn Glu Lys Ser Pro Arg Ala
                435                 440                 445

Trp Tyr Gly Gly Ala Ile Gly Met Val Asn Phe Asn Gly Asp Met Asn
        450                 455                 460

Thr Gly Leu Thr Leu Arg Thr Ile Arg Ile Lys Asp Gly Ile Ala Glu
465                 470                 475                 480

Val Arg Ala Gly Ala Thr Leu Leu Phe Asp Ser Ile Pro Glu Glu Glu
                485                 490                 495

Glu Ala Glu Thr Glu Leu Lys Ala Ser Ala Met Leu Ser Ala Ile Arg
                500                 505                 510

Asp Ala Lys Thr Gly Asn Ser Ala Ser Thr Glu Arg Thr Thr Ala Arg
                515                 520                 525

Val Gly Asp Gly Val Asn Ile Leu Leu Val Asp His Glu Asp Ser Phe
        530                 535                 540

Val His Thr Leu Ala Asn Tyr Phe Arg Gln Thr Gly Ala Asn Val Ser
545                 550                 555                 560

Thr Val Arg Thr Pro Val Pro Asp Glu Val Phe Glu Arg Leu Lys Pro
                565                 570                 575

Asp Leu Val Val Leu Ser Pro Gly Pro Gly Thr Pro Lys Asp Phe Asp
                580                 585                 590

Cys Ala Ala Thr Ile Arg Arg Ala Arg Ala Arg Asp Leu Pro Ile Phe
                595                 600                 605

Gly Val Cys Leu Gly Leu Gln Ala Leu Ala Glu Ala Tyr Gly Gly Glu
        610                 615                 620

Leu Arg Gln Leu His Ile Pro Met His Gly Lys Pro Ser Arg Ile Arg
625                 630                 635                 640

Val Ser Lys Pro Gly Ile Ile Phe Ser Gly Leu Pro Lys Glu Val Thr
                645                 650                 655

Val Gly Arg Tyr His Ser Ile Phe Ala Asp Pro Val Arg Leu Pro Asp
                660                 665                 670

Asp Phe Ile Val Thr Ala Glu Thr Glu Asp Gly Ile Ile Met Ala Phe
                675                 680                 685

Glu His Arg Lys Glu Pro Ile Ala Ala Val Gln Phe His Pro Glu Ser
        690                 695                 700

Ile Met Thr Leu Gly His Asn Ala Gly Met Arg Ile Ile Glu Asn Ile
705                 710                 715                 720

Val Ala His Leu Pro Arg Lys Ala Lys Glu Lys Ala Ala
                725                 730

<210> SEQ ID NO 78
<211> LENGTH: 732
<212> TYPE: PRT
<213> ORGANISM: Azospirillum brasilense

<400> SEQUENCE: 78

Met Tyr Pro Ala Asp Leu Leu Ala Ser Pro Asp Leu Leu Glu Pro Leu
1               5                   10                  15

Arg Phe Gln Thr Arg Gly Gly Val Thr Val Thr Arg Ala Thr Ala
                20                  25                  30

Leu Asp Pro Arg Thr Ala Leu Asp Pro Val Ile Asp Ala Leu Asp Arg
                35                  40                  45

Arg Arg Gly Leu Leu Leu Ser Ser Gly Val Glu Ala Pro Gly Arg Tyr
        50                  55                  60

Arg Arg His Ala Leu Gly Phe Thr Asp Pro Ala Val Ala Leu Thr Ala

-continued

```
             65                  70                  75                  80
Arg Gly Arg Thr Leu Arg Ile Asp Ala Leu Asn Gly Arg Gly Gln Val
                    85                  90                  95

Leu Leu Pro Ala Val Ala Glu Ala Leu Arg Gly Leu Glu Ala Leu Ala
                100                 105                 110

Gly Leu Glu Glu Ala Pro Ser Arg Val Thr Ala Ser Ser Ala Ser Pro
            115                 120                 125

Ala Pro Leu Pro Gly Glu Arg Ser Arg Gln Pro Ser Val Phe Ser
        130                 135                 140

Val Leu Arg Ala Val Leu Asp Leu Phe Ala Ala Pro Asp Asp Pro Leu
145                 150                 155                 160

Leu Gly Leu Tyr Gly Ala Phe Ala Tyr Asp Leu Ala Phe Gln Phe Glu
                165                 170                 175

Pro Ile Arg Gln Arg Leu Glu Arg Pro Asp Asp Gln Arg Asp Leu Leu
                180                 185                 190

Leu Tyr Leu Pro Asp Arg Leu Val Ala Leu Asp Pro Ile Ala Gly Leu
            195                 200                 205

Ala Arg Leu Val Ala Tyr Glu Phe Ile Thr Ala Ala Gly Ser Thr Glu
        210                 215                 220

Gly Leu Glu Cys Gly Gly Arg Asp His Pro Tyr Arg Pro Asp Thr Asn
225                 230                 235                 240

Ala Glu Ala Gly Cys Asp His Ala Pro Gly Asp Tyr Gln Arg Val Val
                245                 250                 255

Glu Ser Ala Lys Ala Ala Phe Arg Arg Gly Asp Leu Phe Glu Val Val
                260                 265                 270

Pro Gly Gln Thr Phe Ala Glu Pro Cys Ala Asp Ala Pro Ser Ser Val
            275                 280                 285

Phe Arg Arg Leu Arg Ala Ala Asn Pro Ala Pro Tyr Glu Ala Phe Val
        290                 295                 300

Asn Leu Gly Arg Gly Glu Phe Leu Val Ala Ala Ser Pro Glu Met Tyr
305                 310                 315                 320

Val Arg Val Ala Gly Gly Arg Val Glu Thr Cys Pro Ile Ser Gly Thr
                325                 330                 335

Val Ala Arg Gly Ala Asp Ala Leu Gly Asp Ala Ala Gln Val Leu Arg
            340                 345                 350

Leu Leu Thr Ser Ala Lys Asp Ala Ala Glu Leu Thr Met Cys Thr Asp
        355                 360                 365

Val Asp Arg Asn Asp Lys Ala Arg Val Cys Glu Pro Gly Ser Val Arg
        370                 375                 380

Val Ile Gly Arg Arg Met Ile Glu Leu Tyr Ser Arg Leu Ile His Thr
385                 390                 395                 400

Val Asp His Val Glu Gly Arg Leu Arg Ser Gly Met Asp Ala Leu Asp
                405                 410                 415

Ala Phe Leu Thr His Ser Trp Ala Val Thr Val Thr Gly Ala Pro Lys
            420                 425                 430

Arg Trp Ala Met Gln Phe Leu Glu Asp Thr Glu Gln Ser Pro Arg Arg
        435                 440                 445

Trp Tyr Gly Gly Ala Phe Gly Arg Leu Gly Phe Asp Gly Gly Met Asp
        450                 455                 460

Thr Gly Leu Thr Leu Arg Thr Ile Arg Met Ala Glu Gly Val Ala Tyr
465                 470                 475                 480

Val Arg Ala Gly Ala Thr Leu Leu Ser Asp Ser Asp Pro Asp Ala Glu
                485                 490                 495
```

```
Asp Ala Glu Cys Arg Leu Lys Ala Ala Phe Arg Asp Ala Ile Arg
            500                 505                 510

Gly Thr Ala Ala Gly Ala Ala Pro Thr Leu Pro Ala Ala Pro Arg Gly
            515                 520                 525

Gly Glu Gly Arg Arg Val Leu Leu Val Asp His Asp Asp Ser Phe Val
            530                 535                 540

His Thr Leu Ala Asp Tyr Leu Arg Gln Thr Gly Ala Ser Val Thr Thr
545                 550                 555                 560

Leu Arg His Ser His Ala Arg Ala Ala Leu Ala Glu Arg Arg Pro Asp
                565                 570                 575

Leu Val Val Leu Ser Pro Gly Pro Gly Arg Pro Ala Asp Phe Asp Val
            580                 585                 590

Ala Gly Thr Ile Asp Ala Ala Leu Ala Leu Gly Leu Pro Val Phe Gly
            595                 600                 605

Val Cys Leu Gly Leu Gln Gly Met Val Glu Arg Phe Gly Gly Ala Leu
            610                 615                 620

Asp Val Leu Pro Glu Pro Val His Gly Lys Ala Thr Glu Val Arg Val
625                 630                 635                 640

Leu Gly Gly Ala Leu Phe Ala Gly Leu Pro Glu Arg Leu Thr Val Gly
                645                 650                 655

Arg Tyr His Ser Leu Val Ala Arg Arg Asp Arg Leu Pro Ala Asp Leu
                660                 665                 670

Thr Val Thr Ala Glu Thr Ala Asp Gly Leu Val Met Ala Val Glu His
            675                 680                 685

Arg Arg Leu Pro Leu Ala Ala Val Gln Phe His Pro Glu Ser Ile Leu
            690                 695                 700

Ser Leu Asp Gly Gly Ala Gly Leu Ala Leu Leu Gly Asn Val Met Asp
705                 710                 715                 720

Arg Leu Ala Ala Gly Ala Leu Thr Asp Ala Ala Ala
                725                 730

<210> SEQ ID NO 79
<211> LENGTH: 731
<212> TYPE: PRT
<213> ORGANISM: Brucella melitensis

<400> SEQUENCE: 79

Met Asn Ala Lys Thr Ala Asp Ser Glu Ile Phe Gln His Glu Thr Ala
1               5                   10                  15

Gly Gly Ile Ile Val Glu Arg Val Arg His Leu Thr Ala Tyr Lys Gly
            20                  25                  30

Ala Ile Glu Ser Tyr Ile Asp Val Leu Asn Glu Trp Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Val Val Ile Thr Ser Arg Ala Arg Thr Met
65                  70                  75                  80

Arg Ile Glu Ala Leu Asn Ala Arg Gly Val Ile Leu Leu Arg Pro Ile
                85                  90                  95

Leu Asp Thr Val Lys Ala Leu Ser Glu Val Lys Ile Asp Gln Ser Gly
            100                 105                 110

Glu Asn Arg Ile Asp Leu Thr Ile Val Glu Pro Val Gly Thr Phe Thr
        115                 120                 125

Glu Glu Glu Arg Ser Arg Met Pro Ser Val Phe Thr Val Leu Arg Ala
```

-continued

```
            130                 135                 140
Ile Val Gly Leu Phe Phe Ser Glu Glu Asp Ala Asn Leu Gly Leu Tyr
145                 150                 155                 160

Gly Ala Phe Gly Tyr Asp Leu Ala Phe Gln Phe Asp Pro Ile Gln Tyr
                165                 170                 175

Lys Leu Lys Arg Pro Asp Asp Gln Arg Asp Leu Val Leu Phe Ile Pro
                180                 185                 190

Asp Glu Ile Phe Val Ala Asp His Tyr Ala Ala Arg Ala Trp Val Asp
                195                 200                 205

Arg Tyr Glu Phe Arg Cys Gly Ser Ser Thr His Gly Leu Asp Arg
210                 215                 220

Ala Thr Pro Val Val Pro Phe Lys Pro Ser Glu Arg Lys Leu Ala Arg
225                 230                 235                 240

Gly Asp His Asn Pro Gly Glu Tyr Ala Arg Leu Val Glu Arg Ala Lys
                245                 250                 255

Glu Ser Phe Lys Arg Gly Asp Leu Phe Glu Val Val Pro Gly Gln Thr
                260                 265                 270

Phe Tyr Glu Arg Cys His Thr Ala Pro Ser Glu Ile Phe Arg Arg Leu
                275                 280                 285

Lys Ser Ile Asn Pro Ser Pro Tyr Ser Phe Phe Ile Asn Leu Gly Glu
                290                 295                 300

Ser Glu Tyr Leu Val Gly Ala Ser Pro Glu Met Phe Val Arg Val Asn
305                 310                 315                 320

Gly Arg Arg Ile Glu Thr Cys Pro Ile Ser Gly Thr Ile Lys Arg Gly
                325                 330                 335

Glu Asp Ala Ile Ser Asp Ser Glu Gln Ile Leu Lys Leu Leu Asn Ser
                340                 345                 350

Lys Lys Asp Glu Ser Glu Leu Thr Met Cys Ser Asp Val Asp Arg Asn
                355                 360                 365

Asp Lys Ser Arg Val Cys Glu Pro Gly Ser Val Arg Val Ile Gly Arg
                370                 375                 380

Arg Gln Ile Glu Met Tyr Ser Arg Leu Ile His Thr Val Asp His Ile
385                 390                 395                 400

Glu Gly Arg Leu Arg Asp Gly Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Leu Glu Glu Asn Glu Arg Ser Pro Arg Ala Trp Tyr Gly Gly
                435                 440                 445

Ala Ile Gly Met Met His Phe Asn Gly Asp Met Asn Thr Gly Leu Thr
450                 455                 460

Leu Arg Thr Ile Arg Ile Lys Asp Gly Val Ala Glu Ile Arg Ala Gly
465                 470                 475                 480

Ala Thr Leu Leu Phe Asp Ser Asn Pro Asp Glu Glu Ala Glu Thr
                485                 490                 495

Glu Leu Lys Ala Ser Ala Met Ile Ala Ala Val Arg Asp Ala Gln Lys
                500                 505                 510

Ser Asn Gln Ile Ala Glu Glu Ser Val Ala Ala Lys Val Gly Glu Gly
                515                 520                 525

Val Ser Ile Leu Leu Val Asp His Glu Asp Ser Phe Val His Thr Leu
530                 535                 540

Ala Asn Tyr Phe Arg Gln Thr Gly Ala Lys Val Ser Thr Val Arg Ser
545                 550                 555                 560
```

```
Pro Val Ala Glu Glu Ile Phe Asp Arg Val Asn Pro Asp Leu Val Val
            565                 570                 575

Leu Ser Pro Gly Pro Gly Ser Pro Gln Asp Phe Asp Cys Lys Ala Thr
        580                 585                 590

Ile Asp Lys Ala Arg Lys Arg Gln Leu Pro Ile Phe Gly Val Cys Leu
        595                 600                 605

Gly Leu Gln Ala Leu Ala Glu Ala Tyr Gly Gly Ala Leu Arg Gln Leu
        610                 615                 620

Arg Val Pro Val His Gly Lys Pro Ser Arg Ile Arg Val Ser Lys Pro
625                 630                 635                 640

Glu Arg Ile Phe Ser Gly Leu Pro Glu Glu Val Thr Val Gly Arg Tyr
            645                 650                 655

His Ser Ile Phe Ala Asp Pro Glu Arg Leu Pro Asp Asp Phe Leu Val
            660                 665                 670

Thr Ala Glu Thr Glu Asp Gly Ile Ile Met Ala Phe Glu His Lys His
        675                 680                 685

Glu Pro Val Ala Ala Val Gln Phe His Pro Glu Ser Ile Met Thr Leu
690                 695                 700

Gly His Asn Ala Gly Met Arg Met Ile Glu Asn Ile Val Thr His Leu
705                 710                 715                 720

Ala Gly Lys His Lys Ala Arg Arg Thr Asn Tyr
            725                 730

<210> SEQ ID NO 80
<211> LENGTH: 735
<212> TYPE: PRT
<213> ORGANISM: Nostoc sp.

<400> SEQUENCE: 80

Met Ile Ala Asp Ser His Ser Tyr Arg Thr Asn Gly Asn Val Arg Val
1               5                   10                  15

Ser Arg Ser Ile Thr Gln Val Lys Met Glu Thr Ala Leu Glu Glu Ile
            20                  25                  30

Leu Phe Tyr Leu Asn Ser Gln Arg Gly Gly Leu Leu Thr Ser Ser Tyr
        35                  40                  45

Glu Tyr Pro Gly Arg Tyr Lys Arg Trp Ala Ile Gly Phe Val Asn Pro
    50                  55                  60

Pro Val Glu Leu Ser Thr Ser Gly Asn Thr Phe Thr Leu Thr Ala Leu
65                  70                  75                  80

Asn Glu Arg Gly Tyr Val Leu Leu Pro Val Ile Phe Glu Cys Leu Ser
            85                  90                  95

Lys Ser Glu Gln Leu Gln Lys Leu Thr Glu His His Lys Ile Thr
            100                 105                 110

Gly Leu Val Lys Ser Thr Pro Glu Phe Phe Ala Glu Glu Arg Ser
        115                 120                 125

Lys Gln Pro Ser Thr Phe Thr Val Ile Arg Glu Ile Leu His Ile Phe
    130                 135                 140

Ser Ser Gln Glu Asp Glu His Leu Gly Leu Tyr Gly Ala Phe Gly Tyr
145                 150                 155                 160

Asp Leu Val Phe Gln Phe Glu Gln Ile Thr Gln Cys Leu Glu Arg Pro
                165                 170                 175

Gln Asp Gln Arg Asp Leu Val Leu Tyr Leu Pro Asp Glu Leu Ile Val
            180                 185                 190

Val Asp Tyr Tyr Gln Gln Gln Ala Phe Arg Leu Glu Tyr Asp Phe Ile
```

```
                195                 200                 205
Thr Ala His Gly Ser Thr Tyr Asp Leu Pro Arg Thr Gly Glu Ser Val
    210                 215                 220

Asp Tyr Arg Gly Gln Cys Leu Thr Pro Pro Gln Asn Ala Asp His Lys
225                 230                 235                 240

Ile Gly Glu Tyr Ala Lys Leu Val Glu Phe Ala Leu Asp Tyr Phe Arg
                245                 250                 255

Arg Gly Asp Leu Phe Glu Val Val Pro Ser Gln Asn Phe Phe Thr Ala
                260                 265                 270

Cys Glu Ala Pro Pro Ser Gln Leu Phe Glu Thr Leu Lys Gln Ile Asn
                275                 280                 285

Pro Ser Pro Tyr Gly Phe Ile Phe Asn Leu Gly Gly Glu Tyr Ile Ile
                290                 295                 300

Gly Ala Ser Pro Glu Met Phe Val Arg Val Glu Gly Arg Val Glu
305                 310                 315                 320

Thr Cys Pro Ile Ser Gly Thr Ile Thr Arg Gly His Asp Ala Ile Asp
                325                 330                 335

Asp Ala Val Gln Ile Arg Gln Leu Leu Asn Ser His Lys Asp Glu Ala
                340                 345                 350

Glu Leu Thr Met Cys Thr Asp Val Asp Arg Asn Asp Lys Ser Arg Ile
                355                 360                 365

Cys Glu Pro Gly Ser Val Lys Val Ile Gly Arg Arg Gln Ile Glu Leu
                370                 375                 380

Tyr Ser His Leu Ile His Thr Val Asp His Val Glu Gly Ile Leu Arg
385                 390                 395                 400

Pro Glu Phe Asp Ala Leu Asp Ala Phe Leu Ser His Thr Trp Ala Val
                405                 410                 415

Thr Val Thr Gly Ala Pro Lys Arg Ala Ala Ile Gln Phe Ile Glu Lys
                420                 425                 430

Asn Glu Arg Ser Val Arg Arg Trp Tyr Gly Gly Ala Val Gly Tyr Leu
                435                 440                 445

Asn Phe Asn Gly Asn Leu Asn Thr Gly Leu Ile Leu Arg Thr Ile Arg
450                 455                 460

Leu Gln Asp Ser Ile Ala Glu Val Arg Val Gly Ala Thr Leu Leu Tyr
465                 470                 475                 480

Asp Ser Ile Pro Gln Ala Glu Gln Glu Thr Ile Thr Lys Ala Ala
                485                 490                 495

Ala Ala Phe Glu Thr Ile Arg Arg Ala Lys Gln Ile Asp Pro Gln Ile
                500                 505                 510

Glu Glu Ser Ser Thr Arg Lys Leu Ser Lys Tyr Leu Pro Asp Gly Gln
                515                 520                 525

Ser Gly Lys His Ile Leu Leu Ile Asp His Glu Asp Ser Phe Val His
                530                 535                 540

Thr Leu Ala Asn Tyr Ile Arg Ser Thr Gly Ala Thr Val Thr Thr Leu
545                 550                 555                 560

Arg His Gly Phe Ser Glu Ser Leu Phe Asp Thr Glu Arg Pro Asp Leu
                565                 570                 575

Val Val Leu Ser Pro Gly Pro Gly Arg Pro Ser Glu Phe Lys Val Gln
                580                 585                 590

Glu Thr Val Ala Ala Cys Val Arg Arg Gln Ile Pro Leu Phe Gly Val
                595                 600                 605

Cys Leu Gly Leu Gln Gly Ile Val Glu Ala Phe Gly Gly Glu Leu Gly
                610                 615                 620
```

```
Val Leu Asn Tyr Pro Gln His Gly Lys Ser Ser Arg Ile Phe Val Thr
625                 630                 635                 640

Ala Pro Asp Ser Val Met Phe Gln Asp Leu Pro Glu Ser Phe Thr Val
            645                 650                 655

Gly Arg Tyr His Ser Leu Phe Ala Leu Ser Gln Arg Leu Pro Lys Glu
        660                 665                 670

Leu Lys Val Thr Ala Ile Ser Asp Asp Glu Val Ile Met Ala Ile Glu
            675                 680                 685

His Gln Thr Leu Pro Ile Ala Ala Val Gln Phe His Pro Glu Ser Ile
        690                 695                 700

Met Thr Leu Ala Gly Glu Val Gly Leu Met Met Ile Lys Asn Val Val
705                 710                 715                 720

Gln Lys Tyr Thr Gln Ser Gln Gln Ser Thr Val Pro Ile Tyr Asp
            725                 730                 735

<210> SEQ ID NO 81
<211> LENGTH: 715
<212> TYPE: PRT
<213> ORGANISM: Nostoc sp.

<400> SEQUENCE: 81

Met Arg Val Ser Arg Ser Thr Thr Glu Val Lys Met Asp Thr Ala Leu
1               5                   10                  15

Asp Glu Ile Leu Phe His Leu Asn Gln Val Arg Gly Gly Leu Leu Thr
            20                  25                  30

Ser Ser Tyr Glu Tyr Pro Gly Arg Tyr Lys Arg Trp Ala Ile Gly Phe
        35                  40                  45

Ile Asn Pro Pro Leu Gln Leu Thr Thr Arg Glu Asn Ala Phe Thr Ile
    50                  55                  60

Ser Ser Leu Asn Pro Arg Gly Gln Val Leu Leu Pro Thr Leu Phe Gln
65                  70                  75                  80

His Leu Ser Ala Gln Ser Gly Leu Gln Gln Ile Ser Leu Asn His Asp
                85                  90                  95

Tyr Ile Thr Gly Glu Ile Arg Pro Thr Lys Gln Leu Phe Thr Glu Glu
            100                 105                 110

Gln Arg Ser Lys Gln Pro Ser Ala Phe Thr Val Ile Arg Glu Ile Leu
        115                 120                 125

Gln Ile Phe Ala Ser Asp Glu Asp Glu His Leu Gly Leu Tyr Gly Ala
    130                 135                 140

Phe Gly Tyr Asp Leu Val Phe Gln Phe Glu Pro Ile Pro Gln Lys Ile
145                 150                 155                 160

Ala Arg Pro Ala Asp Gln Arg Asp Leu Val Leu Tyr Leu Pro Asp Glu
                165                 170                 175

Leu Ile Val Val Asp Tyr Tyr Leu Gln Lys Ala Tyr Arg His Gln Tyr
            180                 185                 190

Glu Phe Ala Thr Glu His Gly Asn Thr Glu His Leu Pro Arg Thr Gly
        195                 200                 205

Gln Ser Ile Asp Tyr Gln Gly Lys His Leu Leu Pro Asn Gln Thr Ala
    210                 215                 220

Asp His Gln Pro Gly Glu Tyr Ala Asn Leu Val Glu Gln Ala Leu Asp
225                 230                 235                 240

Tyr Phe Arg Arg Gly Asp Leu Phe Glu Val Val Pro Ser Gln Asn Phe
                245                 250                 255

Phe Thr Ala Cys Glu Gln Ser Pro Ser Gln Leu Phe Gln Thr Leu Arg
```

-continued

```
               260                 265                 270
Gln Ile Asn Pro Ser Pro Tyr Gly Phe Leu Leu Asn Leu Gly Gly Glu
            275                 280                 285
Tyr Leu Ile Gly Ala Ser Pro Glu Met Phe Val Arg Val Asp Gly Arg
        290                 295                 300
Arg Val Glu Thr Cys Pro Ile Ser Gly Thr Ile Arg Arg Gly Glu Asp
305                 310                 315                 320
Ala Leu Gly Asp Ala Val Gln Ile Arg Gln Leu Leu Asn Ser His Lys
                325                 330                 335
Asp Glu Ala Glu Leu Thr Met Cys Thr Asp Val Asp Arg Asn Asp Lys
            340                 345                 350
Ser Arg Ile Cys Glu Pro Gly Ser Val Arg Val Ile Gly Arg Arg Gln
        355                 360                 365
Ile Glu Leu Tyr Ser His Leu Ile His Thr Val Asp His Val Glu Gly
        370                 375                 380
Ile Leu Arg Pro Glu Phe Asp Ala Leu Asp Ala Phe Leu Ser His Thr
385                 390                 395                 400
Trp Ala Val Thr Val Thr Gly Ala Pro Lys Arg Ala Ala Met Gln Phe
                405                 410                 415
Ile Glu Gln His Glu Arg Ser Ala Arg Arg Trp Tyr Gly Gly Ala Val
            420                 425                 430
Gly Tyr Leu Gly Phe Asn Gly Asn Leu Asn Thr Gly Leu Thr Leu Arg
        435                 440                 445
Thr Ile Arg Leu Gln Asp Ser Ile Ala Glu Val Arg Val Gly Ala Thr
        450                 455                 460
Val Leu Tyr Asp Ser Ile Pro Ser Ala Glu Glu Glu Thr Ile Thr
465                 470                 475                 480
Lys Ala Thr Ala Leu Phe Glu Thr Ile Arg Arg His Thr Thr Ala Asn
                485                 490                 495
Lys Thr Gln Gly Asn Asp Ser His Arg Pro Gly Asp Ile Ala His Asn
            500                 505                 510
Lys Arg Ile Leu Leu Ile Asp Tyr Glu Asp Ser Phe Val His Thr Leu
        515                 520                 525
Ala Asn Tyr Ile Arg Thr Thr Gly Ala Thr Val Thr Thr Leu Arg His
        530                 535                 540
Gly Phe Ala Glu Ser Tyr Phe Asp Ala Glu Arg Pro Asp Leu Val Val
545                 550                 555                 560
Leu Ser Pro Gly Pro Gly Arg Pro Ser Asp Phe Arg Val Pro Gln Thr
                565                 570                 575
Val Ala Ala Leu Val Gly Arg Glu Ile Pro Ile Phe Gly Val Cys Leu
            580                 585                 590
Gly Leu Gln Gly Ile Val Glu Ala Phe Gly Gly Glu Leu Gly Val Leu
        595                 600                 605
Asp Tyr Pro Gln His Gly Lys Pro Ala Arg Ile Ser Val Thr Ala Pro
        610                 615                 620
Asp Ser Val Leu Phe Gln Asn Leu Pro Ala Ser Phe Ile Val Gly Arg
625                 630                 635                 640
Tyr His Ser Leu Phe Ala Gln Pro Gln Thr Ile Pro Gly Glu Leu Lys
                645                 650                 655
Val Thr Ala Ile Ser Glu Asp Asn Val Ile Met Ala Ile Glu His Gln
            660                 665                 670
Thr Leu Pro Ile Ala Ala Val Gln Phe His Pro Glu Ser Ile Met Thr
        675                 680                 685
```

```
Leu Ala Gly Glu Val Gly Gln Thr Ile Ile Lys Asn Val Val Gln Thr
    690             695                 700
Tyr Thr Gln Thr Leu Glu Thr Ser Ile Tyr Ser
705             710                 715

<210> SEQ ID NO 82
<211> LENGTH: 719
<212> TYPE: PRT
<213> ORGANISM: Rhodopseudomonas palustris

<400> SEQUENCE: 82

Met Asn Arg Thr Val Phe Ser Leu Pro Ala Thr Ser Asp Tyr Lys Thr
1               5                   10                  15
Ala Ala Gly Leu Ala Val Thr Arg Ser Ala Gln Pro Phe Ala Gly Gly
            20                  25                  30
Gln Ala Leu Asp Glu Leu Ile Asp Leu Leu Asp His Arg Arg Gly Val
        35                  40                  45
Met Leu Ser Ser Gly Thr Thr Val Pro Gly Arg Tyr Glu Ser Phe Asp
    50                  55                  60
Leu Gly Phe Ala Asp Pro Pro Leu Ala Leu Thr Thr Arg Ala Glu Lys
65                  70                  75                  80
Phe Thr Ile Glu Ala Leu Asn Pro Arg Gly Arg Val Leu Ile Ala Phe
                85                  90                  95
Leu Ser Asp Lys Leu Glu Glu Pro Cys Val Val Glu Gln Ala Cys
            100                 105                 110
Ala Thr Lys Ile Arg Gly His Ile Val Arg Gly Glu Ala Pro Val Asp
        115                 120                 125
Glu Glu Gln Arg Thr Arg Arg Ala Ser Ala Ile Ser Leu Val Arg Ala
    130                 135                 140
Val Ile Ala Ala Phe Ala Ser Pro Ala Asp Pro Met Leu Gly Leu Tyr
145                 150                 155                 160
Gly Ala Phe Ala Tyr Asp Leu Val Phe Gln Phe Glu Asp Leu Lys Gln
                165                 170                 175
Lys Arg Ala Arg Glu Ala Asp Gln Arg Asp Ile Val Leu Tyr Val Pro
            180                 185                 190
Asp Arg Leu Leu Ala Tyr Asp Arg Ala Thr Gly Arg Gly Val Asp Ile
        195                 200                 205
Ser Tyr Glu Phe Ala Trp Lys Gly Gln Ser Thr Ala Gly Leu Pro Asn
    210                 215                 220
Glu Thr Ala Glu Ser Val Tyr Thr Gln Thr Gly Arg Gln Gly Phe Ala
225                 230                 235                 240
Asp His Ala Pro Gly Asp Tyr Pro Lys Val Val Glu Lys Ala Arg Ala
                245                 250                 255
Ala Phe Ala Arg Gly Asp Leu Phe Glu Ala Val Pro Gly Gln Leu Phe
            260                 265                 270
Gly Glu Pro Cys Glu Arg Ser Pro Ala Glu Val Phe Lys Arg Leu Cys
        275                 280                 285
Arg Ile Asn Pro Ser Pro Tyr Gly Gly Leu Leu Asn Leu Gly Asp Gly
    290                 295                 300
Glu Phe Leu Val Ser Ala Ser Pro Glu Met Phe Val Arg Ser Asp Gly
305                 310                 315                 320
Arg Arg Ile Glu Thr Cys Pro Ile Ser Gly Thr Ile Ala Arg Gly Val
                325                 330                 335
Asp Ala Ile Ser Asp Ala Glu Gln Ile Gln Lys Leu Leu Asn Ser Glu
```

-continued

```
            340                 345                 350
Lys Asp Glu Phe Glu Leu Asn Met Cys Thr Asp Val Asp Arg Asn Asp
        355                 360                 365
Lys Ala Arg Val Cys Val Pro Gly Thr Ile Lys Val Leu Ala Arg Arg
    370                 375                 380
Gln Ile Glu Thr Tyr Ser Lys Leu Phe His Thr Val Asp His Val Glu
385                 390                 395                 400
Gly Met Leu Arg Pro Gly Phe Asp Ala Leu Asp Ala Phe Leu Thr His
                405                 410                 415
Ala Trp Ala Val Thr Val Thr Gly Ala Pro Lys Leu Trp Ala Met Gln
            420                 425                 430
Phe Val Glu Asp His Glu Arg Ser Pro Arg Arg Trp Tyr Ala Gly Ala
        435                 440                 445
Phe Gly Val Val Gly Phe Asp Gly Ser Ile Asn Thr Gly Leu Thr Ile
    450                 455                 460
Arg Thr Ile Arg Met Lys Asp Gly Leu Ala Glu Val Arg Val Gly Ala
465                 470                 475                 480
Thr Cys Leu Phe Asp Ser Asn Pro Val Ala Glu Asp Lys Glu Cys Gln
                485                 490                 495
Val Lys Ala Ala Ala Leu Phe Gln Ala Leu Arg Gly Asp Pro Ala Lys
            500                 505                 510
Pro Leu Ser Ala Val Ala Pro Asp Ala Thr Gly Ser Gly Lys Lys Val
        515                 520                 525
Leu Leu Val Asp His Asp Asp Ser Phe Val His Met Leu Ala Asp Tyr
    530                 535                 540
Phe Arg Gln Val Gly Ala Gln Val Thr Val Val Arg Tyr Val His Gly
545                 550                 555                 560
Leu Lys Met Leu Ala Glu Asn Ser Tyr Asp Leu Leu Val Leu Ser Pro
                565                 570                 575
Gly Pro Gly Arg Pro Glu Asp Phe Lys Ile Lys Asp Thr Ile Asp Ala
            580                 585                 590
Ala Leu Ala Lys Lys Leu Pro Ile Phe Gly Val Cys Leu Gly Val Gln
        595                 600                 605
Ala Met Gly Glu Tyr Phe Gly Gly Thr Leu Gly Gln Leu Ala Gln Pro
    610                 615                 620
Ala His Gly Arg Pro Ser Arg Ile Gln Val Arg Gly Gly Ala Leu Met
625                 630                 635                 640
Arg Gly Leu Pro Asn Glu Val Thr Ile Gly Arg Tyr His Ser Leu Tyr
                645                 650                 655
Val Asp Met Arg Asp Met Pro Lys Glu Leu Thr Val Thr Ala Ser Thr
            660                 665                 670
Asp Asp Gly Ile Ala Met Ala Ile Glu His Lys Thr Leu Pro Val Gly
        675                 680                 685
Gly Val Gln Phe His Pro Glu Ser Leu Met Ser Leu Gly Gly Glu Val
    690                 695                 700
Gly Leu Arg Ile Val Glu Asn Ala Phe Arg Leu Gly Gln Ala Ala
705                 710                 715
```

<210> SEQ ID NO 83
<211> LENGTH: 2160
<212> TYPE: DNA
<213> ORGANISM: Rhodopseudomonas palustris

<400> SEQUENCE: 83

-continued

```
atgaacagga ccgttttctc gcttcccgcg accagcgact ataagaccgc cgcgggcctc    60
gcggtgacgc gcagcgccca gccttttgcc ggcggccagg cgctcgacga gctgatcgat   120
ctgctcgacc accgccgcgg cgtgatgctg tcgtccggca caaccgtgcc gggccgctac   180
gagagcttcg acctcggctt tgccgatccg ccgctggcgc tcaccactag gccgaaaaa   240
ttcaccatcg aggcgctcaa tccgcgcggc cgggtgctga tcgcgttcct gtccgacaag   300
cttgaagagc cctgcgtggt ggtggagcag gcctgcgcca ccaagatcag gggccacatc   360
gtccgcggcg aggccccggt cgacgaagaa caacgcaccc gccgcgccag cgcgatctcc   420
ctggtgcgcg cggtgattgc tgccttcgcc tcgccggccg atccgatgct cgggctgtac   480
ggcgccttcg cctacgacct tgtgttccag ttcgaggatc tgaagcagaa gcgtgcccgc   540
gaagccgacc agcgcgacat cgtgctgtac gtgccggatc gcctgctggc ctacgatcgc   600
gccaccggcc gcggcgtcga catttcctac gaattcgcct ggaagggcca gtccaccgcc   660
ggcctgccga acgagaccgc cgagagcgtc tacacccaga ccggccggca gggtttcgcc   720
gaccacgccc cgggcgacta tcccaaggtg gtcgagaagg cccgcgcggc gttcgcccgc   780
ggcgacctgt tcgaggcggt gccggggccag ctgttcggcg agccatgcga gcggtcgccg   840
gccgaagtgt tcaagcggtt gtgccggatc aacccgtcgc cctatggcgg cctgctcaat   900
ctcggcgacg gcgaattcct ggtgtcggcc tcgccggaaa tgttcgtccg ctcggacggc   960
cgccggatcg agacctgccc gatctccggc actatcgccc gcggcgtcga tgcgatcagc  1020
gatgctgagc agatccagaa gctcttgaac tccgagaagg acgagttcga gctgaatatg  1080
tgcaccgacg tcgaccgcaa cgacaaggcg cgggtctgcg tgccgggcac gatcaaagtt  1140
ctcgcgcgcc gccagatcga gacctattcg aagctgttcc acaccgtcga tcacgtcgag  1200
ggcatgctgc gaccgggttt cgacgcgctc gacgccttcc tcacccacgc ctgggcggtc  1260
accgtcaccg gcgcgccgaa gctgtgggcg atgcagttcg tcgaggatca cgagcgtagc  1320
ccgcggcgct ggtatgccgg cgcgttcggc gtggtcggct tcgatggctc gatcaacacc  1380
ggcctcacca tccgcaccat ccggatgaag gacggcctcg ccgaagttcg cgtcggcgcc  1440
acctgcctgt tcgacagcaa tccggtcgcc gaggacaagg aatgccaggt caaggccgcg  1500
gcactgttcc aggcgctgcg cggcgatccc gccaagccgc tgtcggcggt ggcgccggac  1560
gccactggct cgggcaagaa ggtgctgctg gtcgaccacg acgacagctt cgtgcacatg  1620
ctggcggact atttcaggca ggtcggcgcc caggtcaccg tggtgcgcta cgttcacggc  1680
ctgaagatgc tggccgaaaa cagctatgat cttctggtgc tgtcgcccgg tcccggccgg  1740
ccggaggact tcaagatcaa ggatacgatc gacgccgcgc tcgccaagaa gctgccgatc  1800
ttcggcgtct gcctcggcgt ccaggcgatg gcgaatatt ttggcggtac gctcggccag  1860
ctcgcgcagc cggctcacgg ccgcccgtcg cggattcagg tgcgcggcgg cgcgctgatg  1920
cgcggtctcc cgaacgaggt caccatcggc cgctaccact cgctctatgt cgacatgcgc  1980
gacatgccga aggagctgac cgtcaccgcc tccaccgatg acggcatcgc gatggcgatc  2040
gagcacaaga ccctgccggt cggcggcctg cagttccacc ccgagtcgct gatgtcgctc  2100
ggcggcgagg tcgggctgcg gatcgtcgaa aacgccttcc ggctcggcca ggcggcctaa  2160
```

<210> SEQ ID NO 84
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 84

```
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc gttttttttcg tccaactatg aatatccggg ccgttacacc    180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctggcgcgt    540
ccggaagacc agcgtgacat ggtgctgttt ctgcccgatg aaatcctcgt cgttgatcac    600
tattccgcca aggcctggat cgaccgttac gatttcgaga aggacggcat gacgacggac    660
ggcaaatcct ccgacattac ccccgatccc ttcaagacca ccgataccat cccgcccaag    720
ggcgatcacc gtcccggcga atattccgag cttgtggtga aggccaagga aagcttccgc    780
cgcggcgacc tgttcgaggt cgttcccggc cagaaattca tggagcgttg cgaaagcaat    840
ccgtcggcga tttccgccg cctgaaggcg atcaacccgt cgccctattc cttcttcatc     900
aatctcggcg atcaggaata tctggtcggc gcctcgccgg aaatgttcgt gcgcgtctcc    960
ggccgtcgca tcgagacctg cccgatatca ggcaccatca agcgcggcga cgatccgatt   1020
gccgacagcg agcagatttt gaaactgctc aactcgaaaa aggacgaatc cgaactgacc   1080
atgtgctcga acgtggaccg caacgacaag agccgcgtct gcgagccggg ttcggtgaag   1140
gtcattggcc gccgccagat cgagatgtat tcacgcctca tccacaccgt cgatcacatc   1200
gaaggccgc tgcgcgacga tatggacgcc tttgacggtt tcctcagcca cgcctgggcc    1260
gtcaccgtca ccggtgcacc aaagctgtgg gccatgcgct tcatcgaagg tcatgaaaag   1320
agcccgcgcg cctggtatgg cggtgcgatc ggcatggtcg gcttcaacgg cgacatgaat   1380
accggcctga cgctgcgcac catccggatc aaggacggta ttgccgaagt gcgcgccggc   1440
gcgaccctgc tcaatgattc caacccgcag gaagaagaag ccgaaaccga actgaaggcc   1500
tccgccatga tatcagccat cgtgacgca aaaggcacca actctgccgc caccaagcgt    1560
gatgccgcca agtcggcac cggcgtcaag atcctgctcg tcgaccacga agacagcttc   1620
gtgcacacgc tggcgaatta tttccgccag acgggcgcga cggtctcgac cgtcagatca   1680
ccggtcgcag ccgacgtgtt cgatcgcttc cagccggacc tcgttgtcct gtcgcccgga   1740
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
ctgcgccagc ttgctgtgcc catgcacggc aagccttcgc gcatccgcgt gctggaaccc   1920
ggcctcgtct tctccggtct cggcaaggaa gtcacggtcg tcgttaccaa ttcgatcttc   1980
gccgatcccg ccacccttgcc gcgtgatttc atcatcaccg cagaaagcga ggacggcacg   2040
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                      2190
```

<210> SEQ ID NO 85

```
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 85
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc gtattttcg tccaactatg aatatccggg ccgttacacc      180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctggcgcgt     540
ccggaagacc agcgtgacat ggtgctgttt ctgcccgatg aaatcctcgt cgttgatcac     600
tattccgcca aggcctggat cgaccgttac gatttcgaga aggacggcat gacgacggac     660
ggcaaatcct ccgacattac ccccgatccc ttcaagacca ccgataccat cccgcccaag     720
ggcgatcacc gtcccggcga atattccgag cttgtggtga aggccaagga aagcttccgc     780
cgcggcgacc tgttcgaggt cgttcccggc cagaaattca tggagcgttg cgaaagcaat     840
ccgtcggcga tttccgccg cctgaaggcg atcaacccgt cgccctattc cttcttcatc     900
aatctcggcg atcaggaata tctggtcggc gcctcgccgg aaatgttcgt gcgcgtctcc     960
ggccgtcgca tcgagacctg cccgatatca ggcaccatca agcgcggcga cgatccgatt    1020
gccgacagcg agcagatttt gaaactgctc aactcgaaaa aggacgaatc cgaactgacc    1080
atgtgctcgg acgtggaccg caacgacaag agccgcgtct gcgagccggg ttcggtgaag    1140
gtcattggcc gccgcagat cgagatgtat tcacgcctca tccacaccgt cgatcacatc    1200
gaaggccgcc tgcgcgacga tatggacgcc tttgacggtt cctcagcca cgcctgggcc     1260 gtcaccgtca ccggtgcacc aaagctgtgg gccatgcgct tcatcgaagg tcatgaaaag    1320
agcccgcgcg cctggtatgg cggtgcgatc ggcatggtcg gcttcaacgg cgacatgaat    1380
accggcctga cgctgcgcac catccggatc aaggacggta ttgccgaagt gcgcgccggc    1440
gcgaccctgc tcaatgattc caacccgcag gaagaagaag ccgaaaccga actgaaggcc    1500
tccgccatga tatcagccat tcgtgacgca aaaggcacca actctgccgc caccaagcgt    1560
gatgccgcca agtcggcac cggcgtcaag atcctgctcg tcgaccacga agacagcttc    1620
gtgcacacgc tggcgaatta tttccgccag acgggcgcga cggtctcgac cgtcagatca    1680
ccggtcgcag ccgacgtgtt cgatcgcttc cagccggacc tcgttgtcct gtcgcccgga    1740
cccggcagcc cgacggattt cgactgcaag gcaacgatca aggccgcccg cgcccgcgat    1800
ctgccgatct tcggcgtttg cctcggtctg caggcattgg cagaagccta tggcggcgag    1860
ctgcgccagc ttgctgtgcc catgcacggc aagccttcgc gcatccgcgt gctggaaccc    1920
ggcctcgtct tctccggtct cggcaaggaa gtcacggtcg tcgttaccat tcgatcttc     1980 gccgatcccg ccaccctgcc gcgtgatttc atcatcaccg cagaaagcga ggacggcacg    2040
atcatgggca tcgaacacgc caaggaaccg gtggccgccg ttcagttcca cccgaatcg    2100 atcatgacgc tcggacagga cgcgggcatg cggatgatcg agaatgtcgt ggtgcatctg    2160
```

```
acccgcaagg cgaagaccaa ggccgcgtga                                       2190

<210> SEQ ID NO 86
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 86
atggtaacga tcattcagga tgacggagcg gagacctacg agacgaaagg cggcatccag         60
gtcagccgaa agcgccggcc caccgattat gccaacgcca tcgataatta catcgaaaag        120
cttgattccc atcgcggcgc ggttttttcg ttcaactatg aatatccggg ccgttacacc        180
cgctgggata cggccatcgt cgatccgccg ctcggcattt cctgttttgg ccgcaagatg        240
tggatcgaag cctataatgg ccgcggcgaa gtgctgctcg atttcattac ggaaaagctg        300
aaggcgacac ccgatctcac cctcggcgct tcctcgaccc gccggctcga tcttaccgtc        360
aacgaaccgg accgtgtctt caccgaagaa gaacgctcga aaatcccgac ggtcttcacc        420
gctctcagag ccatcgtcga cctcttctat tcgagcgcgg attcggccat cggcctgttc        480
ggtgccttcg gttacgatct cgccttccag ttcgacgcga tcaagctttc gctggcgcgt        540
ccggaagacc agcgtgacat ggtgctgttt ctgcccgatg aaatcctcgt cgttgatcac        600
tattccgcca aggcctggat cgaccgttac gatttcgaga aggacggcat gacgacggac        660
ggcaaatcct ccgacattac ccccgatccc ttcaagacca ccgataccat cccgcccaag        720
ggcgatcacc gtcccggcga atattccgag cttgtggtga aggccaagga aagcttccgc        780
cgcggcgacc tgttcgaggt cgttcccggc cagaaattca tggagcgttg cgaaagcaat        840
ccgtcggcga tttccgccg cctgaaggcg atcaacccgt cgccctattc cttcttcatc        900
aatctcggcg atcaggaata tctggtcggc gcctcgccgg aaatgttcgt gcgcgtctcc        960
ggccgtcgca tcgagacctg cccgatatca ggcaccatca agcgcggcga cgatccgatt       1020
gccgacagcg agcagatttt gaaactgctc aactcgaaaa aggacgaatc cgaactgacc       1080
atgtgctcgg acgtggaccg caacgacaag agccgcgtct gcgagccggg ttcggtgaag       1140
gtcattggcc gccgccagat cgagatgtat tcacgcctca tccacaccgt cgatcacatc       1200
gaaggccgcc tgcgcgacga tatggacgcc tttgacggtt tcctcagcca cgcctgggcc       1260
gtcaccgtca ccggtgcacc aaagctgtgg gccatgcgct tcatcgaagg tcatgaaaag       1320
agcccgcgcg cctggtatgg cggtgcgatc ggcatggtcg gcttcaacgg cgacatgaat       1380 accgcctga cgctgcgcac catcggatc aaggacggta ttgccgaagt gcgcgccggc       1440
gcgaccctgc tcaatgattc caacccgcag gaagaagaag ccgaaaccga actgaaggcc       1500
tccgccatga tatcagccat tcgtgacgca aaaggcacca actctgccgc caccaagcgt       1560
gatgccgcca agtcggcac cggcgtcaag atcctgctcg tcgaccacga agacagcttc       1620
gtgcacacgc tggcgaatta tttccgccag acgggcgcga cggtctcgac cgtcagatca       1680
ccggtcgcag ccgacgtgtt cgatcgcttc cagccggacc tcgttgtcct gtcgcccgga       1740
cccggcagcc cgacggattt cgactgcaag gcaacgatca aggccgcccg cgcccgcgat       1800
ctgccgatct tcggcgtttg cctcggtctg caggcattgg cagaagccta tggcggcgag       1860
ctgcgccagc ttgctgtgcc catgcacggc aagccttcgc gcatccgcgt gctggaaccc       1920
ggcctcgtct tctccggtct cggcaaggaa gtcacggtcg gtcgttacca ttcgatcttc       1980
```

-continued

| | |
|---|---|
| gccgatcccg ccaccctgcc gcgtgatttc atcatcaccg cagaaagcga ggacggcacg | 2040 |
| atcatgggca tcgaacacgc caaggaaccg gtggccgccg ttcagttcca cccggaatcg | 2100 |
| atcatgacgc tcggacagga cgcgggcatg cggatgatcg agaatgtcgt ggtgcatctg | 2160 |
| acccgcaagg cgaagaccaa ggccgcgtga | 2190 |

<210> SEQ ID NO 87
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 87

| | |
|---|---|
| atggtaacga tcattcagga tgacggagcg gagacctacg agacgaaagg cggcatccag | 60 |
| gtcagccgaa agcgccggcc caccgattat gccaacgcca tcgataatta catcgaaaag | 120 |
| cttgattccc atcgcggcgc ggttttttcg tgcaactatg aatatccggg ccgttacacc | 180 |
| cgctgggata cggccatcgt cgatccgccg ctcggcattt cctgttttgg ccgcaagatg | 240 |
| tggatcgaag cctataatgg ccgcggcgaa gtgctgctcg atttcattac ggaaaagctg | 300 |
| aaggcgacac ccgatctcac cctcggcgct tcctcgaccc gccggctcga tcttaccgtc | 360 |
| aacgaaccgg accgtgtctt caccgaagaa gaacgctcga aaatcccgac ggtcttcacc | 420 |
| gctctcagag ccatcgtcga cctcttctat tcgagcgcgg attcggccat cggcctgttc | 480 |
| ggtgccttcg gttacgatct cgccttccag ttcgacgcga tcaagctttc gctggcgcgt | 540 |
| ccggaagacc agcgtgacat ggtgctgttt ctgcccgatg aaatcctcgt cgttgatcac | 600 |
| tattccgcca aggcctggat cgaccgttac gatttcgaga aggacggcat gacgacggac | 660 |
| ggcaaatcct ccgacattac ccccgatccc ttcaagacca ccgataccat cccgcccaag | 720 |
| ggcgatcacc gtcccggcga atattccgag cttgtggtga aggccaagga aagcttccgc | 780 |
| cgcggcgacc tgttcgaggt cgttcccggc cagaaattca tggagcgttg cgaaagcaat | 840 |
| ccgtcggcga tttcccgccg cctgaaggcg atcaacccgt cgccctattc cttcttcatc | 900 |
| aatctcggcg atcaggaata tctggtcggc gcctcgccgg aaatgttcgt gcgcgtctcc | 960 |
| ggccgtcgca tcgagacctg cccgatatca ggcaccatca agcgcggcga cgatccgatt | 1020 |
| gccgacagcg agcagatttt gaaactgctc aactcgaaaa aggacgaatc cgaactgacc | 1080 |
| atgtgctcgg acgtggaccg caacgacaag agccgcgtct gcgagccggg ttcggtgaag | 1140 |
| gtcattggcc gccgccagat cgagatgtat tcacgcctca tccacaccgt cgatcacatc | 1200 |
| gaaggccgcc tgcgcgacga tatggacgcc tttgacggtt tcctcagcca cgcctgggcc | 1260 |
| gtcaccgtca ccggtgcacc aaagctgtgg gccatgcgct tcatcgaagg tcatgaaaag | 1320 |
| agcccgcgcg cctggtatgg cggtgcgatc ggcatggtcg gcttcaacgg cgacatgaat | 1380 |
| accggcctga cgctgcgcac catccggatc aaggacggta ttgccgaagt gcgcgccggc | 1440 |
| gcgacccctgc tcaatgattc caacccgcag gaagaagaag ccgaaaccga actgaaggcc | 1500 |
| tccgccatga tatcagccat tcgtgacgca aaaggcacca actctgccgc caccaagcgt | 1560 |
| gatgccgcca aagtcggcac cggcgtcaag atcctgctcg tcgaccacga agacagcttc | 1620 |
| gtgcacacgc tggcgaatta tttccgccag acgggcgcga cggtctcgac cgtcagatca | 1680 |
| ccggtcgcag ccgacgtgtt cgatcgcttc cagccggacc tcgttgtcct gtcgcccgga | 1740 |
| cccggcagcc cgacggattt cgactgcaag gcaacgatca aggccgcccg cgcccgcgat | 1800 |
| ctgccgatct tcggcgtttg cctcggtctg caggcattgg cagaagccta tgcggcgag | 1860 |

```
ctgcgccagc ttgctgtgcc catgcacggc aagccttcgc gcatccgcgt gctggaaccc    1920
ggcctcgtct tctccggtct cggcaaggaa gtcacggtcg gtcgttacca ttcgatcttc    1980
gccgatcccg ccaccctgcc gcgtgatttc atcatcaccg cagaaagcga ggacggcacg    2040
atcatgggca tcgaacacgc caaggaaccg gtggccgccg ttcagttcca cccggaatcg    2100
atcatgacgc tcggacagga cgcgggcatg cggatgatcg agaatgtcgt ggtgcatctg    2160
acccgcaagg cgaagaccaa ggccgcgtga                                     2190
```

<210> SEQ ID NO 88
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 88

```
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc ggttttttcg tccttctatg aatatccggg ccgttacacc     180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctggcgcgt     540
ccggaagacc agcgtgacat ggtgctgttt ctgcccgatg aaatcctcgt cgttgatcac     600
tattccgcca aggcctggat cgaccgttac gatttcgaga aggacggcat gacgacggac     660
ggcaaatcct ccgacattac ccccgatccc ttcaagacca ccgataccat cccgcccaag     720
ggcgatcacc gtcccggcga atattccgag cttgtggtga aggccaagga aagcttccgc     780
cgcggcgacc tgttcgaggt cgttcccggc cagaaattca tggagcgttg cgaaagcaat     840
ccgtcggcga tttcccgccg cctgaaggcg atcaacccgt cgccctattc cttcttcatc     900
aatctcggcg atcaggaata tctggtcggc gcctcgccgg aaatgttcgt gcgcgtctcc     960
ggccgtcgca tcgagacctg cccgatatca ggcaccatca agcgcggcga cgatccgatt    1020
gccgacagcg agcagatttt gaaactgctc aactcgaaaa aggacgaatc cgaactgacc    1080
atgtgctcgg acgtggaccg caacgacaag agccgcgtct cgagccgggt tcggtgaag    1140 gtcattggcc gccgccagat cgagatgtat tcacgcctca tccacaccgt cgatcacatc    1200
gaaggccgcc tgcgcgacga tatggacgcc tttgacggtt tcctcagcca cgcctgggcc    1260
gtcaccgtca ccggtgcacc aaagctgtgg gccatgcgct tcatcgaagg tcatgaaaag    1320
agcccgcgcg cctggtatgg cggtgcgatc ggcatggtcg gcttcaacgg cgacatgaat    1380
accggcctga cgctgcgcac catccggatc aaggacggta ttgccgaagt gcgcgccggc    1440
gcgaccctgc tcaatgattc caacccgcag gaagaagaag ccgaaaccga actgaaggcc    1500
tccgccatga tatcagccat tcgtgacgca aaaggcacca actctgccgc caccaagcgt    1560
gatgccgcca agtcggcac cggcgtcaag atcctgctcg tcgaccacga agacagcttc    1620
gtgcacacgc tggcgaatta tttccgccag acgggcgcga cggtctcgac cgtcagatca    1680
```

```
ccggtcgcag ccgacgtgtt cgatcgcttc cagccggacc tcgttgtcct gtcgcccgga   1740
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
ctgcgccagc ttgctgtgcc catgcacggc aagccttcgc gcatccgcgt gctggaaccc   1920
ggcctcgtct tctccggtct cggcaaggaa gtcacggtcg gtcgttacca ttcgatcttc   1980
gccgatcccg ccaccctgcc gcgtgatttc atcatcaccg cagaaagcga ggacggcacg   2040
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                    2190
```

<210> SEQ ID NO 89
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 89

```
atggtaacga tcattcagga tgacggagcg gagacctacg agacgaaagg cggcatccag     60
gtcagccgaa agcgccggcc caccgattat gccaacgcca tcgataatta catcgaaaag    120
cttgattccc atcgcggcgc ggttttttcg tccaactatg aatatccggg ccgttacacc    180
cgctgggata cggccatcgt cgatccgccg ctcggcattt cctgttttgg ccgcaagatg    240
tggatcgaag cctataatgg ccgcggcgaa gtgctgctcg atttcattac ggaaaagctg    300
aaggcgacac ccgatctcac cctcggcgct tcctcgaccc gccggctcga tcttaccgtc    360
aacgaaccgg accgtgtctt caccgaagaa gaacgctcga aaatcccgac ggtcttcacc    420
gctctcagag ccatcgtcga cctcttctat tcgagcgcgg attcggccat cggcctgttc    480
ggtgccttcg gttacgatct cgccttccag ttcgacgcga tcaagctttc gctggcgcgt    540
ccggaagacc agcgtgacat ggtgctgttt ctgcccgatg aaatcctcgt cgttgatcac    600
tattccgcca aggcctggat cgaccgttac gatttcgaga aggacggcat gacgacggac    660
ggcaaatcct ccgacattac ccccgatccc ttcaagacca ccgataccat cccgcccaag    720
ggcgatcacc gtcccggcga atattccgag cttgtggtga aggccaagga aagcttccgc    780
cgcggcgacc tgttcgaggt cgttcccggc cagaaattca tggagcgttg cgaaagcaat    840
ccgtcggcga tttccgcccg cctgaaggcg atcaacgcgt cgccctattc cttcttcatc    900
aatctcggcg atcaggaata tctggtcggc gcctcgccgg aaatgttcgt gcgcgtctcc    960
ggccgtcgca tcgagacctg cccgatatca ggcaccatca agcgcggcga cgatccgatt   1020
gccgacagcg agcagatttt gaaactgctc aactcgaaaa aggacgaatc cgaactgacc   1080
atgtgctcga acgtggaccg caacgacaag agccgcgtct cgagccgggt tcggtgaag    1140 gtcattggcc gccgccagat cgagatgtat tcacgcctca tccacaccgt cgatcacatc   1200
gaaggccgct gcgcgacga tatggacgcc tttgacggtt tcctcagcca cgcctgggcc    1260
gtcaccgtca ccggtgcacc aaagctgtgg gccatgcgct tcatcgaagg tcatgaaaag   1320
agcccgcgcg cctggtatgg cggtgcgatc ggcatggtcg gcttcaacgg cgacatgaat   1380
accggcctga cgctgcgcac catccggatc aaggacggta ttgccgaagt gcgcgccggc   1440
gcgaccctgc tcaatgattc caacccgcag gaagaagaag ccgaaaccga actgaaggcc   1500
tccgccatga tatcagccat tcgtgacgca aaaggcacca actctgccgc caccaagcgt   1560
```

```
gatgccgcca aagtcggcac cggcgtcaag atcctgctcg tcgaccacga agacagcttc    1620
gtgcacacgc tggcgaatta tttccgccag acgggcgcga cggtctcgac cgtcagatca    1680
ccggtcgcag ccgacgtgtt cgatcgcttc cagccggacc tcgttgtcct gtcgcccgga    1740
cccggcagcc cgacggattt cgactgcaag gcaacgatca aggccgcccg cgcccgcgat    1800
ctgccgatct tcggcgtttg cctcggtctg caggcattgg cagaagccta tggcggcgag    1860
ctgcgccagc ttgctgtgcc catgcacggc aagccttcgc gcatccgcgt gctggaaccc    1920
ggcctcgtct tctccggtct cggcaaggaa gtcacggtcg tcgttacca ttcgatcttc    1980 gccgatcccg ccaccctgcc gcgtgatttc atcatcaccg cagaaagcga ggacggcacg    2040
atcatgggca tcgaacacgc caaggaaccg gtggccgccg ttcagttcca cccggaatcg    2100
atcatgacgc tcggacagga cgcgggcatg cggatgatcg agaatgtcgt ggtgcatctg    2160
acccgcaagg cgaagaccaa ggccgcgtga                                      2190

<210> SEQ ID NO 90
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 90
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc ggttttttcg tccaactatg aatatccggg ccgttacacc     180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctggcgcgt     540
ccggaagacc agcgtgacat ggtgctgttt ctgcccgatg aaatcctcgt cgttgatcac     600
tattccgcca aggcctggat cgaccgttac gatttcgaga aggacggcat gacgacggac     660
ggcaaatcct ccgacattac ccccgatccc ttcaagacca ccgataccat cccgcccaag     720
ggcgatcacc gtcccggcga atattccgag cttgtggtga aggccaagga aagcttccgc     780
cgcggcgacc tgttcgaggt cgttcccggc cagaaattca tggagcgttg cgaaagcaat     840
ccgtcggcga tttcccgccg cctgaaggcg atcaacgggt cgccctattc cttcttcatc     900
aatctcggcg atcaggaata tctggtcggc gcctcgccgg aaatgttcgt gcgcgtctcc     960
ggccgtcgca tcgagacctg cccgatatca ggcaccatca agcgcggcga cgatccgatt    1020
gccgacagcg agcagatttt gaaactgctc aactcgaaaa aggacgaatc cgaactgacc    1080
atgtgctcgg acgtggaccg caacgacaag agccgcgtct gcgagccggg ttcggtgaag    1140
gtcattggcc gccgcagat cgagatgtat tcacgcctca tccacaccgt cgatcacatc    1200
gaaggccgcc tgcgcgacga tatggacgcc tttgacggtt cctcagcca cgcctgggcc    1260 gtcaccgtca ccggtgcacc aaagctgtgg gccatgcgct tcatcgaagg tcatgaaaag    1320
agcccgcgcg cctggtatgg cggtgcgatc ggcatggtcg gcttcaacgg cgacatgaat    1380
```

-continued

| | |
|---|---|
| accggcctga cgctgcgcac catccggatc aaggacggta ttgccgaagt gcgcgccggc | 1440 |
| gcgaccctgc tcaatgattc caacccgcag gaagaagaag ccgaaaccga actgaaggcc | 1500 |
| tccgccatga tatcagccat tcgtgacgca aaaggcacca actctgccgc caccaagcgt | 1560 |
| gatgccgcca aagtcggcac cggcgtcaag atcctgctcg tcgaccacga agacagcttc | 1620 |
| gtgcacacgc tggcgaatta tttccgccag acgggcgcga cggtctcgac cgtcagatca | 1680 |
| ccggtcgcag ccgacgtgtt cgatcgcttc agccggacc tcgttgtcct gtcgcccgga | 1740 |
| cccggcagcc cgacggattt cgactgcaag gcaacgatca aggccgcccg cgcccgcgat | 1800 |
| ctgccgatct tcggcgtttg cctcggtctg caggcattgg cagaagccta tggcggcgag | 1860 |
| ctgcgccagc ttgctgtgcc catgcacggc aagccttcgc gcatccgcgt gctggaaccc | 1920 |
| ggcctcgtct tctccggtct cggcaaggaa gtcacggtcg tcgttacca ttcgatcttc | 1980 |
| gccgatcccg ccaccctgcc gcgtgatttc atcatcaccg cagaaagcga ggacggcacg | 2040 |
| atcatgggca tcgaacacgc caaggaaccg gtggccgccg ttcagttcca cccggaatcg | 2100 |
| atcatgacgc tcggacagga cgcgggcatg cggatgatcg agaatgtcgt ggtgcatctg | 2160 |
| acccgcaagg cgaagaccaa ggccgcgtga | 2190 |

<210> SEQ ID NO 91
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 91

| | |
|---|---|
| atggtaacga tcattcagga tgacggagcg gagacctacg agacgaaagg cggcatccag | 60 |
| gtcagccgaa agcgccggcc caccgattat gccaacgcca tcgataatta catcgaaaag | 120 |
| cttgattccc atcgcggcgc ggttttttcg tccaactatg aatatccggg ccgttacacc | 180 |
| cgctgggata cggccatcgt cgatccgccg ctcggcattt cctgttttgg ccgcaagatg | 240 |
| tggatcgaag cctataatgg ccgcggcgaa gtgctgctcg atttcattac ggaaaagctg | 300 |
| aaggcgacac ccgatctcac cctcggcgct tcctcgaccc gccggctcga tcttaccgtc | 360 |
| aacgaaccgg accgtgtctt caccgaagaa gaacgctcga aaatcccgac ggtcttcacc | 420 |
| gctctcagag ccatcgtcga cctcttctat tcgagcgcgg attcggccat cggcctgttc | 480 |
| ggtgccttcg gttacgatct cgccttccag ttcgacgcga tcaagctttc gctggcgcgt | 540 |
| ccggaagacc agcgtgacat ggtgctgttt ctgcccgatg aaatcctcgt cgttgatcac | 600 |
| tattccgcca aggcctggat cgaccgttac gatttcgaga aggacggcat gacgacggac | 660 |
| ggcaaatcct ccgacattac ccccgatccc ttcaagacca ccgataccat cccgcccaag | 720 |
| ggcgatcacc gtcccggcga atattccgag cttgtggtga aggccaagga agcttccgc | 780 |
| cgcggcgacc tgttcgaggt cgttcccggc cagaaattca tggagcgttg cgaaagcaat | 840 |
| ccgtcggcga tttccgccg cctgaaggcg atcaaccgt cgccctattc ctggttcatc | 900 |
| aatctcggcg atcaggaata tctggtcggc gcctcgccgg aaatgttcgt gcgcgtctcc | 960 |
| ggccgtcgca tcgagacctg cccgatatca ggcaccatca agcgcggcga cgatccgatt | 1020 |
| gccgacagcg agcagatttt gaaactgctc aactcgaaaa aggacgaatc cgaactgacc | 1080 |
| atgtgctcgg acgtggaccg caacgacaag agccgcgtct gcgagccggg ttcggtgaag | 1140 |
| gtcattggcc gccgcagat cgagatgtat tcacgcctca tccacaccgt cgatcacatc | 1200 |
| gaaggccgcc tgcgcgacga tatggacgcc tttgacggtt tcctcagcca cgcctgggcc | 1260 |

```
gtcaccgtca ccggtgcacc aaagctgtgg gccatgcgct tcatcgaagg tcatgaaaag    1320
agcccgcgcg cctggtatgg cggtgcgatc ggcatggtcg gcttcaacgg cgacatgaat    1380
accggcctga cgctgcgcac catccggatc aaggacggta ttgccgaagt gcgcgccggc    1440
gcgaccctgc tcaatgattc aacccgcag gaagaagaag ccgaaaccga actgaaggcc     1500
tccgccatga tatcagccat tcgtgacgca aaaggcacca actctgccgc caccaagcgt    1560
gatgccgcca agtcggcac cggcgtcaag atcctgctcg tcgaccacga agacagcttc     1620
gtgcacacgc tggcgaatta tttccgccag acgggcgcga cggtctcgac cgtcagatca    1680
ccggtcgcag ccgacgtgtt cgatcgcttc cagccggacc tcgttgtcct gtcgcccgga    1740
cccggcagcc cgacggattt cgactgcaag gcaacgatca aggccgcccg cgcccgcgat    1800
ctgccgatct tcggcgtttg cctcggtctg caggcattgg cagaagccta tggcggcgag    1860 ctgccgccagc ttgctgtgcc catgcacggc aagccttcgc gcatccgcgt gctggaaccc    1920
ggcctcgtct tctccggtct cggcaaggaa gtcacggtcg gtcgttacca ttcgatcttc    1980
gccgatcccg ccaccctgcc gcgtgatttc atcatcaccg cagaaagcga ggacggcacg    2040
atcatgggca tcgaacacgc caaggaaccg gtggccgccg ttcagttcca cccggaatcg    2100
atcatgacgc tcggacagga cgcgggcatg cggatgatcg agaatgtcgt ggtgcatctg    2160
acccgcaagg cgaagaccaa ggccgcgtga                                      2190

<210> SEQ ID NO 92
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 92
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc ggttttttaag tccaactatg aatatccggg ccgttacacc     180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctgcgcgt     540 ccggaagacc agcgtgacat ggtgctgttt ctgcccgatg aaatcctcgt cgttgatcac     600
tattccgcca aggcctggat cgaccgttac gatttcgaga aggacggcat gacgacggac    660
ggcaaatcct ccgacattac ccccgatccc ttcaagacca ccgataccat cccgcccaag    720
ggcgatcacc gtcccggcga atattccgag cttgtggtga aggccaagga aagcttccgc    780
cgcggcgacc tgttcgaggt cgttcccggc cagaaattca tggagcgttg cgaaagcaat    840
ccgtcggcga tttcccgccg cctgaaggcg atcaacccgt cgccctattc cttcttcatc    900
aatctcggcg atcaggaata tctggtcggc gcctcgccgg aaatgttcgt gcgcgtctcc    960
ggccgtcgca tcgagacctg cccgatatca ggcaccatca agcgcggcga cgatccgatt    1020
gccgacagcg agcagatttt gaaactgctc aactcgaaaa aggacgaatc cgaactgacc    1080
```

```
atgtgctcgg acgtggaccg caacgacaag agccgcgtct gcgagccggg ttcggtgaag    1140
gtcattggcc gccgccagat cgagatgtat tcacgcctca tccacaccgt cgatcacatc    1200
gaaggccgcc tgcgcgacga tatggacgcc tttgacggtt tcctcagcca cgcctgggcc    1260
gtcaccgtca ccggtgcacc aaagctgtgg gccatgcgct tcatcgaagg tcatgaaaag    1320
agcccgcgcg cctggtatgg cggtgcgatc ggcatggtcg gcttcaacgg cgacatgaat    1380
accggcctga cgctgcgcac catccggatc aaggacggta ttgccgaagt gcgcgccggc    1440 gcgacccctgc tcaatgattc caacccgcag gaagaagaag ccgaaaccga actgaaggcc    1500
tccgccatga tatcagccat tcgtgacgca aaaggcacca actctgccgc caccaagcgt    1560
gatgccgcca agtcggcac cggcgtcaag atcctgctcg tcgaccacga agacagcttc     1620
gtgcacacgc tggcgaatta tttccgccag acgggcgcga cggtctcgac cgtcagatca    1680
ccggtcgcag ccgacgtgtt cgatcgcttc cagccggacc tcgttgtcct gtcgcccgga    1740
cccggcagcc cgacggattt cgactgcaag gcaacgatca aggccgcccg cgcccgcgat    1800
ctgccgatct tcggcgtttg cctcggtctg caggcattgg cagaagccta tggcggcgag    1860
ctgcgccagc ttgctgtgcc catgcacggc aagccttcgc gcatccgcgt gctggaaccc    1920
ggcctcgtct tctccggtct cggcaaggaa gtcacggtcg gtcgttacca ttcgatcttc    1980
gccgatcccg ccaccctgcc gcgtgatttc atcatcaccg cagaaagcga ggacggcacg    2040
atcatgggca tcgaacacgc caaggaaccg gtggccgccg ttcagttcca cccggaatcg    2100
atcatgacgc tcggacagga cgcgggcatg cggatgatcg agaatgtcgt ggtgcatctg    2160
acccgcaagg cgaagaccaa ggccgcgtga                                     2190
```

<210> SEQ ID NO 93
<211> LENGTH: 2190
<212> TYPE: DNA
<213> ORGANISM: Artificial Sequence
<220> FEATURE:
<223> OTHER INFORMATION: An A. tumefaciens mutant

<400> SEQUENCE: 93

```
atggtaacga tcattcagga tgacggagcg gagacctacg agacgaaagg cggcatccag     60
gtcagccgaa agcgccggcc caccgattat gccaacgcca tcgataatta catcgaaaag    120
cttgattccc atcgcggcgc ggttttttcg tccaactatg aatatccggg ccgttacacc    180
cgctgggata cggccatcgt cgatccgccg ctcggcattt cctgttttgg ccgcaagatg    240
tggatcgaag cctataatgg ccgcggcgaa gtgctgctcg atttcattac ggaaaagctg    300
aaggcgacac ccgatctcac cctcggcgct tcctcgaccc gccggctcga tcttaccgtc    360
aacgaaccgg accgtgtctt caccgaagaa gaacgctcga aaatcccgac ggtcttcacc    420
gctctcagag ccatcgtcga cctcttctat tcgagcgcgg attcggccat cggcctgttc    480
ggtgccttcg gttacgatct cgccttccag ttcgacgcga tcaagctttc gctgcgcgt     540 ccggaagacc agcgtgacat ggtgctgttt ctgcccgatg aaatcctcgt cgttgatcac    600
tattccgcca aggcctggat cgaccgttac gatttcgaga aggacggcat gacgacggac    660
ggcaaatcct ccgacattac ccccgatccc ttcaagacca ccgataccat cccgcccaag    720
ggcgatcacc gtcccggcga atattccgag cttgtggtga aggccaagga agcttccgc     780 cgcgcgacc tgttcgaggt cgttcccggc cagaaattca tggagcgttg cgaaagcaat    840
ccgtcggcga tttcccgccg cctgaaggcg atcaacccgt cgccctattc cgccttcatc    900
aatctcggcg atcaggaata tctggtcggc gcctcgccgg aaatgttcgt gcgcgtctcc    960
```

```
ggccgtcgca tcgagacctg cccgatatca ggcaccatca agcgcggcga cgatccgatt   1020
gccgacagcg agcagatttt gaaactgctc aactcgaaaa aggacgaatc cgaactgacc   1080
atgtgctcgg acgtggaccg caacgacaag agccgcgtct gcgagccggg ttcggtgaag   1140
gtcattggcc gccgccagat cgagatgtat tcacgcctca tccacaccgt cgatcacatc   1200
gaaggccgcc tgcgcgacga tatggacgcc tttgacggtt tcctcagcca cgcctgggcc   1260
gtcaccgtca ccggtgcacc aaagctgtgg gccatgcgct tcatcgaagg tcatgaaaag   1320
agcccgcgcg cctggtatgg cggtgcgatc ggcatggtcg gcttcaacgg cgacatgaat   1380
accggcctga cgctgcgcac catccggatc aaggacggta ttgccgaagt gcgcgccggc   1440
gcgaccctgc tcaatgattc aacccgcag gaagaagaag ccgaaaccga actgaaggcc   1500
tccgccatga tatcagccat cgtgacgca aaaggcacca actctgccgc caccaagcgt   1560
gatgccgcca agtcggcac cggcgtcaag atcctgctcg tcgaccacga agacagcttc   1620
gtgcacacgc tggcgaatta tttccgccag acgggcgcga cggtctcgac cgtcagatca   1680
ccggtcgcag ccgacgtgtt cgatcgcttc cagccgacc tcgttgtcct gtcgcccgga   1740
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
ctgcgccagc ttgctgtgcc catgcacggc aagccttcgc gcatccgcgt gctggaaccc   1920
ggcctcgtct ctccggtct cggcaaggaa gtcacggtcg gtcgttacca ttcgatcttc   1980
gccgatcccg ccaccctgcc gcgtgatttc atcatcaccg cagaaagcga ggacggcacg   2040
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                    2190
```

<210> SEQ ID NO 94
<211> LENGTH: 1821
<212> TYPE: DNA
<213> ORGANISM: Oryza sativa

<400> SEQUENCE: 94

```
atggagtcca tcgccgccgc cacgttcacg ccctcgcgcc tcgccgcccg ccccgccact     60
ccggcggcgg cggcggcccc ggttagagcg agggcggcgg tagcggcagg agggaggagg    120
aggacgagta ggcgcggcgg cgtgaggtgc tccgcgggga agccagaggc aagcgcggtg    180
atcaacggga gcgcggcggc gcgggcggcg gaggaggaca ggaggcgctt cttcgaggcg    240
gcggagcgtg ggagcgggaa gggcaacctg gtgcccatgt gggagtgcat cgtctccgac    300
cacctcaccc ccgtgctcgc ctaccgctgc ctcgtccccg aggacaacat ggagacgccc    360
agcttcctct tcgagtccgt cgagcagggg cccgagggca ccaccaacgt cggtcgctat    420
agcatggtgg gagcccaccc agtgatggag gtcgtggcaa aggagcacaa ggtcacaatc    480
atggaccacg agaagggcaa ggtgacggag caggtcgtgg atgatccat gcagatcccc    540 aggagcatga tggaaggatg gcacccgcag cagatcgatc agctccccga ttccttcacc    600
ggtggatggg tcgggttctt ttcctatgat acagtccgtt atgttgaaaa gaagaagctg    660
cccttctccg gtgctcccca ggacgatagg aaccttcctg atgttcacct tgggctttat    720
gatgatgttc tcgtcttcga caatgtcgag aagaaagtat atgtcatcca ttgggtaaat    780
cttgatcggc atgcaaccac cgaggatgca ttccaagatg gcaagtcccg gctgaacctg    840
```

```
ttgctatcta aagtgcacaa ttcaaatgta cccaagcttt ctccaggatt tgtaaagtta      900
cacactcggc agtttggtac acctttgaac aaatcaacca tgacaagtga tgagtacaag      960
aatgctgtta tgcaggctaa ggagcatatt atggctggtg atattttcca gattgtttta     1020
agccagaggt ttgagaggca gacatacgcc aatccatttg aagtctatcg agctttacga     1080
attgtgaacc caagtccata catggcatat gtacaggcaa gaggctgtgt cctggtagca     1140
tctagtccag aaattcttac tcgtgtgagg aagggtaaaa ttattaaccg tccacttgct     1200
gggactgttc aaggggcaa gacagagaag gaagatgaaa tgcaagagca acaactacta      1260
agtgatgaaa acagtgtgc tgaacatatt atgcttgtag atttgggaag gaatgatgtt      1320
ggaaaggtct ccaaacctgg atctgtgaag gtggagaaat taatgaacat gaacgctac      1380
tcccatgtca tgcacatcag ttccacggtg agtggagagt ggatgatca tctccaaagt      1440
tgggatgccc tgcgagccgc gttgcctgtt ggaacagtta gtggagcacc aaaggtgaaa     1500
gccatggagc tgatagacga gctagaggtc acaagacgag gaccatacag tggcggcctt     1560
ggagggatat catttgacgg ggacatgctt atcgctcttg cactccgcac cattgtgttc     1620
tcaacagcgc caagccacaa cacgatgtac tcatacaaag acaccgagag gcgccgggag     1680
tgggtcgctc acccttcaggc tggtgctggc attgtcgctg atagcagccc agacgacgag     1740
caacgtgaat gcgagaacaa ggcagccgct ctggctcgag ccatcgatct tgctgaatca     1800
gctttcgtag acaaggaata g                                               1821

<210> SEQ ID NO 95
<211> LENGTH: 1498
<212> TYPE: DNA
<213> ORGANISM: Oryza sativa

<400> SEQUENCE: 95
gaattcaaat tttttatata gagtatttct atacatgaat ttttctaact ttttgttttt       60
taaaaaaat ttgtgtggtg tactgtaata ggaagagaag aaggggagga ggaaggaggg       120
agaagaggga ggagtatatg gggaggggg gatgaactga tcgcccagcg tgatagctgg       180
cgatcgagca cccattagaa gggcccaata aaccctggat aattgtcatt gagtggcacc       240
tttcattgag aagacgttat taggaattgt agaagtggca aattatgcta tctgttgtat       300
tgagtgtcac tgtcaccgat aaagctttgc tggttaatgc attgtatttc tccatcaacg       360
cttcatgata caatggtatt tggacgtgtt tataaaataa tatacgtata atgtgggtgg       420
cctagcggcg gccggttaca catagcagcg atcggtccga tgctagtctt cattcattca       480
ggtatgtatt caggtatcag tgtgtgggtg atagtttttt tttttcgttt ttctagttac       540
gatatctcat atctcatagt tgtgatctta taaactttt catgtttatc aatataaatt       600
tcgtgttatc tagtcgttaa aagaaccgta taatgtggca aaaaaatgt ataatgtgtc       660
agagtttgca cgtgtttatc ttgctgcccc gaaacgatta ttcagtgat ttggcaacaa       720
caaaatgtcg tggcggataa gcatatccgt cccaaaagga aaaaagaaa aggaaaaata       780
atctttagaa ataaagccct tactttttcc aagaagcaga ggtaaccgta gctggtattc       840
cgcggctaac tcaatccctt tctctggagt cttggagcgg cacggcggct gcgcacccga       900
cctcgcccac cacctgctcg gcgaaacgcc cggctcggcc gcgacgtgtc ccaccgcacc       960
gcgcgcgcac ccgcgcgccc cgagcccctc gccgcctccg cgcgggcgcc gcacctattt     1020
aaatgcggcc ccgatcccgc attctctcaa ctgcactagt ccccaccaac ggctcggtcc     1080
agtagagttt atccccccacc tatggccagc ctcgtgctct ccctgcgcat cgcccgttcc     1140
```

```
acgccgccgc tggggctggg cggggggcga ttccgcggcc gacgaggggc cgtcgcctgc    1200
cgcgccgcca cgttccagca gctcgacgcc gtcggtgagt ctccgtatca aatgtggggg    1260
ggcatgtctt ggtttgcgga ttggtgggtt gatttgaatg tgtgttctcg tggccgcagc    1320
ggtgagggag gaggagtcca agttcaaggc ggggcggcg gagggttgca acatcctgcc     1380
gctcaagcga tgcatcttct ccgaccacct cacgccggtg ctcgcgtacc gctgcctcgt    1440
cagggaggac gaccgcgagg cgcccagctt cctgtttgag tccgtcgagc agggatcc     1498
```

<210> SEQ ID NO 96
<211> LENGTH: 2073
<212> TYPE: DNA
<213> ORGANISM: Zea mays

<400> SEQUENCE: 96

```
gaattccgcc aaatcgggct atagatcaaa cgctgcactg tagggagcgt gaagccagcg      60
gcgaatggaa tccctagccg ccacctccgt gttcgcgccc tcccgcgtcg ccgtcccggc     120
ggcgcgggcc ctggttaggg cggggacggt ggtaccaacc aggcggacga gcagccggag     180
cggaaccagc ggggtgaaat gctctgctgc cgtgacgccg caggcgagcc cagtgattag     240
caggagcgct gcggcggcga aggcggcgga ggaggacaag aggcggttct tcgaggcggc     300
ggcgcggggg agcgggaagg ggaacctggt gcccatgtgg gagtgcatca agggaacct     360 ggtgcccatg tgggagtgca tcgtgtcgga ccatctcacc cccgtgctcg cctaccgctg     420
cctcgtcccc gaggacaacg tcgacgcccc cagcttcctc ttcgagtccg tcgagcaggg     480
gccccagggc accaccaacg tcggccgcta gcatggtg ggagcccacc cagtgatgga      540
gattgtggcc aaagaccaca aggttacgat catggaccac gagaagagcc aagtgacaga     600
gcaggtagtg gacgacccga tgcagatccc gaggaccatg atggagggat ggcacccaca     660
gcagatcgac gagctccctg aatccttctc cggtggatgg gttgggttct tttcctatga     720
tacggttagg tatgttgaga agaagaagct accgttctcc agtgctcctc aggacgatag     780
gaaccttcct gatgtgcact tgggactcta tgatgatgtt ctagtcttcg ataatgttga     840
gaagaaagta tatgttatcc attgggtcaa tgtggaccgg catgcatctg ttgaggaagc     900
ataccaagat ggcaggtccc gactaaacat gttgctatct aaagtgcaca attccaatgt     960
ccccacactc tctcctggat ttgtgaagct gcacacacgc aagtttggta ccctttgaa     1020 caagtcgacc atgacaagtg atgagtataa gaatgctgtt ctgcaggcta aggaacatat    1080
tatggctggg gatatcttcc agattgttt aagccagagg ttcgagagac gaacatatgc     1140
caacccattt gaggtttatc gagcattacg gattgtgaat cctagcccat acatggcgta    1200
tgtacaggca agaggctgtg tattggttgc gtctagtcct gaaattctta cacgagtcag    1260
taaggggaag attattaatc gaccacttgc tggaactgtt cgaaggggca agacagagaa    1320
ggaagatcaa atgcaagagc agcaactgtt aagtgatgaa aaacagtgtg ccgagcacat    1380
aatgcttgtg gacttgggaa ggaatgatgt tggcaaggta tccaaaccag aggatcagt     1440 gaaggtggag aagttgatta ttgagagata ctcccatgtt atgcacataa gctcaacggt    1500
tagtggacag ttggatgatc atctccagag ttgggatgcc ttgagagctg ccttgcccgt    1560
tggaacagtc agtggtgcac caaaggtgaa ggccatggag ttgattgata agttggaagt    1620
tacgaggcga ggaccatata gtggtggtct aggaggaata tcgtttgatg gtgacatgca    1680
aattgcactt tctctccgca ccatcgtatt ctcaacagcg ccgagccaca acacgatgta    1740
```

```
ctcatacaaa gacgcagata ggcgtcggga gtgggtcgct catcttcagg ctggtgcagg    1800
cattgttgcc gacagtagcc cagatgacga acaacgtgaa tgcgagaata aggctgctgc    1860
actagctcgg gccatcgatc ttgcagagtc agcttttgtg aacaaagaat agtgtgctat    1920
ggttatcgtt tagttcttgt tcatgtttct tttacccact ttccgttaaa aaagatgtc     1980 attagtgggt ggagaaaagc aataagactg ttctctagag aaccgaagaa atatggaaat    2040
tgaggttatg gccggaattc ctgcagcccg ggg                                 2073

<210> SEQ ID NO 97
<211> LENGTH: 504
<212> TYPE: DNA
<213> ORGANISM: Triticum aestivum

<400> SEQUENCE: 97
cccaaacagt ggtggcttag gagggatatc atttgatggt gacatgctta tcgctcttgc      60
tctccgcacc attgtgtttt caacagctcc aagcccccaat aggatgtact catacaaaag    120
ctcagatagg ccccgagagt gggttgctca tcttcaggct ggtgcgggca ttgttgctga    180
tagtatccca gacgatgagc aaaaagaatt tgagaataag gcggctgccc tagctcgggc    240
aattgatctt gcagagtcgg cttttttaga caaagaatag agtgtctatt aaattatttt    300
ttttagttgt tcatcatttt tcacccagtt cattttggaa agttgttcat cgttttttca    360
ccgagttcat attggggaaa aaaagcaata ccgttttgtt gtcctttgaa atgaataaat    420
ttgagctata ataagatgta ttttgctcat cgggcaaaaa aaaaaaaaaa aatataaaaa    480
aaaaaaaaaa aaaaaaaaaa aata                                           504

<210> SEQ ID NO 98
<211> LENGTH: 2161
<212> TYPE: DNA
<213> ORGANISM: Nicotiana tabacum

<400> SEQUENCE: 98
gtcaaaaatc cccatttcac cgtttcctcg tttctcctcc tcactaattt tgtctctttc      60
tcttggtttg ctattgtgct cttgtaggaa tgcagtcgtt acctatctca taccggttgt    120
ttccggccac ccaccggaaa gttctgccat tcgccgtcat ttctagccgg agctcaactt    180
ctgcacttgc gcttcgtgtc cgtacactac aatgccgctg ccttcactct tcatctctag    240
ttatggatga ggacaggttc attgaagctt ctaaaagcgg gaacttgatt ccgctgcaca    300
aaaccatttt ttctgatcat ctgactccgg tgctggctta ccggtgtttg gtgaaagaag    360
acgaccgtga agctccaagc tttctctttg aatccgttga acctggtttt cgaggttcta    420
gtgttggtcg ctacagcgtg gtgggggctc aaccatctat ggaaattgtg gctaaggaac    480
acaatgtgac tatattggac caccacactg gaaaattgac ccagaagact gtccaagatc    540
ccatgacgat tccgaggagt atttctgagg gatggaagcc cagactcatt gatgaacttc    600
ctgatacctt tgtggtgga tgggttggtt atttctcata tgacacagtt cggtatgtag    660
agaacaggaa gttgccattc ctaagggctc cagaggatga ccggaacctt gcagatattc    720
aattaggact atacgaagat gtcattgtgt ttgatcatgt tgagaagaaa gcacatgtga    780
ttcactgggt gcagttggat cagtattcat ctcttcctga ggcatatctt gatgggaaga    840
aacgcttgga atatagtg tctagagtac aaggaattga gtctccaagg ttatctcccg    900
gttctgtgga tttctgtact catgcttttg gaccttcatt aaccaaggga acatgacaa    960 gtgaggagta caagaatgct gtcttacaag caaaggagca cattgctgca ggagacatat   1020
```

-continued

```
ttcaaatcgt tttaagtcaa cgctttgaga gaagaacatt tgctgaccca tttgaagtgt    1080
acagagcatt aagaattgtg aatccaagcc catatatgac ttacatacaa gccagaggct    1140
gtattttagt tgcatcgagc ccagaaattt tgacacgtgt gaagaagaga agaattgtta    1200
atcgaccact ggctgggaca agcagaagag ggaagacacc tgatgaggat gtgatgttgg    1260
aaatgcagat gttaaaagat gagaaacaac gcgcagagca catcatgctg gttgatttag    1320
gacgaaatga tgtaggaaag gtgtcaaaac ctggttctgt gaatgtcgaa aagctcatga    1380
gcgttgagcg gtattcccat gtgatgcaca taagctccac ggtctctgga gagttgcttg    1440
atcatttaac ctgttgggat gcactacgtg ctgcattgcc tgttgggacc gtcagtggag    1500
caccaaaggt aaaggccatg gagttgattg atcagctaga agtagctcgg agagggcctt    1560
acagtggtgg gtttggaggc atttccttt  caggtgacat ggacatcgca ctagctctaa    1620
ggacgatggt attcctcaat ggagctcgtt atgcacacaat gtattcatat acagatgcca    1680
gcaagcgtca ggaatgggtt gctcatctcc aatccggggc tggaattgtg gctgatagta    1740
atcctgatga ggaacagata gaatgcgaga ataaagtagc cggtctgtgc cgagccattg    1800
acttggccga gtcagctttt gtaaagggaa gacacaaacc gtcagtcaag ataaatggtt    1860
ctgtgccaaa tctattttca agggtacaac gtcaaacatc tgttatgtcg aaggacagag    1920
tacatgagaa aagaaactag cgaatatgaa gatgtacata aattctaaag tggttttctt    1980
gttcagttta atcttttact ggattgagac tgtagttgct gaagatagtt gtttagaatg    2040
accttcattt tggtgttcct gaaaggacag tgcacatata tagcaaattg atcaaatgtt    2100
taatccttgt atgcgggtga gaatcaatgc catcagcaat ttggaaaaaa aaaaaaaaa     2160 a                                                                    2161
```

<210> SEQ ID NO 99
<211> LENGTH: 606
<212> TYPE: PRT
<213> ORGANISM: Oryza sativa

<400> SEQUENCE: 99

```
Met Glu Ser Ile Ala Ala Ala Thr Phe Thr Pro Ser Arg Leu Ala Ala
1               5                   10                  15

Arg Pro Ala Thr Pro Ala Ala Ala Ala Pro Val Arg Ala Arg Ala
            20                  25                  30

Ala Val Ala Ala Gly Gly Arg Arg Thr Ser Arg Arg Gly Gly Val
        35                  40                  45

Arg Cys Ser Ala Gly Lys Pro Glu Ala Ser Ala Val Ile Asn Gly Ser
    50                  55                  60

Ala Ala Ala Arg Ala Ala Glu Glu Asp Arg Arg Arg Phe Phe Glu Ala
65                  70                  75                  80

Ala Glu Arg Gly Ser Gly Lys Gly Asn Leu Val Pro Met Trp Glu Cys
                85                  90                  95

Ile Val Ser Asp His Leu Thr Pro Val Leu Ala Tyr Arg Cys Leu Val
            100                 105                 110

Pro Glu Asp Asn Met Glu Thr Pro Ser Phe Leu Phe Glu Ser Val Glu
        115                 120                 125

Gln Gly Pro Glu Gly Thr Thr Asn Val Gly Arg Tyr Ser Met Val Gly
    130                 135                 140

Ala His Pro Val Met Glu Val Val Ala Lys Glu His Lys Val Thr Ile
145                 150                 155                 160
```

-continued

```
Met Asp His Glu Lys Gly Lys Val Thr Glu Gln Val Val Asp Asp Pro
                165                 170                 175
Met Gln Ile Pro Arg Ser Met Met Glu Gly Trp His Pro Gln Gln Ile
            180                 185                 190
Asp Gln Leu Pro Asp Ser Phe Thr Gly Gly Trp Val Gly Phe Phe Ser
        195                 200                 205
Tyr Asp Thr Val Arg Tyr Val Glu Lys Lys Leu Pro Phe Ser Gly
210                 215                 220
Ala Pro Gln Asp Asp Arg Asn Leu Pro Asp Val His Leu Gly Leu Tyr
225                 230                 235                 240
Asp Asp Val Leu Val Phe Asp Asn Val Glu Lys Val Tyr Val Ile
            245                 250                 255
His Trp Val Asn Leu Asp Arg His Ala Thr Thr Glu Asp Ala Phe Gln
        260                 265                 270
Asp Gly Lys Ser Arg Leu Asn Leu Leu Leu Ser Lys Val His Asn Ser
    275                 280                 285
Asn Val Pro Lys Leu Ser Pro Gly Phe Val Lys Leu His Thr Arg Gln
290                 295                 300
Phe Gly Thr Pro Leu Asn Lys Ser Thr Met Thr Ser Asp Glu Tyr Lys
305                 310                 315                 320
Asn Ala Val Met Gln Ala Lys Glu His Ile Met Ala Gly Asp Ile Phe
            325                 330                 335
Gln Ile Val Leu Ser Gln Arg Phe Glu Arg Gln Thr Tyr Ala Asn Pro
        340                 345                 350
Phe Glu Val Tyr Arg Ala Leu Arg Ile Val Asn Pro Ser Pro Tyr Met
    355                 360                 365
Ala Tyr Val Gln Ala Arg Gly Cys Val Leu Val Ala Ser Ser Pro Glu
370                 375                 380
Ile Leu Thr Arg Val Arg Lys Gly Lys Ile Ile Asn Arg Pro Leu Ala
385                 390                 395                 400
Gly Thr Val Arg Arg Gly Lys Thr Glu Lys Glu Asp Glu Met Gln Glu
            405                 410                 415
Gln Gln Leu Leu Ser Asp Glu Lys Gln Cys Ala Glu His Ile Met Leu
        420                 425                 430
Val Asp Leu Gly Arg Asn Asp Val Gly Lys Val Ser Lys Pro Gly Ser
    435                 440                 445
Val Lys Val Glu Lys Leu Met Asn Ile Glu Arg Tyr Ser His Val Met
450                 455                 460
His Ile Ser Ser Thr Val Ser Gly Glu Leu Asp Asp His Leu Gln Ser
465                 470                 475                 480
Trp Asp Ala Leu Arg Ala Ala Leu Pro Val Gly Thr Val Ser Gly Ala
            485                 490                 495
Pro Lys Val Lys Ala Met Glu Leu Ile Asp Glu Leu Glu Val Thr Arg
        500                 505                 510
Arg Gly Pro Tyr Ser Gly Gly Leu Gly Gly Ile Ser Phe Asp Gly Asp
    515                 520                 525
Met Leu Ile Ala Leu Ala Leu Arg Thr Ile Val Phe Ser Thr Ala Pro
530                 535                 540
Ser His Asn Thr Met Tyr Ser Tyr Lys Asp Thr Glu Arg Arg Arg Glu
545                 550                 555                 560
Trp Val Ala His Leu Gln Ala Gly Ala Gly Ile Val Ala Asp Ser Ser
            565                 570                 575
Pro Asp Asp Glu Gln Arg Glu Cys Glu Asn Lys Ala Ala Ala Leu Ala
```

```
                    580                 585                 590
Arg Ala Ile Asp Leu Ala Glu Ser Ala Phe Val Asp Lys Glu
            595                 600                 605

<210> SEQ ID NO 100
<211> LENGTH: 67
<212> TYPE: PRT
<213> ORGANISM: Oryza sativa

<400> SEQUENCE: 100

Met Cys Val Leu Val Ala Ala Val Arg Glu Glu Ser Lys Phe
1               5                   10                  15

Lys Ala Gly Ala Ala Glu Gly Cys Asn Ile Leu Pro Leu Lys Arg Cys
                20                  25                  30

Ile Phe Ser Asp His Leu Thr Pro Val Leu Ala Tyr Arg Cys Leu Val
            35                  40                  45

Arg Glu Asp Asp Arg Glu Ala Pro Ser Phe Leu Phe Glu Ser Val Glu
    50                  55                  60

Gln Gly Ser
65

<210> SEQ ID NO 101
<211> LENGTH: 525
<212> TYPE: PRT
<213> ORGANISM: Zea mays

<400> SEQUENCE: 101

Met Trp Glu Cys Ile Lys Gly Asn Leu Val Pro Met Trp Glu Cys Ile
1               5                   10                  15

Val Ser Asp His Leu Thr Pro Val Leu Ala Tyr Arg Cys Leu Val Pro
                20                  25                  30

Glu Asp Asn Val Asp Ala Pro Ser Phe Leu Phe Glu Ser Val Glu Gln
            35                  40                  45

Gly Pro Gln Gly Thr Thr Asn Val Gly Arg Tyr Ser Met Val Gly Ala
    50                  55                  60

His Pro Val Met Glu Ile Val Ala Lys Asp His Lys Val Thr Ile Met
65                  70                  75                  80

Asp His Glu Lys Ser Gln Val Thr Glu Gln Val Val Asp Asp Pro Met
                85                  90                  95

Gln Ile Pro Arg Thr Met Met Glu Gly Trp His Pro Gln Gln Ile Asp
            100                 105                 110

Glu Leu Pro Glu Ser Phe Ser Gly Gly Trp Val Gly Phe Ser Tyr
    115                 120                 125

Asp Thr Val Arg Tyr Val Glu Lys Lys Leu Pro Phe Ser Ser Ala
    130                 135                 140

Pro Gln Asp Asp Arg Asn Leu Pro Asp Val His Leu Gly Leu Tyr Asp
145                 150                 155                 160

Asp Val Leu Val Phe Asp Asn Val Glu Lys Lys Val Tyr Val Ile His
                165                 170                 175

Trp Val Asn Val Asp Arg His Ala Ser Val Glu Ala Tyr Gln Asp
            180                 185                 190

Gly Arg Ser Arg Leu Asn Met Leu Ser Lys Val His Asn Ser Asn
    195                 200                 205

Val Pro Thr Leu Ser Pro Gly Phe Val Lys Leu His Thr Arg Lys Phe
    210                 215                 220

Gly Thr Pro Leu Asn Lys Ser Thr Met Thr Ser Asp Glu Tyr Lys Asn
```

```
                225                 230                 235                 240
Ala Val Leu Gln Ala Lys Glu His Ile Met Ala Gly Asp Ile Phe Gln
                245                 250                 255

Ile Val Leu Ser Gln Arg Phe Glu Arg Arg Thr Tyr Ala Asn Pro Phe
                260                 265                 270

Glu Val Tyr Arg Ala Leu Arg Ile Val Asn Pro Ser Pro Tyr Met Ala
                275                 280                 285

Tyr Val Gln Ala Arg Gly Cys Val Leu Val Ala Ser Ser Pro Glu Ile
                290                 295                 300

Leu Thr Arg Val Ser Lys Gly Lys Ile Ile Asn Arg Pro Leu Ala Gly
305                 310                 315                 320

Thr Val Arg Arg Gly Lys Thr Glu Lys Glu Asp Gln Met Gln Glu Gln
                325                 330                 335

Gln Leu Leu Ser Asp Glu Lys Gln Cys Ala Glu His Ile Met Leu Val
                340                 345                 350

Asp Leu Gly Arg Asn Asp Val Gly Lys Val Ser Lys Pro Gly Gly Ser
                355                 360                 365

Val Lys Val Glu Lys Leu Ile Ile Glu Arg Tyr Ser His Val Met His
                370                 375                 380

Ile Ser Ser Thr Val Ser Gly Gln Leu Asp Asp His Leu Gln Ser Trp
385                 390                 395                 400

Asp Ala Leu Arg Ala Ala Leu Pro Val Gly Thr Val Ser Gly Ala Pro
                405                 410                 415

Lys Val Lys Ala Met Glu Leu Ile Asp Lys Leu Glu Val Thr Arg Arg
                420                 425                 430

Gly Pro Tyr Ser Gly Gly Leu Gly Gly Ile Ser Phe Asp Gly Asp Met
                435                 440                 445

Gln Ile Ala Leu Ser Leu Arg Thr Ile Val Phe Ser Thr Ala Pro Ser
                450                 455                 460

His Asn Thr Met Tyr Ser Tyr Lys Asp Ala Asp Arg Arg Arg Glu Trp
465                 470                 475                 480

Val Ala His Leu Gln Ala Gly Ala Gly Ile Val Ala Asp Ser Ser Pro
                485                 490                 495

Asp Asp Glu Gln Arg Glu Cys Glu Asn Lys Ala Ala Ala Leu Ala Arg
                500                 505                 510

Ala Ile Asp Leu Ala Glu Ser Ala Phe Val Asn Lys Glu
                515                 520                 525

<210> SEQ ID NO 102
<211> LENGTH: 92
<212> TYPE: PRT
<213> ORGANISM: Triticum aestivum

<400> SEQUENCE: 102

Pro Asn Ser Gly Gly Leu Gly Gly Ile Ser Phe Asp Gly Asp Met Leu
1               5                   10                  15

Ile Ala Leu Ala Leu Arg Thr Ile Val Phe Ser Thr Ala Pro Ser Pro
                20                  25                  30

Asn Arg Met Tyr Ser Tyr Lys Ser Ser Asp Arg Pro Arg Glu Trp Val
                35                  40                  45

Ala His Leu Gln Ala Gly Ala Gly Ile Val Ala Asp Ser Ile Pro Asp
                50                  55                  60

Asp Glu Gln Lys Glu Phe Glu Asn Lys Ala Ala Ala Leu Ala Arg Ala
65                  70                  75                  80
```

```
Ile Asp Leu Ala Glu Ser Ala Phe Leu Asp Lys Glu
            85                  90
```

<210> SEQ ID NO 103
<211> LENGTH: 616
<212> TYPE: PRT
<213> ORGANISM: Nicotiana tabacum

<400> SEQUENCE: 103

```
Met Gln Ser Leu Pro Ile Ser Tyr Arg Leu Phe Pro Ala Thr His Arg
1               5                   10                  15

Lys Val Leu Pro Phe Ala Val Ile Ser Ser Arg Ser Thr Ser Ala
            20                  25                  30

Leu Ala Leu Arg Val Arg Thr Leu Gln Cys Arg Cys Leu His Ser Ser
            35                  40                  45

Ser Leu Val Met Asp Glu Asp Arg Phe Ile Glu Ala Ser Lys Ser Gly
        50                  55                  60

Asn Leu Ile Pro Leu His Lys Thr Ile Phe Ser Asp His Leu Thr Pro
65                  70                  75                  80

Val Leu Ala Tyr Arg Cys Leu Val Lys Glu Asp Asp Arg Glu Ala Pro
                85                  90                  95

Ser Phe Leu Phe Glu Ser Val Glu Pro Gly Phe Arg Gly Ser Ser Val
            100                 105                 110

Gly Arg Tyr Ser Val Val Gly Ala Gln Pro Ser Met Glu Ile Val Ala
            115                 120                 125

Lys Glu His Asn Val Thr Ile Leu Asp His His Thr Gly Lys Leu Thr
130                 135                 140

Gln Lys Thr Val Gln Asp Pro Met Thr Ile Pro Arg Ser Ile Ser Glu
145                 150                 155                 160

Gly Trp Lys Pro Arg Leu Ile Asp Glu Leu Pro Asp Thr Phe Cys Gly
                165                 170                 175

Gly Trp Val Gly Tyr Phe Ser Tyr Asp Thr Val Arg Tyr Val Glu Asn
            180                 185                 190

Arg Lys Leu Pro Phe Leu Arg Ala Pro Glu Asp Asp Arg Asn Leu Ala
        195                 200                 205

Asp Ile Gln Leu Gly Leu Tyr Glu Asp Val Ile Val Phe Asp His Val
210                 215                 220

Glu Lys Lys Ala His Val Ile His Trp Val Gln Leu Asp Gln Tyr Ser
225                 230                 235                 240

Ser Leu Pro Glu Ala Tyr Leu Asp Gly Lys Lys Arg Leu Glu Ile Leu
                245                 250                 255

Val Ser Arg Val Gln Gly Ile Glu Ser Pro Arg Leu Ser Pro Gly Ser
            260                 265                 270

Val Asp Phe Cys Thr His Ala Phe Gly Pro Ser Leu Thr Lys Gly Asn
        275                 280                 285

Met Thr Ser Glu Glu Tyr Lys Asn Ala Val Leu Gln Ala Lys Glu His
    290                 295                 300

Ile Ala Ala Gly Asp Ile Phe Gln Ile Val Leu Ser Gln Arg Phe Glu
305                 310                 315                 320

Arg Arg Thr Phe Ala Asp Pro Phe Glu Val Tyr Arg Ala Leu Arg Ile
                325                 330                 335

Val Asn Pro Ser Pro Tyr Met Thr Tyr Ile Gln Ala Arg Gly Cys Ile
            340                 345                 350

Leu Val Ala Ser Ser Pro Glu Ile Leu Thr Arg Val Lys Lys Arg Arg
        355                 360                 365
```

```
Ile Val Asn Arg Pro Leu Ala Gly Thr Ser Arg Gly Lys Thr Pro
    370                 375                 380

Asp Glu Asp Val Met Leu Glu Met Gln Met Leu Lys Asp Glu Lys Gln
385                 390                 395                 400

Arg Ala Glu His Ile Met Leu Val Asp Leu Gly Arg Asn Asp Val Gly
                405                 410                 415

Lys Val Ser Lys Pro Gly Ser Val Asn Val Glu Lys Leu Met Ser Val
                420                 425                 430

Glu Arg Tyr Ser His Val Met His Ile Ser Ser Thr Val Ser Gly Glu
            435                 440                 445

Leu Leu Asp His Leu Thr Cys Trp Asp Ala Leu Arg Ala Ala Leu Pro
    450                 455                 460

Val Gly Thr Val Ser Gly Ala Pro Lys Val Lys Ala Met Glu Leu Ile
465                 470                 475                 480

Asp Gln Leu Glu Val Ala Arg Arg Gly Pro Tyr Ser Gly Gly Phe Gly
                485                 490                 495

Gly Ile Ser Phe Ser Gly Asp Met Asp Ile Ala Leu Ala Leu Arg Thr
                500                 505                 510

Met Val Phe Leu Asn Gly Ala Arg Tyr Asp Thr Met Tyr Ser Tyr Thr
            515                 520                 525

Asp Ala Ser Lys Arg Gln Glu Trp Val Ala His Leu Gln Ser Gly Ala
    530                 535                 540

Gly Ile Val Ala Asp Ser Asn Pro Asp Glu Glu Gln Ile Glu Cys Glu
545                 550                 555                 560

Asn Lys Val Ala Gly Leu Cys Arg Ala Ile Asp Leu Ala Glu Ser Ala
                565                 570                 575

Phe Val Lys Gly Arg His Lys Pro Ser Val Lys Ile Asn Gly Ser Val
                580                 585                 590

Pro Asn Leu Phe Ser Arg Val Gln Arg Gln Thr Ser Val Met Ser Lys
            595                 600                 605

Asp Arg Val His Glu Lys Arg Asn
    610                 615

<210> SEQ ID NO 104
<211> LENGTH: 1776
<212> TYPE: DNA
<213> ORGANISM: Gossypium hirsutum

<400> SEQUENCE: 104
atgcaggcat ccatgtcggt tacctcgacg aactccacat taccaatgcc agtgcaaagc      60
agccttggat tctctcaccg cttccttcct tcatctcatc ggttttctca acttccgatc     120
acccgctttt ctcccgctcc tacttcactc aaatgcaggg gctctctttc aagcttttcca    180 cttgttaatg atgaaaagaa gtttgtggag gcggccaaaa aagcaaattt agtccccctt     240
tatcgttgca ttttctctga tcaactgact ccagtgcttg cataccggtg tttggttaaa     300
gaagatgata gagaggctcc aagttttctc tttgagtcag tggagcctgg ttctcgggtt     360
tctagtgttg gtcgatatag cgtggttgga gctcaaccga caatggaaat tgtggcaaaa     420
gaaaacaaag ttatgattat ggatcatgag gcagggaatt tgactgagga ggtcgttgag     480
gatccgatgt gtattcccaa gagaatctca gagacttgga aaccccgact tgttgaagat     540
cttcctgatg cgttttgtgg tggatgggtt ggttatttct cctatgatac agttcgttat     600
gtggagaaga aaaagcttcc gttcactaag gcaccacgtg atgacagaaa cctgccagat     660
```

```
atacatctag gactctacaa cgacgtgatt gtatttgatc atgtggaaaa gaaagcatat      720
ataattcact gggtgaggct agataaacac tcgtctgttg agaaagctta taatgaagga      780
gttgaacacc tagagaaatt ggtagctaga gtacaagatg ttgagctacc aaagctatct      840
ccaggctctg tagcattaca aacccatcac tttggccctt ctttaaagaa ctcaaatatg      900
gaaaaggaag agttcaagaa agctgtactg aaagcgaaag agcatattct ggcaggggat      960
attttccaga ttgtattaag ccaacgtttt gaacggagaa catttgctga cccctttgaa     1020
atatatagag ctttgcgagt tgtgaatcca agtccatata tggcctactt gcaagctaga     1080
ggaagtattc tagttgcttc aagtcccgaa attcttacca gggtaaagaa gaataagatt     1140
gtgaataggc cattggctgg aacaacaagg agaggaaaga ctcaggctga agatgagctg     1200
gcagaaaagc tattgctaag taatgaaaag gaatgtgcag aacacatcat gcttgttgat     1260
ttgggtcgca atgatgttgg aaaggtctcc aaatatggtt ctgtaaaggt ggagaagctg     1320
atgaatattg aacgatattc ccatgtgatg cacataagct ccacggttac tggtgagttg     1380
caggatcatc tcactagttg ggatgtcctc cgtgctgcac ttcccgttgg aactgttagt     1440
ggagcaccaa aggtgaaggc gatggagcta atcgatgagt tagaggtgtc aagacgaggt     1500
ccttatagcg gaggatttgg gggcatttcc ttcactgggg atatggatat tgcgttggct     1560
ctcaggacca tggtattccc tacaggtagc cgctatgaca caatgtactc atacaaaggt     1620
tccagcagac gccaagaatg ggtagcttat cttcaagccg gcgctggtgt agttgcagac     1680
agtgatcctg atgccgagca cctcgaatgt caaaacaaag ctgctggcct tgctcgttcc     1740
attgacctag cggaggctgc attcgttcat aaatga                              1776

<210> SEQ ID NO 105
<211> LENGTH: 843
<212> TYPE: DNA
<213> ORGANISM: Gossypium hirsutum

<400> SEQUENCE: 105
atggcagcta atattataac ccaatcatct ctgcttcagc caaaacctgc actttctgct       60
aaaacccttc aaatcccatc tctgcatcgc ttatccggcc tccctcctcc atcaagggtt      120
ggcttttttc tggaaaagaa aacggggatt gttggaaaag ctccattaaa atcggctgta      180
tcggactcaa cctcgtcagt tttggagaac aagaaaaaca gcaagaatcc cattgtcgtc      240
attgacaatt acgacagttt cacttacaat cttttgccagt atattggaga gcttggatgt      300
tacttcgagg ttttttcgaaa tgacgaatta actgtagaag acttaaaaat gaaaaaccct      360
aggggagtgc ttatctctcc tggtccagga acaccccaag attccggaat atcactgcag      420 actgtttttgg aacttggacc tactgtacct ttgtttggtg tttgtatggg tttgcagtgc      480
attggtgagg cttttggagg aaagatagtg cgttctccct atggtgttat gcatggcaaa      540
agttcccctg tatattatga cgaaaagggg gaagacggtt tgttatctgg attgtcaaac      600
cctttcaatg ctggcagata tcatagcctc gtgattgaaa aggacagttt ccctgaggaa      660
gcacttgagg ttactgcttg gacagaagat ggactgataa tggctgctag gcacaaagtt      720
tataagcatc tgcagggtgt tcaattccat ccagagagca tcataaccctc tgaaggaaaa      780 acaattgttc ggaatttcat caaactaatc gagagaaagg aggtggcagg atccaagaat      840
tag                                                                    843

<210> SEQ ID NO 106
<211> LENGTH: 1704
```

```
<212> TYPE: DNA
<213> ORGANISM: Glycine max

<400> SEQUENCE: 106
atggcgactg ttccgcaccc attatccctc gcaagtgtag gttttgctaa ccgaacctcc      60
tccatctcca gatccactct caaatgctgc gctcaatctc cttctccttc actagttgac     120
aacgcccaga gtttctcga agcttccaag aaggggaacg tcattcctct cttccgctgc     180
atattttccg atcacctcac tccggtgctt gcgtaccggt gcctggttaa ggaggacgag     240
agagatgctc cgagttttct ctttgaatcg gtcgagccag gccaaatttc tagcatcgga     300
cggtacagtg tggttggagc acagccgtgt atggaaattg tggcgaaaga gaacgtggtt     360
actattatgg accacgtgga agggcgcagg agtgaggaaa ttgtagagga tcctctggtg     420
attcctcgta ggatcatgga gaagtggacg cctcaactct tagatgaact tcctgaagcg     480
ttttgtggtg gttgggtagg gtatttctct tatgatacaa tgcgctatgt agaaaagaag     540
aaacttccat tttctaatgc cccagtagat gacagaaacc ttcctgatgt tcatctgggc     600
ctttatgaca gtgtgattgt gtttgatcat gttgaaaaga agcatatgt gattcattgg     660
gttcgggtgg atcgatattc ttcagctgag gaggccttcg aagatggaag gaaccggctg     720
gaaactctag tatctcgggt gcatgatata attaccccaa ggctgcctac aggttcgata     780
aagttataca ctcgtctctt tggtcctaaa ctggagatgt caaacatgac aaatgaggag     840
tataagaggg cagtattgaa ggctaaagag cacatacggg ctggtgatat ttttcaaatt     900
gtactaagtc aacgttttga acagagaact tttgcagacc catttgaaat ctacagagca     960
ttgaggattg ttaatcctag tccatatatg acttattac aggccagagg aagtattttg    1020
gttgcttcaa gtcagaaaat tcttacacgg gtgaagaaga gaaagatcac caatcggccc    1080
cttgctggta ctgttagaag aggaaaaaca ccaaaagaag atatcatgtt ggagaaacaa    1140
cttttgaatg atgaaaagca atgtgcagag cacgtaatgc tagttgattt ggggagaaat    1200
gatgttggaa aggtctccaa accgggttct gttcaagttg aaaagcttat gaatattgag    1260
cgctattccc atgttatgca catcagctca acagtcacag gggagttatt agatcactta    1320
acaagctggg atgcattgcg tgctgcttta cctgttggta cagttagcgg agcaccgaag    1380
gtcaaagcca tgcagttgat tgatgagttg aagtcgcaa aaggggggcc ctatagtggg    1440
ggatttggag gtatatcatt caatggcgat atggacatag cccttgctct gaggaccata    1500
gttttcccta caaatgctcg ttatgacaca atgtactcct acaaggataa gaacaaacgc    1560
agagaatggg ttgcccatct ccaggctgga gcgggaattg tggctgacag tgatcctgct    1620
gatgaacaaa gagagtgcga gaacaaagct gcagctcttg ctcgtgccat tgatcttgca    1680
gaatcttcat tgttgataa ataa                                            1704

<210> SEQ ID NO 107
<211> LENGTH: 837
<212> TYPE: DNA
<213> ORGANISM: Glycine max

<400> SEQUENCE: 107
atggctgcca cattcttctc tcacttgtcg cttcttcaat ccaacaacaa cccttctctc      60
tctcacacac cctctcgctt ccctcattct ctcaccaacc gtgtcaaacc ctccctcggt     120
gtggtatctg tggccaaaag ggtaagtgga gtggtgccaa aggccaattt gaatgccttg     180
gaggccaatt cgggtttccc catttcggct aagaagtcca caacaaccc cattgttgtt     240
```

-continued

```
attgacaact atgacagttt cacctataat ctttgccagt atatggggga gttagggttt    300
cactttgagg tctaccgcaa tgatgagttg acagtggagg agttaagaag gaaaaatccc    360
agaggagtgc tgatatcacc tgggccagga gaacctcaag attcaggcat atctttgcaa    420
acggttttgg aacttggacc aactgtgcca ttgtttggtg tgtgcatggg tttgcaatgc    480
attggagagg cttttggagg gaagattgtt cgttctcctc atggtgttat gcatggaaaa    540
agctctatgg tttactatga tgagaaagga gaagatggat tacttgctgg actatcaaat    600
cctttcttgg ctggtagata tcacagcctt gtaattgaaa agagagcctt tcctcatgat    660
gaacttgagg caacagcatg gacagaagat ggtcttataa tggctgctcg tcataagaaa    720
tataagcatc tacagggtgt tcagtttcat ccagagagca tcataacccc agaaggcaag    780
acaattgtcc gtaattttgt caagcttatc gagaaagggg aggctggtgg ctcttga      837
```

<210> SEQ ID NO 108
<211> LENGTH: 591
<212> TYPE: PRT
<213> ORGANISM: Gossypium hirsutum

<400> SEQUENCE: 108

```
Met Gln Ala Ser Met Ser Val Thr Ser Thr Asn Ser Thr Leu Pro Met
1               5                   10                  15

Pro Val Gln Ser Ser Leu Gly Phe Ser His Arg Phe Leu Pro Ser Ser
                20                  25                  30

His Arg Phe Ser Gln Leu Pro Ile Thr Arg Phe Ser Pro Ala Pro Thr
            35                  40                  45

Ser Leu Lys Cys Arg Gly Ser Leu Ser Ser Phe Pro Leu Val Asn Asp
        50                  55                  60

Glu Lys Lys Phe Val Glu Ala Ala Lys Lys Ala Asn Leu Val Pro Leu
65                  70                  75                  80

Tyr Arg Cys Ile Phe Ser Asp Gln Leu Thr Pro Val Leu Ala Tyr Arg
                85                  90                  95

Cys Leu Val Lys Glu Asp Asp Arg Glu Ala Pro Ser Phe Leu Phe Glu
                100                 105                 110

Ser Val Glu Pro Gly Ser Arg Val Ser Ser Val Gly Arg Tyr Ser Val
            115                 120                 125

Val Gly Ala Gln Pro Thr Met Glu Ile Val Ala Lys Glu Asn Lys Val
        130                 135                 140

Met Ile Met Asp His Glu Ala Gly Asn Leu Thr Glu Glu Val Val Glu
145                 150                 155                 160

Asp Pro Met Cys Ile Pro Lys Arg Ile Ser Glu Thr Trp Lys Pro Arg
                165                 170                 175

Leu Val Glu Asp Leu Pro Asp Ala Phe Cys Gly Gly Trp Val Gly Tyr
                180                 185                 190

Phe Ser Tyr Asp Thr Val Arg Tyr Val Glu Lys Lys Leu Pro Phe
            195                 200                 205

Thr Lys Ala Pro Arg Asp Asp Arg Asn Leu Pro Asp Ile His Leu Gly
        210                 215                 220

Leu Tyr Asn Asp Val Ile Val Phe Asp His Val Glu Lys Lys Ala Tyr
225                 230                 235                 240

Ile Ile His Trp Val Arg Leu Asp Lys His Ser Ser Val Glu Lys Ala
                245                 250                 255

Tyr Asn Glu Gly Val Glu His Leu Glu Lys Leu Val Ala Arg Val Gln
            260                 265                 270
```

```
Asp Val Glu Leu Pro Lys Leu Ser Pro Gly Ser Val Ala Leu Gln Thr
            275                 280                 285

His His Phe Gly Pro Ser Leu Lys Asn Ser Asn Met Glu Lys Glu Glu
            290                 295                 300

Phe Lys Lys Ala Val Leu Lys Ala Lys Glu His Ile Leu Ala Gly Asp
305                 310                 315                 320

Ile Phe Gln Ile Val Leu Ser Gln Arg Phe Glu Arg Arg Thr Phe Ala
                325                 330                 335

Asp Pro Phe Glu Ile Tyr Arg Ala Leu Arg Val Val Asn Pro Ser Pro
            340                 345                 350

Tyr Met Ala Tyr Leu Gln Ala Arg Gly Ser Ile Leu Val Ala Ser Ser
            355                 360                 365

Pro Glu Ile Leu Thr Arg Val Lys Lys Asn Lys Ile Val Asn Arg Pro
            370                 375                 380

Leu Ala Gly Thr Thr Arg Arg Gly Lys Thr Gln Ala Glu Asp Glu Leu
385                 390                 395                 400

Ala Glu Lys Leu Leu Leu Ser Asn Glu Lys Glu Cys Ala Glu His Ile
                405                 410                 415

Met Leu Val Asp Leu Gly Arg Asn Asp Val Gly Lys Val Ser Lys Tyr
            420                 425                 430

Gly Ser Val Lys Val Glu Lys Leu Met Asn Ile Glu Arg Tyr Ser His
            435                 440                 445

Val Met His Ile Ser Ser Thr Val Thr Gly Glu Leu Gln Asp His Leu
            450                 455                 460

Thr Ser Trp Asp Val Leu Arg Ala Ala Leu Pro Val Gly Thr Val Ser
465                 470                 475                 480

Gly Ala Pro Lys Val Lys Ala Met Glu Leu Ile Asp Glu Leu Glu Val
                485                 490                 495

Ser Arg Arg Gly Pro Tyr Ser Gly Gly Phe Gly Gly Ile Ser Phe Thr
            500                 505                 510

Gly Asp Met Asp Ile Ala Leu Ala Leu Arg Thr Met Val Phe Pro Thr
            515                 520                 525

Gly Ser Arg Tyr Asp Thr Met Tyr Ser Tyr Lys Gly Ser Ser Arg Arg
            530                 535                 540

Gln Glu Trp Val Ala Tyr Leu Gln Ala Gly Ala Gly Val Val Ala Asp
545                 550                 555                 560

Ser Asp Pro Asp Ala Glu His Leu Glu Cys Gln Asn Lys Ala Ala Gly
                565                 570                 575

Leu Ala Arg Ser Ile Asp Leu Ala Glu Ala Ala Phe Val His Lys
            580                 585                 590

<210> SEQ ID NO 109
<211> LENGTH: 280
<212> TYPE: PRT
<213> ORGANISM: Gossypium hirsutum

<400> SEQUENCE: 109

Met Ala Ala Asn Ile Ile Thr Gln Ser Ser Leu Leu Gln Pro Lys Pro
1               5                   10                  15

Ala Leu Ser Ala Lys Thr Leu Gln Ile Pro Ser Leu His Arg Leu Ser
            20                  25                  30

Gly Leu Pro Pro Pro Ser Arg Val Gly Phe Phe Leu Glu Lys Lys Thr
        35                  40                  45

Gly Ile Val Gly Lys Ala Pro Leu Lys Ser Ala Val Ser Asp Ser Thr
    50                  55                  60
```

-continued

```
Ser Ser Val Leu Glu Asn Lys Lys Asn Ser Lys Asn Pro Ile Val Val
65                  70                  75                  80

Ile Asp Asn Tyr Asp Ser Phe Thr Tyr Asn Leu Cys Gln Tyr Ile Gly
                85                  90                  95

Glu Leu Gly Cys Tyr Phe Glu Val Phe Arg Asn Asp Glu Leu Thr Val
            100                 105                 110

Glu Asp Leu Lys Met Lys Asn Pro Arg Gly Val Leu Ile Ser Pro Gly
        115                 120                 125

Pro Gly Thr Pro Gln Asp Ser Gly Ile Ser Leu Gln Thr Val Leu Glu
    130                 135                 140

Leu Gly Pro Thr Val Pro Leu Phe Gly Val Cys Met Gly Leu Gln Cys
145                 150                 155                 160

Ile Gly Glu Ala Phe Gly Gly Lys Ile Val Arg Ser Pro Tyr Gly Val
                165                 170                 175

Met His Gly Lys Ser Ser Pro Val Tyr Tyr Asp Glu Lys Gly Glu Asp
            180                 185                 190

Gly Leu Leu Ser Gly Leu Ser Asn Pro Phe Asn Ala Gly Arg Tyr His
        195                 200                 205

Ser Leu Val Ile Glu Lys Asp Ser Phe Pro Glu Glu Ala Leu Glu Val
    210                 215                 220

Thr Ala Trp Thr Glu Asp Gly Leu Ile Met Ala Ala Arg His Lys Val
225                 230                 235                 240

Tyr Lys His Leu Gln Gly Val Gln Phe His Pro Glu Ser Ile Ile Thr
                245                 250                 255

Ser Glu Gly Lys Thr Ile Val Arg Asn Phe Ile Lys Leu Ile Glu Arg
            260                 265                 270

Lys Glu Val Ala Gly Ser Lys Asn
        275                 280

<210> SEQ ID NO 110
<211> LENGTH: 567
<212> TYPE: PRT
<213> ORGANISM: Glycine max

<400> SEQUENCE: 110

Met Ala Thr Val Pro His Pro Leu Ser Leu Ala Ser Val Gly Phe Ala
1               5                   10                  15

Asn Arg Thr Ser Ser Ile Ser Arg Ser Thr Leu Lys Cys Cys Ala Gln
                20                  25                  30

Ser Pro Ser Pro Ser Leu Val Asp Asn Ala Gln Lys Phe Leu Glu Ala
            35                  40                  45

Ser Lys Lys Gly Asn Val Ile Pro Leu Phe Arg Cys Ile Phe Ser Asp
        50                  55                  60

His Leu Thr Pro Val Leu Ala Tyr Arg Cys Leu Val Lys Glu Asp Glu
65                  70                  75                  80

Arg Asp Ala Pro Ser Phe Leu Phe Glu Ser Val Glu Pro Gly Gln Ile
                85                  90                  95

Ser Ser Ile Gly Arg Tyr Ser Val Val Gly Ala Gln Pro Cys Met Glu
            100                 105                 110

Ile Val Ala Lys Glu Asn Val Val Thr Ile Met Asp His Val Glu Gly
        115                 120                 125

Arg Arg Ser Glu Glu Ile Val Glu Asp Pro Leu Val Ile Pro Arg Arg
    130                 135                 140

Ile Met Glu Lys Trp Thr Pro Gln Leu Leu Asp Glu Leu Pro Glu Ala
```

-continued

```
        145                 150                 155                 160
    Phe Cys Gly Gly Trp Val Gly Tyr Phe Ser Tyr Asp Thr Met Arg Tyr
                    165                 170                 175

Val Glu Lys Lys Lys Leu Pro Phe Ser Asn Ala Pro Val Asp Asp Arg
                    180                 185                 190

Asn Leu Pro Asp Val His Leu Gly Leu Tyr Asp Ser Val Ile Val Phe
                    195                 200                 205

Asp His Val Glu Lys Lys Ala Tyr Val Ile His Trp Val Arg Val Asp
                    210                 215                 220

Arg Tyr Ser Ser Ala Glu Glu Ala Phe Glu Asp Gly Arg Asn Arg Leu
    225                 230                 235                 240

Glu Thr Leu Val Ser Arg Val His Asp Ile Ile Thr Pro Arg Leu Pro
                    245                 250                 255

Thr Gly Ser Ile Lys Leu Tyr Thr Arg Leu Phe Gly Pro Lys Leu Glu
                    260                 265                 270

Met Ser Asn Met Thr Asn Glu Gly Tyr Lys Arg Ala Val Leu Lys Ala
                    275                 280                 285

Lys Glu His Ile Arg Ala Gly Asp Ile Phe Gln Ile Val Leu Ser Gln
                    290                 295                 300

Arg Phe Glu Gln Arg Thr Phe Ala Asp Pro Phe Glu Ile Tyr Arg Ala
    305                 310                 315                 320

Leu Arg Ile Val Asn Pro Ser Pro Tyr Met Thr Tyr Leu Gln Ala Arg
                    325                 330                 335

Gly Ser Ile Leu Val Ala Ser Ser Pro Glu Ile Leu Thr Arg Val Lys
                    340                 345                 350

Lys Arg Lys Ile Thr Asn Arg Pro Leu Ala Gly Thr Val Arg Arg Gly
                    355                 360                 365

Lys Thr Pro Lys Glu Asp Ile Met Leu Glu Lys Gln Leu Leu Asn Asp
                    370                 375                 380

Glu Lys Gln Cys Ala Glu His Val Met Leu Val Asp Leu Gly Arg Asn
    385                 390                 395                 400

Asp Val Gly Lys Val Ser Lys Pro Gly Ser Val Gln Val Glu Lys Leu
                    405                 410                 415

Met Asn Ile Glu Arg Tyr Ser His Val Met His Ile Ser Ser Thr Val
                    420                 425                 430

Thr Gly Glu Leu Leu Asp His Leu Thr Ser Trp Asp Ala Leu Arg Ala
                    435                 440                 445

Ala Leu Pro Val Gly Thr Val Ser Gly Ala Pro Lys Val Lys Ala Met
                    450                 455                 460

Gln Leu Ile Asp Glu Leu Glu Val Ala Arg Arg Gly Pro Tyr Ser Gly
    465                 470                 475                 480

Gly Phe Gly Gly Ile Ser Phe Asn Gly Asp Met Asp Ile Ala Leu Ala
                    485                 490                 495

Leu Arg Thr Ile Val Phe Pro Thr Asn Ala Arg Tyr Asp Thr Met Tyr
                    500                 505                 510

Ser Tyr Lys Asp Lys Asn Lys Arg Arg Glu Trp Val Ala His Leu Gln
                    515                 520                 525

Ala Gly Ala Gly Ile Val Ala Asp Ser Asp Pro Ala Asp Glu Gln Arg
                    530                 535                 540

Glu Cys Glu Asn Lys Ala Ala Ala Leu Ala Arg Ala Ile Asp Leu Ala
    545                 550                 555                 560

Glu Ser Ser Phe Val Asp Lys
                    565
```

<210> SEQ ID NO 111
<211> LENGTH: 278
<212> TYPE: PRT
<213> ORGANISM: Glycine max

<400> SEQUENCE: 111

Met Ala Ala Thr Phe Phe Ser His Leu Ser Leu Leu Gln Ser Asn Asn
1               5                   10                  15

Asn Pro Ser Leu Ser His Thr Pro Ser Arg Phe Pro His Ser Leu Thr
            20                  25                  30

Asn Arg Val Lys Pro Ser Leu Gly Val Ser Val Ala Lys Arg Val
        35                  40                  45

Ser Gly Val Val Pro Lys Ala Asn Leu Asn Ala Leu Glu Ala Asn Ser
50                  55                  60

Gly Phe Pro Ile Ser Ala Lys Lys Ser Asn Asn Pro Ile Val Val
65                  70                  75                  80

Ile Asp Asn Tyr Asp Ser Phe Thr Tyr Asn Leu Cys Gln Tyr Met Gly
                85                  90                  95

Glu Leu Gly Phe His Phe Glu Val Tyr Arg Asn Asp Glu Leu Thr Val
            100                 105                 110

Glu Glu Leu Arg Arg Lys Asn Pro Arg Gly Val Leu Ile Ser Pro Gly
        115                 120                 125

Pro Gly Glu Pro Gln Asp Ser Gly Ile Ser Leu Gln Thr Val Leu Glu
130                 135                 140

Leu Gly Pro Thr Val Pro Leu Phe Gly Val Cys Met Gly Leu Gln Cys
145                 150                 155                 160

Ile Gly Glu Ala Phe Gly Gly Lys Ile Val Arg Ser Pro His Gly Val
                165                 170                 175

Met His Gly Lys Ser Ser Met Val Tyr Tyr Asp Glu Lys Gly Glu Asp
            180                 185                 190

Gly Leu Leu Ala Gly Leu Ser Asn Pro Phe Leu Ala Gly Arg Tyr His
        195                 200                 205

Ser Leu Val Ile Glu Lys Glu Ser Phe Pro His Asp Glu Leu Glu Ala
210                 215                 220

Thr Ala Trp Thr Glu Asp Gly Leu Ile Met Ala Ala Arg His Lys Lys
225                 230                 235                 240

Tyr Lys His Leu Gln Gly Val Gln Phe His Pro Glu Ser Ile Ile Thr
                245                 250                 255

Pro Glu Gly Lys Thr Ile Val Arg Asn Phe Val Lys Leu Ile Glu Lys
            260                 265                 270

Arg Glu Ala Gly Gly Ser
        275

<210> SEQ ID NO 112
<211> LENGTH: 2210
<212> TYPE: DNA
<213> ORGANISM: Glycine max

<400> SEQUENCE: 112
aaagaaatga cctgaagtct ctatatattc caggtaacga agaccttagc aacccaatga     60
acgcgtcccc atgaacggca cgtgtagcgg agtactaggc cgccgttaca cgctactgct    120
gtccgtcgtc accgtttgaa ttacccaccg ctactttgtc gtcattcttc ttcttcttcc    180
cttttcattg acctttcct tccttcgtcc tccaatggcg actgttccgc acccattatc    240

-continued

```
cctcgcaagt gtaggttttg ctaaccgaac ctcctccatc tccagatcca ctctcaaatg      300
ctgcgctcaa tctccttctc cttcactagt tgacaacgcc cagaagtttc tcgaagcttc      360
caagaagggg aacgtcattc ctctcttccg ctgcatattt tccgatcacc tcactccggt      420
gcttgcgtac cggtgcctgg ttaaggagga cgagagagat gctccgagtt ttctctttga      480
atcggtcgag ccaggccaaa tttctagcat cggacggtac agtgtggttg agcacagcc       540 gtgtatggaa attgtggcga agagaacgt ggttactatt atggaccacg tggaagggcg       600
caggagtgag gaaattgtag aggatcctct ggtgattcct cgtaggatca tggagaagtg      660
gacgcctcaa ctcttagatg aacttcctga agcgttttgt ggtggttggg tagggtattt      720
ctcttatgat acaatgcgct atgtagaaaa aagaaaactt ccattttcta atgccccagt      780
agatgacaga aaccttcctg atgttcatct gggcctttat gacagtgtga ttgtgtttga      840
tcatgttgaa aagaaagcat atgtgattca ttgggttcgg gtggatcgat attcttcagc      900
tgaggaggcc ttcgaagatg gaaggaaccg gctggaaact ctagtatctc gggtgcatga      960
tataattacc ccaaggctgc ctacaggttc gataaagtta tacactcgtc tctttggtcc     1020
taaactggag atgtcaaaca tgacaaatga ggagtataag agggcagtat tgaaggctaa     1080
agagcacata cgggctggtg atattttttca aattgtacta agtcaacgtt ttgaacagag     1140
aacttttgca gacccatttg aaatctacag agcattgagg attgttaatc ctagtccata     1200
tatgacttat ttacaggcca gaggaagtat tttggttgct tcaagtccag aaattcttac     1260
acgggtgaag aagagaaaga tcaccaatcg gccccttgct ggtactgtta aagaggaaa      1320 aacaccaaaa gaagatatca tgttggagaa acaacttttg aatgatgaaa agcaatgtgc     1380
agagcacgta atgctagttg atttgggggag aaatgatgtt ggaaaggtct ccaaaccggg     1440
ttctgttcaa gttgaaaagc ttatgaatat tgagcgctat tcccatgtta tgcacatcag     1500
ctcaacagtc acaggggagt tattagatca cttaacaagc tgggatgcat tgcgtgctgc     1560
tttacctgtt ggtacagtta gcggagcacc gaaggtcaaa gccatgcagt tgattgatga     1620
gttggaagtc gcaagaaggg ggccctatag tgggggatt ggaggtatat cattcaatgg      1680
cgatatggac atagcccttg ctctgaggac catagttttc cctacaaatg ctcgttatga     1740
cacaatgtac tcctacaagg ataagaacaa acgcagagaa tgggttgccc atctccaggc     1800
tggagcggga attgtggctg acagtgatcc tgctgatgaa caaagagagt gcgagaacaa     1860
agctgcagct cttgctcgtg ccattgatct tgcagaatct tcatttgttg ataaataatt     1920
tggattgatc catcatcagt gatgctcctt gataactgag gggcatcctt tttaaatggt     1980
agagaggaag tttgtggtgt gggcagatga tagggggatat gaattacgga gaatctgaaa     2040
ctttgataat gttatgacag aagtgatgaa cataataagg tatttaatga taatgacagc     2100
tttgtgactt tagttaagtc gtcgtttaag agacttcaat agccatttcc gtcggtccat     2160
cttaaaccaa agaaaggtgc ctttgacgga gtttcttttg ctatcataaa               2210
```

<210> SEQ ID NO 113
<211> LENGTH: 988
<212> TYPE: DNA
<213> ORGANISM: Glycine max

<400> SEQUENCE: 113

```
actcggctat gcatccaacg cgttgggagc tctcccatat ggtcgacctg caggcggccg      60
cgaattcact agtgattaac atttgaacat ggctgccaca ttcttctctc acttgtcgct     120
tcttcaatcc aacaacaacc cttctctctc tcacacaccc tctcgcttcc ctcattctct     180
```

```
caccaaccgt gtcaaaccct ccctcggtgt ggtatctgtg gccaaaaggg taagtggagt      240
ggtgccaaag gccaatttga atgccttgga ggccaattcg ggtttcccca tttcggctaa      300
gaagtccaac aacaacccca ttgttgttat tgacaactat gacagtttca cctataatct      360
ttgccagtat atgggggagt tagggtttca ctttgaggtc taccgcaatg atgagttgac      420
agtggaggag ttaagaagga aaaatcccag aggagtgctg atatcacctg gccaggaga       480 acctcaagat tcaggcatat ctttgcaaac ggttttggaa cttggaccaa ctgtgccatt      540
gtttggtgtg tgcatgggtt tgcaatgcat tggagaggct tttggaggga agattgttcg      600
ttctcctcat ggtgttatgc atggaaaaag ctctatggtt tactatgatg agaaaggaga      660
agatggatta cttgctggac tatcaaatcc tttcttggct ggtagatatc acagccttgt      720
aattgaaaaa gagagctttc ctcatgatga acttgaggca acagcatgga cagaagatgg      780
tcttataatg gctgctcgtc ataagaaata taagcatcta cagggtgttc agtttcatcc      840
agagagcatc ataaccccag aaggcaagac aattgtccgt aattttgtca agcttatcga      900
gaaaagggag gctggtggct cttgaaaatc gaattcccgc ggccgccatg gcggccggga      960
gcatgcgacg tcgggccbaw kcggmgtt                                         988

<210> SEQ ID NO 114
<211> LENGTH: 47
<212> TYPE: PRT
<213> ORGANISM: Zea mays

<400> SEQUENCE: 114

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser
        35                  40                  45

<210> SEQ ID NO 115
<211> LENGTH: 32
<212> TYPE: PRT
<213> ORGANISM: Zea mays

<400> SEQUENCE: 115

Met Ala Thr Ala Ser Leu Ala Leu Ser Leu Arg Leu Ala Pro Ser Ser
1               5                   10                  15

Arg Pro Leu Ser Leu Arg Arg Arg Gly Ala Ala Gly Val Thr Cys Arg
            20                  25                  30

<210> SEQ ID NO 116
<211> LENGTH: 849
<212> TYPE: DNA
<213> ORGANISM: Zea mays

<400> SEQUENCE: 116
atggcctgct cccacatcgt cgccgccgcg ggggtctcct ccccgccgc agcggcggct       60 cgttccccgg cgcattctcc cgctgccgcc ttcgcgcgcc tccggtcgac gcctcgtttc     120
gcgagcgctg gcttgtcggt taagggaaac ggagcggcgt tcccgttggt cgccgccgcg     180
gggccggccg cggcggcacc ggtggccgac ctggacggcc gccggccac ggagaagcag      240 cccatcatcg tcatcgacaa ctacgacagc ttcacataca acctctgcca gtatatgggg     300
gagcttggat tgaacttcga agtataccgc aatgatgaac tgaccataga agatgtgaga     360
```

-continued

```
aggaagaacc caaggggaat acttatttct ccaggacctg gtgaaccaca agattcggga    420
atatcattgc agactgttct tgaattaggc ccaaccatcc caatttttgg agtttgcatg    480
ggtctgcaat gcattggaga ggcatttgga ggaaagatta tccgtgctcc ttctggagtg    540
atgcatggga aaagctctcc agtttattac gatgaggaat taggaaaggc attgttcaat    600
ggcttgccaa acccttttac tgccgcgagg taccacagct tggtcattga gcaagaaacc    660
ttcccacatg atgctttgga ggctactgca tggactgaag atggacttat catggctgct    720
cgccacaaga agtacaaaca catccagggt gtccaattcc acccggagag catcatcacc    780
cctgaaggca agaaaatcat cctcaacttt gtcagattca ttgaggaact ggagaagcag    840
cgttcgtag                                                             849
```

```

<210> SEQ ID NO 117
<211> LENGTH: 273
<212> TYPE: PRT
<213> ORGANISM: Oryza sativa

<400> SEQUENCE: 117

Met Ala Thr Ala Ala Arg Leu Leu Pro Lys Ile Gln Ser Pro Ala Ser
1               5                   10                  15

Pro Ala Val Ala Glu Ala Arg Arg Arg Arg Pro Ser Ser Leu Arg Leu
            20                  25                  30

Gly Val Thr Ser Gly Pro Ala Arg Thr Leu Lys Gln Lys Leu Val Ala
        35                  40                  45

Lys Ser Ala Val Ser Val Val Glu Gly Glu Asn Ala Phe Asp Gly Val
    50                  55                  60

Lys Gln Asp Thr Arg Pro Ile Ile Val Ile Asp Asn Tyr Asp Ser Phe
65                  70                  75                  80

Thr Tyr Asn Leu Cys Gln Tyr Met Gly Glu Val Gly Ala Asn Phe Glu
                85                  90                  95

Val Tyr Arg Asn Asp Asp Ile Thr Val Glu Glu Ile Lys Lys Ile Ser
            100                 105                 110

Pro Arg Gly Ile Leu Ile Ser Pro Gly Pro Gly Thr Pro Gln Asp Ser
        115                 120                 125

Gly Ile Ser Leu Gln Thr Val Gln Asp Leu Gly Pro Ser Thr Pro Leu
    130                 135                 140

Phe Gly Val Cys Met Gly Leu Gln Cys Ile Gly Glu Ala Phe Gly Gly
145                 150                 155                 160

Lys Val Val Arg Ser Pro Tyr Gly Val Val His Gly Lys Gly Ser Leu
                165                 170                 175

Val His Tyr Glu Glu Lys Leu Asp Gly Thr Leu Phe Ser Gly Leu Pro
            180                 185                 190

Asn Pro Phe Gln Ala Gly Arg Tyr His Ser Leu Val Ile Glu Lys Asp
        195                 200                 205

Ser Phe Pro His Asp Ala Leu Glu Ile Thr Ala Trp Thr Asp Asp Gly
    210                 215                 220

Leu Ile Met Ala Ala Arg His Arg Lys Tyr Lys His Ile Gln Gly Val
225                 230                 235                 240

Gln Phe His Pro Glu Ser Ile Ile Thr Thr Glu Gly Arg Leu Met Val
                245                 250                 255

Lys Asn Phe Ile Lys Ile Ile Glu Gly Tyr Glu Ala Leu Asn Cys Leu
            260                 265                 270

Pro
```

<210> SEQ ID NO 118
<211> LENGTH: 282
<212> TYPE: PRT
<213> ORGANISM: Zea mays

<400> SEQUENCE: 118

```
Met Ala Cys Ser His Ile Val Ala Ala Gly Val Ser Ser Pro Ala
1               5                   10                  15

Ala Ala Ala Ala Arg Ser Pro Ala His Ser Pro Ala Ala Phe Ala
                20                  25                  30

Arg Leu Arg Ser Thr Pro Arg Phe Ala Ser Ala Gly Leu Ser Val Lys
            35                  40                  45

Gly Asn Gly Ala Ala Phe Pro Leu Val Ala Ala Gly Pro Ala Ala
        50                  55                  60

Ala Ala Pro Val Ala Asp Leu Asp Gly Arg Pro Ala Thr Glu Lys Gln
65                  70                  75                  80

Pro Ile Ile Val Ile Asp Asn Tyr Asp Ser Phe Thr Tyr Asn Leu Cys
                85                  90                  95

Gln Tyr Met Gly Glu Leu Gly Leu Asn Phe Glu Val Tyr Arg Asn Asp
            100                 105                 110

Glu Leu Thr Ile Glu Asp Val Arg Arg Lys Asn Pro Arg Gly Ile Leu
        115                 120                 125

Ile Ser Pro Gly Pro Gly Glu Pro Gln Asp Ser Gly Ile Ser Leu Gln
130                 135                 140

Thr Val Leu Glu Leu Gly Pro Thr Ile Pro Ile Phe Gly Val Cys Met
145                 150                 155                 160

Gly Leu Gln Cys Ile Gly Glu Ala Phe Gly Gly Lys Ile Ile Arg Ala
                165                 170                 175

Pro Ser Gly Val Met His Gly Lys Ser Ser Pro Val Tyr Tyr Asp Glu
            180                 185                 190

Glu Leu Gly Lys Ala Leu Phe Asn Gly Leu Pro Asn Pro Phe Thr Ala
        195                 200                 205

Ala Arg Tyr His Ser Leu Val Ile Glu Gln Thr Phe Pro His Asp
210                 215                 220

Ala Leu Glu Ala Thr Ala Trp Thr Glu Asp Gly Leu Ile Met Ala Ala
225                 230                 235                 240

Arg His Lys Lys Tyr Lys His Ile Gln Gly Val Gln Phe His Pro Glu
                245                 250                 255

Ser Ile Ile Thr Pro Glu Gly Lys Lys Ile Ile Leu Asn Phe Val Arg
            260                 265                 270

Phe Ile Glu Glu Leu Glu Lys Gln Arg Ser
        275                 280
```

<210> SEQ ID NO 119
<211> LENGTH: 822
<212> TYPE: DNA
<213> ORGANISM: Oryza sativa

<400> SEQUENCE: 119

```
atggccaccg ccgcgcggct cctccccaag atccagtccc ccgcctcccc ggccgtcgcg      60
gaggcgcgga ggcgccgccc ctccagtctc cgattaggag ttactagtgg acccgcaaga     120
actctgaagc aaaagcttgt tgctaagagt gctgtttctg tggtggaagg tgaaaacgca     180
tttgatggag taaagcaaga tactagacca atcatagtta tagataacta cgatagcttc     240
```

```
acgtataatt tatgccagta catgggtgag gtgggagcta actttgaggt gtaccgcaat      300
gatgatatca ccgtggaaga aattaagaag atttctccta gaggaatact catctcccct      360
ggccctggca cacctcaaga ttcaggaata tcattgcaaa cagttcaaga tcttggacct      420
tctacacctt tgtttggggt tgcatgggt ttgcagtgta ttggggaggc atttggaggg       480
aaggttgttc gttctcctta tggagttgtg catgggaaag gatcccttgt tcactatgag      540
gagaaacttg atggaacact gttttctggt ctcccaaacc cattccaagc gggaagatac      600
cacagccttg taattgagaa ggatagcttc ccacatgatg ccctggaaat tactgcttgg      660
acagacgatg ggctgatcat ggctgctcgc cacaggaagt acaaacatat acagggtgtg      720
cagttccatc cagagagcat cataacaaca aagggaggc tcatggtcaa gaatttcatc       780
aagattattg aaggctacga ggccttgaat tgcttaccgt ga                         822

<210> SEQ ID NO 120
<211> LENGTH: 867
<212> TYPE: DNA
<213> ORGANISM: Oryza sativa

<400> SEQUENCE: 120
atggcgtgct cccacctggc cgccgccgcc gccgcggcct ccccggcggc cgcgcgttca       60
ccggcggcct ccagcgccgc aaccgcgagc gccttcgcgc gcctctcggc gacgccccgg      120
gtcgcgagcg gcgggttggc cgttagggc cagagggtg tagccgctgt tgtcgccgcc        180
gccgccgggg ccgccgcggc gacgcccgtg gccgacatcg aggaacgccg ggccaccgag      240
aagcagccca tcattgtcat cgataactac gacagcttta cctacaacct ctgccagtat      300 atggggggagc ttggattgaa cttttgaggta tatcgcaatg atgaacttac catagaggat     360
gtaaagagga agaacccaag aggaatactt atttctccag ggcctggtga gccacaagat      420
tcaggtatat cattgcagac tgttctggaa cttggaccta ccatcccaat ttttggtgtc      480
tgcatgggtc tgcagtgtat cggggaagct tttggaggaa agattatccg tgctccttct      540
ggtgtcatgc atggaaaaag ctctccagtt cgctacgatg aggagctagg gaaggccttg      600
ttcaatggct tgccaaaccc atttaccgct gcaagatacc atagcttggt gatcgagcag      660
gagaccttcc cccatgacgc tctggaagcc accgcgtgga ctgaagatgg ccttatcatg      720
gctgctcgcc acaagaagta caggcacatc cagggagtcc aattccaccc agagagcatc      780
atcaccccag aaggcaagag gatcattctc aacttcgtga ggttcatcga ggagctggag      840
aagcagcgtg ccggagagaa gaactag                                          867

<210> SEQ ID NO 121
<211> LENGTH: 2202
<212> TYPE: DNA
<213> ORGANISM: Mesorhizobium loti

<400> SEQUENCE: 121
atggagacgg caatgacgat gaaggttctg gaaaacggcg ctgaaagctt cgtgaccgcg       60
ggtggcatca ccattacgcg tgagcgccac gaccggcct atgcgggtgc gatcgacgct       120
tatgtcgatg gcttgaactc gcgccgcggc gcggtgtttt cctccaacta cgaatatccc      180
ggccgctata cgcgctggga caccgccatc atcgatccgc cgctggtcat ttccgcgcgg      240
ggccgcgcca tgcgcatcga agcgctgaac cgccgcggcg aggcgctgtt gccggtgatc      300
ggcaaaacgc tgggcggcct tgccgacatc accatcgccg agacgacgaa gacgctcatc      360
cgcctcgacg tcgccaagcc cggccgcgtc ttcacggagg aagagcgcag ccgcgtgccc      420
```

-continued

```
tcggtcttca ccgtgctgcg cgccatcacc gctttgttca aaaccgacga ggacgccaat      480
ctcggcctct atggcgcctt cggctacgac ctctccttcc agttcgaccc ggtcgactac      540
aagctcgagc gcaagcccag ccagcgcgac ctcgtgctgt tcctgcccga cgagatcctg      600
gtcgtcgacc actattccgc caaagcctgg accgaccgct acgactattc gggcgaagga      660
ttttcgaccg aaggtctgcc gcgcgacgca atcgccgagc cgttcaagac cgccgaccgc      720
atcccgccgc gcggtgacca tgagccgggc gaatacgcta atctggtgcg cgtgccatg      780 gactcgttca agcgcggcga cctgttcgag gtcgtgcccg ccagatgtt ctacgagcgc      840 tgcgagacgc agccctccga catttcgcgc aagctgaaat cgatcaaccc ctcgccttat      900
tcgttcttca tcaacctcgg cgaaaacgaa tatctgatcg cgcctcgcc cgaaatgttc      960 gtgcgcgtca atggccgccg cgtcgaaacc tgcccgattt cgggcaccat caaacgcggc     1020
gacgacgcca tttccgatag cgagcagatc ctgaagctgc tcaattcgaa gaaggacgaa     1080
tccgagctca caatgtgctc ggacgtcgac cgcaacgaca agtcgcgggt ctgcgagccc     1140
ggctcggtgc gcgtcatcgg ccgccgccag atcgagatgt attcgcgcct catccacacc     1200
gtcgatcaca tcgaaggccg gctgcgcgaa ggcatggacg ctttcgacgc cttcctgtcg     1260
catgcctggg cggtcactgt caccggcgcg ccgaaactgt gggccatgcg cttcatcgag     1320
cagaacgaga gagcccgcg cgcctggtat ggcggcgcaa tcggcatggt caacttcaac     1380
ggcgacatga acaccggcct gacgctgcgc accatccgca tcaaggacgg cattgccgaa     1440
gtgcgggccg gcgcgacatt gctgttcgac agcattcccg aggaagaaga agccgaaacc     1500
gaactgaagg catccgccat gctctccgcc atccgcgacg ccaagacggg caactccgcc     1560
agcaccgagc gcaccaccgc gcgggtcggc gacggcgtca acatcctgct cgtcgaccac     1620
gaggactctt tcgtccacac gctggccaac tacttccgcc agaccggcgc caatgtctcg     1680
accgtgcgca cgccggtgcc ggacgaagtg ttcgagcggc tgaagccgga ccttgtcgtg     1740
ctctcacccg gaccgggtac gccgaaggat ttcgattgcg ccgcgaccat cagacgagcg     1800
cgcgcccgcg acctgccgat cttcggcgtc tgcctaggcc tgcaggcgct ggccgaggcc     1860
tatggcgggg aactgcgcca gctgcatatt cccatgcacg gcaagccctc gcgcatccgc     1920
gtctccaagc ccggcatcat cttctccggc ctgcccaagg aagtcactgt cggccgttac     1980
cactcgatct tcgccgatcc ggtgcgcttg cccgatgatt tcattgtcac ggcagagact     2040
gaggacggca tcatcatggc tttcgagcac cgcaaggagc cgatcgcggc ggtgcagttc     2100
cacccggaat cgatcatgac gctcggccac aatgccggca tgcgcatcat cgagaacatc     2160
gtcgcccatt tgccgcgcaa ggccaaggaa aaggcagcct ga                        2202
```

```
<210> SEQ ID NO 122
<211> LENGTH: 2199
<212> TYPE: DNA
<213> ORGANISM: Azospirillum brasilense

<400> SEQUENCE: 122
atgtaccccg ccgaccttct tgcctcgccc gacctcctcg aaccgctgcg tttccagacg       60
cgcggcggcg tcaccgtcac gcggcgggcg acggcgctcg acccgcggac cgccctcgac      120
ccggtgatcg acgcgctgga ccgccgccgc ggcctgctgc tgtccagcgg ggtggaggcg      180
ccgggccgct accgcgtca cgcgctgggc ttcaccgacc ccgcggtggc gctcacggcg      240
cgtgggcgga cgctgcgcat cgacgcgctg aacgggcggg ggcaagtgct gctgcccgcc      300
```

-continued

```
gtcgccgagg ccctgcgtgg cctggaggcc ctggccggtc tagaggaggc gccgtcgcgg      360
gtcactgcct cgtccgcaag cccagcaccc cttcccggag aggagcggag ccgccagccc      420
tccgttttct cggtcctgcg ggcggtgctg gatctgtttg ccgcccccga cgacccgttg      480
ctcgggctct acggggcctt cgcctacgac ctcgccttcc agttcgagcc gatccgccag      540
cggttggagc ggcccgacga ccagcgcgat ctgctgctct acctgccgga ccggctcgtc      600
gcgctggacc ccatcgcagg actcgcccgg ctcgtcgcgt atgagttcat cacggcggcg      660
ggcagcaccg aggggctgga gtgcggcggg cgcgaccacc cctaccgtcc cgacaccaac      720
gccgaggccg gctgcgacca cgcgcccggt gactatcagc gcgtcgtcga gagcgccaag      780
gccgccttcc gccgcggcga cctgttcgag gtggtgcccg ccagaccctt cgccgagccc      840
tgcgccgacg cgccttcgtc ggtgttccgg cggctgcgcg ccgccaaccc ggcgccttac      900
gaggccttcg tcaacctcgg gcggggcgag ttcctcgtcg ccgccagccc ggagatgtat      960
gtgcgggtgg cgggcgggcg ggtggaaacc tgcccgatct ccggcaccgt ggcgcgcggg     1020
gccgacgcgc tgggcgacgc cgcgcaggtc ctgcgcctgc tgacctcggc caaggacgcg     1080
gcggagctga ccatgtgcac cgacgtggac cgcaacgaca aggcgcgggt gtgcgagccg     1140
ggatccgtcc gggtgatcgg gcggcggatg atcgagctgt actcccgtct gatccacacg     1200
gtggaccatg tggagggacg gctgcggtcc ggaatggacg cgctgacgc cttcctcacc      1260 cacagctggg cggtgacggt gaccggcgcg cccaagcgct gggccatgca gttcctggag     1320
gatacggagc aatcgccgcg ccgctggtac ggcggggcct tcggccggct gggcttcgac     1380
ggcgggatgg acaccggcct gaccctgcgc accatccgca tggccgaggg cgttgcctac     1440
gtgcgggcgg gggcgacgct gctgtccgac agcgatccgg acgcggagga cgcggagtgc     1500
cgcctgaagg ccgccgcctt ccgcgacgcc atccgcggga cggcggcggg tgcggcgccc     1560
acgctgccgg cggctccccg tggcggggag ggcaggcggg tgctgctggt ggatcacgac     1620
gacagcttcg tccacacgct ggccgactat ctgcgccaga cgggcgcttc ggtgacgacg     1680
ctgcgtcaca gtcacgcacg ggcggcgctg gcggagcgga ggccggatct ggtcgtgctg     1740
tcccccggtc cggggcgccc ggcggatttc gacgtggcgg gcaccatcga cgcggcgctg     1800
gcgctcggcc tgccggtgtt cggcgtctgc ctgggcctgc aagggatggt ggagcgcttc     1860
ggcggcgcgc tggacgtgct gccggagccc gtccacggca aggcgacgga ggtccgggtg     1920
ctggccggcg cgctgttcgc cggcctgccg gagcggctga cggtcgggcg ctaccactct     1980
ctggtggccc ggcgcgaccg gctgccggcg gacctcacgg tgaccgcgga gaccgccgac     2040
ggtctggtga tggcggtcga gcaccggcgg cttccgctcg ccgccgtgca gttccacccc     2100
gagtcgatcc tgtcgctcga cggtggggcc ggtcttgccc tgctgggcaa cgtgatggac     2160
cggctggccg ccggcgccct gacggacgct gcggcttga                           2199
```

<210> SEQ ID NO 123
<211> LENGTH: 2196
<212> TYPE: DNA
<213> ORGANISM: Brucella melitensis

<400> SEQUENCE: 123

```
atgaatgcga agactgcgga tagcgagata ttccagcacg aaacggcagg cggtatcatc       60
gtcgagcggg tgcgccacct cacggcctat aagggcgcca ttgaaagcta tatcgatgtg      120
ctgaacgaat ggcgcggtgc ggtgttctcg tccaattacg aatatccggg ccgctatacg      180
cgatgggata ccgcaattgt cgatccgccg gtcgtcatca cgtcgcgtgc ccgcacgatg      240
```

```
cgcatcgagg cgctgaacgc gcgcggcgtc atcctgcttc ggcccattct ggataccgtc    300
aaggcgcttt cggaagtaaa gatcgaccag tccggcgaaa accgtatcga tctgacgatt    360
gtggaaccgg tcgcaccctt cacgaagaa  aacgctcgc  gcatgccctc ggtctttacg    420
gtgctgcgcg ccatagtcgg gcttttcttc tcggaggagg atgccaatct cggcctttat    480
ggcgcctttg gctatgatct ggcgttccag ttcgatccca tccagtacaa gctgaagcgc    540
ccggacgacc agcgtgacct cgtgctgttc attcccgacg aaatcttcgt cgccgaccat    600
tatgcggcgc gcgcctgggt ggaccgttat gaatttcgct gcggcggttc gtccacgcac    660
ggtcttgatc gcgcgacgcc ggtggtgcct ttcaagccat cggagcgcaa gcttgcgcgc    720
ggcgatcata tccgggtga  atatgccagg cttgtcgagc gcgccaagga aagcttcaag    780
cgcggcgacc tgttcgaggt tgtgccgggc cagaccttct atgagcgctg ccacacggcg    840
ccgtcggaga ttttccgccg gctgaagtcg atcaatcctt cgccctattc cttttcatc     900 aatctgggcg agagcgaata tctggtcggc gcatcgccgg aaatgtttgt gcgcgtcaat    960
gggcggcgca tcgagacctg cccgatttcc ggcaccatca agcgcggtga agatgcaatt    1020
tcggattctg agcagatatt gaaactgctt aattccaaga aggacgaatc cgagctgacc    1080
atgtgttcgg atgtgaccg  caacgacaag agccgcgttt gcgagccggg ttcggtgcgt    1140
gttatcggtc gccgccagat cgagatgtat tcccgcctga tccatacggt cgatcatatc    1200
gaaggccgcc tgcgtgacgg catggatgcg tttgacggct tcctcagcca tgcatgggct    1260
gtgacggtga caggcgcgcc gaagctgtgg gcaatgcgct tcttgagga  aaacgaacgc    1320 agcccgcgcg catggtatgg cggcgcgatc ggcatgatgc atttcaatgg cgatatgaat    1380
acagggctga cgctgcgcac catccgcatc aaggatggtg tggcggaaat ccgtgcaggg    1440
gcgacgcttc tgttcgattc caaccctgac gaggaagaag ccgagaccga attgaaggca    1500
tcggccatga ttgcggctgt gcgggacgca cagaagagca atcagatcgc ggaagaaagt    1560
gtggcggcaa aggtgggtga gggggtttcg atcctgctgg tcgatcacga ggattccttc    1620
gtccatacgc ttgccaatta tttccgccag acgggcgcca aggtttccac cgtgcgttca    1680
ccggtggcag aggagatatt cgaccgcgtc aatcccgatc tggtggtgtt atcgccggga    1740
ccgggctcgc cgcaggattt cgattgcaag gcgaccatcg ataaggcgcg caagcgccag    1800
cttccgattt ttggcgtctg cctcggcctt caggccctgg cggaagccta tgcggggcg    1860 ttgcgccagc ttcgcgttcc ggtgcatggc aagccttcac gcatccgcgt atcaaagccg    1920
gagcgcattt tctccggctt gccggaggaa gtgacggtgg ggcgttatca ttcgatcttc    1980
gccgatcctg aacgcctgcc ggatgatttt tcgtcacag  ccgaaacgga agacgggatc    2040
atcatggctt ttgaacataa acatgaaccg gtggcagccg ttcaattcca tcccgaatcc    2100
atcatgacgc ttggccataa tgccggtatg cgcatgatcg agaatatcgt gacgcatctt    2160
gcaggcaagc acaaggcgcg ccgcaccaac tattga                              2196
```

<210> SEQ ID NO 124
<211> LENGTH: 2148
<212> TYPE: DNA
<213> ORGANISM: Nostoc sp.

<400> SEQUENCE: 124

```
gtgcgcgtat ctcgtagcac aaccgaggtg aagatggaca ctgcactaga tgaaattctc     60
tttcacctaa atcaagtacg tggaggtttg ttaaccagta gttacgaata tccagggcga    120
```

```
tacaaaagat gggcgattgg attcattaat cccccattac aactgacaac aagagagaac    180
gcatttacca tctcttcact caatcctcgc ggacaggtgc tactaccaac cttgttccag    240
catctatcag cccagtcgca actacaacaa atcagcctca atcatgacta catcacaggt    300
gaaattcgac ccacaaaaca gttattcaca gaagaacaac ggagtaaaca accgtcagcc    360
tttacagtca tccgcgaaat tctccagatt tttgcgagtg atgaagacga gcatttaggg    420
ttatatggtg catttggtta cgacttagta tttcaatttg aaccaattcc ccaaaaaatt    480
gctcgtcccg cagaccaacg ggatttagtc ctgtatctac ccgatgaact catagttgta    540
gattactatc tacaaaaagc atatcgtcac cagtatgaat tgccacaga acatggcaac    600 accgagcatc ttccacggac aggccagtcc atcgactacc agggtaaaca tcttctacca    660
aaccaaactg ctgaccatca accaggagaa atgccaacc tagttgagca agcactcgac    720
tacttccgcc ggggtgactt atttgaagta gttcctagtc aaaacttttt tacagcctgt    780
gaacaatcac ccagtcaact attccagacc ttaaggcaaa ttaatcctag tccttatgga    840
tttctgttga atttgggtgg tgaatatctc ataggtgcat caccagaaat gtttgtgcga    900
gttgatggta ggcgagtgga aacctgtccc attagtggca ctattagacg gggagaagat    960
gctttaggcg acgctgtaca aattcgtcag ttgcttaact cccataaaga tgaagccgag   1020
ttaacaatgt gtactgacgt agaccgcaac gataaatcgc ggatttgtga acccggttca   1080
gtcagggtga ttggtcgtcg ccagattgaa ctgtacagcc acctcattca tacagtagac   1140
catgtagaag ggatactgag gccggaattt gacgctttag atgccttctt gagtcatact   1200
tgggcagtta cagtcacagg cgcacccaaa cgagccgcca tgcagttcat cgaacagcat   1260
gaacgcagcg cccgtcgttg gtatggggga gcagttggtt atttaggctt taatggtaac   1320
ttgaataccg gattaaccct gcggacaatt cgtttacaag actccatcgc cgaagtgcga   1380
gttggtgcaa cagtccttta cgactccatt ccgtcagccg aagaagagga aacaattact   1440
aaagcgactg cattatttga gaccattcgc cgtcatacca ctgccaataa aactcaagga   1500
aacgatagtc atcgccctgg ggatatcgcc cacaataagc gtatcctcct catcgactac   1560
gaagattcat tgttcacac attagccaat tacatccgca ccaccggcgc aaccgtcacc   1620
accctacgtc atggttttgc tgaatcatat tttgatgcag aacgcccaga cttagtggta   1680
ttgtctcccg gccctggtag acccagtgac ttccgagttc cccaaacggt tgcagccttg   1740
gtaggtcgag aaatccccat tttttggcgtt tgtctgggat tacaaggcat agtggaagct   1800
tttggcggag aattaggcgt gcttgattat ccccaacacg gtaaaccgc acggatttca   1860 gtgactgcac ctgattctgt gctgtttcaa aatttaccag catccttcat cgtgggtaga   1920
taccattcct tatttgccca accccaaact atacccggtg aactcaaagt cacagcgatt   1980
tctgaggaca atgtaattat ggcaattgaa caccaaacac tacctatagc cgccgtccaa   2040
tttcatccag agtcaatcat gaccctagca ggagaagttg gtcagacaat cattaaaaat   2100
gtggtgcaga catatacccca aactttagaa acatcaattt actcttag                2148
```

<210> SEQ ID NO 125
<211> LENGTH: 2208
<212> TYPE: DNA
<213> ORGANISM: Nostoc sp.

<400> SEQUENCE: 125

```
atgattgccg attcccacag ctacagaact aatggtaacg tgcgtgtctc tcgctccatc     60
acacaagtta aaatggagac agctttagaa gagattcttt tctacttaaa ctctcagcgt    120
```

| | |
|---|---|
| ggtggattgc tgactagtag ctatgaatat ccaggaagat ataaaagatg ggcaattggt | 180 |
| tttgttaatc cacctgtaga attatccaca agcggaaata cttttactct cacagcatta | 240 |
| aatgagcgtg ctatgtact tttaccagtg atctttgagt gtttatcaaa atcagaacaa | 300 |
| ctccagaaac tcactgaaca tcatcataaa attactggat tagttaaatc tacaccagaa | 360 |
| ttttttgccg aagaagaacg tagtaaacaa ccttctacat ttacggttat tcgggaaata | 420 |
| ctacatatct tctctagtca agaagacgaa catttaggat tatatggtgc gtttggttat | 480 |
| gacttagttt tccaatttga gcaaataacc caatgcttag aacgtccaca agaccaacga | 540 |
| gatttagttc tatatttacc cgacgaattg atagttgtag actactatca acaacaagca | 600 |
| tttcggctag agtatgactt catcacagcg catggtagta cttatgattt gccccgcacg | 660 |
| ggagaatctg ttgattatcg aggtcaatgt ttaacacctc tcaaaatgc tgaccataaa | 720 |
| ataggtgagt atgccaaact agtagaattt gcccttgatt atttccgtcg gggtgactta | 780 |
| tttgaagtgg ttcccagtca gaattttttc acagcttgcg aagcaccacc aagccaacta | 840 |
| tttgaaactt taaaacaaat aaatcctagt ccctatggat ttattttaa tcttggtgga | 900 |
| gaatacatca ttggcgcttc accagaaatg tttgtacggg tggaaggtag gcgtgtagaa | 960 |
| acttgtccta ttagtggcac tattactaga gggcatgatg ctatagatga tgctgtgcag | 1020 |
| attcgtcagt tactcaactc ccacaaagac gaagcagagt tgactatgtg tactgacgta | 1080 |
| gaccgtaacg ataagtctcg catctgtgaa cccggttcag tcaaggtgat tggtcgccgg | 1140 |
| caaattgaat tatatagcca cttaattcat acggtagacc atgtagaagg cattctccga | 1200 |
| ccagagtttg atgctttaga tgctttcctc agtcacactt gggctgttac agtcacaggc | 1260 |
| gcaccgaaaa gggctgctat tcaattcatc gaaaagaacg aacgcagcgt cagacgttgg | 1320 |
| tatggtggcg cggttgggta tttgaatttt aacgggaatt taaatactgg gttaattta | 1380 |
| aggacaatca gattgcaaga ctcaattgct gaagtgcgag ttggtgctac tctactgtat | 1440 |
| gactccatac cccaagcaga agaacaagaa accatcacta agctgcggc tgcttttgaa | 1500 |
| acgattcggc gtgctaaaca aatagaccca cagattgaag aatctagtac tagaaagtta | 1560 |
| agcaaatatc ttcccgatgg acaatcaggt aaacacatct tactaattga ccatgaagac | 1620 |
| tcatttgttc atacccctagc taactacatc cgttccactg gtgcaactgt caccacactg | 1680 |
| cgtcacggct tctcagaatc cctatttgat acagaacgcc cagacttagt agtattatct | 1740 |
| cctggccccg gtagaccgag tgaatttaaa gtacaggaaa ccgtcgccgc ctgcgtccgt | 1800 |
| cgccaaatac ctctgtttgg tgtctgttta ggactgcaag gtattgtgga agctttcggt | 1860 |
| ggagaattgg gagtattgaa ttatccccaa catggtaaat cttcgcggat ttttgttaca | 1920 |
| gcacccgatt ctgtgatgtt tcaagatttg cccgaatctt ttacagtcgg gagatatcat | 1980 |
| tcattatttg cactatcaca acgcttacca aaagaactga aggtgacagc gatttctgat | 2040 |
| gatgaggtga ttatggcgat tgaacatcag acactaccta tcgccgccgt ccagtttcat | 2100 |
| ccagaatcaa tcatgactct agctggagaa gttggttaa tgatgatcaa aaatgtggtg | 2160 |
| caaaaatata cacaaagtca acagtcaaca gttcccatct atgactaa | 2208 |

<210> SEQ ID NO 126
<211> LENGTH: 2160
<212> TYPE: DNA
<213> ORGANISM: Rhodopseudomonas palustris

<400> SEQUENCE: 126

```
atgaacagga ccgttttctc gcttcccgcg accagcgact ataagaccgc cgcgggcctc      60
gcggtgacgc gcagcgccca gccttttgcc ggcggccagg cgctcgacga gctgatcgat     120
ctgctcgacc accgccgcgg cgtgatgctg tcgtccggca caaccgtgcc gggccgctac     180
gagagcttcg acctcggctt tgccgatccg ccgctggcgc tcaccactag ggccgaaaaa     240
ttcaccatcg aggcgctcaa tccgcgcggc cgggtgctga tcgcgttcct gtccgacaag     300
cttgaagagc cctgcgtggt ggtggagcag gcctgcgcca ccaagatcag gggccacatc     360
gtccgcggcg aggccccggt cgacgaagaa caacgcaccc gccgcgccag cgcgatctcc     420
ctggtgcgcg cggtgattgc tgccttcgcc tcgccggcca tccgatgct cgggctgtac      480
ggcgccttcg cctacgacct tgtgttccag ttcgaggatc tgaagcagaa gcgtgcccgc     540
gaagccgacc agcgcgacat cgtgctgtac gtgccggatc gcctgctggc ctacgatcgc     600
gccaccggcc gcggcgtcga catttcctac gaattcgcct ggaagggcca gtccaccgcc     660
ggcctgccga acgagaccgc cgagagcgtc tacacccaga ccggccggca gggtttcgcc     720
gaccacgccc cgggcgacta tcccaaggtg gtcgagaagg cccgcgcggc gttcgcccgc     780
ggcgacctgt tcgaggcggt gccggggcca ctgttcggcg agccatgcga gcggtcgccg     840
gccgaagtgt tcaagcggtt gtgccggatc aacccgtcgc cctatggcgg cctgctcaat     900
ctcggcgacg cgaattcct ggtgtcggcc tcgccggaaa tgttcgtccg ctcggacggc      960
cgccggatcg agacctgccc gatctccggc actatcgccc gcggcgtcga tgcgatcagc    1020
gatgctgagc agatccagaa gctcttgaac tccgagaagg acgagttcga gctgaatatg    1080
tgcaccgacg tcgaccgcaa cgacaaggcg cgggtctgcg tgccgggcac gatcaaagtt    1140
ctcgcgcgcc gccagatcga gacctattcg aagctgttcc acaccgtcga tcacgtcgag    1200
ggcatgctgc gaccgggttt cgacgcgctc gacgccttcc tcacccacgc ctgggcggtc    1260
accgtcaccg gcgcgccgaa gctgtgggcg atgcagttcg tcgaggatca cgagcgtagc    1320
ccgcggcgct ggtatgccgg cgcgttcggc gtggtcggct tcgatggctc gatcaacacc    1380
ggcctcacca tccgcaccat ccggatgaag gacggcctcg ccgaagttcg cgtcggcgcc    1440
acctgcctgt tcgacagcaa tccggtcgcc gaggacaagg aatgccaggt caaggccgcg    1500
gcactgttcc aggcgctgcg cggcgatccc gccaagccgc tgtcggcggt ggcgccggac    1560
gccactggct cgggcaagaa ggtgctgctg gtcgaccacg acgacagctt cgtgcacatg    1620
ctggcggact atttcaggca ggtcggcgcc caggtcaccg tggtgcgcta cgttcacggc    1680
ctgaagatgc tggccgaaaa cagctatgat cttctggtgc tgtcgcccgg tcccggccgg    1740
ccggaggact tcaagatcaa ggatacgatc gacgccgcgc tcgccaagaa gctgccgatc    1800
ttcggcgtct gcctcggcgt ccaggcgatg gcgaatatt tggcggtac gctcggccag       1860
ctcgcgcagc cggctcacgg ccgcccgtcg cggattcagg tgcgcggcgg cgcgctgatg    1920
cgcggtctcc cgaacgaggt caccatcggc cgctaccact cgctctatgt cgacatgcgc    1980
gacatgccga aggagctgac cgtcaccgcc tccaccgatg acggcatcgc gatggcgatc    2040
gagcacaaga ccctgccggt cggcggcctg cagttccacc ccgagtcgct gatgtcgctc    2100
ggcggcgagg tcgggctgcg gatcgtcgaa aacgccttcc ggctcggcca ggcggcctaa    2160
```

<210> SEQ ID NO 127
<211> LENGTH: 2166
<212> TYPE: DNA
<213> ORGANISM: Bradyrhizobium japonicum

<400> SEQUENCE: 127

```
atgaacagga cagtctttgc cctcccggcc agaagcgatt acgtgacccg cggcggtctc      60
gcgatcacgc gcgtggcgga gcagtttacc ggcggcgcga gccggctcga cgatctcgtc     120
aacctgctcg accgccgccg cggcgtggtg ctgtcctcgg gcacgaccgt gccgggccgc     180
tacgagagct tcgacctcgg cttctccgat ccgccgctca agctcgagac cacaggcgtc     240
aatttcaagc tggaagccct gaacgagcgc ggccaggtgc tgatcgcctt ccttgccgat     300
gtcctgcgcg agccctgcgt ggtgatatcc gaaaagaccg cttcgcgcct cgccggccac     360
atcatccgcg gcgatgcccc ggtcgaggaa gaccagcgca cccggcgcgc cagcgtggtg     420
tcgctggtgc gcgacctcgt cgccgccttc tccgccaatg acgacgggct gctcggcctg     480
ttcggcgcct tcgcctacga tctcgtgttc cagatcgagg atctcgtgca gaagcgcgcg     540
cgcgagagcg accagcgcga catcgtgctc tacgttcccg atcgcctgct ggcctatgac     600
cgcgccaccg gccgcggcgt cgtgctcagc tacgacttca cgtggaaggg cagatccacc     660
gagggcctgc cgcgcgagac ccgccgacagc ccgtacatga agacaccgcg ccagggcttt     720
gccgatcatg cgcccggcga ataccaggcc accgtcgaga ccgcgcgcgc ggcctttgcc     780
cgcggcgatc tgttcgaggc cgtgccgggc cagctgttcg ccgagccctg cgatcgttct     840
ccggcggaag tgttccagcg cctctgtgtc atcaacccgt cgccctacgg cgcgctgatg     900
aatctcggcg acggcgagtt tctcgtctcc gcctcgcccg agatgttcgt gcgttcggac     960
ggccgccgcg tcgagacctg cccgatctcg gcaccatcg cgcgcggcac cgatgcgatc    1020
ggcgatgccg agcagatccg ccagctcctg aattcggaga aggacgagtt cgagctcaac    1080
atgtgcaccg acgttgatcg caacgacaag gcgcgcgtct gcgtccccgg caccatcaag    1140
gtgctggcgc gccggcagat cgagacctac tcaaaactgt tccacaccgt cgaccacgtc    1200
gagggcatgc tgcgtcccgg cttcgacgcg ctcgatgcct tcctcaccca tgcctgggcc    1260
gtcaccgtga caggtgcgcc gaagctctgg gcgatgcagt tcgtcgagga tcacgagcgg    1320
tcgccgcggc gctggtatgc gggtgcgatc ggcgcggtga atttcgacgg cagcatcaat    1380
accgcctca ccatccgcac catccgcatg aaggatggtc tcgccgaggt gcgcgtcggc    1440
gccacctgcc tgttcgattc cgatcccgct gccgaggacc gcgaatgcca ggtcaaggcg    1500
gcggcgctgt ccaggcgct gcgcggcgat ccgccaaaac cgctctcgac ctttgcgccc    1560
gatgcgaccg gaagcggcaa gcgggtgctg ctgatcgacc acgacgacag cttcgtgcac    1620
atgctcgccc actatttccg ccaggtcggc gccagcgtca ccgtggtccg ctatgtgcat    1680
gcgctcgaca tgctcaagca gaagaggtgg gatttgctgg tgctgtcgcc cggcccgggc    1740
aggcccgaag atttcgggat caggaagacg atcgatgcgg cgctggagaa caagctgccg    1800
gtgttcggcg tctgcctcgg cgtgcaggcg atcggcgaat attttggcgg cgagctcggc    1860
cagctcacgc atcccgccca cggccggccc tcgcgggtgc aggtgcgcgg cggccgcctg    1920
atgcgcaatt tgccgagcga gatcgtgatc ggccgctatc actcgctcta tgtcgagcgc    1980
gacagcatgc cggaggtttt gtccgtcacc gccagcaccg aggacggcgt cgctatggcg    2040
ctggagcaca gaccctgcc ggtcgcgggc gtgcaattcc acccggagtc gctgatgtcg    2100
ctcggcggcg aggtgggctt gaggattgtc gagaacgcgt tccggctgga tgcgcgtgtt    2160
gattga                                                               2166
```

<210> SEQ ID NO 128
<211> LENGTH: 2187
<212> TYPE: DNA

<213> ORGANISM: Rhodospirillum rubrum

<400> SEQUENCE: 128

| | | | | | |
|---|---|---|---|---|---|
| atgcaaacat | cgaccttcac | caccgccggc | ggttttacca | tcagcagttg | cctacgcccg | 60 |
| cttgccgggg | cggatggcgc | cttcgaggcg | ctgatcgacc | gactcgatcg | ccatcgcggc | 120 |
| atggtgatcg | cctcgaccta | tgagtatccc | ggccgctatc | gccgccacgc | cctgggtttt | 180 |
| tgcgatccgc | cgctggtgct | ggagggcaag | gggcgcgagg | cccatctgct | ggcgctcaat | 240 |
| cgccgggggc | gggccctgct | gccggccctg | gccgttggct | tggaggggc | ggccgggctg | 300 |
| gagggcctgc | gccgcgaggc | cgaccggctg | gtcttgcgtg | tcaaggccat | ggcgccctgg | 360 |
| ttccccgagg | aggagcgctc | gcgccaaccc | tcgctgatgt | cggtggtgcg | cgccctcgcc | 420 |
| gggctgttcg | ccgccgaaaa | cgacccgttt | ttcgggcttg | tcggcgcctt | tggctatgac | 480 |
| ctgggcttgg | ctttcgagcg | cctgccccat | gcccggccgc | gatcggccga | tcaccgcgat | 540 |
| ctggtgcttt | acctgcccga | ccgtctgctg | atcgacgatc | ccgaagcggc | ggccttgcc | 600 |
| gaacgccttt | acgacatcac | cgcggccgat | ggggcaagca | ccgccggctt | ggcgcgggaa | 660 |
| accgccgctt | acaccgccga | ccaccccgcc | ggcggcgtgc | cgatcgagga | tgatatgccc | 720 |
| ccgggcgctt | acggggcgat | cgtccgtggg | ctgaaggagg | ccttcgccgc | cggggatctg | 780 |
| ttcgaggcgg | tgccctcgcg | cgccctgcgc | cggccttgcg | ccgaggcgcc | gagccgtttg | 840 |
| taccggcggc | tgcgcgcggc | caatccggcg | ccctatctgt | tcctggccaa | tctggggcg | 900 |
| ggcgaacatc | tgatcggcgc | ctcgcccgaa | atgttcgtgc | gcgtcggtgg | agcgccgggg | 960 |
| gcgcggcggg | tggaaaacctg | cccgatctcg | gcaccatcg | cccgggggcc | cgacgccctg | 1020 |
| ggcgatgccg | aggccatccg | caccctgctc | aattcgacca | aggacgaggc | cgaattgacc | 1080 |
| atgtgcaccg | atgtcgaccg | caacgacaag | gcgcgggtct | gcgtggccgg | cagcgttacc | 1140 |
| gtcatcggtc | gccgccagat | cgagctatat | tcccggctga | tccacacggt | cgaccatgtg | 1200 |
| gagggccggc | tgcgccccga | gcttgacgcc | cttgacgcct | ttctcagcca | ctgctgggcg | 1260 |
| gtgacggtga | ccggagcgcc | caagcgcgcc | gccatggccg | ccgtcgaagc | cgtggagcgg | 1320 |
| gcgccgcgcg | cctggtatgg | cggcgccatc | ggccgcctgg | gcttcgacgg | taccctcgac | 1380 |
| accggactgg | tgctgcgcac | catccgcctg | cgtcacggcg | tcgccgaggt | gcgggtgggg | 1440 |
| gcgacgctgc | tccaccgttc | cgatcccgag | gaggaggagg | ccgaaaccct | gctcaaggcc | 1500 |
| tcggccctgc | tcgccctgct | cgatgccacc | accccggcca | agccgaatgc | cccgcatctt | 1560 |
| ccgttgcgcg | gccgggcgcc | gcgcgtgctg | gtcatcgacc | acgaggacag | cttcgtccat | 1620 |
| accctggcgt | cttatctgcg | caatgccggg | gccgagacca | ccgtgctgcg | ctgggacgtg | 1680 |
| ccggcggcg | tgcgcgccgg | cgtcgaggcc | gatctgctgg | tgctgtcgcc | gggaccgggc | 1740 |
| acgccgtcgc | gcttcgccct | gggggccagc | ctggactggg | cggtggcgcg | cggcttgccg | 1800 |
| gtcttcggcg | tctgcctggg | gctgcagggc | atcgtcgaac | aggccggggg | ccgccttgcc | 1860 |
| cggctggcgg | ttcccgccca | tggcatggcc | tcgacgctgc | ggctggtcgc | ccccggggac | 1920 |
| ccgctgttcg | ccggcctgcc | cacgaccatg | agagtgggcc | gctaccacag | cctgcacgcc | 1980 |
| gagcgcgcca | gcctgcccga | cagcctggag | atcctggccg | aaagcgacga | cggggtgatc | 2040 |
| atggcgctgc | gccaccgcct | gctgcccttc | agcgccgtgc | aattccaccc | cgaaagcctg | 2100 |
| atgaccctgg | acggcggcgc | cggaccccga | ttgatcgcca | atcttctgga | aaccctaagc | 2160 |
| gtcccgcgaa | cgcgccacgc | cgcctaa | | | | 2187 |

<210> SEQ ID NO 129
<211> LENGTH: 2181
<212> TYPE: DNA
<213> ORGANISM: Thermobifida fusca

<400> SEQUENCE: 129

```
gtggacgaca actcctacac caccagtggt ggtatcaccg tgcaccgcac ggcagtgccg      60
tgcgatcccc gtgcgctcgc cgatctgacg gtcaacgtgg aacagcgccg aggcggcgtg     120
ctctcctccg ggatggagta tcccggccgc tacagccgtt ggcatttggg atacgtggac     180
ccgtgcctgg aagttgtcgc gcgcggccgc acgatcgggg cgacggccct caacgaccgc     240
ggccgtgtcc tgctgcccgc ggtagcccgg gcgctcaccg cgcacggcgc ggtggtggag     300
cacaccgacg acacggtcgc tgtcacggtc cctgaaccgg atcccaccga gttcttcact     360
gaggaagagc gcagccgccg gctcagtgtt ttttctgcgc tccgcgccct cgtgggcgtg     420
ttcttccacg cggaagaacc ccacctgggg ttgtacgggg cgttcggcta cgatctggcg     480
ttccagttcg aaccgatcga gcaggtgctg ccgcgcgacc ggaggaccg ggacctggtg      540
ttgcacctgc ccgacgagat catcgtccac gaccggaaac gggagatctg ccagcgctac     600
tcctacgact tcacgctgcc ggaggagttg cgcggcccgg caggggcgac cacgcggggc     660
ctgccacgcc acaccgagcc cacaccccg gtgaccccgg ctgccgaggt gccgccgcag      720
ccggaacccg ggtcgtatgc gcggatcgtg gctgaggcca aggagcggtt ccgccgcggc     780
gacttgttcg aagtggtgcc cagccaccgc ttgtacgcgc cgtgtgcgtc gcctgcgcgg     840
ttctacgagc ggctgcggga acgcaaccct gccccgtacg agttcttcct caacctgggg     900
gagggcgagt acctggtcgg cgcgtccccg gaaatgtttg tgcgggtcac gggccgtccc     960
ggagaggggc agcgggtgga gacctgcccg atctccggca cgatcaagcg tggcgcggac    1020
gcggtcggcg acgcggagaa catcaaggag ctgctgtcgt ccgcgaagga agagtcggag    1080
ctgaccatgt gcaccgacgt ggaccgcaac gacaagtccc gggtgtgcgt gccaggcagt    1140
gtgcgggtga tcggccgccg gcagatcgaa atgtacagtc ggctcatcca cacggtcgac    1200
cacattgagg ggattctgcg ccccgagttg acgctattg acgcgttcct cacccacatg     1260
tgggcggtga ccgtgacggg ggcgccgaag acgtgggcga tgcggttcat cgaacagcat    1320
gagagttcgc cgcgccgctg gtatgggggc gcggtcggtg tcatcaatt tgatggttcg     1380
atgaacaccg ggttgacgtt gcggaccgcg cacatccggg acggggtggc gacggtgcgg    1440
gcgggcgcca cactgctgta cgactctgat ccggaagctg aagagcggga gactttcctc    1500
aaagcccgtg ccctgttgga gaccctcacc gacgagggtg aggaaacctc caaggctgcg    1560
cctgcggtgg agcaggtggg ggcggggatg cgggtgctgc tcgtcgacca cgaagactcg    1620
ttcgtcaaca cgctcgcgga ctacgtccgg cggcacggcg ccgaggtcac cacggtgcgc    1680
tacgggttcg acccggccct gctcgaccag atgcgtcccg acctggtggt gctctccccg    1740
gggccggggc tgcccgccga tttcgcgatg agcgcgctgt tgaaggagtt ggacgcgcgc    1800
ggcctgcctg tgttcgggga tgtgcctggg ctgcaggcga tggtggagta cgcgggcggg    1860
gagctgctca cttttggacac gccggtgcac ggtaaacccg ccgggttcg ggtcaccggg     1920
ggcgcgctgc tggctgggct gggagaggac ggggagttca ccgcggcccg ctaccactcc    1980
gtgtacgcga ccccggaccg ggtgaaaggg ttcgaggtga cggcggtgac ggaggacgac    2040
ggtttccccg tggtcatggc gatcgagaat gctgaggcgc ggcggtgggc ggtccagttc    2100
cacccccgagt cgatcctcac cggccgggtg ggggagcaga tcgtgcgcaa cgtgctgcgc    2160
```

```
ttggccaggg agagcagctg a                                              2181
```

<210> SEQ ID NO 130
<211> LENGTH: 721
<212> TYPE: PRT
<213> ORGANISM: Bradyrhizobium japonicum

<400> SEQUENCE: 130

| | | | | | | | | | | | | | | |
|---|---|---|---|---|---|---|---|---|---|---|---|---|---|---|
| Met | Asn | Arg | Thr | Val | Phe | Ala | Leu | Pro | Ala | Arg | Ser | Asp | Tyr | Val | Thr |
| 1 | | | | 5 | | | | | 10 | | | | | 15 | |
| Arg | Gly | Gly | Leu | Ala | Ile | Thr | Arg | Val | Ala | Glu | Gln | Phe | Thr | Gly | Gly |
| | | | 20 | | | | | 25 | | | | | 30 | | |
| Ala | Ser | Arg | Leu | Asp | Asp | Leu | Val | Asn | Leu | Leu | Asp | Arg | Arg | Arg | Gly |
| | | | | 35 | | | | | 40 | | | | | 45 | |
| Val | Val | Leu | Ser | Ser | Gly | Thr | Thr | Val | Pro | Gly | Arg | Tyr | Glu | Ser | Phe |
| | 50 | | | | | 55 | | | | | 60 | | | | |
| Asp | Leu | Gly | Phe | Ser | Asp | Pro | Pro | Leu | Lys | Leu | Glu | Thr | Thr | Gly | Val |
| 65 | | | | | 70 | | | | | 75 | | | | | 80 |
| Asn | Phe | Lys | Leu | Glu | Ala | Leu | Asn | Glu | Arg | Gly | Gln | Val | Leu | Ile | Ala |
| | | | | 85 | | | | | 90 | | | | | 95 | |
| Phe | Leu | Ala | Asp | Val | Leu | Arg | Glu | Pro | Cys | Val | Val | Ile | Ser | Glu | Lys |
| | | | 100 | | | | | 105 | | | | | 110 | | |
| Thr | Ala | Ser | Arg | Leu | Ala | Gly | His | Ile | Ile | Arg | Gly | Asp | Ala | Pro | Val |
| | | | | 115 | | | | | 120 | | | | | 125 | |
| Glu | Glu | Asp | Gln | Arg | Thr | Arg | Arg | Ala | Ser | Val | Val | Ser | Leu | Val | Arg |
| | 130 | | | | | 135 | | | | | 140 | | | | |
| Asp | Leu | Val | Ala | Ala | Phe | Ser | Ala | Asn | Asp | Asp | Gly | Leu | Leu | Gly | Leu |
| 145 | | | | | 150 | | | | | 155 | | | | | 160 |
| Phe | Gly | Ala | Phe | Ala | Tyr | Asp | Leu | Val | Phe | Gln | Ile | Glu | Asp | Leu | Val |
| | | | | 165 | | | | | 170 | | | | | 175 | |
| Gln | Lys | Arg | Ala | Arg | Glu | Ser | Asp | Gln | Arg | Asp | Ile | Val | Leu | Tyr | Val |
| | | | 180 | | | | | 185 | | | | | 190 | | |
| Pro | Asp | Arg | Leu | Leu | Ala | Tyr | Asp | Arg | Ala | Thr | Gly | Arg | Gly | Val | Val |
| | | | | 195 | | | | | 200 | | | | | 205 | |
| Leu | Ser | Tyr | Asp | Phe | Thr | Trp | Lys | Gly | Arg | Ser | Thr | Glu | Gly | Leu | Pro |
| | 210 | | | | | 215 | | | | | 220 | | | | |
| Arg | Glu | Thr | Ala | Asp | Ser | Pro | Tyr | Met | Lys | Thr | Pro | Arg | Gln | Gly | Phe |
| 225 | | | | | 230 | | | | | 235 | | | | | 240 |
| Ala | Asp | His | Ala | Pro | Gly | Glu | Tyr | Gln | Ala | Thr | Val | Glu | Thr | Ala | Arg |
| | | | | 245 | | | | | 250 | | | | | 255 | |
| Ala | Ala | Phe | Ala | Arg | Gly | Asp | Leu | Phe | Glu | Ala | Val | Pro | Gly | Gln | Leu |
| | | | 260 | | | | | 265 | | | | | 270 | | |
| Phe | Ala | Glu | Pro | Cys | Asp | Arg | Ser | Pro | Ala | Glu | Val | Phe | Gln | Arg | Leu |
| | | | | 275 | | | | | 280 | | | | | 285 | |
| Cys | Val | Ile | Asn | Pro | Ser | Pro | Tyr | Gly | Ala | Leu | Met | Asn | Leu | Gly | Asp |
| | 290 | | | | | 295 | | | | | 300 | | | | |
| Gly | Glu | Phe | Leu | Val | Ser | Ala | Ser | Pro | Glu | Met | Phe | Val | Arg | Ser | Asp |
| 305 | | | | | 310 | | | | | 315 | | | | | 320 |
| Gly | Arg | Arg | Val | Glu | Thr | Cys | Pro | Ile | Ser | Gly | Thr | Ile | Ala | Arg | Gly |
| | | | | 325 | | | | | 330 | | | | | 335 | |
| Thr | Asp | Ala | Ile | Gly | Asp | Ala | Glu | Gln | Ile | Arg | Gln | Leu | Leu | Asn | Ser |
| | | | 340 | | | | | 345 | | | | | 350 | | |
| Glu | Lys | Asp | Glu | Phe | Glu | Leu | Asn | Met | Cys | Thr | Asp | Val | Asp | Arg | Asn |
| | | | | 355 | | | | | 360 | | | | | 365 | |

-continued

```
Asp Lys Ala Arg Val Cys Val Pro Gly Thr Ile Lys Val Leu Ala Arg
370                 375                 380

Arg Gln Ile Glu Thr Tyr Ser Lys Leu Phe His Thr Val Asp His Val
385                 390                 395                 400

Glu Gly Met Leu Arg Pro Gly Phe Asp Ala Leu Asp Ala Phe Leu Thr
                405                 410                 415

His Ala Trp Ala Val Thr Val Thr Gly Ala Pro Lys Leu Trp Ala Met
            420                 425                 430

Gln Phe Val Glu Asp His Glu Arg Ser Pro Arg Arg Trp Tyr Ala Gly
        435                 440                 445

Ala Ile Gly Ala Val Asn Phe Asp Gly Ser Ile Asn Thr Gly Leu Thr
    450                 455                 460

Ile Arg Thr Ile Arg Met Lys Asp Gly Leu Ala Glu Val Arg Val Gly
465                 470                 475                 480

Ala Thr Cys Leu Phe Asp Ser Asp Pro Ala Ala Glu Asp Arg Glu Cys
                485                 490                 495

Gln Val Lys Ala Ala Ala Leu Phe Gln Ala Leu Arg Gly Asp Pro Pro
            500                 505                 510

Lys Pro Leu Ser Thr Phe Ala Pro Asp Ala Thr Gly Ser Gly Lys Arg
        515                 520                 525

Val Leu Leu Ile Asp His Asp Asp Ser Phe Val His Met Leu Ala Asp
530                 535                 540

Tyr Phe Arg Gln Val Gly Ala Ser Val Thr Val Val Arg Tyr Val His
545                 550                 555                 560

Ala Leu Asp Met Leu Lys Gln Lys Arg Trp Asp Leu Leu Val Leu Ser
                565                 570                 575

Pro Gly Pro Gly Arg Pro Glu Asp Phe Gly Ile Arg Lys Thr Ile Asp
            580                 585                 590

Ala Ala Leu Glu Asn Lys Leu Pro Val Phe Gly Val Cys Leu Gly Val
        595                 600                 605

Gln Ala Ile Gly Glu Tyr Phe Gly Gly Glu Leu Gly Gln Leu Thr His
    610                 615                 620

Pro Ala His Gly Arg Pro Ser Arg Val Gln Arg Gly Gly Arg Leu
625                 630                 635                 640

Met Arg Asn Leu Pro Ser Glu Ile Val Ile Gly Arg Tyr His Ser Leu
                645                 650                 655

Tyr Val Glu Arg Asp Ser Met Pro Glu Val Leu Ser Val Thr Ala Ser
            660                 665                 670

Thr Glu Asp Gly Val Ala Met Ala Leu Glu His Lys Thr Leu Pro Val
        675                 680                 685

Ala Gly Val Gln Phe His Pro Glu Ser Leu Met Ser Leu Gly Gly Glu
    690                 695                 700

Val Gly Leu Arg Ile Val Glu Asn Ala Phe Arg Leu Asp Ala Arg Val
705                 710                 715                 720

Asp

<210> SEQ ID NO 131
<211> LENGTH: 728
<212> TYPE: PRT
<213> ORGANISM: Rhodospirillum rubrum

<400> SEQUENCE: 131

Met Gln Thr Ser Thr Phe Thr Thr Ala Gly Gly Phe Thr Ile Ser Ser
1               5                   10                  15
```

```
Cys Leu Arg Pro Leu Ala Gly Ala Asp Gly Ala Phe Glu Ala Leu Ile
         20                  25                  30

Asp Arg Leu Asp Arg His Arg Gly Met Val Ile Ala Ser Thr Tyr Glu
         35                  40                  45

Tyr Pro Gly Arg Tyr Arg His Ala Leu Gly Phe Cys Asp Pro Pro
 50                  55                  60

Leu Val Leu Glu Gly Lys Gly Arg Glu Ala His Leu Leu Ala Leu Asn
 65                  70                  75                  80

Arg Arg Gly Arg Ala Leu Leu Pro Ala Leu Ala Val Gly Leu Glu Gly
                 85                  90                  95

Ala Ala Gly Leu Glu Gly Leu Arg Arg Glu Ala Asp Arg Leu Val Leu
             100                 105                 110

Arg Val Lys Ala Met Ala Pro Trp Phe Pro Glu Glu Glu Arg Ser Arg
         115                 120                 125

Gln Pro Ser Leu Met Ser Val Val Arg Ala Leu Ala Gly Leu Phe Ala
 130                 135                 140

Ala Glu Asn Asp Pro Phe Phe Gly Leu Val Gly Ala Phe Gly Tyr Asp
145                 150                 155                 160

Leu Gly Leu Ala Phe Glu Arg Leu Pro His Ala Arg Pro Arg Ser Ala
                 165                 170                 175

Asp His Arg Asp Leu Val Leu Tyr Leu Pro Asp Arg Leu Leu Ile Asp
             180                 185                 190

Asp Pro Glu Ala Gly Gly Leu Ala Glu Arg Leu Tyr Asp Ile Thr Ala
         195                 200                 205

Ala Asp Gly Ala Ser Thr Ala Gly Leu Ala Arg Glu Thr Ala Ala Tyr
210                 215                 220

Thr Ala Asp His Pro Ala Gly Gly Val Pro Ile Glu Asp Asp Met Pro
225                 230                 235                 240

Pro Gly Ala Tyr Gly Ala Ile Val Arg Gly Leu Lys Glu Ala Phe Ala
                 245                 250                 255

Ala Gly Asp Leu Phe Glu Ala Val Pro Ser Arg Ala Leu Arg Arg Pro
             260                 265                 270

Cys Ala Glu Ala Pro Ser Arg Leu Tyr Arg Arg Leu Arg Ala Ala Asn
         275                 280                 285

Pro Ala Pro Tyr Leu Phe Leu Ala Asn Leu Gly Ala Gly Glu His Leu
290                 295                 300

Ile Gly Ala Ser Pro Glu Met Phe Val Arg Val Gly Ala Pro Gly
305                 310                 315                 320

Ala Arg Arg Val Glu Thr Cys Pro Ile Ser Gly Thr Ile Ala Arg Gly
                 325                 330                 335

Pro Asp Ala Leu Gly Asp Ala Glu Ala Ile Arg Thr Leu Leu Asn Ser
             340                 345                 350

Thr Lys Asp Glu Ala Glu Leu Thr Met Cys Thr Asp Val Asp Arg Asn
         355                 360                 365

Asp Lys Ala Arg Val Cys Val Ala Gly Ser Val Thr Val Ile Gly Arg
370                 375                 380

Arg Gln Ile Glu Leu Tyr Ser Arg Leu Ile His Thr Val Asp His Val
385                 390                 395                 400

Glu Gly Arg Leu Arg Pro Glu Leu Asp Ala Leu Asp Ala Phe Leu Ser
                 405                 410                 415

His Cys Trp Ala Val Thr Val Thr Gly Ala Pro Lys Arg Ala Ala Met
             420                 425                 430

Ala Ala Val Glu Ala Val Glu Arg Ala Pro Arg Ala Trp Tyr Gly Gly
```

-continued

```
                435                 440                 445
Ala Ile Gly Arg Leu Gly Phe Asp Gly Thr Leu Asp Thr Gly Leu Val
450                 455                 460

Leu Arg Thr Ile Arg Leu Arg His Gly Val Ala Glu Val Arg Val Gly
465                 470                 475                 480

Ala Thr Leu Leu His Arg Ser Asp Pro Glu Glu Glu Ala Glu Thr
                485                 490                 495

Leu Leu Lys Ala Ser Ala Leu Leu Ala Leu Leu Asp Ala Thr Thr Pro
                500                 505                 510

Ala Lys Pro Asn Ala Pro His Leu Pro Leu Arg Gly Arg Ala Pro Arg
                515                 520                 525

Val Leu Val Ile Asp His Glu Asp Ser Phe Val His Thr Leu Ala Ser
530                 535                 540

Tyr Leu Arg Asn Ala Gly Ala Glu Thr Thr Val Leu Arg Trp Asp Val
545                 550                 555                 560

Pro Ala Ala Val Arg Ala Gly Val Glu Ala Asp Leu Leu Val Leu Ser
                565                 570                 575

Pro Gly Pro Gly Thr Pro Ser Arg Phe Ala Leu Gly Ala Ser Leu Asp
                580                 585                 590

Trp Ala Val Ala Arg Gly Leu Pro Val Phe Gly Val Cys Leu Gly Leu
                595                 600                 605

Gln Gly Ile Val Glu Gln Ala Gly Gly Arg Leu Ala Arg Leu Ala Val
                610                 615                 620

Pro Ala His Gly Met Ala Ser Thr Leu Arg Leu Val Ala Pro Gly Asp
625                 630                 635                 640

Pro Leu Phe Ala Gly Leu Pro Thr Thr Met Arg Val Gly Arg Tyr His
                645                 650                 655

Ser Leu His Ala Glu Arg Ala Ser Leu Pro Asp Ser Leu Glu Ile Leu
                660                 665                 670

Ala Glu Ser Asp Asp Gly Val Ile Met Ala Leu Arg His Arg Leu Leu
                675                 680                 685

Pro Phe Ser Ala Val Gln Phe His Pro Glu Ser Leu Met Thr Leu Asp
                690                 695                 700

Gly Gly Ala Gly Pro Arg Leu Ile Ala Asn Leu Leu Glu Thr Leu Ser
705                 710                 715                 720

Val Pro Arg Thr Arg His Ala Ala
                725

<210> SEQ ID NO 132
<211> LENGTH: 726
<212> TYPE: PRT
<213> ORGANISM: Thermobifida fusca

<400> SEQUENCE: 132

Val Asp Asp Asn Ser Tyr Thr Thr Ser Gly Gly Ile Thr Val His Arg
1               5                   10                  15

Thr Ala Val Pro Cys Asp Pro Arg Ala Leu Ala Asp Leu Thr Val Asn
                20                  25                  30

Val Glu Gln Arg Arg Gly Gly Val Leu Ser Ser Gly Met Glu Tyr Pro
                35                  40                  45

Gly Arg Tyr Ser Arg Trp His Leu Gly Tyr Val Asp Pro Cys Leu Glu
                50                  55                  60

Val Val Ala Arg Gly Arg Thr Ile Gly Ala Thr Ala Leu Asn Asp Arg
65                  70                  75                  80
```

-continued

```
Gly Arg Val Leu Leu Pro Ala Val Ala Arg Ala Leu Thr Ala His Gly
            85                  90                  95

Ala Val Val Glu His Thr Asp Asp Thr Val Ala Val Thr Val Pro Glu
        100                 105                 110

Pro Asp Pro Thr Glu Phe Phe Thr Glu Glu Arg Ser Arg Arg Leu
    115                 120                 125

Ser Val Phe Ser Ala Leu Arg Ala Leu Val Gly Val Phe Phe His Ala
    130                 135                 140

Glu Glu Pro His Leu Gly Leu Tyr Gly Ala Phe Gly Tyr Asp Leu Ala
145                 150                 155                 160

Phe Gln Phe Glu Pro Ile Glu Gln Val Leu Pro Arg Asp Pro Glu Asp
                165                 170                 175

Arg Asp Leu Val Leu His Leu Pro Asp Glu Ile Ile Val His Asp Arg
            180                 185                 190

Lys Arg Glu Ile Cys Gln Arg Tyr Ser Tyr Asp Phe Thr Leu Pro Glu
        195                 200                 205

Glu Leu Arg Gly Pro Ala Gly Ala Thr Thr Arg Gly Leu Pro Arg His
    210                 215                 220

Thr Glu Pro Thr Pro Val Thr Pro Ala Ala Glu Val Pro Pro Gln
225                 230                 235                 240

Pro Glu Pro Gly Ser Tyr Ala Arg Ile Val Ala Glu Ala Lys Glu Arg
                245                 250                 255

Phe Arg Arg Gly Asp Leu Phe Glu Val Val Pro Ser His Arg Leu Tyr
            260                 265                 270

Ala Pro Cys Ala Ser Pro Ala Arg Phe Tyr Glu Arg Leu Arg Glu Arg
        275                 280                 285

Asn Pro Ala Pro Tyr Glu Phe Phe Leu Asn Leu Gly Glu Gly Glu Tyr
    290                 295                 300

Leu Val Gly Ala Ser Pro Glu Met Phe Val Arg Val Thr Gly Arg Pro
305                 310                 315                 320

Gly Glu Gly Gln Arg Val Glu Thr Cys Pro Ile Ser Gly Thr Ile Lys
                325                 330                 335

Arg Gly Ala Asp Ala Val Gly Asp Ala Glu Asn Ile Lys Glu Leu Leu
            340                 345                 350

Ser Ser Ala Lys Glu Glu Ser Glu Leu Thr Met Cys Thr Asp Val Asp
        355                 360                 365

Arg Asn Asp Lys Ser Arg Val Cys Val Pro Gly Ser Val Arg Val Ile
    370                 375                 380

Gly Arg Arg Gln Ile Glu Met Tyr Ser Arg Leu Ile His Thr Val Asp
385                 390                 395                 400

His Ile Glu Gly Ile Leu Arg Pro Glu Leu Asp Ala Ile Asp Ala Phe
                405                 410                 415

Leu Thr His Met Trp Ala Val Thr Val Thr Gly Ala Pro Lys Thr Trp
            420                 425                 430

Ala Met Arg Phe Ile Glu Gln His Glu Ser Ser Pro Arg Arg Trp Tyr
        435                 440                 445

Gly Gly Ala Val Gly Val Ile Asn Phe Asp Gly Ser Met Asn Thr Gly
    450                 455                 460

Leu Thr Leu Arg Thr Ala His Ile Arg Asp Gly Val Ala Thr Val Arg
465                 470                 475                 480

Ala Gly Ala Thr Leu Leu Tyr Asp Ser Asp Pro Glu Ala Glu Arg
                485                 490                 495

Glu Thr Phe Leu Lys Ala Arg Ala Leu Leu Glu Thr Leu Thr Asp Glu
```

```
                      500                 505                 510
Gly Glu Glu Thr Ser Lys Ala Ala Pro Ala Val Glu Gln Val Gly Ala
            515                 520                 525

Gly Met Arg Val Leu Leu Val Asp His Glu Asp Ser Phe Val Asn Thr
        530                 535                 540

Leu Ala Asp Tyr Val Arg Arg His Gly Ala Glu Val Thr Thr Val Arg
545                 550                 555                 560

Tyr Gly Phe Asp Pro Ala Leu Leu Asp Gln Met Arg Pro Asp Leu Val
                565                 570                 575

Val Leu Ser Pro Gly Pro Gly Leu Pro Ala Asp Phe Ala Met Ser Ala
            580                 585                 590

Leu Leu Lys Glu Leu Asp Ala Arg Gly Leu Pro Val Phe Gly Val Cys
        595                 600                 605

Leu Gly Leu Gln Ala Met Val Glu Tyr Ala Gly Gly Glu Leu Leu Thr
    610                 615                 620

Leu Asp Thr Pro Val His Gly Lys Pro Gly Arg Val Arg Val Thr Gly
625                 630                 635                 640

Gly Ala Leu Leu Ala Gly Leu Gly Glu Asp Gly Glu Phe Thr Ala Ala
                645                 650                 655

Arg Tyr His Ser Val Tyr Ala Thr Pro Asp Arg Val Lys Gly Phe Glu
            660                 665                 670

Val Thr Ala Val Thr Glu Asp Gly Phe Pro Val Val Met Ala Ile
        675                 680                 685

Glu Asn Ala Glu Ala Arg Arg Trp Ala Val Gln Phe His Pro Glu Ser
    690                 695                 700

Ile Leu Thr Gly Arg Val Gly Glu Gln Ile Val Ala Asn Val Leu Arg
705                 710                 715                 720

Leu Ala Arg Glu Ser Ser
                725

<210> SEQ ID NO 133
<211> LENGTH: 281
<212> TYPE: PRT
<213> ORGANISM: Sorghum bicolor

<400> SEQUENCE: 133

Met Val Cys Ser Gln Leu Thr Ala Ala Gly Ala Ser Ser Leu Ala Ala
1               5                   10                  15

Ala Ala Val Arg Ser Arg Ala His Ser Pro Ala Ala Phe Ala Gln
            20                  25                  30

Leu Arg Ser Thr Pro Arg Ile Ala Ser Ala Gly Leu Ser Val Lys Gly
        35                  40                  45

Asn Arg Ala Ala Leu Pro Leu Val Ala Ala Ala Gly Pro Ala Ala Ala
    50                  55                  60

Ala Pro Val Ala Asp Leu Asp Gly Pro Ala Thr Glu Lys Gln Pro
65                  70                  75                  80

Ile Ile Val Ile Asp Asn Tyr Asp Ser Phe Thr Tyr Asn Leu Cys Gln
                85                  90                  95

Tyr Met Gly Glu Leu Gly Leu Asn Phe Glu Val Tyr Arg Asn Asp Glu
            100                 105                 110

Leu Thr Ile Glu Asp Val Lys Arg Lys Asn Pro Arg Gly Ile Leu Ile
        115                 120                 125

Ser Pro Gly Pro Gly Glu Pro Gln Asp Ser Gly Ile Ser Leu Gln Ala
    130                 135                 140
```

```
Val Leu Glu Leu Gly Pro Thr Ile Pro Ile Phe Gly Val Cys Met Gly
145                 150                 155                 160

Leu Gln Cys Ile Gly Glu Ala Phe Gly Gly Lys Ile Ile Arg Ala Pro
            165                 170                 175

Ser Gly Val Met His Gly Lys Ser Ser Pro Val Tyr Tyr Asp Glu Glu
        180                 185                 190

Leu Gly Lys Ala Leu Phe Asn Gly Leu Pro Asn Pro Phe Thr Ala Ala
    195                 200                 205

Arg Tyr His Ser Leu Val Ile Glu Glu Thr Phe Pro His Asp Ala
210                 215                 220

Leu Glu Ala Thr Ala Trp Thr Glu Asp Gly Leu Ile Met Ala Ala Arg
225                 230                 235                 240

His Lys Lys Tyr Lys His Ile Gln Gly Val Gln Phe His Pro Glu Ser
                245                 250                 255

Ile Ile Thr Pro Asp Gly Lys Lys Ile Ile Leu Asn Phe Val Arg Phe
                260                 265                 270

Ile Glu Glu Leu Glu Lys Gln Arg Ser
275                 280
```

<210> SEQ ID NO 134
<211> LENGTH: 1122
<212> TYPE: DNA
<213> ORGANISM: Sorghum bicolor

<400> SEQUENCE: 134

```
gtcgacccac gcgtccgccg cctccccacc ctcgctccct ctcaccgccc gccaccgccg      60
agatggtctg ctcccagctc accgccgcgg gggcctcctc cctcgccgcc gcagcggttc     120
gttcccgggc gcattcccca gccgccgcct tcgcgcaact acgtcgacg cctcgcattg      180
cgagcgctgg cttgtcggtt aagggaaaca gggcggctct tccgttggtc gccgccgcgg     240
ggccggccgc ggcggcgccg gtggccgacc tggacggccc cccggccacg gagaagcagc     300
ccatcattgt catcgataac tacgacagct tcacctacaa cctctgccag tatatggggg     360
agcttggatt gaactttgaa gtataccgca atgatgaact gaccatagaa gatgtaaaga     420
ggaagaaccc aagaggaata cttatttctc cagggcctgg tgaaccacaa gattcaggaa     480
tatcattgca ggctgttctt gaattaggcc caaccatccc aatttttgga gtttgcatgg     540
gcctgcagtg cattggggag gcatttgggg gaaagattat ccgtgctcct tctggagtga     600
tgcatgggaa aagctctcca gtttattacg acgaggaatt aggaaaggcc ttattcaatg     660
gcttgccaaa ccctttacc gctgcgaggt accacagctt ggtcattgag aagaaaccct      720
tcccgcatga tgctttagag gccactgcat ggactgaaga tggacttatc atggctgctc     780
gccacaagaa gtacaaacac atccagggtg tccaattcca cccggagagc atcatcaccc     840
ctgacggcaa gaaaatcatc ctcaatttcg tcagattcat tgaggaactg gagaagcagc     900
gttcctaggg aggtagatgc caccggtggc ttcatagatc agtcagaagc agagacaaag     960
gcgcttgaag ctgcgtagta ccgggtctgg cagtggaagt tagctaggaa acagcctttt    1020
tcctccctta attcgttgtg ctcgtggtaa tataatctgt gtggactgaa tttcgaataa    1080
agtccagctg ttcaaataaa aaaaaaaaa aagggcggcc gc                        1122
```

<210> SEQ ID NO 135
<211> LENGTH: 1934
<212> TYPE: DNA
<213> ORGANISM: Sorghum bicolor

<400> SEQUENCE: 135

```
gtcgacccac gcgtccgcgt gacacccgc cggcacctc cgcctcccca ccctcgctcc      60
ctctcaccgc ccgccaccgc cgagatggtc tgctcccagc tcaccgccgc ggggcctcc    120
tccctcgccg ccgcagcggt tcgttcccgg gcgcattccc cagccgccgc cttcgcgcaa   180
ctacggtcga cgcctcgcat tgcgagcgct ggcttgtcgg ttaagggaaa cagggcggct   240
cttccgttgg tcgccgccgc ggggccggcc gcggcggcgc cggtgccgga cctggacggc   300
cccccggcca cggagaagca gcccatcatt gtcatcgata actacgacag cttcacctac   360
aacctctgcc agtatatggg ggagcttgga ttgaactttg aagtataccg caatgatgaa   420
ctgaccatag aagatgtaaa gaggaagaac ccaagaggaa tacttatttc tccagggcct   480
ggtgaaccac aagattcagg aatatcattg caggctgttc ttgaattagg cccaaccatc   540
ccaattttg gagtttgcat gggcctgcag tgcattgggg aggcatttgg gggaaagatt    600
atccgtgctc cttctggagt gatgcatggg aaaagctctc cagtttatta cgacgaggaa   660
ttaggaaagg ccttattcaa tggcttgcca aaccctttta ccgctgcgag gtaccacagc   720
ttggtcattg aggaagaaac cttcccgcat gatgctttag aggccactgc atggactgaa   780
gatggactta tcatggctgc tcgccacaag aagtacaaac acatccaggg tgtccaattc   840
cacccggaga gcatcatcac ccctgacggc aagaaaatca tcctcaattt cgtcagattc   900
attgaggaac tggagaagca gcgttcctag ggaggtagat gccaccggtg gcttcataga   960
tcagtcagaa gcagagacaa aggcgcttga agctgcgtag taccgggtct ggcagtggaa  1020
gttagctagg aaacagcctt tttcctccct taattcgttg tgctcgtggt aatataatct  1080
gtgtggactg aatttcgaat aaagtccagc tgttcaaata aaaaaaaaaa aaagggcgg   1140
ccgctaccct cgaggccggc cgggccggga agccgcgatg ttaaatgtgt ggtccttagc  1200
aatcaaatct gcgtacaaga tggaatctct attattttca gcgaaaccaa gggattccgt  1260
gagcgcatcc gagggaggaa ggtgggcgta cctttaggct tctttccgac ctccgggaag  1320
tgcggcgagg gtttcatggc gatgttggcg gctgcaaggc cggcgcgccg gatagaggcg  1380
ggggcagggg aactgacaag ggtttaacta cgcgaacgcg cactgcagga atggacgagc  1440
tcgctctctc aaatcggccg aatgcgctcg tcccaccgag acgccgtctt gctccgtctc  1500
cctgtctcgc tcacgcggac gctccacgcg agcagggcag gccgaggagg gcgacggcgc  1560
agccgggcga cggcgcgagg agagcgatgg cgcgaagagt gcagaacgcg cggctcggcg  1620
gcggcgcagc tgtgcggcgg cgcggttggg ccgcggtggc ggagaacggt gaacggaaga  1680
acgaagaaga aagggaaaga agcctttgta tgacacgtgg gtcccgcagt tagaagggtt  1740
aaaatctgttg tctcatccat cacgtagtct taattttttt ttcactagtc tgtgttaatg  1800
ctacgatctt aagaagccag cgacaataag agtagctcta ataaaaaaaa aaaaaaaag   1860
aaaaaaaaaa aaaaaaaaa aaaaaaaa aaaacaaaaa aaaaaaaaaa aaaggcccct    1920
agggccctcg agct                                                    1934
```

<210> SEQ ID NO 136
<211> LENGTH: 2055
<212> TYPE: DNA
<213> ORGANISM: Zea mays

<400> SEQUENCE: 136

```
ggccggccgg gactccactc cactccactc gcccgcgccc gccgcccgcg tgctcctccc      60
tcgcgcccgc cccgccccgc tccgccccta tctatatcca ttcccgctcg tccccctcaa    120
```

```
caaccctcct cacggcgcac tcgtgttcgt gtcatcccgc ccgcaggccg cagtccatgg    180
ccaccgccag cctcgcgctc tcgctgcgcc tcgcgccgta ctcgcacccg ctgagcctcc    240
gccgccgggg ggccgccggc gtcacctgcc gcgccaccac cgccacgttc caccagcttg    300
acgccgtcgc ggtgagggag gaggagtcca ggttccggac ggcggcggcg agggccgca    360 acctgctgcc gctcacgagg tgcatcttct ccgatcacct cacgcccgtg ctcgcctacc    420
gctgcctcgt caaggaggac gaacgcgagg cgcccagctt tctattcgag tctgtcgagc    480
aggggtccga gggcaccaat gtggggaggt acagcgtggt cggggcgcag ccttctatgg    540
aggtcgtggc caaggctaac catgtgacgg tcatggacca tgagatgaag tcgaggaggg    600
agcacttcgt gcctgatccc atgaggatcc ccaggacaat catggagcag tggaacccgc    660
agattgctga cagcctccct gatgcatttt gtggaggatg ggttggattc ttctcatatg    720
atacagtgcg ttatgttgaa acaaagaagc ttcctttcag taaggcacca catgatgata    780
ggaaccttcc tgatattcat ttaggcctct atagtgacgt cattgtgttt gatcatgttg    840
aaaagaaaac acatgttatt cattgggtga ggacagactg ctatcgttct gttgatgaag    900
catatgaaga tggaagaaat cggcttgaag ctttgttatc aagattacat tgcctcaatg    960
tcccaacact ttcttctggt tctataaaac tcaatgttga aactttggc ccagtaatgc    1020 aaaaatcaac gatgtcaagc gaagaatata aaaatatcgt tgtccaagct aaagaacaca    1080
tcttggccgg tgacattttc caagttgttt taagccagcg ttttgagaga cggacattcg    1140
ccgacccctt tgaaatctat cgtgcattgc gcatcgtaaa tcctagtcca tatatggcct    1200
atctacaggc acgaggttgt attctcgtgg catcgagtcc tgaaattctt acccgggtac    1260
aaaagaggac aataatcaat cgtccgcttg ctggaaccat aagaagaggc aaaacaaaag    1320
cagaagacaa aactttagaa caattgcttt tgagtgacga aaagcagtgt gctgaacata    1380
ttatgctagt agatcttggc cgaaatgatg ttgggaaggt gtccaaacca ggttcagtaa    1440
aggtagagaa attgatgaat atcgaacgat attctcatgt catgcacatc agctcaacag    1500
taactggaga gctacgcgat gatcttacgt gttgggatgc gctacgagcc gcattgccag    1560
ttggaaccgt tagtggcgct ccaaaggtga gagcaatgga gttgattgat cagctagaag    1620
tgagtatgcg tgggccgtat agtggtggct ttggagggat ttccttttcgc ggcgacatgg    1680 acattgcact ggctcttcgc actatcgtct tccccaccgc atctcggttt gataccatgt    1740
actcgtacac agacagtaag tcccgacagg agtgggtggc tcacctccag gccggagctg    1800
gcatagttgc tgatagcaaa ccggatgacg agcaccaaga gtgtataaac aaggctgcag    1860
gtgttgctcg tgccattgac cttgctgaat ctacatttct tgaagactag tctagtctaa    1920
tgaaggaaat gtatgtttaa gttctctgta caattatgga ttgtcctaga aacaggctt    1980 tcttaggccg aataaaaact caattgtaat aaagttaata aatggacaac tttagctaaa    2040
aaaaaaaaaa aaaaa                                                    2055
```

```
<210> SEQ ID NO 137
<211> LENGTH: 577
<212> TYPE: PRT
<213> ORGANISM: Zea mays

<400> SEQUENCE: 137

Met Ala Thr Ala Ser Leu Ala Leu Ser Leu Arg Leu Ala Pro Tyr Ser
1               5                   10                  15

His Pro Leu Ser Leu Arg Arg Arg Gly Ala Ala Gly Val Thr Cys Arg
```

-continued

```
                20                  25                  30
Ala Thr Thr Ala Thr Phe His Gln Leu Asp Ala Val Ala Val Arg Glu
                35                  40                  45

Glu Glu Ser Arg Phe Arg Thr Ala Ala Ala Glu Gly Arg Asn Leu Leu
     50                  55                  60

Pro Leu Thr Arg Cys Ile Phe Ser Asp His Leu Thr Pro Val Leu Ala
 65                  70                  75                  80

Tyr Arg Cys Leu Val Lys Glu Asp Glu Arg Glu Ala Pro Ser Phe Leu
                 85                  90                  95

Phe Glu Ser Val Glu Gln Gly Ser Glu Gly Thr Asn Val Gly Arg Tyr
            100                 105                 110

Ser Val Val Gly Ala Gln Pro Ser Met Glu Val Val Ala Lys Ala Asn
        115                 120                 125

His Val Thr Val Met Asp His Glu Met Lys Ser Arg Arg Glu His Phe
    130                 135                 140

Val Pro Asp Pro Met Arg Ile Pro Arg Thr Ile Met Glu Gln Trp Asn
145                 150                 155                 160

Pro Gln Ile Ala Asp Ser Leu Pro Asp Ala Phe Cys Gly Gly Trp Val
                165                 170                 175

Gly Phe Phe Ser Tyr Asp Thr Val Arg Tyr Val Glu Thr Lys Lys Leu
            180                 185                 190

Pro Phe Ser Lys Ala Pro His Asp Asp Arg Asn Leu Pro Asp Ile His
        195                 200                 205

Leu Gly Leu Tyr Ser Asp Val Ile Val Phe Asp His Val Glu Lys Lys
    210                 215                 220

Thr His Val Ile His Trp Val Arg Thr Asp Cys Tyr Arg Ser Val Asp
225                 230                 235                 240

Glu Ala Tyr Glu Asp Gly Arg Asn Arg Leu Glu Ala Leu Leu Ser Arg
                245                 250                 255

Leu His Cys Leu Asn Val Pro Thr Leu Ser Ser Gly Ser Ile Lys Leu
            260                 265                 270

Asn Val Glu Asn Phe Gly Pro Val Met Gln Lys Ser Thr Met Ser Ser
        275                 280                 285

Glu Glu Tyr Lys Asn Ile Val Val Gln Ala Lys Glu His Ile Leu Ala
    290                 295                 300

Gly Asp Ile Phe Gln Val Val Leu Ser Gln Arg Phe Glu Arg Arg Thr
305                 310                 315                 320

Phe Ala Asp Pro Phe Glu Ile Tyr Arg Ala Leu Arg Ile Val Asn Pro
                325                 330                 335

Ser Pro Tyr Met Ala Tyr Leu Gln Ala Arg Gly Cys Ile Leu Val Ala
            340                 345                 350

Ser Ser Pro Glu Ile Leu Thr Arg Val Gln Lys Arg Thr Ile Ile Asn
        355                 360                 365

Arg Pro Leu Ala Gly Thr Ile Arg Arg Gly Lys Thr Lys Ala Glu Asp
    370                 375                 380

Lys Thr Leu Glu Gln Leu Leu Ser Asp Lys Gln Cys Ala Glu
385                 390                 395                 400

His Ile Met Leu Val Asp Leu Gly Arg Asn Asp Val Gly Lys Val Ser
                405                 410                 415

Lys Pro Gly Ser Val Lys Val Glu Lys Leu Met Asn Ile Glu Arg Tyr
            420                 425                 430

Ser His Val Met His Ile Ser Ser Thr Val Thr Gly Glu Leu Arg Asp
        435                 440                 445
```

-continued

```
Asp Leu Thr Cys Trp Asp Ala Leu Arg Ala Ala Leu Pro Val Gly Thr
        450                 455                 460
Val Ser Gly Ala Pro Lys Val Arg Ala Met Glu Leu Ile Asp Gln Leu
465                 470                 475                 480
Glu Val Ser Met Arg Gly Pro Tyr Ser Gly Phe Gly Gly Ile Ser
                485                 490                 495
Phe Arg Gly Asp Met Asp Ile Ala Leu Ala Leu Arg Thr Ile Val Phe
            500                 505                 510
Pro Thr Ala Ser Arg Phe Asp Thr Met Tyr Ser Tyr Thr Asp Ser Lys
        515                 520                 525
Ser Arg Gln Glu Trp Val Ala His Leu Gln Ala Gly Ala Gly Ile Val
    530                 535                 540
Ala Asp Ser Lys Pro Asp Glu His Gln Glu Cys Ile Asn Lys Ala
545                 550                 555                 560
Ala Gly Val Ala Arg Ala Ile Asp Leu Ala Glu Ser Thr Phe Leu Glu
                565                 570                 575
Asp
```

```
<210> SEQ ID NO 138
<211> LENGTH: 22
<212> TYPE: DNA
<213> ORGANISM: Artificial sequence
<220> FEATURE:
<223> OTHER INFORMATION: A primer

<400> SEQUENCE: 138
atggcagcgg taattctgga ag                                          22

<210> SEQ ID NO 139
<211> LENGTH: 19
<212> TYPE: DNA
<213> ORGANISM: Artificial sequence
<220> FEATURE:
<223> OTHER INFORMATION: A primer

<400> SEQUENCE: 139
tcaggctgcc ttggtcttc                                              19

<210> SEQ ID NO 140
<211> LENGTH: 30
<212> TYPE: DNA
<213> ORGANISM: Artificial sequence
<220> FEATURE:
<223> OTHER INFORMATION: A primer

<400> SEQUENCE: 140
actgactcca tggcagcggt aattctggaa                                  30

<210> SEQ ID NO 141
<211> LENGTH: 20
<212> TYPE: DNA
<213> ORGANISM: Artificial sequence
<220> FEATURE:
<223> OTHER INFORMATION: A primer

<400> SEQUENCE: 141
ctgactagtt caggctgctt                                             20

<210> SEQ ID NO 142
<211> LENGTH: 30
<212> TYPE: DNA
```

<213> ORGANISM: Artificial sequence
<220> FEATURE:
<223> OTHER INFORMATION: A primer

<400> SEQUENCE: 142

| tgctgaccat ggcctgctcc cacatcgtcg | 30 |

<210> SEQ ID NO 143
<211> LENGTH: 34
<212> TYPE: DNA
<213> ORGANISM: Artificial sequence
<220> FEATURE:
<223> OTHER INFORMATION: A primer

<400> SEQUENCE: 143

| cagtgaattc ctacgaacgc tgcttctcca gttc | 34 |

<210> SEQ ID NO 144
<211> LENGTH: 2193
<212> TYPE: DNA
<213> ORGANISM: Artificial Sequence
<220> FEATURE:
<223> OTHER INFORMATION: A codon-optimized A. tumefaciens mutant

<400> SEQUENCE: 144

| atggtgacca tcattcagga cgacggcgct gagacctacg agactaaggg cggtatccaa | 60 |
| gtgagccgta agcgtaggcc cactgactac gctaacgcca tcgacaacta catcgagaag | 120 |
| ctagactccc atcgcggcgc tgtgttctcc ttcaactacg aatacctgg gcgctacacg | 180 |
| aggtgggata ccgccatcgt cgatcctcca ttgggcatct cctgttttgg gcgtaagatg | 240 |
| tggatcgagg cgtacaacgg ccgtggcgaa gtcttgctgg acttcatcac ggagaagctc | 300 |
| aaggccacac cggacctcac cctcggcgct tcctcgaccc gccgcctcga ccttacggtc | 360 |
| aacgagccgg accgcgtgtt caccgaggaa gagcgtagca agatcccgac tgtcttcacc | 420 |
| gcgctcagag ccatcgtgga cctattctac tcttctgcgg acagcgccat cgggttgttc | 480 |
| ggtgccttcg gttacgacct cgcgttccag ttcgacgcca tcaagctctc gctcgcgcgg | 540 |
| ccggaggacc agcgagacat ggtgctcttc ctccctgacg agatcctggt cgtcgatcac | 600 |
| tattccgcga aggcgtggat cgaccggtac gacttcgaga aggatggcat gaccacggat | 660 |
| ggcaagagca gcgacatcac tcccgaccca ttcaagacca ccgacaccat ccctccaaag | 720 |
| ggcgatcacc gccctggcga gtattccgaa ctcgtggtga aggccaagga atccttccgg | 780 |
| cgcggcgatc tgtttgaggt ggttcccggc caaaagttca tggagaggtg cgagtcgaat | 840 |
| ccgtctgcga tcagtcgccg actgaaagcg atcaacccga gccgtattc cttcttcatc | 900 |
| aacctcggcg atcaggaata tctggtcgga gcctcacccg agatgttcgt cagggtctcc | 960 |
| ggccgccgga tcgagacgtg cccaattttcc ggaaccatca gcgcggaga tgacccgata | 1020 |
| gccgactctg agcagatcct gaaactcttg aacagcaaga aggacgagtc cgagctgact | 1080 |
| atgtgctcag atgtggaccg aaacgacaag tcacgtgtct gcgagcccgg tagcgtcaag | 1140 |
| gtcattggcc gccgtcagat cgagatgtac tccaggctga ttcacacggt cgatcatatc | 1200 |
| gaagggcggc tgcgcgacga tatggacgca ttcgacgggt tcctcagtca cgcctgggcc | 1260 |
| gttactgtca ccggagcgcc taagctctgg gctatgaggt tcatcgaggg ccacgagaag | 1320 |
| agccctaggg cttggtatgg tggtgccatc ggcatggttg ggttcaacgg cgacatgaac | 1380 |
| accgggctga cgctccggac catcaggatc aaagacggca ttgccgaggt gagggccggt | 1440 |
| gccacgcttc tcaacgatag caaccctcag gaggaagagg cggagaccga gctgaaagcc | 1500 |

```
tctgcgatga tctccgcgat tagagatgca aagggtacga acagtgctgc caccaagcgg   1560
gacgcagcca aggtgggcac cggcgtcaag attttacttg tcgatcacga ggactccttc   1620
gtgcacactc tggcgaacta cttccgccag acaggcgcga cggtctccac cgttaggtca   1680
ccggtggccg ctgacgtgtt cgataggttc cagcccgacc ttgtggtgct ctctcccggt   1740
cccggctcgc ccacggactt cgactgcaag gccaccatta aggccgccag gccagggat    1800 ctgccaatct tcggcgtttg cctcgggctt caggcattgg ccgaggcata cggtggagag   1860
ctgaggcagc tcgccgtccc gatgcacggg aagccatccc gcatcagagt cctggagccc   1920
ggcctcgtct tctccggtct cgggaaggag gtcacggtcg gtcggtatca ttcgatcttc   1980
gccgatccgg caaccctccc gcgcgacttc atcataaccg ccgagtcgga ggacggaacg   2040
atcatgggaa tcgaacacgc caaggagccc gtagctgcgg ttcagttcca ccctgagtcc   2100
atcatgaccc tcggtcaaga tgcgggtatg cggatgatcg agaatgtggt ggttcacctc   2160
acccgcaagg ccaagaccaa ggcagcatga tag                                2193
```

<210> SEQ ID NO 145
<211> LENGTH: 2193
<212> TYPE: DNA
<213> ORGANISM: Artificial Sequence
<220> FEATURE:
<223> OTHER INFORMATION: A codon-optimized A. tumefaciens mutant

<400> SEQUENCE: 145

```
atggtgacca tcattcagga cgacggcgct gagacctacg agactaaggg cggtatccaa     60
gtgagccgta agcgtaggcc cactgactac gctaacgcca tcgacaacta catcgagaag    120
ctagactccc atcgcggcgc tgtgttctcc tgcaactacg aataccctgg gcgctacacg    180
aggtgggata ccgccatcgt cgatcctcca ttgggcatct cctgttttgg gcgtaagatg    240
tggatcgagg cgtacaacgg ccgtggcgaa gtcttgctgg acttcatcac ggagaagctc    300
aaggccacac cggacctcac cctcggcgct tcctcgaccc gccgcctcga ccttacggtc    360
aacgagccgg accgcgtgtt caccgaggaa gagcgtagca agatcccgac tgtcttcacc    420
gcgctcagag ccatcgtgga cctattctac tcttctgcgg acagcgccat cgggttgttc    480
ggtgccttcg gttacgacct cgcgttccag ttcgacgcca tcaagctctc gctcgcgcgg    540
ccggaggacc agcgagacat ggtgctcttc ctccctgacg agatcctggt cgtcgatcac    600
tattccgcga aggcgtggat cgaccggtac gacttcgaga aggatggcat gaccacggat    660
ggcaagagca gcgacatcac tcccgaccca ttcaagacca ccgacaccat ccctccaaag    720
ggcgatcacc gccctggcga gtattccgaa ctcgtggtga aggccaagga atccttccgg    780
cgcggcgatc tgtttgaggt ggttcccggc caaaagttca tggagaggtg cgagtcgaat    840
ccgtctgcga tcagtcgccg actgaaagcg atcaacccga cccgtattc cttcttcatc     900 aacctcggcg atcaggaata tctggtcgga gcctcacccg agatgttcgt cagggtctcc    960
ggccgccgga tcgagacgtg cccaatttcc ggaaccatca gcgcggaga tgacccgata   1020 gccgactctg agcagatcct gaaactcttg aacagcaaga aggacgagtc cgagctgact   1080
atgtgctcag atgtggaccg aaacgacaag tcacgtgtct gcgagccgg tagcgtcaag   1140 gtcattggcc gccgtcagat cgagatgtac tccaggctga ttcacacggt cgatcatatc   1200
gaagggcggc tgcgcgacga tatggacgca ttcgacgggt cctcagtca cgcctgggcc    1260 gttactgtca ccggagcgcc taagctctgg gctatgaggt tcatcgaggg ccacgagaag   1320
```

-continued

```
agccctaggg cttggtatgg tggtgccatc ggcatggttg ggttcaacgg cgacatgaac    1380
accgggctga cgctccggac catcaggatc aaagacggca ttgccgaggt gagggccggt    1440
gccacgcttc tcaacgatag caaccctcag gaggaagagg cggagaccga gctgaaagcc    1500
tctgcgatga tctccgcgat tagagatgca aagggtacga acagtgctgc caccaagcgg    1560
gacgcagcca aggtgggcac cggcgtcaag attttacttg tcgatcacga ggactccttc    1620
gtgcacactc tggcgaacta cttccgccag acaggcgcga cggtctccac cgttaggtca    1680
ccggtggccg ctgacgtgtt cgataggttc cagcccgacc ttgtggtgct ctctcccggt    1740
cccggctcgc ccacggactt cgactgcaag gccaccatta aggccgccag gccagggat    1800 ctgccaatct cggcgtttg cctcgggctt caggcattgg ccgaggcata cggtggagag    1860
ctgaggcagc tcgccgtccc gatgcacggg aagccatccc gcatcagagt cctggagccc    1920
ggcctcgtct tctccggtct cgggaaggag gtcacggtcg gtcggtatca ttcgatcttc    1980
gccgatccgg caaccctccc gcgcgacttc atcataaccg ccgagtcgga ggacggaacg    2040
atcatgggaa tcgaacacgc caaggagccc gtagctgcgg ttcagttcca ccctgagtcc    2100
atcatgaccc tcggtcaaga tgcgggtatg cggatgatcg agaatgtggt ggttcacctc    2160
acccgcaagg ccaagaccaa ggcagcatga tag                                2193
```

<210> SEQ ID NO 146
<211> LENGTH: 195
<212> TYPE: DNA
<213> ORGANISM: Artificial Sequence
<220> FEATURE:
<223> OTHER INFORMATION: A Zea mays CTP fused to 18 amino acids from the
      N-terminus of the Zea mays anthranilate synthase a2 protein
      (ZmASA2)

<400> SEQUENCE: 146

```
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc tgctgccgtg acgccgcagg cgagcccagt gattagcagg     180
agcgctgcgg cggcc                                                      195
```

<210> SEQ ID NO 147
<211> LENGTH: 65
<212> TYPE: PRT
<213> ORGANISM: Artificial Sequence
<220> FEATURE:
<223> OTHER INFORMATION: A Zea mays CTP fused to 18 amino acids from the
      N-terminus of the Zea mays anthranilate synthase a2 protein
      (ZmASA2)

<400> SEQUENCE: 147

```
Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65
```

<210> SEQ ID NO 148

<211> LENGTH: 232
<212> TYPE: DNA
<213> ORGANISM: Artificial Sequence
<220> FEATURE:
<223> OTHER INFORMATION: Oryza sativa glutelin 1 gene 3'-UTR

<400> SEQUENCE: 148

| | | |
|---|---|---|
| gttggcaatg cggataaaga ataactaaat aaataaataa ataaattgca agcaattgcg | 60 |
| ttgctgctat gtactgtaaa agtttcttat aatatcagtt ctgaatgcta aggacatccc | 120 |
| tcaagatggt ctttctattt tgtgttccc gttccaatgt actgttggta tcctcttgga | 180 |
| gattcatcaa tatgagaaaa cagagaatgg acaaccctcc cttatcttat gg | 232 |

<210> SEQ ID NO 149
<211> LENGTH: 7562
<212> TYPE: DNA
<213> ORGANISM: Artificial Sequence
<220> FEATURE:
<223> OTHER INFORMATION: Transcription units of pMON66879

<400> SEQUENCE: 149

| | | |
|---|---|---|
| ttttcagggt acacctagtg aggcaacggg gcagcgagtg gcacaacccc ccttccacgt | 60 |
| gtaccgagtc aagagttacc tttaatagac ggattggccg agtcaagacg catctttggt | 120 |
| tgtacgttcg aggtggccca cgtttcgccg tcgccgccgt cctatataag ttaacattta | 180 |
| ccgaagtaca ggcccttag atgtacctag tcgttactca tactaccagt tatacctctt | 240 |
| tttctttctc attaatggtt aaaaaaaagt taagttttta catctacagg cgtcgcaata | 300 |
| atatttact ttcatgtaaa actattttgc tgtttaatgc taggcagcat aaatatccgc | 360 |
| tttcgttatt tgtttaataa gattaagcct ttagaaataa agctgcacag atgtaagtgc | 420 |
| aggtttaccc ccgaatctac tctttgaagt gctagctact ccggaggtga gctgtattga | 480 |
| agcatattac atacgatatg cttcaataga gctcgtcgta aggtctaacc caagttagtt | 540 |
| gttccatgct cggtatagtg aaataagttt aaccatagcg gttttggttc ttccttgagg | 600 |
| gtaggagttt ccaaacattc cttcttaaga gtcaggtttc ggagttgttc cagtcccatg | 660 |
| tctcagaggt ttggtaatcg gttttcgatg tcctctagtt acttcttaga agttagtttc | 720 |
| atttgatgac aaggtcgtgt acgtagtacc agtcattcaa agtctttttc tgtaggtggc | 780 |
| ttctgaattt caatcacccg tagaaacttt cattagaaca gttgtagctc gtcgaccgaa | 840 |
| caccctggt ctgttttttc cttaccacgt cttaacaatc cgcgtggatg ttttcgtag | 900 |
| aaacggaaat aacgtttcta tttcgtctaa ggagatcatg ttcacccctt gttttattgc | 960 |
| accttttctc gacaggactg tcgggtgagt gattacgcat actgcttgcg tcactgctgg | 1020 |
| tgttttctta agggagatat attcttccgt aagtaagggt aaacttcctg tgtcttttta | 1080 |
| aacgatgtaa caaagtgttt gaagtttata ataagtaaat aaacagtcga agtttgaga | 1140 |
| aacaaagaac aaacaactaa ctcttataaa ttttggtacc gcgttcaatc gtcttagacg | 1200 |
| ttaccacacg tcttgggtag agaatagagg ttagagagct ttaggtcagt tgcgtttaga | 1260 |
| gggaatagcc aaagagactt ctgcgtcgtc gtaggtgctc gaataggcta aagcagcagc | 1320 |
| accctaact tcttctcacc ctactgcaat taaccgagac tcgaagcagg agaattccag | 1380 |
| tacagaagac aaaggtgccg cacgtacgaa gtgccacgtt cgtcggcagg tcgttgacga | 1440 |
| gcattcagga gaccagaaag accttggcag gcataaggtc cactgttcag atagagggtg | 1500 |
| tccaggaagt acaaacctcc agagcgatcg ccactttgag catagtggcc agaaaacctt | 1560 |
| ccacttctac aatagttgtg accattccga tacgttcgat acccacggtc ttaggcattc | 1620 |

```
cttccactat gaacctagta actaccacaa ccattgccac ctgaggaacg aggactccga    1680
ggagagctaa agccattgcg acgttgacca acggcaaact gatacccaga acaaccacaa    1740
atgctaaagc tatcgtgaaa gtaaccactg cgaagagagt gattcgcagg ttacccagca    1800
cacaacttgg gtgaagcgct ttacccacac gtccacttca gacttctgcc actagcagaa    1860
ggtcaatgga acgcacctgg tttctgaggt tgcggttagt ggatgtccca tggataccga    1920
aggcgagttc acttcaggcg acaagacgaa cgaccagagt tgtgggtcc atagtggtga     1980 caatagctcg gttagtactg agcactggtg tgacttttct acgaagttcc aaaaccacga    2040
ttggaatggc aactctgact acgactgcca cacgcatggt aggcagaact tccagcacca    2100
ttcgagtggc cagttcacta actacaaggt ccactaggta ggagatgacg aaagggtaac    2160
caacgacgga acgaacaagg tccaaggctg cagtggtagg aattgcaaaa ctacttgggt    2220
tgggcatgac cagagtagaa ctgagacgtc ctttacccac ggctgtagct tcactagttg    2280
ggtgcagaac gaccacctct tctgcaccga ctgaacgcac aagcaagaag atgaaacttc    2340
ccacaatgac aaggtcttct ggcacgagga agatactagc tgctcatagg ttaagagcga    2400
caacgtcgac gtaagcgact tccacgatgg caatacttgc caaaccttct tgaggcacaa    2460
ttcctttcgc tggcagaaag acgacagcgt ttgccagagt tcgagttgcc acaactaacg    2520
ctacttccac tctgaagaga gcagcacgca ccagcaggac tgccattccc agagccattg    2580
cgaagacctc gtcgcagcg atgggtggag ctagtggcat agcgatactc gaaggagcaa     2640
tacccagagc aaagactttt gggacaatga caactactac gatgatacta gcgatgatcg    2700
aagggtctca agtacctaaa ctaccgacca gaacctcgat tctagcttga gaggctgtga    2760
ttccgacgaa ctactcggtc gaaagcaagc atagtagcca aagctgttgc aagcagttca    2820
agttacgtag tcaaagtaac gcgtgtgtgg tcttaggatg actcaagctc ataataccgt    2880 aaccctttg acaaaagaa catggtaaac aacacgaaca ttaaatgaca caaaaaataa      2940
gccaaaagcg atagcttgac actttacctt tacctacctc ttctcaatta cttactatac    3000
caggaaaaca agtaagagtt taattataat aaacaaaaaa gagaataaac aacacacaac    3060
ttaaacttta atattctcta tacgtttgta aaacaaaact catttttaca cagtttagca    3120
ccggagatta ctggcttcaa ttatactcct cattttgtga acatcaacat ggtaatacga    3180
ataagtgatc cgttgtttat ataaaagtct ggatcttttc gacgtttaca atgacttatg    3240
ttcatacagg agaacacaaa atctgtaaat acttgaaagg aaatacatta aaaggtctta    3300
ggaacagtct aagattagta acgaaatatt aatatcaata tgagtaccta aacatcaact    3360 catacttta taaaaaatta cgtaaaatac tgaacggtta actaactgtt gtacgtagtt      3420
agctggacgt cggtgagctc tattgaagca tattacatac gatatgcttc aatacgccgg    3480
cgcaagttcg aacgtacgga cgtccagctg agatctccta ggggccgttt ttgtaaatta    3540
tgcataataa attctttttt tatacattat tatataaata taaattata gataagaata     3600 cataaaaaat ttttagataa tatataacta gttgatttta taaaaatata gatgtgaata    3660
aaacgtaaaa atagttaaaa gaacgcaaaa aaccgtataa attattactg ataagaaatt    3720
attagttagt aataagaatg taccatgtat aacaaccttg gtatacttca caagtaacgt    3780
aaactgatac acctatcaca aaactaggta cgggaagtaa acggcgataa ttaattaaac    3840
cattgtctaa gcaagattag tcaatgaatt aggaaggagt agtattaatt agaccatcaa    3900
gcttacggta ttataactaa tcaaaaaacc tggtattctt tttcggttcc ttgttttctt    3960
```

```
ctgttttgtg ttactctcat aggaaacgta tcgttacaga ttcaagtatt ttaagtttgt    4020
ttttgcgtta gtgtgtgtca cctgtagtga ataggtgatc gactagtcct agcggcgcag    4080 ttctttttt ttgacctggg gttttcggta cgtgttgttg tgcatgagtg tttccgcagt     4140
tagctcgtcg ggttttgtaa gtggttgagt tgggtagtac tcgggtgtgt aaacaacaaa    4200
gattgggttg gagtttgagc ataagagaag gcggtggagt aaaaacaaat aaagttgtgg    4260
gcagtttgac gtagggtggg gcaccggttt acaagtacgt acaattgttc tggatactga    4320
tatttataga cgttagagcc gggttcaaaa gtagtagttc ttggcccatg gctcgagctc    4380
tagaggtgtt accgaaggag atacgagaga aggcgatgat accaacgag aggccgagtc     4440 cggtgatacc agcgaggaaa gttgcctgaa ttcaggaggc gacggaaggg tcggtgggcg    4500
ttccgattgt tgctgtaatg aaggtagtgt tcgttgccgc cttctcaatt gacgtacgtc    4560
cacaccggag gctaaccttt cttcttcaaa ctctgagaga aatggaagg actggaatgg      4620 ctaaggccac cagcgcagtt gacgtacgtc cggtaccatt gctagtaagt cctactgcct    4680
cgcctctgga tgctctgctt tccgccgtag gtccagtcgg cttcgcggc cgggtggcta     4740 atacggttgc ggtagctatt aatgtagctt ttcgaactaa gggtagcgcc gcgccaaaaa    4800
agcacgttga tacttatagg cccggcaatg tgggcgaccc tatgccggta gcagctaggc    4860
ggcgagccgt aaaggacaaa accggcgttc tacacctagc ttcggatatt accgcgccg     4920 cttcacgacg agctaaagta atgccttttc gacttccgct gtgggctaga gtgggagccg    4980
cgaaggagct gggcggccga gctagaatgg cagttgcttg gcctggcaca gaagtggctt    5040
cttcttgcga gcttttaggg ctgccagaag tggcgagagt ctcggtagca gctggagaag    5100
ataagctcgc gcctaagccg gtagccggac aagccacgga agccaatgct agagcggaag    5160
gtcaagctgc gctagttcga aagcgaccgc gcaggccttc tggtcgcact gtaccacgac    5220
aaagacgggc tactttagga gcagcaacta gtgataaggc ggttccggac ctagctggca    5280
atgctaaagc tcttcctgcc gtactgctgc ctgccgttta ggaggctgta atgggggcta    5340
gggaagttct ggtggctatg gtagggcggg ttccccgcta gtggcagggc cgcttataag    5400
gctcgaacac cacttccggt tcctttcgaa ggcggcgccg ctggacaagc tccagcaagg    5460 gccggtctt aagtacctcg caacgctttc gttaggcagc cgctaaaggg cggcggactt     5520
ccgctagttg ggcagcggga taaggaagaa gtagttagag ccgctagtcc ttatagacca    5580
gccgcggagc ggcctttaca agcacgcgca gaggccggca gctagctct ggacgggcta     5640 tagtccgtgg tagttcgcgc cgctgctagg ctaacggctg tcgctcgtct aaaactttga    5700
cgagttgagc tttttcctgc ttaggcttga ctggtacacg agcctgcacc tggcgttgct    5760
gttctcggcg cagacgctcg gcccaagcca cttccagtaa ccggcggcgg tctagctcta    5820
cataagtgcg gagtaggtgt ggcagctagt gtagcttccg gcggacgcgc tgctatacct    5880
gcggaaactg ccaaaggagt cggtgcggac ccggcagtgg cagtggccac gtggtttcga    5940
cacccggtac gcgaagtagc ttccagtact tttctcgggc gcgcggacca taccgccacg    6000
ctagccgtac cagccgaagt tgccgctgta cttatggccg gactgcgacg cgtggtaggc    6060
ctagttcctg ccataacggc ttcacgcgcg gccgcgctgg gacgagttac taaggttggg    6120
cgtccttctt cttcggcttt ggcttgactt ccggaggcgg tactatagtc ggtaagcact    6180
gcgttttccg tggttgagac ggcggtggtt cgcactacgg cggtttcagc cgtggccgca    6240
gttctaggac gagcagctgg tgcttctgtc gaagcacgtg tgcgaccgct taataaaggc    6300
ggtctgcccg cgctgccaga gctggcagtc tagtggccag cgtcggctgc acaagctagc    6360
```

```
gaaggtcggc ctggagcaac aggacagcgg gcctgggccg tcgggctgcc taaagctgac      6420
gttccgttgc tagttccggc gggcgcgggc gctagacggc tagaagccgc aaacggagcc      6480
agacgtccgt aaccgtcttc ggataccgcc gctcgacgcg gtcgaacgac acgggtacgt      6540
gccgttcgga agcgcgtagg cgcacgacct tgggccggag cagaagaggc cagagccgtt      6600
ccttcagtgc cagccagcaa tggtaagcta gaagcggcta gggcggtggg acggcgcact      6660
aaagtagtag tggcgtcttt cgctcctgcc gtgctagtac ccgtagcttg tgcggttcct      6720
tggccaccgg cggcaagtca aggtgggcct tagctagtac tgcgagcctg tcctgcgccc      6780
gtacgcctac tagctcttac agcaccacgt agactgggcg ttccgcttct ggttccggcg      6840
cactaccgcg agctactgtg ccaatttagt gatcacgccg gtaggttaag ggctagcaag      6900
tttgtaaacc gttatttcaa agaattctaa cttaggacaa cggccagaac gctactaata      6960
gtatattaaa gacaacttaa tgcaattcgt acattattaa ttgtacatta cgtactgcaa      7020
taaatactct acccaaaaat actaatctca gggcgttaat atgtaaatta tgcgctatct      7080
tttgttttat atcgcgcgtt tgatcctatt taatagcgcg cgccacagta gatacaatga      7140
tctagcccct agctaggggc ccgccggcgc cggctgaacc ggccgcgcgg aattaattcg      7200
ggcccgaaac cgatggaatt ctctcagtac aaatttgata gtcacaaact gtcctatata      7260
accgcccatt tggattctct tttctcgcaa ataatcttat tgcctataaa ttttcccgca      7320
cttttccaaa taggcaagca ggtaaacata cacgtacggt tggtgtccca aggggagccc      7380
tcacgaaccg taaggcatgc tattactgaa gacaagttgg tgggtttgca gcctttcgga      7440
ctgctgcctc gtcgtaaggt tttctaggg aaccgagcag acccagccga tctccagctc      7500
acccgacgac accgaactag ggagttgcgc cakcgcctgc atcgcgtcgc ggcttttag      7560 ga                                                                    7562

<210> SEQ ID NO 150
<211> LENGTH: 35
<212> TYPE: DNA
<213> ORGANISM: Artificial sequence
<220> FEATURE:
<223> OTHER INFORMATION: A primer

<400> SEQUENCE: 150
acgcggatcc gttggcaatg cggataaaga ataac                                35

<210> SEQ ID NO 151
<211> LENGTH: 34
<212> TYPE: DNA
<213> ORGANISM: Artificial sequence
<220> FEATURE:
<223> OTHER INFORMATION: A primer

<400> SEQUENCE: 151
tacgctcgag ccataagata agggagggtt gtcc                                 34
```

HIGH TRYPTOPHAN MAIZE

This application is a Continuation-in-Part of U.S. application Ser. No. 10/430,011, filed May 5, 2003, which claims the priority of U.S. Provisional Application Ser. No. 60/377,727, filed May 3, 2002; each of which applications is incorporated herein by reference.

INCORPORATION OF SEQUENCE LISTING

A computer readable form of the sequence listing is contained in the file named "MONS109US.txt" which is 351 kb (measured in MS-Windows) and was created on Aug. 11, 2006 and is located on a CDROM, which is filed herewith and is herein incorporated by reference.

BACKGROUND OF THE INVENTION

1. Field of the Invention

The present invention relates generally to methods and compositions for improving expression of heterologous genes in order to enhance the nutritional content of plants.

2. Description of Related Art

The seeds of a number of important crops, including soybean and maize do not contain sufficient quantities of several amino acids to be nutritionally complete. These amino acids include, but are not limited to: tryptophan, isoleucine, valine, arginine, lysine, methionine, and threonine. Therefore, the biosynthetic pathways for these amino acids, and/or biosynthetic pathways for metabolites that feed into those pathways, are potential targets for manipulation in order to increase the amino acid content of these plants.

Anthranilate synthase (AS, EC 4.1.3.27) catalyzes the first reaction branching from the aromatic amino acid pathway to the biosynthesis of tryptophan in plants, fungi, and bacteria. The most common form of anthranilate synthase (for example, the maize anthranilate synthase) is a heterotetrameric enzyme consisting of two subunits, the α or TrpE subunit and the β or TrpG subunit. Two α-subunits and two β-subunits assemble to form the heterotetrameric anthranilate synthases. "Monomeric" forms of AS have also been discovered that comprise a single polypeptide chain having the activities of both TrpE and TrpG subunits (for example from *Rhizobium meliloti*). While monomeric anthranilate synthases comprise just one type of polypeptide, the enzymatically active form of a monomeric anthranilate synthase is typically a homodimer consisting of two such monomeric polypeptides. Both heterotetrameric and monomeric anthranilate synthases catalyze the formation of anthranilate in a reaction utilizing glutamine and chorismate. The domain found on the α-subunit (referred to herein as the "α-domain") binds chorismate and eliminates the enolpyruvate side chain, and the domain found on the β-subunit (referred to herein as the "β-domain") transfers an amino group from glutamine to the position on the chorismate phenyl ring that resides between the carboxylate and the enolpyruvate moieties.

The next reaction in the synthesis of tryptophan is the transfer of the phosphoribosyl moiety of phosphoribosyl pyrophosphate to anthranilate. The indole ring is formed in two steps involving an isomerization converting the ribose group to a ribulose followed by a cyclization reaction to yield indole glycerol phosphate. The final reaction in the pathway is catalyzed by a single enzyme that may contain either one or two subunits. The reaction accomplishes the cleavage of indole glyceraldehyde-3-phosphate and condensation of the indole group with serine (Umbarger, 1978).

Metabolite flow in the tryptophan pathway in higher plants and microorganisms is apparently regulated through feedback inhibition of anthranilate synthase by tryptophan. Tryptophan may block the conformational rearrangement that is required to activate the β-domain and to create a channel for passage of ammonia toward the active site of the α-domain. Such feedback inhibition by tryptophan is believed to depress the production of tryptophan by anthranilate synthase (see Li and Last, 1996).

Several amino acid residues have been identified as being involved in the feedback regulation of the anthranilate synthase complex from *Salmonella typhimurium*. Such information provides evidence of an amino-terminal regulatory site (Caligiuri and Bauerle, 1991). Niyogi et al. have further characterized the anthranilate synthase from certain plants employing a molecular approach (Niyogi and Fink, 1992 and Niyogi et al., 1993). They found that the α-subunits of the *Arabidopsis* anthranilate synthase are encoded by two closely related, nonallelic genes that are differentially regulated. One of these α-subunit genes, ASA1, is induced by wounding and bacterial pathogen infiltration, implicating its involvement in a defense response, whereas the other α-subunit gene, ASA2, is expressed at constitutive basal levels. Both predicted proteins share regions of homology with bacterial and fungal anthranilate synthase proteins, and contain conserved amino acid residues at positions that have been shown to be involved in tryptophan feedback inhibition in bacteria (Caligiuri et al., 1991).

Amino acid analogs of tryptophan and analogs of the intermediates in the tryptophan biosynthetic pathway (e.g., 5-methyltryptophan, 4-methyltryptophan, 5-fluorotryptophan, 5-hydroxytryptophan, 7-azatryptophan, 3β-indoleacrylic acid, 3-methylanthranilic acid), have been shown to inhibit the growth of both prokaryotic and eukaryotic organisms. Plant cell cultures can be selected for resistance to these amino acid analogs. For example, cultured tobacco, carrot, potato, corn and *Datura innoxia* cell lines have been selected that are resistant to growth inhibition by 5-methyltryptophan (5-MT), an amino acid analog of tryptophan, due to expression of an altered anthranilate synthase.

Ranch et al. (1983) selected for 5-MT resistance in cell cultures of *Datura innoxia*, a dicot weed, and reported that the resistant cell cultures contained increased tryptophan levels (8 to 30 times higher than the wild type level) and an anthranilate synthase with less sensitivity to tryptophan feedback inhibition. Regenerated plants were also resistant to 5-MT, contained an altered anthranilate synthase, and had greater concentrations of free tryptophan (4 to 44 times) in the leaves than did the leaves of the control plants. In contrast to the studies with *N. tabacum*, where the altered enzyme was not expressed in plants regenerated from resistant cell lines, these results indicated that the amino acid overproduction phenotype could be selected at the cellular level and expressed in whole plants regenerated from the selected cells in *Datura innoxia*.

Hibberd et al. (U.S. Pat. No. 4,581,847) described 5-MT resistant maize cell lines that contained an anthranilate synthase that was less sensitive to feedback inhibition than wild-type anthranilate synthase. One 5-MT resistant cell line accumulated free tryptophan at levels almost twenty-fold greater than that of non-transformed cell lines.

Anderson et al. (U.S. Pat. No. 6,118,047) disclose the use of a tryptophan-insensitive α-domain of anthranilate synthase from C28 maize in a transgene to prepare transgenic maize plants (*Zea mays*) exhibiting elevated levels of free tryptophan in the seed(s).

Although it is possible to select for 5-MT resistance in certain cell cultures and plants, this characteristic does not necessarily correlate with the overproduction of free tryptophan in whole plants. Additionally, plants regenerated from 5-MT resistant lines frequently do not express an altered form of the enzyme. Nor is it predictable that this characteristic will be stable over a period of time and will be passed along as a heritable trait.

Anthranilate synthase has also been partially purified from crude extracts of cell cultures of higher plants (Hankins et al., 1976; Widholm, 1973). However, it was found to be very unstable. Thus, there is a need to provide plants with a source of anthranilate synthase that can increase the tryptophan content of plants.

SUMMARY OF THE INVENTION

The present invention provides nucleic acids encoding an anthranilate synthase (AS) that can be used to generate transgenic plants. When such anthranilate synthase nucleic acids are expressed in a transgenic plant, elevated levels of tryptophan can be achieved within the cells of the plant. In one embodiment, the present invention is directed to DNA molecules that encode a monomeric anthranilate synthase, where such a monomeric anthranilate synthase is a natural or genetically engineered chimeric fusion of the α- and β-domains of an anthranilate synthase. The anthranilate synthase gene from a few species (e.g., some bacteria and other microbes) naturally gives rise to a monomeric anthranilate synthase that constitutes a single polypeptide chain. However, most species have a heterotetrameric anthranilate synthase composed of two α- and two β-domains found on separate subunits. The present invention also contemplates formation of chimeric anthranilate synthase fusion proteins comprising any anthranilate synthase α-domain linked to any β-domain.

In general, the sequence identity of naturally occurring monomeric anthranilate synthases with most plant anthranilate synthases is quite low. However, according to the invention, such monomeric anthranilate synthases can provide high levels of tryptophan when expressed in a plant, despite a low sequence identity with the plant's endogenous anthranilate synthase enzyme. Accordingly, the present invention provides monomeric anthranilate synthases that can have divergent sequences and that are capable of efficiently providing high levels of tryptophan in a plant host. For example, transgenic soybean plants containing the monomeric *Agrobacterium tumefaciens* anthranilate synthase can produce from up to about 10,000 to about 12,000 ppm tryptophan in seeds, with average trp levels ranging up to about 7,000 to about 8,000 ppm. In contrast, non-transgenic soybean plants normally have up to only about 100 to about 200 ppm tryptophan in seeds.

Accordingly, the present invention provides an isolated DNA sequence encoding a monomeric anthranilate synthase, wherein the monomeric anthranilate synthase has an anthranilate α-domain and an anthranilate β-domain and wherein the monomeric anthranilate synthase is expressed in a plant. Such expression can elevate the level of L-tryptophan in the plant.

The monomeric anthranilate synthase can be naturally monomeric. Examples of organisms from which naturally monomeric anthranilate synthase nucleic acids may be isolated, include but are not limited to organisms such as *Agrobacterium tumefaciens, Rhizobium meliloti* (e.g., Genbank Accession No. GI 95177), *Mesorhizobium loti* (e.g., Genbank Accession No. GI 13472468), *Brucella melitensis* (e.g., Genbank Accession No. GI 17982357), *Nostoc* sp. PCC7120 (e.g., Genbank Accession Nos. GI 17227910 or GI 17230725), *Azospirillum brasilense* (e.g., Genbank Accession No. GI 1174156) and *Anabaena* M22983 (e.g., Genbank Accession No. GI 152445). In some embodiments, the isolated DNA encodes an *Agrobacterium tumefaciens* anthranilate synthase having, for example, an amino acid sequence having SEQ ID NO: 4 or a nucleotide sequence having any one of SEQ ID NOs: 1 or 75.

Alternatively, the monomeric anthranilate synthase can be a fusion of any available anthranilate synthase α and β domain. Such α and β domains can be derived from *Zea mays, Ruta graveolens, Sulfolobus solfataricus, Salmonella typhimurium, Serratia marcescens, Escherichia coli, Agrobacterium tumefaciens, Arabidopsis thaliana, Rhizobium meliloti* (e.g., Genbank Accession No. GI 95177), *Mesorhizobium loti* (e.g., Genbank Accession No. GI 13472468), *Brucella melitensis* (e.g., Genbank Accession No. GI 17982357), *Nostoc* sp. PCC7120 (e.g., Genbank Accession No. GI 17227910 or GI 17230725), *Azospirillum brasilense* (e.g., Genbank Accession No. GI 1174156) and *Anabaena* M22983 (e.g., Genbank Accession No. GI 152445), soybean, rice, cotton, wheat, tobacco or any gene encoding α subunit or domain of anthranilate synthase. For example, nucleic acids encoding such an α or β domain can be obtained by using the sequence information in any of SEQ ID NOs: 1-70, 75-113, and 116-137.

In another embodiment, the invention provides an isolated DNA encoding an α domain of anthranilate synthase from *Zea mays* that comprises SEQ ID NOs: 5 or 66. Such an isolated DNA can have nucleotide sequence SEQ ID NOs: 2, 67, or 68. The isolated DNA can be operably linked to a promoter and, when expressed in a plant can provide elevated levels of L-tryptophan in the plant.

In yet another embodiment, the invention provides an isolated DNA molecule encoding an anthranilate synthase wherein the DNA molecule encodes a protein substantially homologous to an anthranilate synthase protein exemplified by SEQ ID NOs: 66, 108-111, 133, and 137. The isolated DNA encoding an anthranilate synthase comprises a DNA molecule substantially homologous to a DNA molecule exemplified by SEQ ID NOs: 67, 68, 104-107, and 134-136.

In still another embodiment, the present invention provides a DNA construct comprising an expression cassette, wherein the expression cassette in operable linkage comprises (i) a heterologous promoter; (ii) a DNA molecule encoding a monomeric anthranilate synthase protein, wherein the monomeric anthranilate synthase comprises a single polypeptide comprising an anthranilate synthase α-domain and an anthranilate synthase β-domain, and (iii) a transcriptional terminator. The monomeric anthranilate synthase protein may comprise a protein substantially homologous to proteins exemplified by SEQ ID NOs: 4, 7, 43, 57, 77-82, and 130-132. The DNA molecule may comprise a DNA molecule substantially homologous to a DNA molecule exemplified by SEQ ID NOs: 1, 75, 76, 83, and 121-129.

In a further embodiment, the present invention provides a DNA construct comprising a first expression cassette, wherein the first expression cassette in operable linkage comprises (i) a heterologous promoter; (ii) a DNA molecule encoding an anthranilate synthase α-domain protein and (iii) a transcriptional terminator.

The above DNA construct may further comprise a second expression cassette in operable linkage comprising (i) a heterologous promoter; (ii) a DNA molecule encoding an anthranilate synthase β-domain protein and (iii) a transcriptional terminator. The DNA construct may comprise an α-domain or β-domain protein substantially homologous to a protein exemplified by SEQ ID NOs: 5, 6, 8, 44, 45, 66, 99, 100, 101, 102, 103, 108, 109, 110, 111, 117, 118, 133, or 137. The DNA molecule encoding an anthranilate synthase α-domain or β-domain protein may comprise a DNA molecule substantially homologous to a DNA molecule exemplified by SEQ ID NOs: 2, 3, 67, 94, 95, 96, 97, 98, 104, 105, 106, 112, 116, 119, 120, 134, 135, or 136. A specific example comprises a DNA construct where the α-domain anthranilate synthase protein is SEQ ID NO: 66 and the β-domain protein is SEQ ID NO: 118.

The isolated DNA can also encode a mutant anthranilate synthase, or a mutant anthranilate synthase domain. Such a mutant anthranilate synthase, or domain thereof, can have one or more mutations. As is known to one of skill in the art, mutations can be silent, can give rise to variant gene products having enzymatic activity similar to wild type or can give rise to derivative gene products that have altered enzymatic activity. The present invention contemplates all such mutations.

The mutated isolated DNA can be generated from a wild type anthranilate synthase nucleic acid either in vitro or in vivo and can encode, for example, one or more amino acid substitutions, deletions or insertions. Mutant isolated DNAs that generate a mutant anthranilate synthase having increased activity, greater stability, or less sensitivity to feedback inhibition by tryptophan or tryptophan analogs are desirable. In one embodiment, the anthranilate synthase, or a domain thereof, is resistant to inhibition by endogenous L-tryptophan or by tryptophan analogs. For example, the anthranilate synthase can have one or more mutations in the tryptophan-binding pocket or elsewhere that reduces the sensitivity of the anthranilate synthase, or the domain thereof, to tryptophan inhibition. Among the amino acid residues contemplated for mutation are residues, for example, at about positions 48, 51, 52, 293, and 298. For example, the mutation can be:
  a) at about position 48 replace Val with Phe;
  b) at about position 48 replace Val with Tyr;
  c) at about position 51 replace Ser with Phe;
  d) at about position 51 replace Ser with Cys;
  e) at about position 52 replace Asn with Phe;
  f) at about position 293 replace Pro with Ala;
  g) at about position 293 replace Pro with Gly; or
  h) at about position 298 replace Phe with Trp;
wherein the position of the mutation is determined by alignment of the amino acid sequence of the selected anthranilate synthase with an *Agrobacterium tumefaciens* anthranilate synthase amino acid sequence. Examples of anthranilate synthases having such mutations include those with SEQ ID NOs: 58-65, 69, 70, and 84-94.

Alternatively, the DNA that encodes a mutant anthranilate synthase can be an artificial polynucleotide having one or more mutations in the tryptophan-binding pocket or elsewhere that reduces the sensitivity of the anthranilate synthase, or the domain thereof, to tryptophan inhibition. Among the amino acid residues contemplated for mutation are residues, for example, at about positions 48, 51, 52, 293, and 298. For example, the mutation can be:
  a) at about position 48 replace Val with Phe;
  b) at about position 48 replace Val with Tyr;
  c) at about position 51 replace Ser with Phe;
  d) at about position 51 replace Ser with Cys;
  e) at about position 52 replace Asn with Phe;
  f) at about position 293 replace Pro with Ala;
  g) at about position 293 replace Pro with Gly; or
  h) at about position 298 replace Phe with Trp;
wherein the position of the mutation is determined by alignment of the amino acid sequence of the selected anthranilate synthase with an *Agrobacterium tumefaciens* anthranilate synthase (AgroAS) amino acid sequence. Examples of anthranilate synthases having such mutations include the polypeptides of SEQ ID NOs:60-61, encoded by the nucleic acid sequences of SEQ ID NOs:144-145.

The isolated DNA can encode other elements and functions. Any element or function contemplated by one of skill in the art can be included. For example, the isolated DNA can also include a promoter that can function in a plant cell that is operably linked to the DNA encoding the anthranilate synthase. The isolated DNA can further encode a plastid transit peptide. The isolated DNA can also encode a selectable marker or a reporter gene. Such a selectable marker gene can impart herbicide resistance to cells of said plant, high protein content, high oil content, high lysine content, high isoleucine content, high tocopherol content and the like. The DNA sequence can also comprise a sequence encoding one or more of the insecticidal proteins derived from *Bacillus thuringiensis*.

The present invention further provides vectors comprising an isolated DNA of the invention. Such vectors can be used to express anthranilate synthase polypeptides in prokaryotic and eukaryotic cells, to transform plant cells and to generate transgenic plants.

The present invention also provides a transgenic plant comprising an isolated DNA of the invention. Expression of these isolated DNAs in the transgenic plant can result in an elevated level of L-tryptophan, preferably free L-tryptophan, in the transgenic plant, e.g., in the seeds or other parts of the plant. The level is increased above the level of L-tryptophan in the cells of a plant that differ from the cells of the transgenic soybean plant by the absence of the DNA, e.g., the corresponding untransformed cells or an untransformed plant with the same genetic background. The DNA is preferably heritable in that it is preferably transmitted through a complete normal sexual cycle of the fertile plant to its progeny and to further generations.

Transgenic plants that can have such an isolated DNA include dicotyledonous plants (dicots), for example, soybean or canola. Alternatively, the transgenic plants can be monocotyledonous plants (monocots), for example, maize, rice, wheat, barley, millet, oat, or sorghum.

The present invention also provides a seed of any of the transgenic plants containing any of the isolated DNAs, anthranilate synthase polypeptides, transgenes or vectors of the invention.

The present invention further provides an animal feed or human food that contains at least a portion of a plant having an isolated DNA or DNA construct of the invention. Portions of plants that can be included in the animal feed or human food include, for example, seeds, leaves, stems, roots, tubers, or fruits. Desirable portions of plants have increased levels of tryptophan provided by expression of an anthranilate synthase encoded by an isolated DNA of the invention.

The present invention further provides a method for altering, preferably increasing, the tryptophan content of a plant (dicot or a monocot) by introducing an isolated DNA of the invention into regenerable cells of the plant. The DNA sequence is preferably operably linked to at least one promoter operable in the plant cells. The transformed cells are identified or selected, and then regenerated to yield a plant comprising cells that can express a functional anthranilate synthase polypeptide. In some embodiments, the DNA encoding the anthranilate synthase, or domain thereof, is a mutant DNA. In other embodiments, the DNA encoding the anthranilate synthase, or domain thereof, is an artificial polynucleotide. The introduced DNA is preferably heritable and the plant is preferably a fertile plant. For example, the introduced DNA preferably can be passed by a complete sexual cycle to progeny plants, and can impart the high tryptophan phenotype to subsequent generations of progeny.

The anthranilate synthase-encoding DNAs, are preferably incorporated into vectors or "transgenes" that can also include DNA sequences encoding transit peptides, such as plastid transit peptides, and selectable marker or reporter genes, operably linked to one or more promoters that are functional in cells of the target plant. The promoter can be, for example, an inducible promoter, a tissue specific promoter, a strong promoter or a weak promoter. Other transcription or translation regulatory elements, e.g., enhancers or terminators, can also be functionally linked to the anthranilate synthase-encoding DNA segment.

Cells in suspension culture or as embryos, intact tissues or organs can be transformed by a wide variety of transformation techniques, for example, by microprojectile bombardment, electroporation and *Agrobacterium tumefaciens*-mediated transformation, and other procedures available to the art.

Thus, the cells of the transformed plant comprise a native anthranilate synthase gene and a transgene or other DNA segment encoding an exogenous anthranilate synthase. The expression of the exogenous anthranilate synthase in the cells of the plant can lead to increased levels of tryptophan and its secondary metabolites. In some embodiments, such expression confers tolerance to an amount of endogenous L-tryptophan analogue, for example, so that at least about 10% more anthranilate synthase activity is present than in a plant cell having a wild type or tryptophan-sensitive anthranilate synthase.

The present invention also provides a method for altering the tryptophan content in a plant comprising: (a) introducing into regenerable cells of a plant a transgene comprising an isolated DNA encoding an anthranilate synthase domain and a plastid transit peptide, operably linked to a promoter functional in the plant cell to yield transformed cells; and (b) regenerating a transformed plant from said transformed plant cells wherein the cells of the plant express the anthranilate synthase domain encoded by the isolated DNA in an amount effective to increase the tryptophan content in said plant relative to the tryptophan content in an untransformed plant of the same genetic background. The domain can be an anthranilate synthase α-domain. The anthranilate synthase domain can have one or more mutations, for example, mutations that reduce the sensitivity of the domain to tryptophan inhibition. Such mutations can be, for example, in the tryptophan-binding pocket. Such a domain can be, for example, an anthranilate synthase domain from *Agrobacterium tumefaciens, Anabaena* M22983, *Arabidopsis thaliana, Azospirillum brasilense, Brucella melitensis, Escherichia coli, Euglena gracilis, Mesorhizobium loti, Nostoc* sp. PCC7120, *Rhizobium meliloti, Ruta graveolens, Rhodopseudomonas palustris, Salmonella typhimurium, Serratia marcescens, Sulfolobus solfataricus*, soybean, rice, cotton or *Zea mays. Ruta graveolens* has its own chloroplast transport sequence that may be used with the anthranilate synthase transgene. Accordingly, one of skill in the art may not need to add a plastid transport sequence when using a *Ruta graveolens* DNA.

The present invention also provides novel isolated and purified DNA molecules comprising a DNA encoding a monomeric anthranilate synthase, or a domain thereof. Such an anthranilate synthase DNA can provide high levels of tryptophan when expressed within a plant. In some embodiments, the anthranilate synthase is substantially resistant to inhibition by free L-tryptophan or an analog thereof. Examples of novel DNA sequences contemplated by the invention include but are not limited to DNA molecules isolated from *Agrobacterium tumefaciens, Anabaena* M22983, *Arabidopsis thaliana, Azospirillum brasilense, Bradyrhizobium japonicum, Brucella melitensis, Escherichia coli, Euglena gracilis, Mesorhizobium loti, Nostoc* sp. PCC7120, *Rhizobium meliloti, Ruta graveolens, Rhodopseudomonas palustris, Rhodospirillum rubrum, Salmonella typhimurium, Serratia marcescens, Sorghum bicolor, Sulfolobus solfataricus, Thermobifida fiisca*, or *Zea mays*(maize), or other such anthranilate synthases.

These DNA sequences include synthetic or naturally-occurring monomeric forms of anthranilate synthase that have the α-domain of anthranilate synthase linked to at least one other anthranilate synthase domain on a single polypeptide chain. The monomeric anthranilate synthase can, for example, be a fusion of an anthranilate synthase α or β domain. Such an anthranilate synthase α or β domain can be derived from *Agrobacterium tumefaciens, Anabaena* M22983, *Arabidopsis thaliana, Azospirillum brasilense, Bradyrhizobium japonicum, Brucella melitensis, Escherichia coli, Euglena gracilis, Mesorhizobium loti, Nostoc* sp. PCC7120, *Rhizobium meliloti, Ruta graveolens, Rhodopseudomonas palustris, Rhodospirillum rubrum, Salmonella typhimurium, Serratia marcescens, Sorghum bicolor, Sulfolobus solfataricus, Thermobifida fusca*, sorghum, soybean, rice, cotton, wheat, tobacco, or *Zea mays* (maize) or any gene encoding a subunit or domain of anthranilate synthase. Such anthranilate synthases and domains thereof are also exemplified herein by the anthranilate synthase nucleic acids isolated from *Agrobacterium tumefaciens*, (SEQ ID NOs: 1, 75, or 84-94), *Zea mays*, (SEQ ID NOs: 2, 67, 68, 96, 116, or 136), *Ruta graveolens* (SEQ ID NO: 3), *Anabaena* M22983, *Arabidopsis thaliana* (SEQ ID NO: 45), *Azospirillum brasilense* (SEQ ID NO: 122), *Brucella melitensis* (SEQ ID NO: 123), *Mesorhizobium loti* (SEQ ID NO: 121), *Nostoc* sp. PCC7120 (SEQ ID NOs: 124 or 125), *Rhizobium meliloti, Rhodopseudomonas palustris* (SEQ ID NO: 126), *Sulfolobus solfataricus*, rice (SEQ ID NOs: 94, 95, 119, or 120), wheat (SEQ ID NO: 97), tobacco (SEQ ID NO: 98), *Gossypium hirsutum* (SEQ ID NOs: 104 or 105), *Glycine max* (SEQ ID NOs: 106, 107, 112, or 113), *Bradyrhizobium janonicum* (SEQ ID NO: 127), *Rhodospirillum rubrum* (SEQ ID NO: 128), *Thermobifida fusca* (SEQ ID NO: 129) or *Sorghum bicolor* (SEQ ID NOs: 134 or 135). These nucleotide sequences encode anthranilate synthases or α-domains or β domains thereof from *Agrobacterium tumefaciens* (SEQ ID NOs: 4, 58-65, 69, or 70); *Zea mays* (SEQ ID NOs: 5, 66, 101, 118, or 137) and *Ruta graveolens* (SEQ ID NO: 6), *Anabaena* M22983, *Azospirillum brasilense* (SEQ ID NO: 78), *Brucella melitensis* (SEQ ID NO: 79), *Mesorhizobium loti* (SEQ ID NO: 77), *Nostoc* sp. PCC7120 (SEQ ID NOs: 80 or 81), *Rhizobium meliloti* (SEQ ID NOs: 7 or 43), *Rhodopseudomonas palustris* (SEQ ID NOs: 57 or 82), *Sulfolobus solfataricus* (SEQ ID NOs: 8 or 44), rice (SEQ ID NOs: 99, 100, or 117), wheat (SEQ ID NO: 102), tobacco (SEQ ID NO: 103), *Gossypium hirsutum* (SEQ ID NOs: 108 or 109), *Glycine max* (SEQ ID NOs: 110 or 111), *Bradyrhizobium japonicum* (SEQ ID NO: 130), *Rhodospirillum rubrum* (SEQ ID NO: 131), *Thermobifida fusca* (SEQ ID NO: 132) or *Sorghum bicolor* (SEQ ID NO: 133).

The present invention also provides an isolated DNA molecule comprising a DNA sequence encoding an *Agrobacterium tumefaciens* anthranilate synthase or a domain thereof having enzymatic activity. Such a DNA molecule can encode an anthranilate synthase having SEQ ID NOs: 4, 58-65, 69, or 70, a domain or variant thereof having anthranilate synthase activity. The DNA molecule can also have a sequence comprising SEQ ID NOs: 1, 75, 84-93 or 144-145, or a domain or variant thereof. Coding regions of any DNA molecule provided herein can also be optimized for expression in a selected organism, for example, a selected plant or microbe. Examples of DNA molecules having optimized codon usage for a selected plant are *Agrobacterium tumefaciens* anthranilate synthase-encoding DNA molecules having SEQ ID NOs: 75, 144 and 145.

The present invention also provides an isolated and purified DNA molecule comprising a DNA sequence encoding a *Zea mays* anthranilate synthase domain. Such a DNA molecule can encode an anthranilate synthase domain having SEQ ID NOs: 5 or 66, or a variant or derivative thereof having anthranilate synthase activity. The DNA molecule can also have a sequence comprising SEQ ID NOs: 2, 67, or 68, or a domain or variant thereof.

The present invention further provides an isolated DNA molecule of at least 8 nucleotides that hybridizes to the complement of a DNA molecule comprising any one of SEQ ID NOs: 1, 75, or 84-94 under stringent conditions. Such a DNA molecule can be a probe or a primer, for example, a nucleic acid having any one of SEQ ID NOs: 9-42, 47-56, or 138-143. Alternatively, the DNA can include up to an entire coding region for a selected anthranilate synthase, or a domain thereof. Such a DNA can also include a DNA sequence encoding a promoter operable in plant cells and/or a DNA sequence encoding a plastid transit peptide. The present invention further contemplates vectors for transformation and expression of these types of DNA molecules in plants and/or microbes.

Functional anthranilate synthase DNA sequences and functional anthranilate synthase polypeptides that exhibit 50%, preferably 60%, more preferably 70%, even more preferably 84%, most preferably 90%, e.g., 95% to 99%, sequence identity to the DNA sequences and amino acid sequences explicitly described herein are also within the scope of the present invention. For example, 85% identity means that 85% of the amino acids are identical when the 2 sequences are aligned for maximum matching. Gaps (in either of the 2 sequences being matched) are allowed in maximizing matching; gap lengths of 5 or less are preferred with 2 or less being more preferred.

Alternatively and preferably, two polypeptide sequences are homologous, as this term is used herein, if they have an alignment score of more than 5 (in standard deviation units) using the program ALIGN with the mutation data matrix and a gap penalty of 6 or greater. See Dayhoff (1972). The 2 sequences or parts thereof are more preferably homologous if their amino acids are greater than or equal to 50% identical when optimally aligned using the ALIGN program. The present invention further provides expression vectors for generating a transgenic plant with high seed levels of tryptophan comprising an isolated DNA sequence encoding a monomeric anthranilate synthase comprising an anthranilate synthase α-domain linked to an anthranilate synthase β-domain and a plastid transit peptide, operably linked to a promoter functional in a plant cell. Such a monomeric anthranilate synthase can, for example, be an *Agrobacterium tumefaciens, Rhizobium meliloti, Mesorhizobium loti, Brucella melitensis, Nostoc* sp. PCC7120, *Azospirillum brasilense, Anabaena* M22983, *Bradyrhizobium japonicum, Rhodospirillum rubrum*, or *Thermobifida fusca* anthranilate synthase. The monomeric anthranilate synthase can also be a fusion of anthranilate synthase α- and β-domains derived from *Agrobacterium tumefaciens, Anabaena* M22983, *Arabidopsis thaliana, Azospirillum brasilense, Brucella melitensis, Mesorhizobium loti, Nostoc* sp. PCC7120, *Rhizobium meliloti, Rhodopseudomonas palustris, Ruta graveolens, Sulfolobus solfataricus, Salmonella typhimurium, Serratia marcescens, Bradyrhizobium japonicum, Rhodospirillum rubrum, Thermobifida fusca, Sorghum bicolor*, soybean, rice, cotton, wheat, tobacco, *Zea mays*, or any gene encoding a subunit or domain of anthranilate synthase.

The transmission of the isolated and purified anthranilate synthase DNA providing increased levels of tryptophan can be evaluated at a molecular level, e.g., Southern or Northern blot analysis, PCR-based methodologies, the biochemical or immunological detection of anthranilate synthase, or by phenotypic analyses, i.e., whether cells of the transformed progeny can grow in the presence of an amount of an amino acid analog of tryptophan that inhibits the growth of untransformed plant cells.

The present invention also provides a method of producing anthranilate synthase in a prokaryotic or eukaryotic host cell, such as a yeast, insect cell, or bacterium, which can be cultured, preferably on a commercial scale. The method includes the steps of introducing a transgene comprising a DNA segment encoding an anthranilate synthase, or a domain thereof, such as a monomeric anthranilate synthase, comprising at least the α and β anthranilate synthase domains, or functional variant thereof, into a host cell and expressing anthranilate synthase in the host cell so as to yield functional anthranilate synthase or domain thereof. A transgene generally includes transcription and translation regulatory elements, e.g., a promoter, functional in host cell, either of eukaryotic or prokaryotic origin. Preferably, the transgene is introduced into a prokaryotic cell, such as *Escherichia coli*, or a eukaryotic cell, such as a yeast or insect cell, that is known to be useful for production of recombinant proteins. Culturing the transformed cells can lead to enhanced production of tryptophan and its derivatives, which can be recovered from the cells or from the culture media. Accumulation of tryptophan may also lead to the increased production of secondary metabolites in microbes and plants, for example, indole containing metabolites such as simple indoles, indole conjugates, indole alkaloids, indole phytoalexins and indole glucosinalates in plants.

Anthranilate synthases insensitive to tryptophan have the potential to increase a variety of chorismate-derived metabolites, including those derived from phenylalanine due to the stimulation of phenylalanine synthesis by tryptophan via chorismate mutase (Siehl, 1999). Other chorismate-derived metabolites that may increase when feedback insensitive anthranilate synthase s are present include phenylpropanoids, flavonoids, and isoflavonoids, as well as those derived from anthranilate, such as indole, indole alkaloids, and indole glucosinolates. Many of these compounds are important plant hormones, plant defense compounds, chemopreventive agents of various health conditions, and/or pharmacologically active compounds. The range of these compounds whose synthesis might be increased by expression of anthranilate synthase depends on the organism in which the anthranilate synthase is expressed. The present invention contemplates synthesis of tryptophan and other useful compounds in a variety of prokaryotic and eukaryotic cells or organisms, including plant cells, microbes, fungi, yeast, bacteria, insect cells, and mammalian cells.

Hence, the present invention provides a method for producing tryptophan comprising: culturing a prokaryotic or eukaryotic host cell comprising an isolated DNA under conditions sufficient to express a monomeric anthranilate synthase encoded by the isolated DNA, wherein the monomeric anthranilate synthase comprises an anthranilate synthase α domain and an anthranilate synthase β domain, and wherein the conditions sufficient to express a monomeric anthranilate synthase comprise nutrients and precursors sufficient for the host cell to synthesize tryptophan utilizing the monomeric anthranilate synthase.

Examples of useful compounds that may be generated upon expression in a variety of host cells and/or organisms include indole acetic acid and other auxins, isoflavonoid compounds important to cardiovascular health found in soy, volatile indole compounds which act as signals to natural enemies of herbivorous insects in maize, anticarcinogens such as indole glucosinolates (indole-3-carbinol) found in the Cruciferae plant family, as well as indole alkaloids such as ergot compounds produced by certain species of fungi. (Barnes et al, 1996; Frey et al., 2000; Muller et al., 2000; Mantegani et al., 1999; Zeligs, 1998; Mash et al., 1998; Melanson et al., 1997; Broadbent et al., 1998).

The present invention also provides an isolated and purified DNA molecule of at least seven nucleotide bases that hybridizes under moderate, and preferably, high stringency conditions to the complement of an anthranilate synthase encoding DNA molecule. Such isolated and purified DNA molecules comprise novel DNA segments encoding anthranilate synthase or a domain or mutant thereof. The mutant DNA can encode an anthranilate synthase that is substantially resistant to inhibition by free L-tryptophan or an amino acid analog of tryptophan. Such anthranilate synthase DNA molecules can hybridize, for example, to an *Agrobacterium tumefaciens*, *Rhodopseudomonas palustris* or *Ruta graveolens* anthranilate synthase, or an α-domain thereof, including functional mutants thereof. When these DNA molecules encode a functional anthranilate synthase or an anthranilate synthase domain, they are termed "variants" of the primary DNA molecules encoding anthranilate synthase, anthranilate synthase domains or mutants thereof. Shorter DNA molecules or oligonucleotides can be employed as primers for amplification of target DNA sequences by PCR, or as intermediates in the synthesis of full-length genes.

Also provided is a hybridization probe comprising a novel isolated and purified DNA segment of at least seven nucleotide bases, which is detectably labeled or which can bind to a detectable label, which DNA segment hybridizes under moderate or, preferably, high stringency conditions to the non-coding strand of a DNA molecule comprising a DNA segment encoding an anthranilate synthase such as a monomeric anthranilate synthase, or a domain thereof, such as the α-domain, including functional mutants thereof, that are substantially resistant to inhibition by an amino acid analog of tryptophan. Moderate and stringent hybridization conditions are well known to the art, see, for example sections 0.47-9.51 of Sambrook et al., (1989); see, also, Sambrook and Russell, (2001). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% sodium dodecylsulfate (SDS), and 10% dextran sulfate at 42° C., with washes at 42° C. in 0.2×SSC and 0.1% SDS.

The present invention also provides methods and compositions for providing a polynucleotide molecule that encodes a tryptophan feedback insensitive anthranilate synthase comprising an artificial polynucleotide molecule substantially identical to SEQ ID NO: 145; wherein said artificial polynucleotide molecule provides enhanced levels of at least one amino acid in a transgenic corn cell comprising said artificial polynucleotide molecule when compared to a corn cell not comprising said artificial polynucleotide molecule.

The artificial polynucleotide molecules of the present invention encode proteins that provide nutritionally enhanced phenotypes to a transgenic cell containing a DNA construct comprising said artificial polynucleotide molecules. The nutritionally enhanced phenotypes include, but are not limited to, the production of elevated levels of tryptophan in the cell when compared to tryptophan levels seen in cells not comprising said artificial polynucleotide molecules.

The present invention further provides a method of providing an increased level of tryptophan in the seed of a plant comprising: a) constructing an artificial polynucleotide molecule; b) constructing a DNA construct containing said artificial polynucleotide molecule; c) transforming said DNA construct into a plant cell; and d) regenerating said plant cell into a fertile transgenic plant.

The present invention further provides nutritionally enhanced feed products and methods of making such products comprising seed of transgenic corn cells with an increased level of tryptophan; and processing such seed into a meal, protein or oil.

DESCRIPTION OF THE FIGURES

FIG. 1 depicts the translated sequence of the *Agrobacterium tumefaciens* anthranilate synthase DNA sequence (upper sequence) (SEQ ID NO: 4) and the translated sequence of the anthranilate synthase DNA sequence from *Rhizobium meliloti* (lower sequence) (SEQ ID NO: 7).

FIG. 3A-B depicts an anthranilate synthase amino acid sequence alignment comparing the *Agrobacterium tumefaciens* α-domain sequence (SEQ ID NO: 4) and the *Sulfolobus solfataricus* α-domain sequence (SEQ ID NO: 8).

FIG. 4A-B depicts the sequences of the 34 primers (SEQ ID NOs: 9-42) used to mutate SEQ ID NO: 1. The mutated codons are underlined and the changed bases are in lower case.

FIG. 7A-D depicts a multiple sequence alignment of monomeric "TrpEG" anthranilate synthases having SEQ ID NOs: 4 and 43 (derived from *Agrobacterium tumefaciens* and *Rhizobium meliloti*, respectively) with the TrpE (α) and TrpG (β) domains of heterotetrameric anthranilate synthases from *Sulfolobus solfataricus* (SEQ ID NO: 44) and *Arabidopsis thaliana* (SEQ ID NO: 45). Linker regions are underlined.

FIG. 10 depicts the sequence of the truncated trpE gene of *Escherichia coli* EMG2 (K-12 wt F+) (SEQ ID NO: 46). The first 30 bp and the last 150 bp of this trpE nucleic acid are connected by an EcoR1 restriction site. The beginning of the trpG gene follows the trpE stop codon.

FIG. 12A-C depicts the DNA (SEQ ID NO: 1) and amino acid (SEQ ID NO: 4) sequences of the α-domain of the anthranilate synthase gene isolated from *Agrobacterium tumefaciens*.

FIG. 13A-C depicts the DNA (SEQ ID NO: 2) sequence of the α-domain of the anthranilate synthase gene isolated from Zea mays. FIG. 13D depicts the amino acid (SEQ ID NO: 5) sequence of the α-domain of the anthranilate synthase gene isolated from Zea mays.

FIG. 15A-E provides a sequence comparison of anthranilate synthase amino acid sequences from Agrobacterium tumefaciens (AgrTu__15889565) (SEQ ID NO: 4), Rhizobium meliloti (RhiMe__136328) (SEQ ID NO: 7), Mesorhizobium loti (MesLo__13472468) (SEQ ID NO: 77), Azospirillum brasilense (AzoBr__1717765) (SEQ ID NO: 78), Brucella melitensis(BruMe__17986732) (SEQ ID NO: 79), Nostoc sp. (Nostoc__17227910) (SEQ ID NO: 80), Nostoc sp. (Nostoc__17230725) (SEQ ID NO: 81), and Rhodopseudomonas palustris (RhoPa_TrpEG) (SEQ ID NO: 82).

FIG. 16A-B provides an optimized nucleotide sequence for Agrobacterium tumefaciens anthranilate synthase (SEQ ID NO: 75).

Figure 17A:
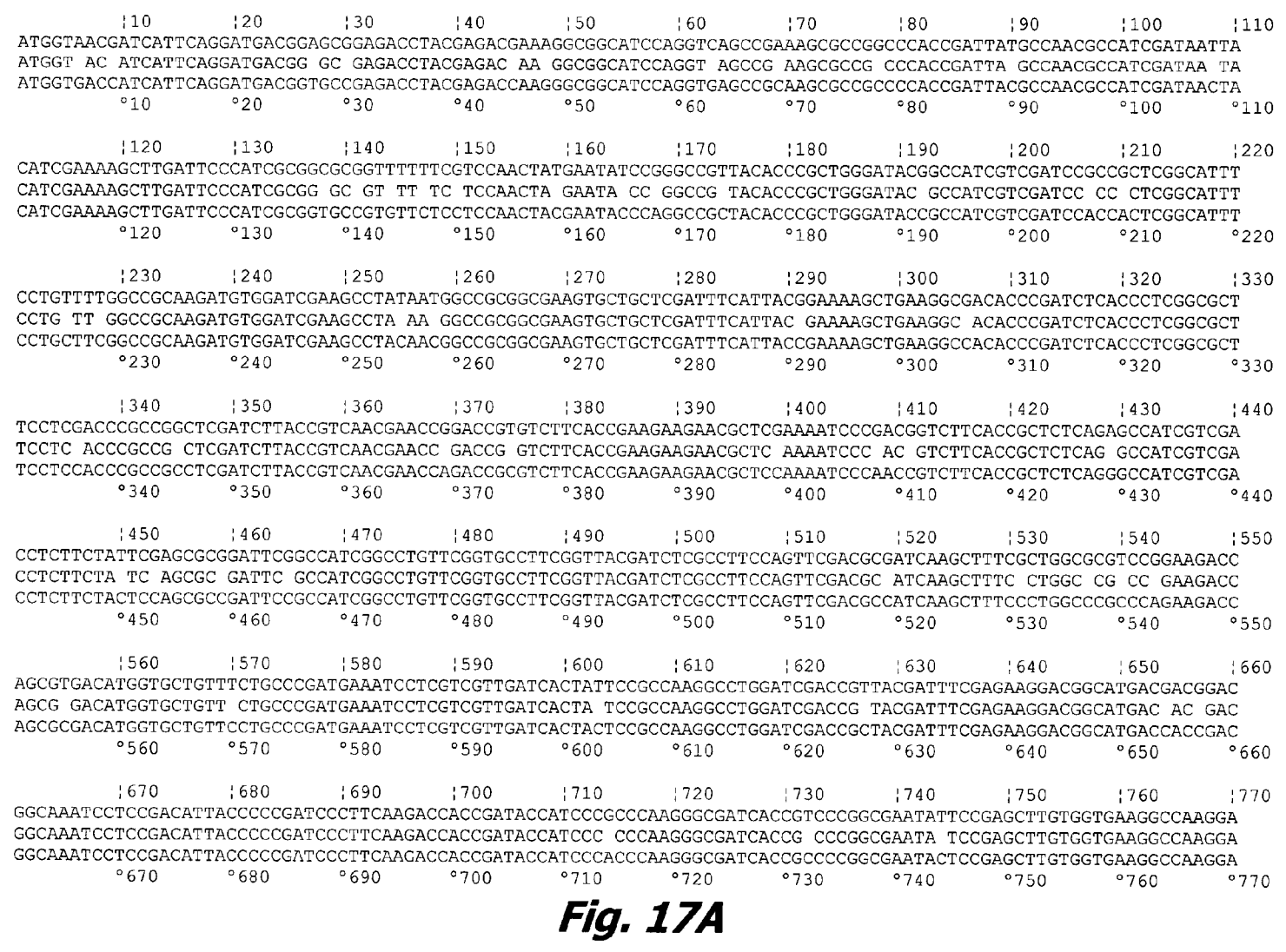
Figure 17B:
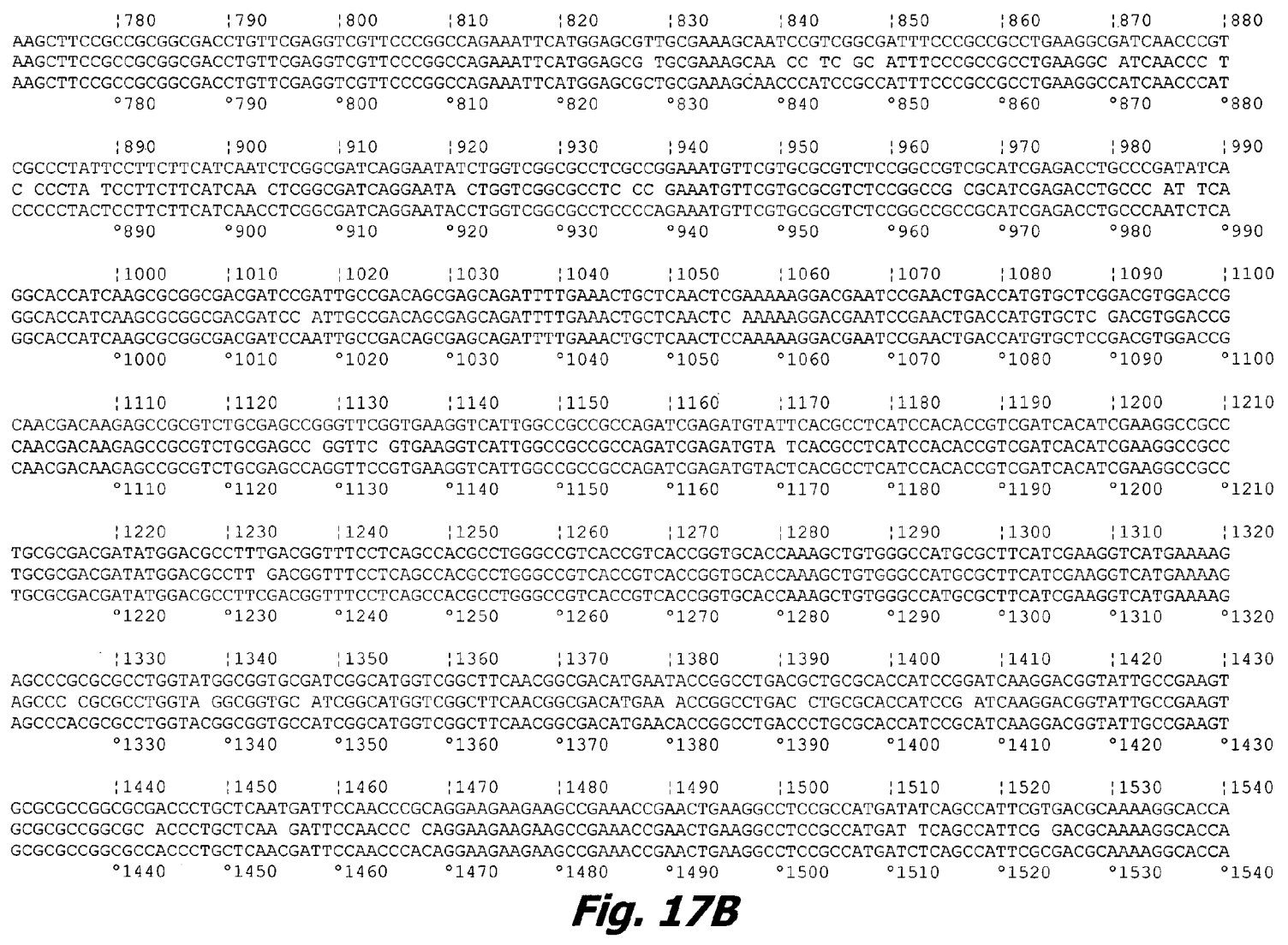

FIG. 17A-C provides an alignment of the wild type (top strand) and optimized (bottom strand) Agrobacterium tumefaciens anthranilate synthase nucleotide sequences (SEQ ID NOs: 1 and 75). These two sequences are 94% identical, as demonstrated by the middle strand.

FIG. 22 A-B provides a codon-optimized nucleotide sequence for the mutant S51F allele of Agrobacterium tumefaciens anthranilate synthase (SEQ ID NO: 144).

FIG. 23 A-C provides an alignment of the non-optimized (top strand; AS-S51F; SEQ ID NO: 86) and codon-optimized (bottom strand; AS (S51F) Codon_Opt; SEQ ID NO: 144) nucleotide sequences for the mutant S51F allele of Agrobacterium tumefaciens anthranilate synthase (AgroAS). The alignment was carried out using the ClustalW (Slow/Accurate, IUB) program. These two sequences are 82.9% identical and have no polynucleotide sequence lengths of more than 29 consecutive nucleotides that have 100% identity.

FIG. 24 A-B provides an alignment of the amino acid sequences of the non-optimized S51F mutant Agrobacterium tumefaciens anthranilate synthase (top strand; AgroAS-S51F; SEQ ID NO: 60) with the amino acid translation of the codon-optimized S51F mutant Agrobacterium tumefaciens anthranilate synthase (bottom strand; AS (S51F) Codon_Opt-Final; translation of SEQ ID NO: 144). The alignment was carried out using the ClustalW (Slow/Accurate, IUB) program. These two sequences are 100% identical.

FIG. 25 A-B provides a codon-optimized nucleotide sequence for the mutant S51C allele of tumefaciens anthranilate synthase (AgroAS-S51C-nno (non-native optimized gene); pMON68066; SEQ ID NO: 145).

FIG. 26 provides the amino acid translation of SEQ ID NO: 144, the codon-optimized mutant S51F allele of Agrobacterium tumefaciens anthranilate synthase (same as SEQ ID NO: 60).

DETAILED DESCRIPTION OF THE INVENTION

Figure 2:
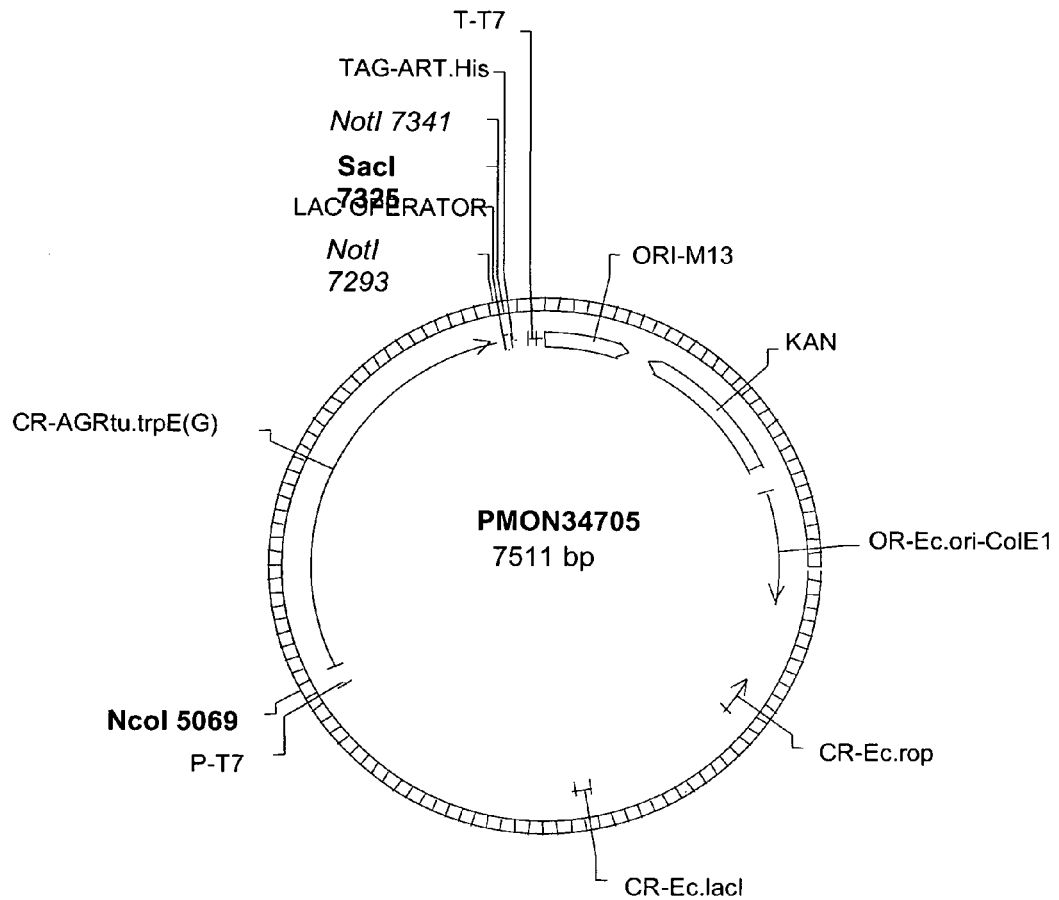
FIG. 2 is a restriction map of plasmid pMON34705.

The present invention provides isolated DNAs, vectors, host cells and transgenic plants comprising an isolated nucleic acid encoding an anthranilate synthase capable of providing high levels of tryptophan upon expression within the plant. In one embodiment, the isolated nucleic acid encodes a monomeric anthranilate synthase (AS). In other embodiments, the isolated nucleic acid encodes an anthranilate synthase, or a domain thereof, that is substantially resistant to inhibition by free L-tryptophan or an amino acid analog of tryptophan. Expression of the anthranilate synthase, or domain thereof, elevates the level of tryptophan, e.g., free tryptophan in the seed, over the level present in the plant absent such expression.

Methods are also provided for producing transgenic plants having nucleic acids associated with increased anthranilate synthase activity, and producing cultured cells, plant tissues, plants, plant parts and seeds that produce high levels of tryptophan. Such transgenic plants can preferably sexually transmit the ability to produce high levels of tryptophan to their progeny. Also described are methods for producing isolated DNAs encoding mutant anthranilate synthases, and cell culture selection techniques to select for novel genotypes that overproduce tryptophan and/or are resistant to tryptophan analogs. For example, to produce soybean lines capable of producing high levels of tryptophan, transgenic soybean cells that contain at least on of the isolated DNAs of the present invention, are prepared and characterized, then regenerated into plants. Some of the isolated DNAs are resistant to growth inhibition by the tryptophan analog. The methods provided in the present invention may also be used to produce increased levels of free tryptophan in dicot plants, such as other legumes, as well as in monocots, such as the cereal grains.

DEFINITIONS

As used herein, "altered" levels of tryptophan in a transformed plant, plant tissue, plant part or plant cell are levels which are greater or lesser than the levels found in the corresponding untransformed plant, plant tissue, plant part or plant cell.

As used herein, a "α-domain" is a portion of an enzyme or enzymatic complex that binds chorismate and eliminates the enolpyruvate side chain. Such an α-domain can be encoded by a TrpE gene. In some instances, the α-domain is a single polypeptide that functions only to bind chorismate and to eliminate the enolpyruvate side chain from chorismate. In other instances, the α-domain is part of a larger polypeptide that can carry out other enzymatic functions in addition to binding chorismate and eliminating the enolpyruvate side chain from chorismate.

The term "β-domain" refers to a portion of an enzyme or enzymatic complex that transfers an amino group from glutamine to the position on the chorismate ring that resides between the carboxylate and the enolpyruvate moieties. Such a β-domain can be encoded by a TrpG gene. In some instances, the β-domain is a single polypeptide that functions only to transfer an amino group from glutamine to the position on the chorismate ring that resides between the carboxylate and the enolpyruvate moieties. In other instances, the β-domain is part of a larger polypeptide that can carry out other enzymatic functions in addition to transferring an amino group from glutamine to the position on the chorismate ring that resides between the carboxylate and the enolpyruvate moieties.

As used herein, "an amino acid analog of tryptophan" is an amino acid that is structurally related to tryptophan and that can bind to the tryptophan-binding site in a wild type anthranilate synthase. These analogs include, but are not limited to, 6-methylanthranilate, 5-methyltryptophan, 4-methyltryptophan, 5-fluorotryptophan, 5-hydroxytryptophan, 7-azatryptophan, 3'-indoleacrylic acid, 3-methylanthranilic acid, and the like.

The phrase "consists essentially of" as used with respect to the present DNA molecules, sequences or segments is defined to mean that a major portion of the DNA molecule, sequence or segment encodes an anthranilate synthase. Unless otherwise indicated, the DNA molecule, sequence or segment generally does not encode proteins other than an anthranilate synthase.

The term "complementary to" is used herein to mean that the sequence of a nucleic acid strand could hybridize to all, or a portion, of a reference polynucleotide sequence. For illustration, the nucleotide sequence "TATAC" has 100% identity to a reference sequence 5'-TATAC-3' but is 100% complementary to a reference sequence 5'-GTATA-3'.

As used herein, an "exogenous" anthranilate synthase is an anthranilate synthase that is encoded by an isolated DNA that has been introduced into a host cell, and that is preferably not identical to any DNA sequence present in the cell in its native, untransformed state. An "endogenous" or "native" anthranilate synthase is an anthranilate synthase that is naturally present in a host cell or organism.

As used herein, "increased," "high" or "elevated" levels of free L-tryptophan in a plant cell, plant tissue, plant part or plant are levels that are about 2 to 200 times, preferably about 5 to 150 times, and more preferably about 10-100 times, the levels found in an untransformed plant cell, plant tissue, plant part or plant, i.e., one where the genome has not been altered by the presence of an exogenous anthranilate synthase nucleic acid or domain thereof. For example, the levels of free L-tryptophan in a transformed plant seed are compared with those in an untransformed plant seed ("the starting material").

DNA molecules encoding an anthranilate synthase, and DNA molecules encoding a transit peptide or marker/reporter gene are "isolated" in that they were taken from their natural source and are no longer within the cell where they normally exist. Such isolated DNA molecules may have been at least partially prepared or manipulated in vitro, e.g., isolated from a cell in which they are normally found, purified, and amplified. Such isolated DNA molecules can also be "recombinant" in that they have been combined with exogenous DNA molecules or segments. For example, a recombinant DNA can be an isolated DNA that is operably linked to an exogenous promoter, or to a promoter that is endogenous to the host cell. The term embraces nucleic acids that are biochemically purified so as to substantially remove contaminating nucleic acids and other cellular components. The term also embraces recombinant nucleic acids and chemically synthesized nucleic acids.

As used herein with respect to anthranilate synthase, the term "monomeric" means that two or more anthranilate synthase domains are incorporated in a functional manner into a single polypeptide chain. The monomeric anthranilate synthase may be assembled in vivo into a dimeric form. Monomeric anthranilate synthase nucleic acids and polypeptides can be isolated from various organisms such as *Agrobacterium tumefaciens, Anabaena* M22983, *Azospirillum brasilense, Brucella melitensis, Euglena gracilis, Mesorhizobium loti, Nostoc* sp. PCC7120 or *Rhizobium meliloti*. Alternatively, monomeric anthranilate synthase nucleic acids and polypeptides can be constructed from a combination of domains selected from any convenient monomeric or multimeric anthranilate synthase gene. Such organisms include, for example, *Agrobacterium tumefaciens, Anabaena* M22983, *Arabidopsis thaliana, Azospirillum brasilense, Brucella melitensis, Mesorhizobium loti, Nostoc* sp. PCC7120, *Rhizobium meliloti, Rhodopseudomonas palustris, Ruta graveolens, Sulfolobus solfataricus, Salmonella typhimurium, Serratia marcescens*, soybean, rice, cotton, *Zea mays*, or any gene encoding a subunit or domain of anthranilate synthase. Nucleic acids encoding the selected domains can be linked recombinantly. For example, a nucleic acid encoding the C-terminus of an α-domain can be linked to a nucleic acid encoding the N-terminus of the β-domain, or vice versa, by forming a phosphodiester bond. As an alternative, such single domain polypeptides can be linked chemically. For example, the α-domain can be linked via its C-terminus to the N-terminus of the β-domain, or vice versa, by forming a peptide bond.

As used herein, a "native" gene means a gene that has not been changed in vitro, i.e., a "wild-type" gene that has not been mutated in vitro.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as a "chloroplast genome," a circular DNA molecule that ranges in size from about 120 to about 217 kb, depending upon the plant species, and which usually contains an inverted repeat region.

As used herein, "polypeptide" means a continuous chain of amino acids that are all linked together by peptide bonds, except for the N-terminal and C-terminal amino acids that have amino and carboxylate groups, respectively, and that are not linked in peptide bonds. Polypeptides can have any length and can be post-translationally modified, for example, by glycosylation or phosphorylation.

As used herein, a plant cell, plant tissue or plant that is "resistant or tolerant to inhibition by an amino acid analog of tryptophan" is a plant cell, plant tissue, or plant that retains at least about 10% more anthranilate synthase activity in the presence of an analog of L-tryptophan, than a corresponding wild type anthranilate synthase. In general, a plant cell, plant tissue, or plant that is "resistant or tolerant to inhibition by an amino acid analog of tryptophan" can grow in an amount of an amino acid analog of tryptophan that normally inhibits growth of the untransformed plant cell, plant tissue, or plant, as determined by methodologies known to the art. For example, a homozygous backcross converted inbred plant transformed with a DNA molecule that encodes an anthranilate synthase that is substantially resistant or tolerant to inhibition by an amino acid analog of tryptophan grows in an amount of an amino acid analog of tryptophan that inhibits the growth of the corresponding, i.e., substantially isogenic, recurrent inbred plant.

As used herein, an anthranilate synthase that is "resistant or tolerant to inhibition by tryptophan or an amino acid analog of tryptophan" is an anthranilate synthase that retains greater than about 10% more activity than a corresponding wild-type or native susceptible anthranilate synthase, when the tolerant/resistant and wild type anthranilate synthases are exposed to equivalent amounts of tryptophan or an amino acid analog of tryptophan. Preferably the resistant or tolerant anthranilate synthase retains greater than about 20% more activity than a corresponding wild-type or native susceptible anthranilate synthase.

As used herein with respect to anthranilate synthase, the phrase "a domain thereof," includes a structural or functional segment of a full-length anthranilate synthase. A structural domain includes an identifiable structure within the anthranilate synthase. An example of a structural domain includes an alpha helix, a beta sheet, an active site, a substrate or inhibitor binding site and the like. A functional domain includes a segment of an anthranilate synthase that performs an identifiable function such as a tryptophan binding pocket, an active site or a substrate or inhibitor binding site. Functional domains of anthranilate synthase include those portions of anthranilate synthase that can catalyze one step in the biosynthetic pathway of tryptophan. For example, an α-domain is a domain that can be encoded by trpE and that can transfer $NH_3$ to chorismate and form anthranilate. A β-domain can be encoded by trpG and can remove an amino group from glutamine to form ammonia. Hence, a functional domain includes enzymatically active fragments and domains of an anthranilate synthase. Mutant domains of anthranilate synthase are also contemplated. Wild type anthranilate synthase nucleic acids utilized to make mutant domains include, for example, any nucleic acid encoding a domain of *Agrobacterium tumefaciens, Anabaena* M22983, *Arabidopsis thaliana, Azospirillum brasilense, Brucella melitensis, Mesorhizobium loti, Nostoc* sp. PCC7120, *Rhizobium meliloti, Rhodopseudomonas palustris, Ruta graveolens, Sulfolobus solfataricus, Salmonella typhimurium, Serratia marcescens*, soybean, rice, cotton, wheat, tobacco, *Zea mays*, or any gene encoding a subunit or domain of anthranilate synthase that can comprise at least one amino acid substitution in the coding region thereof. Domains that are mutated or joined to form a monomeric anthranilate synthase having increased tryptophan biosynthetic activity, greater stability, reduced sensitivity to tryptophan or an analog thereof, and the like, are of particular interest.

The term "5' UTR" refers to the untranslated region of DNA upstream, or 5', of the coding region of a gene.

The term "3' UTR" refers to the untranslated region of DNA downstream, or 3', of the coding region of a gene.

The term "substantially homologous" refers to two sequences which are at least about 90% identical in sequence, as measured by the BestFit program described herein (Version 10; Genetics Computer Group, Inc., University of Wisconsin Biotechnology Center, Madison, Wis.), using default parameters.

The percent of sequence identity is preferably determined using the "Best Fit" or "Gap" program of the Sequence Analysis Software Package (Version 10; Genetics Computer Group, Inc., University of Wisconsin Biotechnology Center, Madison, Wis.). "Gap" utilizes the algorithm of Needleman and Wunsch (1970) to find the alignment of two sequences that maximizes the number of matches and minimizes the number of gaps.

"BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the Best Fit program using default parameters. As used herein, the term "operatively linked" means that a promoter is connected to a coding region in such a way that the transcription of that coding region is controlled and regulated by that promoter. Means for operatively linking a promoter to a coding region are well known in the art.

The term "substantially identical" as used herein, refers to a comparison of polynucleotide molecules that encode the same or nearly the same protein or polypeptide. The four letter genetic code (A, G, C, and T/U) comprises three letter codons that direct t-RNA molecules to assemble amino acids into a polypeptide from an mRNA template. Having more than one codon that may code for the same amino acid is referred to as degenerate. Degenerate codons are used to construct substantially identical polynucleotide molecules that encode the same polypeptide where these polynucleotide molecules have a sequence of nucleotides when compared along their entire length in which they are at least 85% identical to one another, more preferably 86 to 90% identical to one another, even more preferably 91 to 95% identical to one another, or most preferably 96 to 99% identical to one another. Such sequences may differ due to changes at one or more bases, including a coding region with a truncation or deletion, yet still encode a polypeptide with anthranilate synthase activity.

An "artificial polynucleotide" as used in the present invention is a DNA sequence designed according to the methods of the present invention and created as an isolated DNA molecule for use in a DNA construct that provides expression of a protein in host cells, and for the purposes of cloning into appropriate constructs or other uses known to those skilled in the art. Computer programs are available for these purposes, including but not limited to the "BestFit" or "Gap" programs of the Sequence Analysis Software Package, Genetics Computer Group (GCG), Inc., University of Wisconsin Biotechnology Center, Madison, Wis. 53711. The artificial polynucleotide may be created by one or more methods known in the art that include, but are not limited to, overlapping PCR and chemical synthesis. An artificial polynucleotide molecule of the present invention is substantially identical to other polynucleotides that code for the identical or nearly identical protein.

"Codon optimization" as used in the present invention is a method of adjusting the frequency of codon usage of a polynucleotide encoding a protein derived from a foreign source to provide a pattern of codon usage that will result in enhanced expression of the protein in the host cell (see, for example, Fischhoff and Perlak, U.S. Pat. No. 5,500,365). In particular, codons to be used to optimize the artificial polynucleotides of the present invention are selected from a monocot high usage table according to the following criteria: a) after a known polynucleotide sequence is scanned using a sequence optimizer computer program, codons 1 through 50 are selected from the most abundant codons from a monocot high usage table, avoiding the use of rare codons; b) codons 51 to the end of the molecule are selected randomly from a monocot high usage table; c) codon repeats are avoided; d) regions that are A+T-rich or which many contain cryptic mRNA processing sites are identified and modified to increase the GC content and to avoid truncation of the processed molecule; and e) the resulting polynucleotide sequence is manually edited to remove unwanted restriction sites, insert stops, cryptic polyadenylation signals and other undesirable sequences. Computer programs such as the "BestFit" or "Gap" programs of the Sequence Analysis Software Package, Genetics Computer Group (GCG), Inc., University of Wisconsin Biotechnology Center, Madison, Wis. 53711, as well as other such programs designed for this purpose, may be used to adjust the frequency of codon utilization to provide enhanced expression of the protein in the host cell. A DNA sequence that has been subjected to such adjustment of codon usage is said to be "codon-optimized".

The term "translation" refers to the production the corresponding gene product, i.e., a peptide, polypeptide, or protein from an mRNA.

As used herein, the term "nutritionally enhanced" refers to an elevated, increased or high level of a particular amino acid in a plant cell as compared to the level of the same amino acid found in an untransformed plant cell, plant tissue, plant part or plant, i.e., one where the genome has not been altered by the presence of an exogenous nucleic acid. For example, the levels of free L-tryptophan in a transformed plant seed are compared with those in an untransformed plant seed ("the starting material").

As used herein, an "isogenic" line or event or cell is identical to the transgenic line or event or cell with respect to its genetic composition except that the transgenic line or event or cell contains additional DNA that has been introduced into its genome that is not present in the isogenic line or event or cell.

General Concepts

The present invention relates to novel nucleic acids and methods for obtaining plants that produce elevated levels of free L-tryptophan. The overproduction results from the introduction and expression of a nucleic acid encoding anthranilate synthase, or a domain thereof. Such anthranilate synthase nucleic acids include wild type or mutant α-domains, or monomeric forms of anthranilate synthase. A monomeric form of anthranilate synthase comprises at least two anthranilate synthase domains in a single polypeptide chain, e.g., an α-domain linked to a β-domain.

Native plant anthranilate synthases are generally quite sensitive to feedback inhibition by L-tryptophan and analogs thereof. Such inhibition constitutes a key mechanism for regulating the tryptophan synthetic pathway. Therefore, an anthranilate synthase or a domain thereof that is highly active, more efficient or that is inhibited to a lesser extent by tryptophan or an analog thereof will likely produce elevated levels of tryptophan. According to the invention, the *Agrobacterium tumefaciens* anthranilate synthase is particularly useful for producing high levels of tryptophan.

To generate high levels of tryptophan in a plant or a selected host cell, the selected anthranilate synthase nucleic acid is isolated and may be manipulated in vitro to include regulatory signals required for gene expression in plant cells or other cell types. Because the tryptophan biosynthetic pathway in plants is reported to be present within plastids, the exogenous anthranilate synthase nucleic acids are either introduced into plastids or are modified by adding a nucleic acid segment encoding an amino-terminal plastid transit peptide. Such a plastid transit peptide can direct the anthranilate synthase gene product into plastids. In some instances the anthranilate synthase may already contain a plastid transport sequence, in which case there is no need to add one.

In order to alter the biosynthesis of tryptophan, the nucleic acid encoding an anthranilate synthase activity must be introduced into plant cells or other host cells and these transformed cells identified, either directly or indirectly. An entire anthranilate synthase or a useful portion or domain thereof can be used. The anthranilate synthase is stably incorporated into the plant cell genome. The transcriptional signals controlling expression of the anthranilate synthase must be recognized by and be functional within the plant cells or other host cells. That is, the anthranilate synthase must be transcribed into messenger RNA (mRNA), and the mRNA must be stable in the plant cell nucleus and be transported intact to the cytoplasm for translation. The anthranilate synthase mRNA must have appropriate translational signals to be recognized and properly translated by plant cell ribosomes. The polypeptide gene product must substantially escape proteolytic attack in the cytoplasm, be transported into the correct cellular compartment (e.g. a plastid) and be able to assume a three-dimensional conformation that will confer enzymatic activity. The anthranilate synthase must further be able to function in the biosynthesis of tryptophan and its derivatives; that is, it must be localized near the native plant enzymes catalyzing the flanking steps in biosynthesis (presumably in a plastid) in order to obtain the required substrates and to pass on the appropriate product.

Even if all these conditions are met, successful overproduction of tryptophan is not a predictable event. The expression of some transgenes may be negatively affected by nearby chromosomal elements. If the high level of tryptophan is achieved by mutation to reduce feedback inhibition, there may be other control mechanisms compensating for the reduced regulation at the anthranilate synthase step. There may be mechanisms that increase the rate of breakdown of the accumulated amino acids. Tryptophan and related amino acids must be also overproduced at levels that are not toxic to the plant. Finally, the introduced trait must be stable and heritable in order to permit commercial development and use.

Isolation and Identification of DNA Coding for an Anthranilate Synthase

Nucleic acids encoding an anthranilate synthase can be identified and isolated by standard methods, for example, as described by Sambrook et al., (1989); Sambrook and Russell, (2001). For example, a DNA sequence encoding an anthranilate synthase or a domain thereof can be identified by screening of a DNA or cDNA library generated from nucleic acid derived from a particular cell type, cell line, primary cells, or tissue. Examples of libraries useful for identifying and isolating an anthranilate synthase include, but are not limited to, a cDNA library derived from *Agrobacterium tumefaciens* strain A348, maize inbred line B73 (Stratagene, La Jolla, Calif., Cat. #937005, Clontech, Palo Alto, Calif., Cat. # FL1032a, #FL1032b, and FL1032n), genomic library from maize inbred line Mo17 (Stratagene, Cat. #946102), genomic library from maize inbred line B73 (Clontech, Cat. # FL1032d), genomic DNA from Anabaena M22983 (e.g., Genbank Accession No. GI 152445), *Arabidopsis thaliana*, Azospirillum brasilense (e.g., Genbank Accession No. GI 1174156), *Brucella melitensis* (GI 17982357), *Escherichia coli, Euglena gracilis, Mesorhizobium loti* (e.g., Genbank Accession No. GI 13472468), *Nostoc* sp. PCC7120 (e.g., Genbank Accession No. GI 17227910 or GI 17230725), *Rhizobium meliloti* (e.g., Genbank Accession No. GI 95177), *Ruta graveolens, Rhodopseudomonas palustris, Salmonella typhimurium, Serratia marcescens, Sulfolobus solfataricus*, soybean, rice, cotton, wheat, tobacco, *Zea mays* (maize), or other species. Moreover, anthranilate synthase nucleic acids can be isolated by nucleic acid amplification procedures using genomic DNA, mRNA or cDNA isolated from any of these species.

Screening for DNA fragments that encode all or a portion of the sequence encoding an anthranilate synthase can be accomplished by screening plaques from a genomic or cDNA library for hybridization to a probe of an anthranilate synthase gene from other organisms or by screening plaques from a cDNA expression library for binding to antibodies that specifically recognize anthranilate synthase. DNA fragments that hybridize to anthranilate synthase probes from other organisms and/or plaques carrying DNA fragments that are immunoreactive with antibodies to anthranilate synthase can be subcloned into a vector and sequenced and/or used as probes to identify other cDNA or genomic sequences encoding all or a portion of the desired anthranilate synthase gene. Preferred cDNA probes for screening a maize or plant library can be obtained from plasmid clones pDPG600 or pDPG602.

A cDNA library can be prepared, for example, by random oligo priming or oligo dT priming. Plaques containing DNA fragments can be screened with probes or antibodies specific for anthranilate synthase. DNA fragments encoding a portion of an anthranilate synthase gene can be subcloned and sequenced and used as probes to identify a genomic anthranilate synthase gene. DNA fragments encoding a portion of a bacterial or plant anthranilate synthase can be verified by determining sequence homology with other known anthranilate synthase genes or by hybridization to anthranilate synthase-specific messenger RNA. Once cDNA fragments encoding portions of the 5', middle and 3' ends of an anthranilate synthase are obtained, they can be used as probes to identify and clone a complete genomic copy of the anthranilate synthase gene from a genomic library.

Portions of the genomic copy or copies of an anthranilate synthase gene can be sequenced and the 5' end of the gene identified by standard methods including either by DNA sequence homology to other anthranilate synthase genes or by RNAase protection analysis, for example, as described by Sambrook et al., (1989); (2001). The 3' and 5' ends of the target gene can also be located by computer searches of genomic sequence databases using known AS coding regions. Once portions of the 5' end of the gene are identified, complete copies of the anthranilate synthase gene can be obtained by standard methods, including cloning or polymerase chain reaction (PCR) synthesis using oligonucleotide primers complementary to the DNA sequence at the 5' end of the gene. The presence of an isolated full-length copy of the anthranilate synthase gene can be verified by hybridization, partial sequence analysis, or by expression of a maize anthranilate synthase enzyme.

Exemplary isolated DNAs of the invention include DNAs having the following nucleotide SEQ ID NO:
SEQ ID NO: 1 *Agrobacterium tumefaciens* (wild type)
SEQ ID NO: 2 *Zea mays* (wild type, alpha2)
SEQ ID NO: 3 *Ruta graveolens*
SEQ ID NO: 46 truncated trpE gene of *E. coli* EMG2 (K-12 wt F+)
SEQ ID NO: 67 *Zea mays* (C28 mutant)
SEQ ID NO: 68 *Zea mays* (C28+terminator)
SEQ ID NO: 71 Chloroplast Targeting Peptide (g)
SEQ ID NO: 73 Chloroplast Targeting Peptide (a)
SEQ ID NO: 75 *Agrobacterium tumefaciens* (optimized)
SEQ ID NO: 76 *Rhodopseudomonas palustris*
SEQ ID NO: 83 *Rhodopseudomonas palustris* (RhoPa_TrpEG)
SEQ ID NO: 84 *Agrobacterium tumefaciens* V48F mutant
SEQ ID NO: 85 *Agrobacterium tumefaciens* V48Y mutant
SEQ ID NO: 86 *Agrobacterium tumefaciens* S51F mutant
SEQ ID NO: 87 *Agrobacterium tumefaciens* S51C mutant
SEQ ID NO: 88 *Agrobacterium tumefaciens* N52F mutant
SEQ ID NO: 89 *Agrobacterium tumefaciens* P293A mutant
SEQ ID NO: 90 *Agrobacterium tumefaciens* P293G mutant
SEQ ID NO: 91 *Agrobacterium tumefaciens* F298W mutant
SEQ ID NO: 92 *Agrobacterium tumefaciens* S50K mutant
SEQ ID NO: 93 *Agrobacterium tumefaciens* F298A mutant
SEQ ID NO: 94 rice
SEQ ID NO: 95 rice isozyme
SEQ ID NO: 96 maize (U.S. Pat. No. 6,118,047 to Anderson)
SEQ ID NO: 97 wheat
SEQ ID NO: 98 tobacco
SEQ ID NO: 104 *Gossypium hirsutum* (alpha)
SEQ ID NO: 105 *Gossypium hirsutum* (beta)
SEQ ID NO: 106 *Glycine max* (alpha)
SEQ ID NO: 107 *Glycine max* (beta)
SEQ ID NO: 112 *Glycine max* (alpha) with 5' and 3'UTRs
SEQ ID NO: 113 *Glycine max* (beta) with 5' and 3'UTRs
SEQ ID NO: 116 *Zea mays* (beta)
SEQ ID NO: 119 *Oryza sativa* (beta1)
SEQ ID NO: 120 *Oryza sativa* (beta2)
SEQ ID NO: 121 *Mesorhizobium* loti
SEQ ID NO: 122 *Azospirillum brasilense*
SEQ ID NO: 123 *Brucella melitensis*
SEQ ID NO: 124 *Nostoc sp.*
SEQ ID NO: 125 *Nostoc sp.*
SEQ ID NO: 126 *Rhodopseudomonas palustris*
SEQ ID NO: 127 *Bradyrhizobium japonicum*
SEQ ID NO: 128 *Rhodospirillum rubrum*
SEQ ID NO: 129 *Thermobifida fusca*
SEQ ID NO: 134 *Sorghum bicolor* (beta1)
SEQ ID NO: 135 *Sorghum bicolor* (beta2)
SEQ ID NO: 136 *Zea mays* (alpha1)
SEQ ID NO: 144 *Agrobacterium tumefaciens* codon-optimized S51F mutant
SEQ ID NO: 145 *Agrobacterium tumefaciens* codon-optimized S51C mutant
SEQ ID NO: 146 ASA2(+18); *Zea mays* sequence encoding a chloroplast targeting peptide (CTP) fused to 18 amino acids from the N-terminus of the *Zea mays* anthranilate synthase a2 protein (ZmASA2).
SEQ ID NO: 148 *Oryza sativa* glutelin 1 (Os-gt1) 3'-UTR
SEQ ID NO: 149 DNA sequence of transformation vector comprising transcription units of pMON66879

Certain primers are also useful for the practice of the present invention, for example, primers having SEQ ID NOs: 9-42, 47-56, or 138-143.

The present invention also contemplates any isolated nucleic acid encoding an anthranilate synthase having, for example, any one of the following amino acid sequences.
SEQ ID NO: 4 *Agrobacterium tumefaciens* (wild type)
SEQ ID NO: 5 *Zea mays* (wild type)
SEQ ID NO: 6 *Ruta graveolens*
SEQ ID NO: 7 *Rhizobium meliloti*
SEQ ID NO: 8 *Sulfolobus solfataricus*
SEQ ID NO: 43 *Rhizobium meliloti*
SEQ ID NO: 44 *Sulfolobus solfataricus*
SEQ ID NO: 45 *Arabidopsis thaliana*
SEQ ID NO: 57 *Rhodopseudomonas palustris*
SEQ ID NO: 58 *Agrobacterium tumefaciens* V48F mutant
SEQ ID NO: 59 *Agrobacterium tumefaciens* V48Y mutant
SEQ ID NO: 60 *Agrobacterium tumefaciens* S51F mutant
SEQ ID NO: 61 *Agrobacterium tumefaciens* S51C mutant
SEQ ID NO: 62 *Agrobacterium tumefaciens* N52F mutant
SEQ ID NO: 63 *Agrobacterium tumefaciens* P293A mutant
SEQ ID NO: 64 *Agrobacterium tumefaciens* P293G mutant
SEQ ID NO: 65 *Agrobacterium tumefaciens* F298W mutant
SEQ ID NO: 66 *Zea mays* C28 mutant
SEQ ID NO: 69 *Agrobacterium tumefaciens* S50K mutant
SEQ ID NO: 70 *Agrobacterium tumefaciens* F298A mutant
SEQ ID NO: 74 Chloroplast Targeting Peptide (a)
SEQ ID NO: 72 Chloroplast Targeting Peptide (g)
SEQ ID NO: 77 *Mesorhizobium loti* (MesLo__13472468)
SEQ ID NO: 78 *Azospirillum brasilense* (AzoBr__1717765)
SEQ ID NO: 79 *Brucella melitensis* (BruMe__17986732)
SEQ ID NO: 80 *Nostoc* sp. (*Nostoc*__17227910)
SEQ ID NO: 81 *Nostoc* sp. (*Nostoc*__17230725)

SEQ ID NO: 82 *Rhodopseudomonas palustris* RhoPa_TrpEG
SEQ ID NO: 99 rice
SEQ ID NO: 100 rice isozyme
SEQ ID NO: 101 maize (U.S. Pat. No. 6,118,047 to Anderson)
SEQ ID NO: 102 wheat
SEQ ID NO: 103 tobacco
SEQ ID NO: 108 *Gossypium hirsutum* (alpha)
SEQ ID NO: 109 *Gossypium hirsutum* (beta)
SEQ ID NO: 110 *Glycine max* (alpha)
SEQ ID NO: 111 *Glycine max* (beta)
SEQ ID NO: 114 *Zea mays* (ASalpha2) chloroplast targeting peptide
SEQ ID NO: 115 *Zea mays* (ASalpha1) chloroplast targeting peptide
SEQ ID NO: 117 *Oryza sativa* (beta)
SEQ ID NO: 118 *Zea mays* (beta)
SEQ ID NO: 130 *Bradyrhizobium japonicum*
SEQ ID NO: 131 *Rhodospirillum rubrum*
SEQ ID NO: 132 *Thermobifida fusca*
SEQ ID NO: 133 *Sorghum bicolor* (beta)
SEQ ID NO: 137 *Zea mays* (ASalpha1)
SEQ ID NO: 147 ASA2(+18); *Zea mays* chloroplast targeting peptide (CTP) fused to 18 amino acids from the N-terminus of the *Zea mays* anthranilate synthase a2 protein Any of these nucleic acids and polypeptides can be utilized in the practice of the invention, as well as any mutant, variant or derivative thereof.

Monomeric Anthranilate Synthases

According to the present invention, monomeric anthranilate synthases from plant and non-plant species are functional in plants and can provide high levels of tryptophan. Surprisingly, monomeric anthranilate synthases from non-plant species function very well in plants even though the sequences of these monomeric anthranilate synthases have low homology with most plant anthranilate synthases. For example, monomeric anthranilate synthases from species as diverse as bacteria, protists, and microbes can be used successfully. In particular, monomeric anthranilate synthases from bacterial species such as *Agrobacterium tumefaciens, Rhizobium meliloti, Mesorhizobium loti, Brucella melitensis, Nostoc* sp. PCC7120, *Azospirillum brasilense, Anabaena* M22983, *Bradyrhizobium janonicum, Rhodospirillum rubrum*, and *Thermobidfida fusca* are functional in plants and can provide high levels of tryptophan, despite the rather low sequence identity of these monomeric anthranilate synthases with most plant anthranilate synthases.

Transgenic plants containing, for example, the wild type monomeric *Agrobacterium tumefaciens* anthranilate synthase can produce up to about 10,000 to about 12,000 ppm tryptophan in seeds, with average trp levels ranging up to about 7,000 to about 8,000 ppm. Non-transgenic soybean plants normally have up to only about 100 to about 200 ppm tryptophan in seeds. By comparison transgenic plants containing an added mutant *Zea mays*α domain produce somewhat lower levels of tryptophan (e.g., averages up to about 3000 to about 4000 ppm).

Monomeric enzymes may have certain advantages over multimeric enzymes. For example, while the present invention is not to be limited to a specific mechanism, a monomeric enzyme may provide greater stability, coordinated expression, and the like. When domains or subunits of a heterotetrameric anthranilate synthase are synthesized in vivo, those domains/subunits must properly assemble into a heterotetrameric form before the enzyme becomes active. Addition of a single domain of anthranilate synthase by transgenic means to a plant may not provide overproduction of the entire heterotetrameric enzyme because there may not be sufficient endogenous amounts of the non-transgenic domains to substantially increase levels of the functional tetramer. Hence, nucleic acids, vectors and enzymes encoding a monomeric anthranilate synthase can advantageously be used to overproduce all of the enzymatic functions of anthranilate synthase.

According to the present invention, anthranilate synthase domains from species that naturally produce heterotetrameric anthranilate synthases can be fused or linked to provide monomeric anthranilate synthases that can generate high tryptophan levels when expressed within a plant cell, plant tissue or seed. For example, a monomeric anthranilate synthase can be made by fusing or linking the α- and β-domains of anthranilate synthase so that the sequence of the α-β fusion generally aligns with an anthranilate synthase that is naturally monomeric. Examples of sequence alignments of monomeric and heterotetrameric anthranilate synthases are shown in FIGS. 7 and 15. Using such sequence alignments, the spacing and orientation of anthranilate synthase domains can be adjusted or modified to generate a monomeric anthranilate construct from heterotetrameric domains that optimally aligns with naturally monomeric anthranilate synthases. Such a fusion protein can be used to increase tryptophan levels in the tissues of a plant.

Heterotetrameric anthranilate synthases, such as the *Sulfolobus solfataricus* anthranilate synthase (e.g., Genbank Accession No. GI1004323), share between about 30% to about 87% sequence homology with heterotetrameric anthranilate synthases from other plant and microbial species. Monomeric anthranilate synthases, such as the *A. tumefaciens* anthranilate synthase, have between about 84% and about 52% identity to the other monomeric enzymes (e.g. *Rhizobium meliloti* (Genbank Accession No. GI 15966140) and *Azospirillum brasilense* (Genbank Accession No. 1717765), respectively; and Bae et al., (1989); De Troch et al., (1997).

However, the overall sequence identity shared between naturally monomeric and naturally heterotetrameric anthranilate synthases can be less than 30%. Hence, visual alignment rather than computer-generated alignment, may be needed to optimally align monomeric and heterotetrameric anthranilate synthases. Landmark structures and sequences within the anthranilate synthases can facilitate sequences alignments. For example, the motif "LLES" is part of a β-sheet of the β-sandwich that forms the tryptophan-binding pocket of anthranilate synthases. Such landmark sequences can be used to more confidently align divergent anthranilate synthase sequences, and are especially useful for determination of key residues involved in tryptophan binding.

To accomplish the fusion or linkage of anthranilate synthase domains, the C-terminus of the selected TrpE or α-domain is linked to the N-terminus of the TrpG domain or β-domain. In some cases, a linker peptide may be utilized between the domains to provide the appropriate spacing and/or flexibility. Appropriate linker sequences can be identified by sequence alignment of monomeric and heterotetrameric anthranilate synthases.

The selected β-domains can be cloned, for example, by hybridization, PCR amplification or as described in Anderson et al., U.S. Pat. No. 6,118,047. A plastid transit peptide sequence can also be linked to the anthranilate synthase coding region using standard methods. For example, an *Arabidopsis* small subunit (SSU) chloroplast targeting peptide (CTP, SEQ ID NOs: 71-74) may be used for this purpose. See also Stark et al., (1992). The fused gene can then be inserted into a suitable vector for plant transformation as described herein.

Anthranilate Synthase Mutants

Mutant anthranilate synthases contemplated by the present invention can have any type of mutation including, for example, amino acid substitutions, deletions, insertions, and/or rearrangements. Such mutants can be derivatives or variants of anthranilate synthase nucleic acids and polypeptides specifically identified herein. Alternatively, mutant anthranilate synthases can be obtained from any available species, including those not explicitly identified herein. The mutants, derivatives and variants can have identity with at least about 30% of the amino acid positions of any one of SEQ ID NOs: 4-8, 43-45, 57-66, 69-70, 77-82, 99-111, 117-118, 130-133 and 137, and have anthranilate synthase activity. In a preferred embodiment, polypeptide derivatives and variants have identity with at least about 50% of the amino acid positions of any one of SEQ ID NOs: 4-8, 43-45, 57-66, 69-70, 77-82, 99-111, 117-118, 130-133 and 137, and have anthranilate synthase activity. In a more preferred embodiment, polypeptide derivatives and variants have identity with at least about 60% of the amino acid positions of any one of SEQ ID NOs: 4-8, 43-45, 57-66, 69-70, 77-82, 99-111, 117-118, 130-133 and 137, and have anthranilate synthase activity. In a more preferred embodiment, polypeptide derivatives and variants have identity with at least about 70% of the amino acid positions of any one of SEQ ID NOs: 4-8, 43-45, 57-66, 69-70, 77-82, 99-111, 117-118, 130-133 and 137, and have anthranilate synthase activity. In an even more preferred embodiment, polypeptide derivatives and variants have identity with at least about 80% of the amino acid positions of any one of SEQ ID NOs: 4-8, 43-45, 57-66, 69-70, 77-82, 99-111, 117-118, 130-133 and 137, and have anthranilate synthase activity. In an even more preferred embodiment, polypeptide derivatives and variants have identity with at least about 90% of the amino acid positions of any one of SEQ ID NOs: 4-8, 43-45, 57-66, 69-70, 77-82, 99-111, 117-118, 130-133 and 137, and have anthranilate synthase activity. In an even more preferred embodiment, polypeptide derivatives and variants have identity with at least about 95% of the amino acid positions of any one of SEQ ID NOs: 4-8, 43-45, 57-66, 69-70, 77-82, 99-111, 117-118, 130-133 and 137, and have anthranilate synthase activity.

In one embodiment, anthranilate synthase mutants, variants and derivatives can be identified by hybridization of any one of SEQ ID NOs: 1-3, 46, 47-56, 67-68, 75-76, 83-98, 104-107, 112, 113, 116, 119-129, 134-136, and 138-145, or a fragment or primer thereof under moderate or, preferably, high stringency conditions to a selected source of nucleic acids. Moderate and stringent hybridization conditions are well known to the art, (e.g. sections 0.47-9.51 of Sambrook et al., (1989); and Sambrook and Russell, (2001)). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS.

The present invention further provides hybridization probes and primers comprising a novel isolated and purified DNA segment of at least seven nucleotide bases, which can be detectably labeled or bind to a detectable label. Such a hybridization probe or primer can hybridize under moderate or high stringency conditions to either strand of a DNA molecule that encodes an anthranilate synthase. Examples of such hybridization probes and primers include any one of SEQ ID NOs: 9-42, 47-56, and 138-143.

The anthranilate synthase can be any anthranilate synthase, or a mutant or domain thereof, such as the α-domain. The anthranilate synthase can be a monomeric anthranilate synthase. Functional mutants are preferred, particularly those that can generate high levels of tryptophan in a plant, for example, those mutants that are substantially resistant to inhibition by an amino acid analog of tryptophan.

Nucleic acids encoding mutant anthranilate synthases can also be generated from any convenient species, for example, from nucleic acids encoding any domain of *Agrobacterium tumefaciens*, *Anabaena* M22983 (e.g. Genbank Accession No. GI 152445), *Arabidopsis thaliana*, *Azospirillum brasilense* (e.g., Genbank Accession No. GI 1174156), *Brucella melitensis* (e.g., Genbank Accession No. GI 17982357), *Escherichia coli, Euglena gracilis, Mesorhizobium loti* (e.g., Genbank Accession No. GI 13472468), *Nostoc* sp. PCC7120 (e.g., Genbank Accession No. GI 17227910 or GI 17230725), *Rhizobium meliloti* (e.g., Genbank Accession No. GI 95177), *Ruta graveolens, Rhodopseudomonas palustris, Salmonella typhimurium, Serratia marcescens, Sulfolobus solfataricus, Bradyrhizobium japonicum, Rhodospirillum rubrum, Thermobifida fusca, Sorghum bicolor*, soybean, rice, cotton, wheat, tobacco, *Zea mays* (maize), or any gene encoding a subunit or domain of anthranilate synthase.

Mutants having increased anthranilate synthase activity, reduced sensitivity to feedback inhibition by tryptophan or analogs thereof, and/or the ability to generate increased amounts of tryptophan in a plant are desirable. Such mutants do have a functional change in the level or type of activity they exhibit and are sometimes referred to as "derivatives" of the anthranilate synthase nucleic acids and polypeptides provided herein.

However, the present invention also contemplates anthranilate synthase variants as well as anthranilate synthase nucleic acids with "silent" mutations. As used herein, a silent mutation is a mutation that changes the nucleotide sequence of the anthranilate synthase but that does not change the amino acid sequence of the encoded anthranilate synthase. A variant anthranilate synthase is encoded by a mutant nucleic acid and the variant has one or more amino acid changes that do not substantially change its activity when compared to the corresponding wild type anthranilate synthase. The invention is directed to all such derivatives, variants and anthranilate synthases nucleic acids with silent mutations.

DNA encoding a mutated anthranilate synthase that is resistant and/or tolerant to L-tryptophan or amino acid analogs of tryptophan can be obtained by several methods. The methods include, but are not limited to:

1. spontaneous variation and direct mutant selection in cultures;
2. direct or indirect mutagenesis procedures on tissue cultures of any cell types or tissue, seeds or plants;
3. mutation of the cloned anthranilate synthase gene by methods such as by chemical mutagenesis; site specific or site directed mutagenesis Sambrook et al., cited supra), transposon mediated mutagenesis (Berg et al., 1983), and deletion mutagenesis (Mitra et al., 1989);

4. rational design of mutations in key residues; and

5. DNA shuffling to incorporate mutations of interest into various anthranilate synthase nucleic acids.

For example, protein structural information from available anthranilate synthase proteins can be used to rationally design anthranilate synthase mutants that have a high probability of having increased activity or reduced sensitivity to tryptophan or tryptophan analogs. Such protein structural information is available, for example, on the *Solfolobus solfataricus* anthranilate synthase (Knochel et al., 1999). Rational design of mutations can be accomplished by alignment of the selected anthranilate synthase amino acid sequence with the anthranilate synthase amino acid sequence from an anthranilate synthase of known structure, for example, *Sulfolobus solfataricus*. See FIGS. 3, 7, and 15. The predicted tryptophan binding and catalysis regions of the anthranilate synthase protein can be assigned by combining the knowledge of the structural information with the sequence homology. For example, residues in the tryptophan binding pocket can be identified as potential candidates for mutation to alter the resistance of the enzyme to feedback inhibition by tryptophan. Using such structural information, several *Agrobacterium tumefaciens* anthranilate synthase mutants were rationally designed in the site or domain involved in tryptophan binding.

Using such sequence and structural analysis, regions analogous to the monomeric *Agrobacterium tumefaciens* anthranilate synthase at approximately positions 25-60 or 200-225 or 290-300 or 370-375 were identified in the monomeric *Agrobacterium tumefaciens* anthranilate synthase as being potentially useful residues for mutation to produce active anthranilate synthases that may have less sensitivity to tryptophan feedback inhibition. More specifically, amino acids analogous to P29, E30, S31, I32, S42, V43, V48, S50, S51, N52, N204, P205, M209, F210, G221, N292, P293, F298, and A373 in the monomeric *Agrobacterium tumefaciens* anthranilate synthase are identified as being potentially useful residues for mutation to produce active anthranilate synthases that may have less sensitivity to tryptophan feedback inhibition. The present invention contemplates any amino acid substitution or insertion at any of these positions. Alternatively, the amino acid at any of these positions can be deleted.

Site directed mutagenesis can be used to generate amino acid substitutions, deletions and insertions at a variety of sites. Examples of specific mutations made within the *Agrobacterium tumefaciens* anthranilate synthase coding region include the following:

at about position 48 replace Val with Phe (see e.g., SEQ ID NO: 58);

at about position 48 replace Val with Tyr (see e.g., SEQ ID NO: 59);

at about position 51 replace Ser with Phe (see e.g., SEQ ID NO: 60);

at about position 51 replace Ser with Cys (see e.g., SEQ ID NO: 61);

at about position 52 replace Asn with Phe (see e.g., SEQ ID NO: 62);

at about position 293 replace Pro with Ala (see e.g., SEQ ID NO: 63);

at about position 293 replace Pro with Gly (see e.g., SEQ ID NO: 64); or at about position 298 replace Phe with Trp (see e.g., SEQ ID NO: 65).

Similar mutations can be made in analogous positions of any anthranilate synthase by alignment of the amino acid sequence of the anthranilate synthase to be mutated with an *Agrobacterium tumefaciens* anthranilate synthase amino acid sequence. One example of an *Agrobacterium tumefaciens* anthranilate synthase amino acid sequence that can be used for alignment is SEQ ID NO: 4.

Useful mutants can also be identified by classical mutagenesis and genetic selection. A functional change can be detected in the activity of the enzyme encoded by the gene by exposing the enzyme to free L-tryptophan or amino acid analogs of tryptophan, or by detecting a change in the DNA molecule using restriction enzyme mapping or DNA sequence analysis.

For example, a gene encoding an anthranilate synthase substantially tolerant to 5-methyltryptophan (5-MT) can be isolated from a 5-methyltryptophan tolerant cell line. See U.S. Pat. No. 4,581,847, the disclosure of which is incorporated by reference herein. Briefly, partially differentiated plant cell cultures are grown and subcultured with continuous exposures to low levels of 5-methyltryptophan. 5-methyltryptophan concentrations are then gradually increased over several subculture intervals. Cells or tissues growing in the presence of normally toxic 5-methyltryptophan levels are repeatedly subcultured in the presence of 5-methyltryptophan and characterized. Stability of the 5-methyltryptophan tolerance trait of the cultured cells may be evaluated by growing the selected cell lines in the absence of 5-methyltryptophan for various periods of time and then analyzing growth after exposing the tissue to 5-methyltryptophan. Cell lines that are tolerant by virtue of having an altered anthranilate synthase enzyme can be selected by identifying cell lines having enzyme activity in the presence of normally toxic, i.e., growth inhibitor, levels of 5-methyltryptophan.

The anthranilate synthase gene cloned from a 5-MT- or 6-methylanthramilate (6-MA)-resistant cell line can be assessed for tolerance to 5-MT, 6-MA, or other amino acid analogs of tryptophan by standard methods, as described in U.S. Pat. No. 4,581,847, the disclosure of which is incorporated by reference herein.

Cell lines with an anthranilate synthase of reduced sensitivity to 5-methyltryptophan inhibition can be used to isolate a 5-methyltryptophan-resistant anthranilate synthase. A DNA library from a cell line tolerant to 5-methyltryptophan can be generated and DNA fragments encoding all or a portion of an anthranilate synthase gene can be identified by hybridization to a cDNA probe encoding a portion of an anthranilate synthase gene. A complete copy of the altered gene can be obtained either by cloning and ligation or by PCR synthesis using appropriate primers. The isolation of the altered gene coding for anthranilate synthase can be confirmed in transformed plant cells by determining whether the anthranilate synthase being expressed retains enzyme activity when exposed to normally toxic levels of 5-methyltryptophan (Anderson et al., U.S. Pat. No. 6,118,047).

Codon Optimization

In general, expression of bacterial genes in plants may often result in inefficient protein accumulation. This can be attributed to suboptimal usage of amino acid codons in the host plant, resulting in limitation of some of the tRNAs corresponding to rare codons of the bacterial gene, presence of cryptic mRNA processing sites, or due to inefficient initiation of translation. The major block to efficient bacterial gene expression in plants appears to be at the translational level, as evidenced by low level expression of wild-type cry1A(b) and cry1A(c) genes in tobacco, tomato and cotton (Perlak et al., 1991). One of the efficient methods to optimize or to correct low levels of protein expression is to modify the transgene DNA sequence in accordance with the favorable codon usage preference of the host organism. In addition, modification of the regions that are A+T-rich resembling plant introns (Goodall and Filipowich, 1989) or potential polyadenylation signal sequences and mRNA splicing sites (Dean et al., 1986) may enhance the stability of the mRNA in the host organism.

Coding regions of any DNA molecule provided herein can also be optimized for expression in a selected organism, for example, a selected plant or other host cell type. An example of a DNA molecule having optimized codon usage for a selected plant is an *Agrobacterium tumefaciens* anthranilate synthase DNA molecule having SEQ ID NO: 75. This optimized *Agrobacterium tumefaciens* anthranilate synthase DNA (SEQ ID NO: 75) has 94% identity with SEQ ID NO: 1. A further example of a DNA molecule having optimized codon usage for a selected plant is an artificial polynucleotide sequence having SEQ ID NO: 144. This codon-optimized S51F mutant of *Agrobacterium tumefaciens* anthranilate synthase DNA (SEQ ID NO: 144) has 82.9% identity with SEQ ID NO: 86. Yet another example of a DNA molecule having optimized codon usage for a selected plant is an artificial polynucleotide sequence having SEQ ID NO: 145. This codon-optimized S51C mutant of *Agrobacterium tumefaciens* anthranilate synthase DNA (SEQ ID NO: 145) has 82.9% identity with SEQ ID NO: 87.

Transgenes and Vectors

Once a nucleic acid encoding anthranilate synthase or a domain thereof is obtained and amplified, it is operably combined with a promoter and, optionally, with other elements to form a transgene.

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous genes, that is, a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in a transgene of the present invention can provide for expression of anthranilate synthase from a DNA sequence encoding anthranilate synthase. Preferably, the coding sequence is expressed so as to result in an increase in tryptophan levels within plant tissues, for example, within the seeds of the plant. In another embodiment, the coding sequence is expressed so as to result in increased tolerance of the plant cells to feedback inhibition or to growth inhibition by an amino acid analog of tryptophan or so as to result in an increase in the total tryptophan content of the cells. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression in plants. Many promoters useful in the practice of the invention are available to those of skill in the art.

Preferred promoters will generally include, but are not limited to, promoters that function in bacteria, bacteriophage, plastids or plant cells. Useful promoters include the CaMV 35S promoter (Odell et al., 1985), the CaMV 19S (Lawton et al., 1987), nos (Ebert et al., 1987), Adh (Walker et al., 1987), sucrose synthase (Yang et al., 1990), α-tubulin, napin, actin (Wang et al., 1992), cab (Sullivan et al., 1989), PEPCase promoter (Hudspeth et al., 1989), maize L3 oleosin promoter, P-Zm.L3 (U.S. Pat. No. 6,433,252) the 7S-alpha'-conglycinin promoter (Beachy et al., 1985) or those associated with the R gene complex (Chandler et al., 1989). Other useful promoters include the bacteriophage SP6, T3, and T7 promoters.

Plastid promoters can be also be used. Most plastid genes contain a promoter for the multi-subunit plastid-encoded RNA polymerase (PEP) as well as the single-subunit nuclear-encoded RNA polymerase. A consensus sequence for the nuclear-encoded polymerase (NEP) promoters and listing of specific promoter sequences for several native plastid genes can be found in Hajdukiewicz et al. (1997), which is hereby in its entirety incorporated by reference.

Examples of plastid promoters that can be used include the *Zea mays* plastid RRN (ZMRRN) promoter. The ZMRRN promoter can drive expression of a gene when the *Arabidopsis thaliana* plastid RNA polymerase is present. Similar promoters that can be used in the present invention are the *Glycine max* plastid RRN (SOYRRN) and the *Nicotiana tabacum* plastid RRN (NTRRN) promoters. All three promoters can be recognized by the *Arabidopsis* plastid RNA polymerase. The general features of RRN promoters are described by Hajdukiewicz et al. and U.S. Pat. No. 6,218,145.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924). For example, it is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of monocot transformation. Tissue-specific promoters, including but not limited to, root-cell promoters (Conkling et al., 1990), and tissue-specific enhancers (Fromm et al., 1989) are also contemplated to be particularly useful, as are inducible promoters such as ABA- and turgor-inducible promoters, and the like.

As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987). The choice of such sequences is at the discretion of those of skill in the art. Sequences that are derived from genes that are highly expressed in dicots, and in soybean in particular, are contemplated.

In some cases, extremely high expression of anthranilate synthase or a domain thereof, is not necessary. For example, using the methods of the invention such high levels of anthranilate synthase may be generated that the availability of substrate, rather than enzyme, may limit the levels of tryptophan generated. In such cases, more moderate or regulated levels of expression can be selected by one of skill in the art. Such a skilled artisan can readily modulate or regulate the levels of expression, for example, by use of a weaker promoter or by use of a developmentally regulated or tissue specific promoter.

Nucleic acids encoding the anthranilate synthase of interest can also include a plastid transit peptide (e.g. SEQ ID NOs: 72, 74, 114, or 147) to facilitate transport of the anthranilate synthase polypeptide into plastids, for example, into chloroplasts. A nucleic acid encoding the selected plastid transit peptide (e.g. SEQ ID NOs: 71, 73 or 146) is generally linked in-frame with the coding sequence of the anthranilate synthase. However, the plastid transit peptide can be placed at either the N-terminal or C-terminal end of the anthranilate synthase.

Constructs also include the nucleic acid of interest (e.g. DNA encoding an anthranilate synthase) along with a nucleic acid sequence that acts as a transcription termination signal and that allows for the polyadenylation of the resultant mRNA. Such transcription termination signals are placed 3' or downstream of the coding region of interest. Preferred transcription termination signals contemplated include the transcription termination signal from the nopaline synthase gene of *Agrobacterium tumefaciens* (Bevan et al., 1983), the terminator from the octopine synthase gene of *Agrobacterium tumefaciens*, the 3'-UTR of the glutelin 1 gene of *Oryza sativa* (Os-gt1; SEQ ID NO: 148), and the 3' end of genes encoding protease inhibitor I or II from potato or tomato, although other transcription termination signals known to those of skill in the art are also contemplated. Regulatory elements such as Adh intron 1 (Callis et al., 1987), sucrose synthase intron (Vasil et al., 1989) or TMV omega element (Gallie et al., *The Plant Cell*, 1:301 (1989)) may further be included where desired. These 3' nontranslated regulatory sequences can be obtained as described in An (1987) or are already present in plasmids available from commercial sources such as Clontech, (Palo Alto, Calif.). The 3' nontranslated regulatory sequences can be operably linked to the 3 terminus of an anthranilate synthase gene by standard methods. Other such regulatory elements useful in the practice of the invention are known to those of skill in the art.

A DNA construct may comprise a first expression cassette, comprised of, in operable linkage, a heterologous promoter, a DNA molecule encoding an anthranilate synthase α-domain protein and a transcriptional terminator. This DNA construct may further comprise a second expression cassette in operable linkage, comprising a heterologous promoter, a DNA molecule encoding an anthranilate synthase β-domain protein and a transcriptional terminator.

Selectable marker genes or reporter genes are also useful in the present invention. Such genes can impart a distinct phenotype to cells expressing the marker gene and thus allow such transformed cells to be distinguished from cells that do not have the marker. Selectable marker genes confer a trait that one can "select" for by chemical means, i.e., through the use of a selective agent (e.g., a herbicide, antibiotic, or the like). Reporter genes, or screenable genes, confer a trait that one can identify through observation or testing, i.e., by "screening" (e.g., the R-locus trait). Of course, many examples of suitable marker genes are known to the art and can be employed in the practice of the present invention.

Possible selectable markers for use in connection with the present invention include, but are not limited to, a neo gene (Potrykus et al., 1985) which codes for neomycin resistance and can be selected for using kanamycin, G418, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) that confers resistance to imidazolinone, sulfonylurea or other ALS-inhibiting chemicals (EP 154 204 (1985)); a methotrexate-resistant DHFR gene (Thillet et al., 1988); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable plastid transit peptide (CTP).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al, 1986; Twell et al., 1989) causing rapid accumulation of ammonia and cell death.

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) that encodes a catechol dioxygenase that can convert chromogenic catechols; an α-amylase gene (Ikuta et al., 1990); a tyrosinase gene (Katz et al., 1983) that encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995). The presence of the lux gene in transformed cells may be detected using, for example, X-ray film, scintillation counting, fluorescent spectrophotometry, low-light video cameras, photon-counting cameras, or multiwell luminometry. It is also envisioned that this system may be developed for populational screening for bioluminescence, such as on tissue culture plates, or even for whole plant screening.

Additionally, transgenes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and may then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences may increase the accumulation of gene product.

A particular example of such a use concerns the direction of an anthranilate synthase to a particular organelle, such as the plastid, rather than to the cytoplasm. This is exemplified by the use of the *Arabidopsis* SSU1A transit peptide that confers plastid-specific targeting of proteins. Alternatively, the transgene can comprise a plastid transit peptide-encoding DNA sequence or a DNA sequence encoding the rbcS (RuBISCO) transit peptide operably linked between a promoter and the DNA sequence encoding an anthranilate synthase (for a review of plastid targeting peptides, see Heijne et al. (1989); Keegstra et al. (1989). If the transgene is to be introduced into a plant cell, the transgene can also contain plant transcriptional termination and polyadenylation signals and translational signals linked to the 3' terminus of a plant anthranilate synthase gene.

An exogenous plastid transit peptide can be used which is not encoded within a native plant anthranilate synthase gene. A plastid transit peptide is typically 40 to 70 amino acids in length and functions post-translationally to direct a protein to the plastid. The transit peptide is cleaved either during or just after import into the plastid to yield the mature protein. The complete copy of a gene encoding a plant anthranilate synthase may contain a plastid transit peptide sequence. In that case, it may not be necessary to combine an exogenously obtained plastid transit peptide sequence into the transgene.

Exogenous plastid transit peptide encoding sequences can be obtained from a variety of plant nuclear genes, so long as the products of the genes are expressed as preproteins comprising an amino terminal transit peptide and transported into plastid. Examples of plant gene products known to include such transit peptide sequences include, but are not limited to, the small subunit of ribulose biphosphate carboxylase, chlorophyll a/b binding protein, plastid ribosomal proteins encoded by nuclear genes, certain heatshock proteins, amino acid biosynthetic enzymes such as acetolactate acid synthase, 3-enolpyruvylphosphoshikimate synthase, dihydrodipicolinate synthase, anthranilate synthase and the like. In some instances a plastid transport protein already may be encoded in the anthranilate synthase gene of interest, in which case there may be no need to add such plastid transit sequences. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon, for example, an ATG codon, and be expressed as an amino acid sequence that is recognized by and will function properly in plastids of the host plant. Attention should also be given to the amino acid sequence at the junction between the transit peptide and the anthranilate synthase enzyme where it is cleaved to yield the mature enzyme. Certain conserved amino acid sequences have been identified and may serve as a guideline. Precise fusion of the transit peptide coding sequence with the anthranilate synthase coding sequence may require manipulation of one or both DNA sequences to introduce, for example, a convenient restriction site. This may be accomplished by methods including site-directed mutagenesis, insertion of chemically synthesized oligonucleotide linkers, and the like.

Precise fusion of the nucleic acids encoding the plastid transport protein may not be necessary so long as the coding sequence of the plastid transport protein is in-frame with that of the anthranilate synthase. For example, additional peptidyl or amino acids can often be included without adversely affecting the expression or localization of the protein of interest.

Once obtained, the plastid transit peptide sequence can be appropriately linked to the promoter and an anthranilate synthase coding region in a transgene using standard methods. A plasmid containing a promoter functional in plant cells and having multiple cloning sites downstream can be constructed or obtained from commercial sources. The plastid transit peptide sequence can be inserted downstream from the promoter using restriction enzymes. An anthranilate synthase coding region can then be translationally fused or inserted immediately downstream from and in frame with the 3' terminus of the plastid transit peptide sequence. Hence, the plastid transit peptide is preferably linked to the amino terminus of the anthranilate synthase. Once formed, the transgene can be subcloned into other plasmids or vectors.

In addition to nuclear plant transformation, the present invention also extends to direct transformation of the plastid genome of plants. Hence, targeting of the gene product to an intracellular compartment within plant cells may also be achieved by direct delivery of a gene to the intracellular compartment. Direct transformation of plastid genome may provide additional benefits over nuclear transformation. For example, direct plastid transformation of anthranilate synthase eliminates the requirement for a plastid targeting peptide and post-translational transport and processing of the pre-protein derived from the corresponding nuclear transformants. Plastid transformation of plants has been described by Maliga (2002); Heifetz (2000); Bock (2001); and Daniell et al. (2002), and references within.

After constructing a transgene containing an anthranilate synthase gene, the cassette can then be introduced into a plant cell. Depending on the type of plant cell, the level of gene expression, and the activity of the enzyme encoded by the gene, introduction of DNA encoding an anthranilate synthase into the plant cell can lead to the overproduction of tryptophan, confer tolerance to an amino acid analog of tryptophan, such as 5-methyltryptophan or 6-methylanthranilate, and/or otherwise alter the tryptophan content of the plant cell.

Transformation of Host Cells

A transgene comprising an anthranilate synthase gene can be subcloned into a known expression vector, and AS expression can be detected and/or quantitated. This method of screening is useful to identify transgenes providing for an expression of an anthranilate synthase gene, and expression of an anthranilate synthase in the plastid of a transformed plant cell.

Plasmid vectors include additional DNA sequences that provide for easy selection, amplification, and transformation of the transgene in prokaryotic and eukaryotic cells, e.g., pUC-derived vectors, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An, cited supra. This binary Ti vector can be replicated in prokaryotic bacteria such as *E. coli* and *Agrobacterium*. The *Agrobacterium* plasmid vectors can also be used to transfer the transgene to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying a transgene of the invention can be used to transform both prokaryotic and eukaryotic cells, but is preferably used to transform plant cells. See, for example, Glassman et al., U.S. Pat. No. 5,258,300.

The expression vector can then be introduced into prokaryotic or eukaryotic cells by available methods. Methods of transformation especially effective for monocots and dicots, include, but are not limited to, microprojectile bombardment of immature embryos (U.S. Pat. No. 5,990,390) or Type II embryogenic callus cells as described by Gordon-Kamm et al. (1990); Fromm et al. (1990); Walters et al. (1992), or by electroporation of type I embryogenic calluses described by D'Halluin et al. (1992) or by Krzyzek (U.S. Pat. No. 5,384,253). Transformation of plant cells by vortexing with DNA-coated tungsten whiskers (Coffee et al., U.S. Pat. No. 5,302,523) and transformation by exposure of cells to DNA-containing liposomes can also be used.

After transformation of the selected anthranilate synthase construct into a host cell, the host cell may be used for production of useful products generated by the transgenic anthranilate synthase in combination with the host cell's enzymatic machinery. Culturing the transformed cells can lead to enhanced production of tryptophan and other useful compounds, which can be recovered from the cells or from the culture media. Examples of useful compounds that may be generated upon expression in a variety of host cells and/or organisms include tryptophan, indole acetic acid and other auxins, isoflavonoid compounds important to cardiovascular health found in soy, volatile indole compounds which act as signals to natural enemies of herbivorous insects in maize, anticarcinogens such as indole glucosinolates (indole-3-carbinol) found in the Cruciferae plant family, as well as indole alkaloids such as ergot compounds produced by certain species of fungi. (Barnes et al., 1996; Frey et al., 2000; Muller et al., 2000; Mantegani et al., 1999; Zeligs, 1998; Mash et al., 1998; Melanson et al., 1997; Broadbent et al., 1998).

Accumulation of tryptophan may also lead to the increased production of secondary metabolites in microbes and plants, for example, indole containing metabolites such as simple indoles, indole conjugates, indole alkaloids, indole phytoalexins and indole glucosinalates in plants.

Anthranilate synthases insensitive to tryptophan have the potential to increase a variety of chorismate-derived metabolites, including those derived from phenylalanine due to the stimulation of phenylalanine synthesis by tryptophan via chorismate mutase (Siehl, 1999). Other chorismate-derived metabolites that may increase when feedback insensitive anthranilate synthases are present include phenylpropanoids, flavonoids, and isoflavonoids, as well as those derived from anthranilate, such as indole, indole alkaloids, and indole glucosinolates. Many of these compounds are important plant hormones, plant defense compounds, chemopreventive agents of various health conditions, and/or pharmacologically active compounds.

The range of these compounds whose synthesis might be increased by expression of anthranilate synthase depends on the organism in which the anthranilate synthase is expressed. One of skill in the art can readily assess which organisms and host cells to use and/or test in order to generate the desired compounds. The present invention contemplates synthesis of tryptophan and other useful compounds in a variety of organisms, including plants, microbes, fungi, yeast, bacteria, insect cells, and mammalian cells.

Strategy for Selection of Tryptophan Overproducer Cell Lines

Efficient selection of a desired tryptophan analog resistant, tryptophan overproducer variant using tissue culture techniques requires careful determination of selection conditions. These conditions are optimized to allow growth and accumulation of tryptophan analog resistant, tryptophan overproducer cells in the culture while inhibiting the growth of the bulk of the cell population. The situation is complicated by the fact that the vitality of individual cells in a population can be highly dependent on the vitality of neighboring cells.

Conditions under which cell cultures are exposed to tryptophan analog are determined by the characteristics of the interaction of the compound with the tissue. Such factors as the degree of toxicity and the rate of inhibition should be considered. The accumulation of the compounds by cells in culture, and the persistence and stability of the compounds, both in the media and in the cells, also need to be considered along with the extent of uptake and transmission to the desired cellular compartment. Additionally, it is important to determine whether the effects of the compounds can be readily reversed by the addition of tryptophan.

The effects of the analog on culture viability and morphology is carefully evaluated. It is especially important to choose analog exposure conditions that have no impact on plant regeneration capability of cultures. Choice of analog exposure conditions is also influenced by whether the analog kills cells or simply inhibits cell divisions.

The choice of a selection protocol is dependent upon the considerations described above. The protocols briefly described below can be utilized in the selection procedure. For example, to select for cells that are resistant to growth inhibition by a tryptophan analog, finely divided cells in liquid suspension culture can be exposed to high tryptophan analog levels for brief periods of time. Surviving cells are then allowed to recover and accumulate and are then reexposed for subsequently longer periods of time. Alternatively, organized partially differentiated cell cultures are grown and subcultured with continuous exposure to initially low levels of a tryptophan analog. Concentrations are then gradually increased over several subculture intervals. While these protocols can be utilized in a selection procedure, the present invention is not limited to these procedures.

Genes for Plant Modification

As described herein above, genes that function as selectable marker genes and reporter genes can be operably combined with the DNA sequence encoding the anthranilate synthase, or domain thereof, in transgenes, vectors and plants of the present invention. Additionally, other agronomical traits can be added to the transgenes, vectors and plants of the present invention. Such traits include, but are not limited to, insect resistance or tolerance; disease resistance or tolerance (viral, bacterial, fungal, nematode); stress resistance or tolerance, as exemplified by resistance or tolerance to drought, heat, chilling, freezing, excessive moisture, salt stress, oxidative stress, increased yields, food content and makeup, physical appearance, male sterility, drydown, standability, prolificacy, starch properties, oil quantity and quality, and the like. One may incorporate one or more genes conferring such traits into the plants of the present invention.

Insect Resistance or Tolerance

*Bacillus thuringiensis* (or "Bt") bacteria include nearly 20 known subspecies of bacteria which produce endotoxin polypeptides that are toxic when ingested by a wide variety of insect species. The biology and molecular biology of the endotoxin proteins (Bt proteins) and corresponding genes (Bt genes) has been reviewed by Whitely et al. (1986) and by Hofte et al. (1989). Genes coding for a variety of Bt proteins have been cloned and sequenced. A segment of the Bt polypeptide is essential for toxicity to a variety of Lepidoptera pests and is contained within approximately the first 50% of the Bt polypeptide molecule. Consequently, a truncated Bt polypeptide coded by a truncated Bt gene will in many cases retain its toxicity towards a number of Lepidoptera insect pests. For example, the HD73 and HD1 Bt polypeptides have been shown to be toxic to the larvae of the important Lepidoptera insect pests of plants in the U.S.A. such as the European corn borer, cutworms and earworms. The genes coding for the HD1 and HD73 Bt polypeptides have been cloned and sequenced by Geiser et al. (1986) and Adang et al. (1985), respectively, and can be cloned from HD1 and HD73 strains obtained from culture collections (e.g. *Bacillus* Genetic Stock Center, Columbus, Ohio or USDA Bt stock collection Peoria, Ill.) using standard protocols. Examples of Bt genes and polypeptides are described, for example, in U.S. Pat. Nos. 6,329,574; 6,303,364; 6,320,100; and 6,331,655.

DNA coding for new, previously uncharacterized Bt toxins, may be cloned from the host *Bacillus* organism using protocols that have previously been used to clone Bt genes, and new synthetic forms of Bt toxins may also be produced.

A Bt gene useful in the present invention may include a 5' DNA sequence including a sequence of DNA which will allow for the initiation of transcription and translation of a downstream located Bt sequence in a plant. The Bt gene may also comprise a 3' DNA sequence that includes a sequence derived from the 3' non-coding region of a gene that can be expressed in the plant of interest. The Bt gene would also include a DNA sequence coding for a toxic Bt polypeptide produced by *Bacillus thuringiensis* or toxic portions thereof or having substantial amino sequence homology thereto. The Bt coding sequence may include: (i) DNA sequences which code for insecticidal proteins that have substantial homology to Bt endotoxins that are active against insect pests of the plant of interest, e.g., the HD73 or HD1 Bt sequences; (ii) sequences coding for insecticidally-active segments of the Bt endotoxin polypeptide, e.g., insecticidally active HD73 or HD1 polypeptides truncated from the carboxy and/or amino termini; and/or (iii) a truncated Bt sequence fused in frame with a sequence(s) that codes for a polypeptide that provides some additional advantage such as: (a) genes that are selectable, e.g., genes that confer resistance to antibiotics or herbicides, (b) reporter genes whose products are easy to detect or assay, e.g., luciferase or beta-glucuronidase; (c) DNA sequences that code for polypeptide sequences that have some additional use in stabilizing the Bt protein against degradation or enhance the efficacy of the Bt protein against insects, e.g., protease inhibitors; and (d) sequences that help direct the Bt protein to a specific compartment inside or outside the plant cell, e.g., a signal sequence.

To obtain optimum synthesis of a Bt protein or other heterologous protein in the plant, it may also be appropriate to adjust the DNA sequence of the gene encoding such a protein to more resemble the genes that are efficiently expressed in the plant of interest. Since the codon usage of Bt genes may be dissimilar to that used by genes that are expressed in the plant of interest, the expression of a Bt gene in plant cells may be improved by the replacement of codons with those that are more efficiently expressed in plants, e.g., are used more frequently in the plants of interest (See Murray et al., 1989). Such replacement of codons may require the substitution of bases without changing the amino acid sequence of the resulting Bt polypeptide. The Bt polypeptide may be identical in sequence to the bacterial gene or segments thereof. The complete Bt coding sequence, or sections thereof, containing a higher proportion of preferred codons than the original bacterial gene could be synthesized using standard chemical synthesis protocols, and introduced or assembled into the Bt gene using standard protocols, such as site-directed mutagenesis or DNA polymerization and ligation and the like.

Protease inhibitors may also provide insect resistance. For example, use of a protease inhibitor II gene, pinII, from tomato or potato may be useful. Also advantageous is the use of a pinII gene in combination with a Bt toxin gene. Other genes which encode inhibitors of the insects' digestive system, or those that encode enzymes or co-factors that facilitate the production of inhibitors, may also be useful. This group includes oryzacystatin and amylase inhibitors such as those from wheat and barley.

Genes encoding lectins may confer additional or alternative insecticide properties. (Murdock et al., 1990; Czapla and Lang, 1990. Lectin genes contemplated to be useful include, for example, barley and wheat germ agglutinin (WGA) and rice lectins. (Gatehouse et al., 1984).

Genes controlling the production of large or small polypeptides active against insects when introduced into the insect pests such as lytic peptides, peptide hormones and toxins and venoms, may also be useful. For example, the expression of juvenile hormone esterase, directed towards specific insect pests, may also result in insecticidal activity, or perhaps cause cessation of metamorphosis. (Hammock et al., 1990).

Transgenic plants expressing genes encoding enzymes that affect the integrity of the insect cuticle may also be useful. Such genes include those encoding, for example, chitinase, proteases, lipases and also genes for the production of nikkomycin. Genes that code for activities that affect insect molting, such those affecting the production of ecdysteroid UDP-glucosyl transferase, may also be useful.

Genes that code for enzymes that facilitate the production of compounds that reduce the nutritional quality of the plant to insect pests, may also be useful. It may be possible, for instance, to confer insecticidal activity to a plant by altering its sterol composition. Further embodiments of the present invention concern transgenic plants with enhanced lipoxygenase activity.

The present invention also provides methods and compositions useful in altering plant secondary metabolites. One example concerns altering plants to produce DIMBOA which, it is contemplated, will confer resistance to European corn borer, rootworm and several other insect pests. See, e.g., U.S. Pat. No. 6,331,880. DIMBOA is derived from indole-related compounds. The present invention provides methods for increasing the content of indole-related compounds like tryptophan within plant cells and tissues. Hence, according to the invention the methods provided herein may also increase the levels of DIMBOA, and thereby increase the resistance of plants to insects.

The introduction of genes that can regulate the production of maysin, and genes involved in the production of dhurrin in sorghum, is also contemplated to be of use in facilitating resistance to earworm and rootworm, respectively.

Further genes encoding proteins characterized as having potential insecticidal activity may also be used. Such genes include, for example, the cowpea trypsin inhibitor (CpTI; Hilder et al., 1987) which may be used as a rootworm deterrent; genes encoding avermectin (Campbell, 1989; Ikeda et al., 1987) which may prove useful as a corn rootworm deterrent; ribosome inactivating protein genes; and genes that regulate plant structures. Transgenic plants including anti-insect antibody genes and genes that code for enzymes that can convert a non-toxic insecticide (pro-insecticide) applied to the outside of the plant into an insecticide inside the plant are also contemplated.

Environmental or Stress Resistance or Tolerance

Improvement of a plant's ability to tolerate various environmental stresses can be effected through expression of genes. For example, increased resistance to freezing temperatures may be conferred through the introduction of an "antifreeze" protein such as that of the Winter Flounder (Cutler et al., 1989) or synthetic gene derivatives thereof. Improved chilling tolerance may also be conferred through increased expression of glycerol-3-phosphate acetyltransferase in plastids (Wolter et al., 1992). Resistance to oxidative stress can be conferred by expression of superoxide dismutase (Gupta et al., 1993), and can be improved by glutathione reductase (Bowler et al., 1992).

It is contemplated that the expression of genes that favorably affect plant water content, total water potential, osmotic potential, and turgor will enhance the ability of the plant to tolerate drought and will therefore be useful. It is proposed, for example, that the expression of genes encoding for the biosynthesis of osmotically-active solutes may impart protection against drought. Within this class are genes encoding for mannitol dehydrogenase (Lee and Saier, 1982) and trehalose-6-phosphate synthase (Kaasen et al., 1992).

Similarly, other metabolites may protect either enzyme function or membrane integrity (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol, sorbitol, dulcitol, glucosylglycerol, sucrose, stachyose, raffinose, proline, glycine, betaine, ononitol and pinitol. See, e.g., U.S. Pat. No. 6,281,411.

Three classes of Late Embryogenic Proteins have been assigned based on structural similarities (see Dure et al., 1989). Expression of structural genes from all three LEA groups may confer drought tolerance. Other types of proteins induced during water stress, which may be useful, include thiol proteases, aldolases and transmembrane transporters, which may confer various protective and/or repair-type functions during drought stress. See, e.g., PCT/CA99/00219 (Na+/H+ exchanger polypeptide genes). Genes that effect lipid biosynthesis might also be useful in conferring drought resistance.

The expression of genes involved with specific morphological traits that allow for increased water extractions from drying soil may also be useful. The expression of genes that enhance reproductive fitness during times of stress may also be useful. It is also proposed that expression of genes that minimize kernel abortion during times of stress would increase the amount of grain to be harvested and hence be of value.

Enabling plants to utilize water more efficiently, through the introduction and expression of genes, may improve the overall performance even when soil water availability is not limiting. By introducing genes that improve the ability of plants to maximize water usage across a full range of stresses relating to water availability, yield stability or consistency of yield performance may be realized.

Disease Resistance or Tolerance

Resistance to viruses may be produced through expression of genes. For example, expression of antisense genes targeted at essential viral functions or expression of genes encoding viral coat proteins may impart resistance to the virus.

Resistance to diseases caused by bacteria and fungi may be conferred through introduction of genes. For example, genes encoding so-called "peptide antibiotics," pathogenesis related (PR) proteins, toxin resistance, and proteins affecting host-pathogen interactions such as morphological characteristics may be useful.

Mycotoxin Reduction/Elimination

Production of mycotoxins, including aflatoxin and fumonisin, by fungi associated with plants is a significant factor in rendering grain not useful. Inhibition of the growth of these fungi may reduce the synthesis of these toxic substances and therefore reduce grain losses due to mycotoxin contamination. It may be possible to introduce genes into plants such that would inhibit synthesis of the mycotoxin without interfering with fungal growth. Further, expression of a novel gene which encodes an enzyme capable of rendering the mycotoxin nontoxic would be useful in order to achieve reduced mycotoxin contamination of grain.

Plant Composition or Quality

The composition of the plant may be altered, for example, to improve the balance of amino acids in a variety of ways including elevating expression of native proteins, decreasing expression of those with poor composition, changing the composition of native proteins, or introducing genes encoding entirely new proteins possessing superior composition (see, e.g., U.S. Pat. No. 6,160,208 (alteration of seed storage protein expression)). The introduction of genes that alter the oil content of the plant may be of value (see, e.g., U.S. Pat. Nos. 6,069,289 and 6,268,550 (ACCase gene)). Genes may be introduced that enhance the nutritive value of the starch component of the plant, for example by increasing the degree of branching, resulting in improved utilization of the starch in cows by delaying its metabolism.

Plant Agronomic Characteristics

Two of the factors determining where plants can be grown are the average daily temperature during the growing season and the length of time between frosts. Expression of genes that are involved in regulation of plant development may be useful, e.g., the liguleless and rough sheath genes that have been identified in corn.

Genes may be introduced into corn that would improve standability and other plant growth characteristics. Expression of genes which confer stronger stalks, improved root systems, or prevent or reduce ear droppage would be of value to the farmer Nutrient Utilization The ability to utilize available nutrients may be a limiting factor in growth of plants. It may be possible to alter nutrient uptake, tolerate pH extremes, mobilization through the plant, storage pools, and availability for metabolic activities by the introduction of genes. These modifications would allow a plant to more efficiently utilize available nutrients. For example, an increase in the activity of an enzyme that is normally present in the plant and involved in nutrient utilization may increase the availability of a nutrient. An example of such an enzyme would be phytase.

Male Sterility

Male sterility is useful in the production of hybrid seed, and male sterility may be produced through expression of genes. It may be possible through the introduction of TURF-13 via transformation to separate male sterility from disease sensitivity. See Levings (1990). As it may be necessary to restore male fertility for breeding purposes and for grain production, genes encoding restoration of male fertility may also be introduced.

Selection and Characterization of Resistant Cell Lines

Selections are carried out until cells or tissue are recovered which are observed to be growing well in the presence of normally inhibitory levels of a tryptophan analog thereof. These cell "lines" are subcultured several additional times in the presence of a tryptophan analog to remove non-resistant cells and then characterized. The amount of resistance that has been obtained is determined by comparing the growth of these cell lines with the growth of unselected cells or tissue in the presence of various tryptophan analogs at various concentrations. Stability of the resistance trait of the cultured cells may be evaluated by simply growing the selected cell lines in the absence of the tryptophan analog for various periods of time and then analyzing growth after re-exposing the tissue to the analog. The resistant cell lines may also be evaluated using in vitro chemical studies to verify that the site of action of the analog is altered to a form that is less sensitive to inhibition by tryptophan analogs.

Transient expression of an anthranilate synthase gene can be detected and quantitated in the transformed cells. Gene expression can be quantitated by RT-PCR analysis, a quantitative Western blot using antibodies specific for the cloned anthranilate synthase or by detecting enzyme activity in the presence of tryptophan or an amino acid analog of tryptophan. The tissue and subcellular location of the cloned anthranilate synthase can be determined by immunochemical staining methods using antibodies specific for the cloned anthranilate synthase or subcellular fractionation and subsequent biochemical and/or immunological analyses. Sensitivity of the cloned anthranilate synthase to agents can also be assessed. Transgenes providing for expression of an anthranilate synthase or anthranilate synthase tolerant to inhibition by an amino acid analog of tryptophan or free L-tryptophan can then be used to transform monocot and/or dicot plant tissue cells and to regenerate transformed plants and seeds. Transformed cells can be selected by detecting the presence of a selectable marker gene or a reporter gene, for example, by detecting a selectable herbicide resistance marker. Transient expression of an anthranilate synthase gene can be detected in the transgenic embryogenic calli using antibodies specific for the cloned anthranilate synthase, or by RT-PCR analyses.

Plant Regeneration and Production of Seed

Transformed embryogenic calli, meristematic tissue, embryos, leaf discs and the like can then be used to generate transgenic plants that exhibit stable inheritance of the transformed anthranilate synthase gene. Plant cell lines exhibiting satisfactory levels of tolerance to an amino acid analog of tryptophan are put through a plant regeneration protocol to obtain mature plants and seeds expressing the tolerance traits by methods well known in the art (for example, see U.S. Pat. Nos. 5,990,390 and 5,489,520; and Laursen et al., (1994)). The plant regeneration protocol allows the development of somatic embryos and the subsequent growth of roots and shoots. To determine that the tolerance trait is expressed in differentiated organs of the plant, and not solely in undifferentiated cell culture, regenerated plants can be assayed for the levels of tryptophan present in various portions of the plant relative to regenerated, non-transformed plants. Transgenic plants and seeds can be generated from transformed cells and tissues showing a change in tryptophan content or in resistance to a tryptophan analog using standard methods. It is especially preferred that the tryptophan content of the leaves or seeds is increased. A change in specific activity of the enzyme in the presence of inhibitory amounts of tryptophan or an analog thereof can be detected by measuring enzyme activity in the transformed cells as described by Widholm (1972). A change in total tryptophan content can also be examined by standard methods as described by Jones et al. (1981).

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

The commercial value of tryptophan overproducer soybeans, cereals and other plants is greatest if many different hybrid combinations are available for sale. The farmer typically grows more than one kind of hybrid based on such differences as maturity, standability or other agronomic traits. Additionally, hybrids adapted to one part of the country are not adapted to another part because of differences in such traits as maturity, disease, and insect resistance. Because of this, it is necessary to breed tryptophan overproduction into a large number of parental inbred lines so that many hybrid combinations can be produced.

A conversion process (backcrossing) is carried out by crossing the original overproducer line to normal elite lines and crossing the progeny back to the normal parent. Subsequent to the backcrossing, the new overproducer lines and the appropriate combinations of lines which make good commercial hybrids are evaluated for overproduction as well as a battery of important agronomic traits. Overproducer lines and hybrids are produced which are true to type of the original normal lines and hybrids. This requires evaluation under a range of environmental conditions where the lines or hybrids will generally be grown commercially. For production of high tryptophan soybeans, it may be necessary that both parents of the hybrid seed be homozygous for the high tryptophan character. Parental lines of hybrids that perform satisfactorily are increased and used for hybrid production using standard hybrid seed production practices.

The transgenic plants produced herein are expected to be useful for a variety of commercial and research purposes. Transgenic plants can be created for use in traditional agriculture to possess traits beneficial to the consumer of the grain harvested from the plant (e.g., improved nutritive content in human food or animal feed). In such uses, the plants are generally grown for the use of their grain in human or animal foods. However, other parts of the plants, including stalks, husks, vegetative parts, and the like, may also have utility, including use as part of animal silage, fermentation feed, biocatalysis, or for ornamental purposes.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from soybean cells to cells of other species, e.g., by protoplast fusion.

In one embodiment, a transgene comprised of a maize anthranilate α-domain isolated from a maize cell line tolerant to 5-MT and linked to the 35S CaMV promoter is introduced into a 5-MT sensitive monocot or dicot tissue using microprojectile bombardment. Transformed embryos or meristems are selected and used to generate transgenic plants. Transformed calli and transgenic plants can be evaluated for tolerance to 5-MT or 6-MA and for stable inheritance of the tolerance trait.

EXAMPLES

The following examples further illustrate the invention and are not intended to be limiting thereof. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation and E. Coli Expression of Anthranilate Synthase from Agrobacterium tumefaciens This example describes the isolation of anthranilate synthase from Agrobacterium tumefaciens and its expression in E. coli.

Cloning of Agrobacterium tumefaciens AS

The nucleotide and amino acid sequences of the anthranilate synthase coding region from Rhizobium meliloti (GenBank accession number: P15395) was used to search an Agrobacterium tumefaciens C58 genomic sequence database (Goodner et al., 2001). The search consisted of tblastn using blosum62 matrix, (Altschul et al., 1997).

The identified AS homolog in the Agrobacterium tumefaciens C58 genomic sequence database was cloned by PCR using genomic DNA from Agrobacterium tumefaciens strain C58 (ATCC No. 33970) as the template. The primary PCR reaction was carried out using the following primers:

```
5'-TTATGCCGCCTGTCATCG-3';    (SEQ ID NO: 47)
and

5'-ATAGGCTTAATGGTAACCG-3'.   (SEQ ID NO: 48)
```

Gene amplification parameters were as follows: (a) denature at 95° C. for 30 seconds, (b) anneal at 50° C. for 30 seconds and (c) extend at 72° C. for 2 minutes, using Expand high fidelity PCR (Roche Biochemicals), according to manufacturer directions.

An additional round of PCR amplification, yielding a product of approximately 2.3 Kb in length, was carried out using the amplified template from above and the following nested primers:

```
5'-CTGAACAACAGAAGTACG-3';    (SEQ ID NO: 49)
and

5'-TAACCGTGTCATCGAGCG-3'.    (SEQ ID NO: 50)
```

The purified PCR product was ligated into pGEM-T easy (Promega Biotech, Madison, Wis.) resulting in the plasmid pMON61600. pMON61600 was sequenced using standard sequencing methodology. Confirmation of the correct sequence was obtained by comparison of the sequence the Rhizobium meliloti anthranilate synthase sequence (FIG. 1). The translated amino acid sequence from the isolated clone (SEQ ID NO: 4) shared 88% identity with the Rhizobium meliloti enzyme (SEQ ID NO: 7) (FIG. 1).

The abbreviation "AgroAS" or A. tumefaciens AS is sometimes used herein to refer to Agrobacterium tumefaciens anthranilate synthase.

E. coli Expression of Agrobacterium tumefaciens AS

The following vectors were constructed to facilitate subcloning of the Agrobacterium tumefaciens AS gene into a suitable expression vector.

A 2215 base pair PCR fragment was generated using pMON61600 as the template and the following primers:

```
                                             (SEQ ID NO: 51)
  5'-AAAAAGATCTCCATGGTAACGATCATTCAGG-3';
  and (SEQ ID NO: 52)
  5'-AAAAGAATTCTTATCACGCGGCCTTGGTCTTCGCC-3'.
```

The plasmid pMON61600 was digested with restriction enzymes NcoI and RsrII. In addition, a 409 bp fragment (derived by digesting the 2215 base pair PCR product with NcoI and RsrII) was then ligated into the digested pMON61600 plasmid, thereby replacing the NcoI/RsrII fragment, and resulting in a NcoI site in frame with the translation initiation codon (ATG) of Agrobacterium tumefaciens AS to yield plasmid pMON34692.

The base T7 E. coli expression plasmid, pMON34697, was generated by restriction digestion of pET30a (Novagen, Inc, Madison, Wis.)) with SphI and BamHI. The resulting 4,969 bp fragment was purified and subcloned with a 338 bp SphI and BamHI fragment from pET11d (Novagen, Inc).

The plasmid pMON34705 (FIG. 2) was generated by restriction digestion of pMON34697 with NcoI and SacI. The resulting 5,263 bp fragment was then purified and ligated with a 2,256 bp NcoI and SacI fragment from pMON34692 containing Agrobacterium tumefaciens AS.

The plasmid pMON34705 was transformed into *E. coli* BL21(DE3) (F-ompT HsdS$_b$(r$_B^-$m$_B^-$)gal dcm (DE3)) according to manufacturer's instructions (Novagen, Inc). DE3 is a host lysogen of λDE3 containing a chromosomal copy of T7 RNA polymerase under control of an isopropyl-1-thio-D-galactopyranoside (IPTG) inducible lacUV5.

Transformed cells were selected on kanamycin plates that had been incubated at 37° C. overnight (10 hours). Single colonies were transferred to 2 ml of LB (Luria Broth; per liter, 10 g tryptone, 5 g yeast extract, 10 g NaCl, and 1 g glucose (optional)) or 2X-YT broth (per liter, 16 g tryptone, 10 g yeast extract, 5 g NaCl) and then placed in a 37° C. incubator and shaken at 225 rpm for 3 hours. The cells were removed and 4 μL of 100 mM IPTG was added to the culture and returned to the 37° C. incubator for an additional 2 to 3 hours. A 1 mL aliquot of the cells was removed and sonicated in sonication buffer, (50 mM potassium phosphate (pH 7.3), 10% glycerol, 10 mM 2-mercaptoethanol and 10 mM MgCl$_2$). The resulting lysed cell extract was the source material for the standard AS assay described below. The results established that the expression system based on plasmid pMON34705 was able to produce soluble and enzymatically active *Agrobacterium tumefaciens* AS protein that accounts for approximately 50% of total soluble extracted protein.

Example 2

High Trp Seed Levels are Achieved by Transformation of Plants with Wild Type *Agrobacterium* Anthranilate Synthase Expression Vector pMON58120

The vector pMON58120 (FIG. 26) encodes a fusion between a 264 base pair *Arabidopsis* small subunit (SSU) chloroplast targeting peptide (CTP, SEQ ID NO: 71) and a 2187 base pair wild type *Agrobacterium* anthranilate synthase (AgroAS) open reading frame (SEQ ID NO: 1) (see Stark et al., 1992). Expression of this open reading frame is driven by the soy 7S alpha prime (7Sα') promoter.

Upon translation on cytoplasmic ribosomes, the fusion (immature protein) is imported into chloroplast where the chloroplast targeting sequence is removed. There are two cleavage sites in the CTP1. The first site is 30 base pairs upstream of the CDS start (C/M), and the other is at the initial methionine (C/M). The second cleavage site does not seem to be processed efficiently. The cleavage is predicted to yield a mature protein of about 70 Kd that has AS activity as shown by enzyme activity data and trp efficacy data.

The AS gene was transformed with the synthetic CP4 gene that confers glyphosate resistance, however the CP4 gene is processed separately from the AS gene. Expression of the CP4 gene was driven by the FMV promoter, which is a 35S promoter from Figwort Mosaic Virus. Glyphosate resistance allows for selection of the transformed plants.

Western Analysis of AS Protein

Thirty-five transformation events of pMON58120 were analyzed for AgroAS protein presence. AgroAS protein was detected with a polyclonal antibody raised in rabbits against purified His-tagged AgroAS. The His-tagged, full-length Agro-AS polypeptide was used as an antigen to generate a population of polyclonal antibodies in rabbits by CoCalico Biological, Inc. The recombinant His-tagged Agro-AS DNA was placed into a pMON 34701 (pet-30a-agroAS) expression vector. The His-AgroAS fusion protein was expressed in *E. coli* BL21(DE3) and purified by Ni-NTA resin system (Qiagen protocol). For western analysis, primary rabbit anti-AgroAS antibodies were used at 1:5,000 dilution. Secondary, goat anti-rabbit alkaline phosphatase-conjugated antibodies were used at 1:5,000 dilution. In transgenic lines carrying 7Salpha'-AgroAS genes, western blot analysis consistently revealed the presence of a single band that specifically cross-reacted with anti-AgroAS antibodies. This band was not detected in the nontransgenic control line.

Free Amino Acid Analysis of Soy and *Arabidopsis* Seed

Amino Acid Extraction: About 50 mg of crushed soy seed (5 mg of *Arabidopsis*) material was placed in each centrifuge vial. One milliliter of 5% trichloroacetic acid was added to each sample (100 μl for *Arabidopsis*). The samples were vortexed, and allowed to sit, with agitation, at room temperature for 15 min. They were then microcentrifuged for 15 min at 14000 rpm. Some of the supernatant was then removed, placed in a HPLC vial and sealed. Samples were kept at 4° C. in the analysis queue.

Amino Acid Analysis: The reagents utilized for amino acid analysis included the OPA reagent (o-phthalaldehyde and 3-mercaptopropionic acid in borate buffer (Hewlett-Packard, PN 5061-3335)) where the borate buffer (0.4 N in water, pH 10.2). The analysis was performed using the Agilent 1100 series HPLC system as described in the Agilent Technical Publication, "Amino Acid Analysis Using Zorbax Eclipse-AAA Columns and the Agilent 1100 HPLC", Mar. 17, 2000. First, 0.5 μl of the sample was derivatized with 2.5 μl of OPA reagent in 10 μl of borate buffer. Second, the derivative is injected onto a Eclipse XDB-C18

5 μm, 4.6×150 mm column using a flow rate of 1.2 ml/min. Amino acid concentrations were measured using fluorescence: excitation at 340 nm, emission at 450 nm. Elution was with a gradient of HPLC Buffers A and B according to Table A, where HPLC Buffer A was 40 mM Na$_2$HPO$_4$, pH=7.8 and HPLC Buffer B was 9:9:2::Methanol:Acetonitrile:Water.

TABLE A

| | Amino Acid Elution | | | | |
| --- | --- | --- | --- | --- | --- |
| | | Time | | | |
| | 0 | 20 | 21 | 26 | 27 |
| % Buffer B | 5 | 65 | 100 | 100 | 100 |

Amino acid standards were prepared from the dry chemicals, using all amino acids of interest. Proline analysis required an additional derivatization step with 9-fluorenylmethyl-chloroformate (FMOC). Amino acid standards were also sometimes purchased in concentrations ranging from 0 to 100 μg/ml. Samples were reported in μg/g of seed powder.

Expression of Wild Type *Agrobacterium* Anthranilate Synthase in *Arabidopsis*

The vector pMON58120 was transformed into *Arabidopsis* plants by vacuum infiltration of the secondary influorescences, and plants were allowed to set transgenic seed. The seed was collected and screened for the presence of a selectable marker (glyphosate resistance). Glyphosate resistant plants were grown to maturity and seed from each plant, which was designated a transformation event, and analyzed for tryptophan content (Table B). Selected transformation events were also analyzed for the presence of the expressed *Agrobacterium* anthranilate synthase protein in the mature seed by Western blot analysis as shown in Table B.

TABLE B

Analysis of Transformants

| Transformation Event | Trp (ppm) | Protein present |
|---|---|---|
| 7317 | 2547 | + |
| 7315 | 2960 | + |
| 7319 | 3628 | + |
| 7313 | 3979 | + |

Expression of Wild Type *Agrobacterium* Anthranilate Synthase in Soy (*Glycine max*)

Thirty-three out of thirty-five soy transformation events analyzed had an increase in seed trp levels, for example, from above 500 ppm and up to 12,000 ppm. In nontransgenic soy seeds, the trp level is less than 200 ppm. All seeds that contained high amounts of trp demonstrated anthranilate synthase protein expression by western blotting. Table C presents data for nineteen soy events that contain high trp levels and also are positive for anthranilate synthase anthranilate synthase protein by western blot analysis.

TABLE C

Correlation between the Presence of the AgroAS Protein and Tryptophan Levels in Nineteen Soy Transgenic Events bearing pMON58120

| Pedigree | Trp max (ppm) | Trp average (ppm) | Protein present? |
|---|---|---|---|
| A3244 (ctr) | 306 | 96 | NO |
| GM_A20380:@. | 6444 | 2246.4 | YES |
| GM_A20532:@. | 6055 | 2556.6 | YES |
| GM_A22043:@. | 10422 | 2557.2 | YES |
| GM_A20598:@. | 8861 | 2859.9 | YES |
| GM_A20744:@. | 7121 | 3373.3 | YES |
| GM_A20381:@. | 6392 | 3572.9 | YES |
| GM_A20536:@. | 9951 | 3581.5 | YES |
| GM_A20510:@. | 8916 | 3592.7 | YES |
| GM_A20459:@. | 8043 | 3900.4 | YES |
| GM_A20337:@. | 7674 | 4088.6 | YES |
| GM_A20533:@. | 9666 | 4183.2 | YES |
| GM_A20577:@. | 6276 | 4434.1 | YES |
| GM_A20339:@. | 9028 | 4687.8 | YES |
| GM_A20386:@. | 8487 | 5285.3 | YES |
| GM_A20457:@. | 11007 | 5888.9 | YES |
| GM_A20379:@. | 7672 | 6416.1 | YES |
| GM_A20537:@. | 9163 | 6695.8 | YES |
| GM_A20534:@. | 12676 | 7618.2 | YES |
| GM_A20576:@. | 10814 | 7870.1 | YES |

The AgroAS Enzyme Assay

The specific activity of anthranilate synthase was measured in eleven transformation events carrying the pMON58120 construct. Individual soybean immature seeds were analyzed using an HPLC-based end-point assay based on the method described by Paulsen (1991). Briefly, desalted extracts were generated from individual seeds in grinding buffer (100 mM Tris pH7.5, 10% glycerol, 1 mM EDTA, 1 mM DTT) and incubated for 30 min with reaction buffer (100 mM tris pH 7.5, 1 mM chorismate, 20 mM glutamine, and 10 mM $MgCl_2$). AgroAS activity was measured in the presence or absence of 25 mM trp. The reaction was stopped with phosphoric acid and the amount of anthranilate formed was quantified by HPLC using a fluorescence detector set at 340 mm/excitation and 410 nm/emission.

The specific activity of AS in immature segregating transgenic seeds ranged from 1.5-fold up to 70-fold increase compared to a nontransgenic control, reaching as high as 6,000 pmoles/mg/min. As shown in the last column of Table D, the anthranilate synthase activity in transgenic plants is resistant to tryptophan inhibition (see Table D).

TABLE D

AgroAS Enzyme Activity in Transgenic Event 20576

| Event | Seed No. | Specific Activity (pmoles/mg/min) | Specific Activity (pmoles/mg/min) (+25 micromolar Trp) |
|---|---|---|---|
| Control | 3244-1 | 95.4 | 42.4 |
| Control | 3244-2 | 85.5 | 40.6 |
| 20576 | 20576-1 | 6060.2 | 4407.1 |
| 20576 | 20576-2 | 3783.8 | 1709.4 |
| 20576 | 20576-3 | 2768.3 | 2431.7 |
| 20576 | 20576-4 | 4244.08 | 2125.2 |

Example 3

Soybean Transformation with a Vector Containing a Maize Anthranilate Synthase α-Subunit Gene The coding sequence for a maize anthranilate synthase α-subunit was isolated from pMON52214 by digesting with XbaI in combination with a partial NcoI digest (see Anderson et al., U.S. Pat. No. 6,118,047). The resulting 1952 bp DNA fragment representing the anthranilate synthase a coding region was gel purified, and the ends were made blunt. The plasmid pMON53901 was digested with BglII and EcoRI, to generate a 6.8 Kb fragment. After isolation, the ends of the 6.8 Kb fragment were made blunt and dephosphorylated. The 1952 Kb fragment containing the ASα gene was then ligated into the blunt-ended 6.8 Kb pMON53901 fragment to generate pMON39324, a maize 7S promoter-maize ASα-NOS 3' UTR expression vector.

Figure 8:
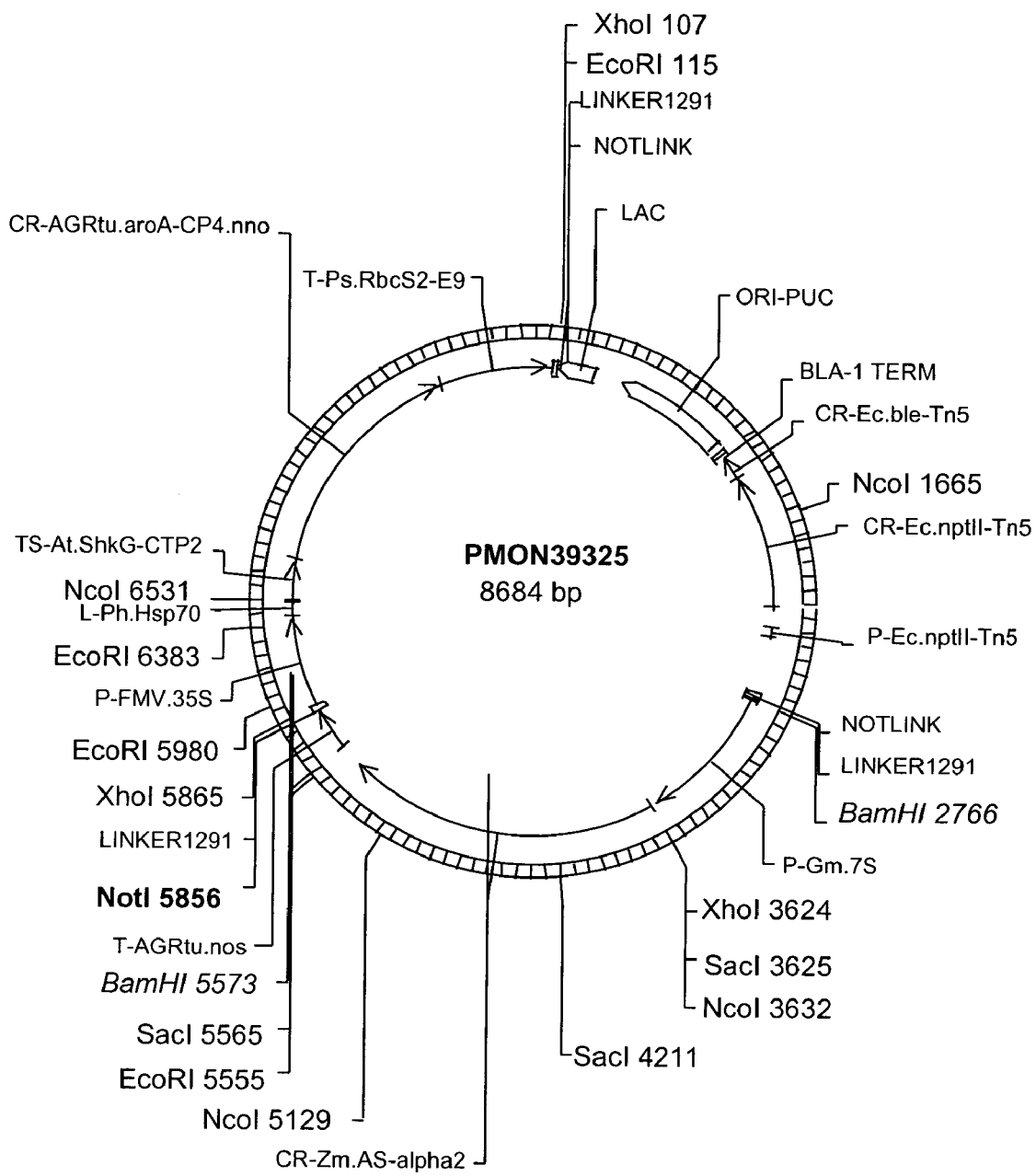
FIG. 8 is a restriction map of plasmid pMON39325.

This pMON39324, a maize 7S promoter-maize ASα-NOS 3' UTR cassette, was subsequently digested with BamHI resulting in a 2.84 Kb DNA fragment, containing the 7S promoter and maize ASα coding sequence. The plasmid pMON39322 was digested with BamHI resulting in a 5.88 kb DNA fragment. These two fragments were then ligated together to create pMON39325 (FIG. 8), a transformation vector containing 7S promoter-maize ASα-NOS 3' UTR cassette subcloned into pMON39322.

Using similar procedures, the coding sequence for a maize anthranilate synthase α-subunit was cloned downstream from the USP promoter to generate a pMON58130 expression vector, downstream from the Arc5 promoter to generate a pMON69662 expression vector, downstream from the Lea9 promoter to generate a pMON69650 expression vector, and downstream from the Per1 promoter to generate a pMON69651 expression vector. A list with these expression vectors is presented in Table E.

TABLE E

C28-Maize Anthranilate Synthase Constructs

| Seed Generation | Expression Cassette | Vector Name |
|---|---|---|
| R4 | 7Sa'-maize ASα | PMON39325 |
| R2 | Napin-maize ASα | PMON58023 |
| R1 | USP-maize ASα | PMON58130 |
| R1 | Arc5-maize ASα | PMON69662 |
| R1 | Lea9-maize ASα | PMON69650 |
| R1 | Per1-maize ASα | PMON69651 |

These vectors were used for plant transformation and propagation experiments. Soybean plants were transformed with the maize AS-containing vectors using the microprojectile bombardment technology as described herein. Several transgenic soybean lines were established for each type of vector and propagated through the number of generations indicated in Table E.

For example, three homozygous lines were established that carried the 7Sα'-maize AS transgene from pMON39325. These three lines were grown in a randomized block design in two different locations. Mature seed was produced and analyzed for free amino acid content. Controls were included to establish baseline trp levels, i.e. the three corresponding negative isolines and the nontransgenic controls.

Figure 9:
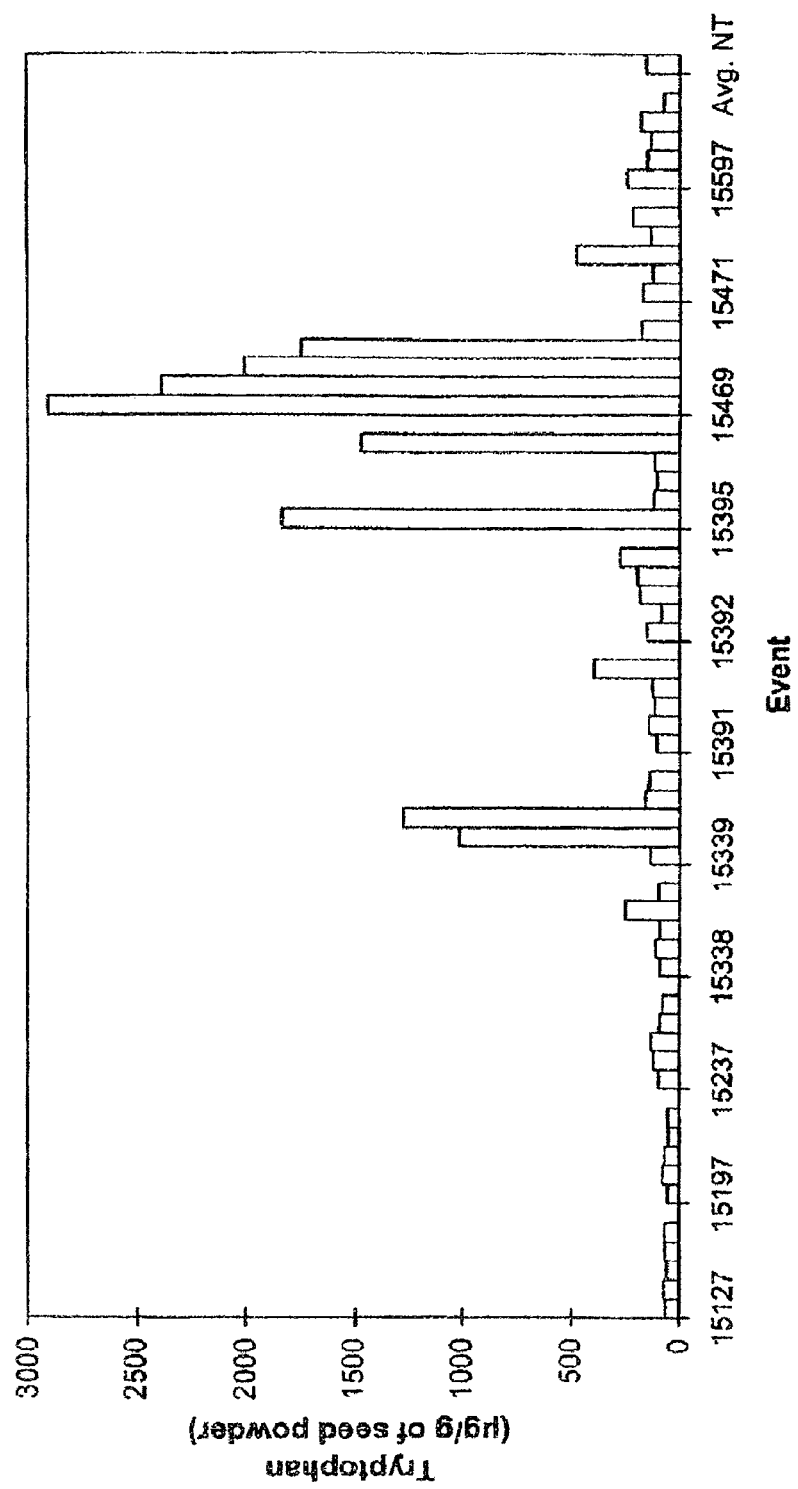
FIG. 9 is a graph depicting free tryptophan levels in soybean seeds transformed with pMON39325. There were five observations from each event. NT represents non-transgenic soybean seed.
Figure 11:
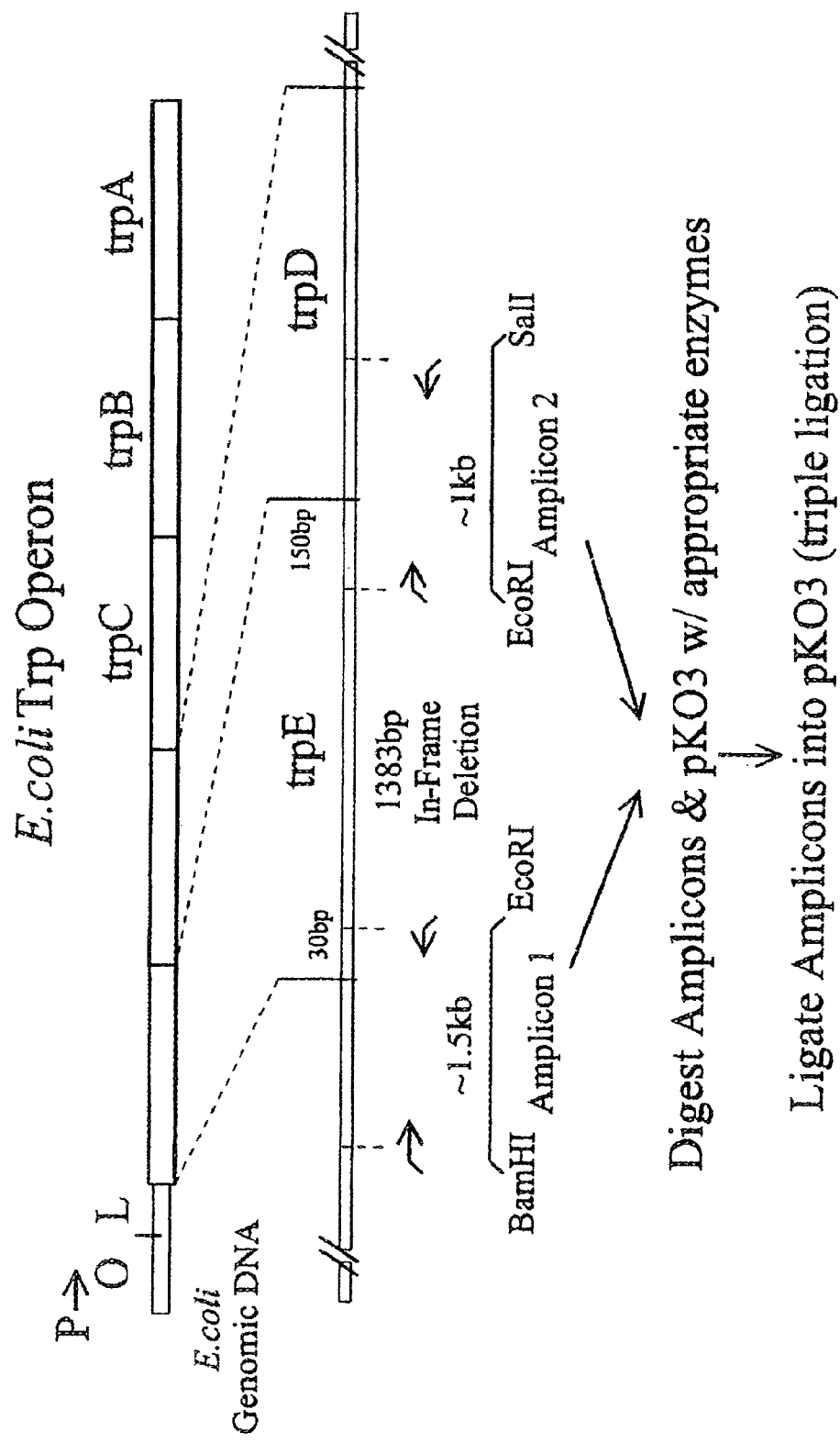
FIG. 11 schematically depicts construction of the in-frame deletion in the *E. coli* trpE gene.
Figure 14:
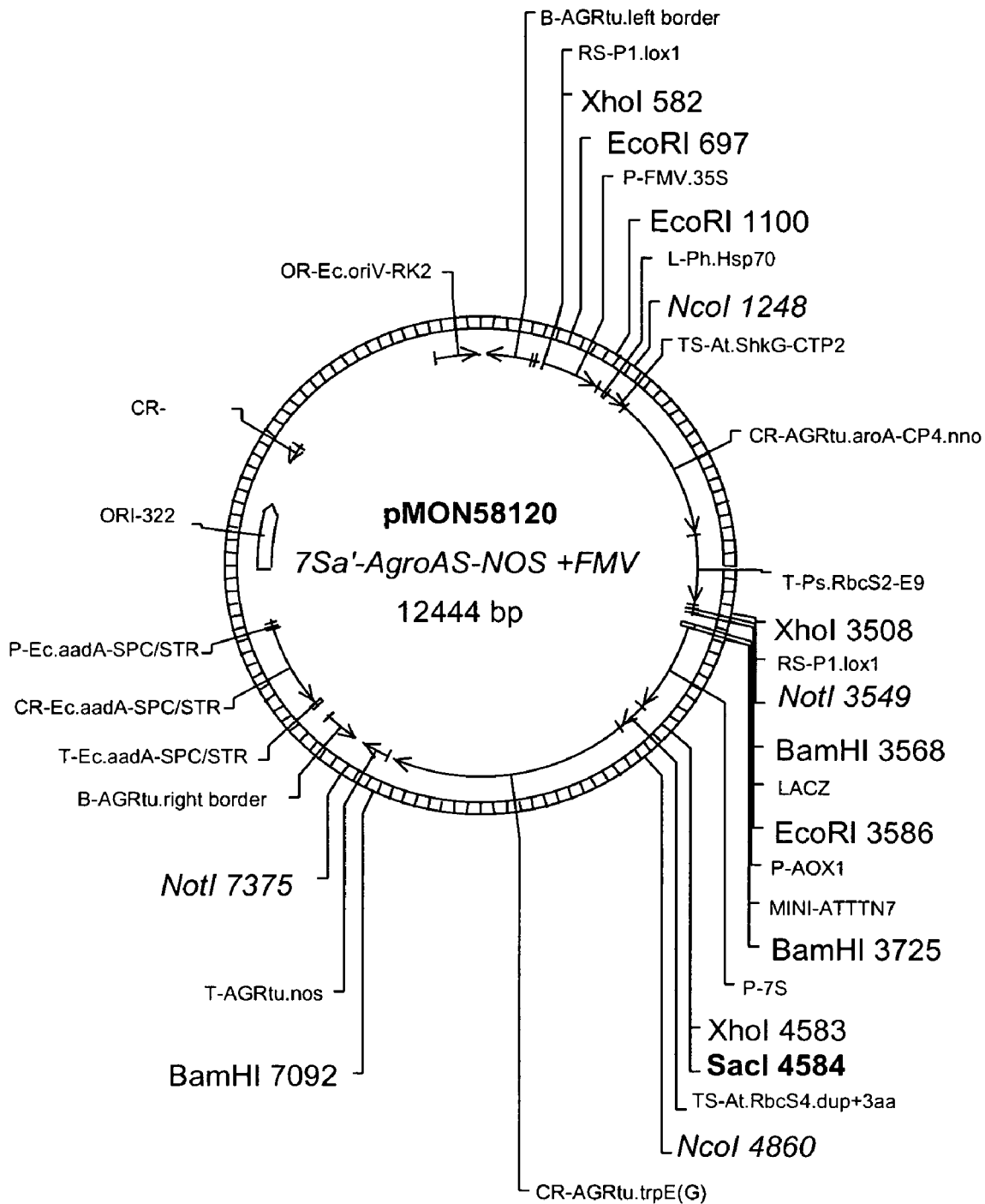
FIG. 14 is a restriction map of plasmid pMON58120.
Figure 18:
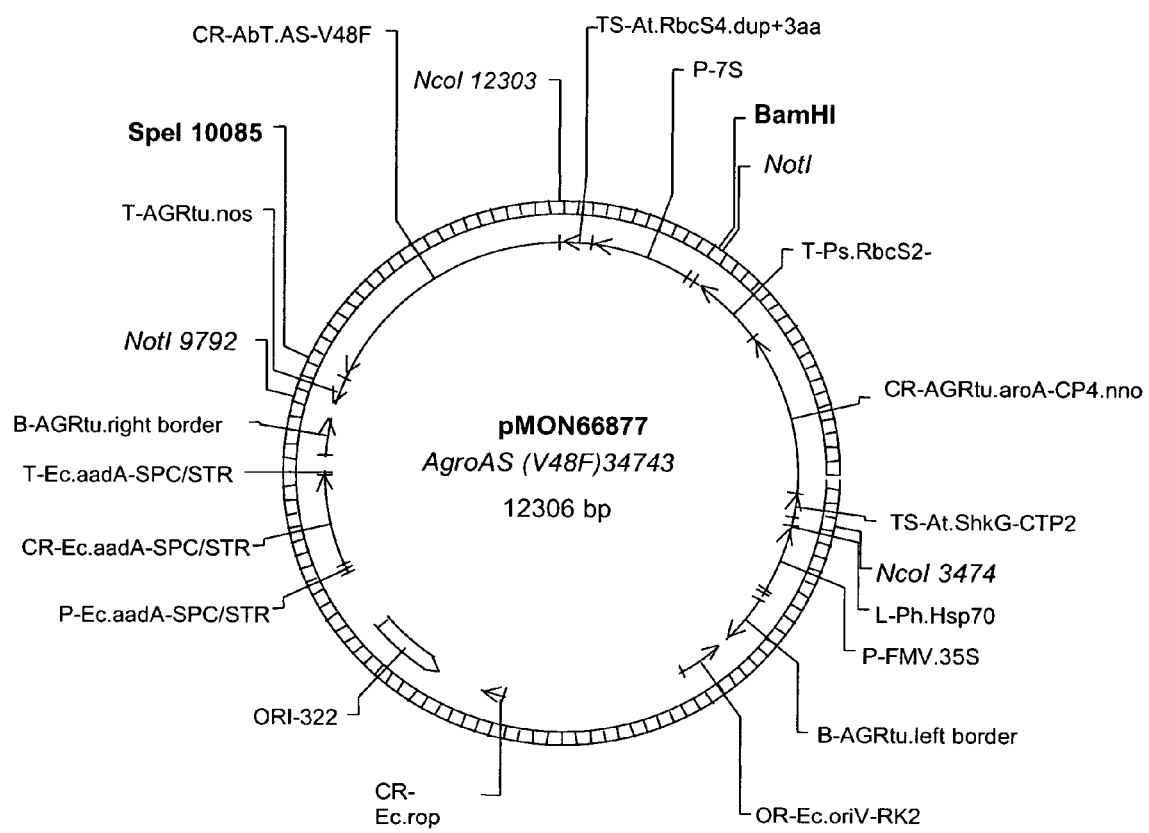
FIG. 18 is a restriction map of plasmid pMON66877.
Figure 19:
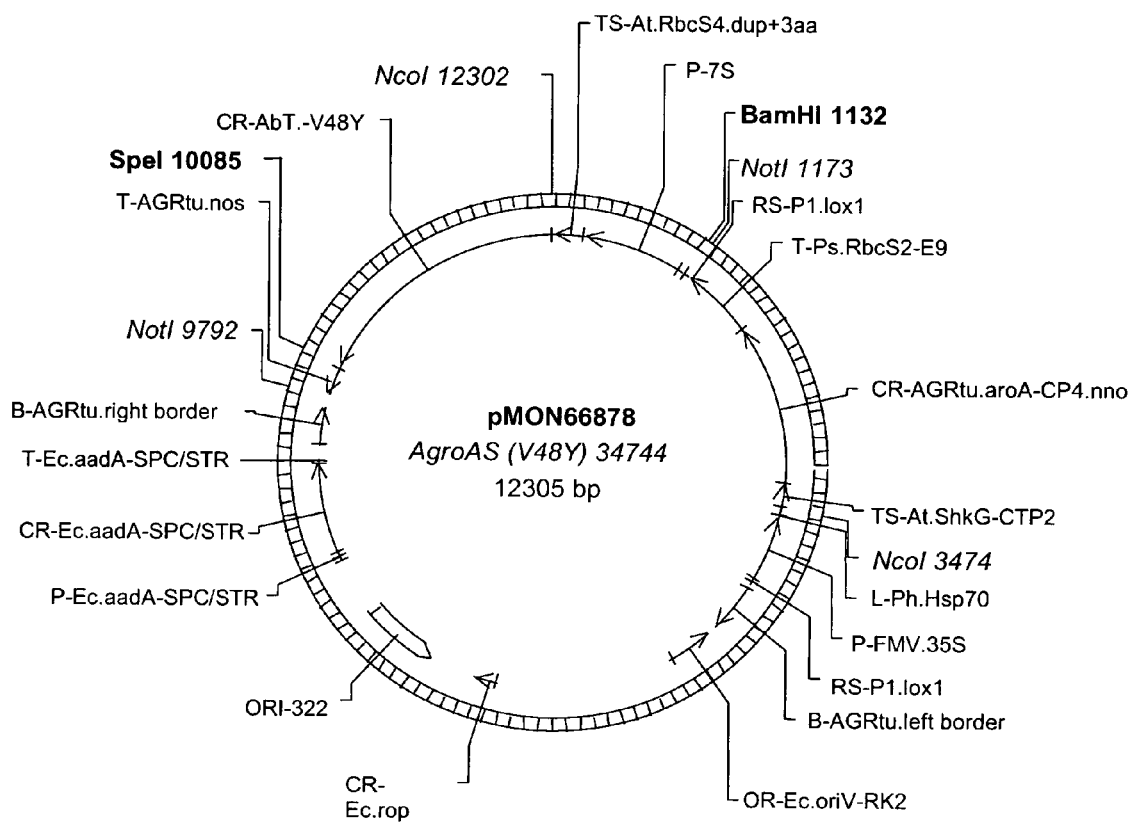
FIG. 19 is a restriction map of plasmid pMON66878.

Table F provides R4 seed tryptophan in ppm for pMON39325 transformant and control lines, showing that the average non-transgenic soybeans contain about 100-200 μg tryptophan/g seed powder whereas the pMON39325 transformants contain substantially more Trp. See also, FIG. 9.

TABLE F

Trp Levels in seeds of Soybean Plants Transformed with the C28 *Zea mays* mutant (pMON39325)

| Positive isoline number | Average trp of Positive Isoline (ppm) | Standard deviation | Average trp of corresponding Negative isoline (ppm) | Standard deviation |
| --- | --- | --- | --- | --- |
| 39325-1 | 3467 | 377 | 226 | 55 |
| 35325-2 | 2623 | 307 | 164 | 20 |
| 35325-3 | 3715 | 152 | 184 | 64 |
| 35325-4 | 2833 | 165 | 202 | 146 |
| 35325-5 | 3315 | 161 | 173 | 34 |
| 35325-6 | 2394 | 318 | 144 | 22 |
| nontransgenic control-7 | | | 191 | 24 |
| nontransgenic control-8 | | | 118 | 23 |

Five other constructs, expressing the C28 maize anthranilate synthase under the control of five different promoters (Table E) were transformed into soy and transgenic plants were obtained. Each construct generated events high in trp. An example illustrating events generated by Per1-C28 maize anthranilate synthase is shown in Tables G and H.

TABLE G

C28 maize AS Protein Expression Correlates with Increased Trp Levels in Three Transgenic Events bearing Per1-C28 maize AS (pMON69651)

| Pedigree | Trp average (ppm) | Protein present? |
| --- | --- | --- |
| Control | 96 | No |
| 22689 | 2375 | Yes |
| 22787 | 1707 | Yes |
| 22631 | 1116 | Yes |

Table H illustrates the enzymatic activity of C28 maize AS in R1 seeds from soybean plants transformed with the pMON69651 expression vector.

TABLE H

Specific Activity of C28 maize AS in R1 Seeds of pMON69651 Transformants

| Event | Seed number | Specific activity (pmoles/mg/min) | Specific activity (pmoles/mg/min) (+25 micromolar tryptophan) |
| --- | --- | --- | --- |
| Control | | 51.6 | 2.6 |
| 22689 | 22689-1 | 130.9 | 64.7 |
| | 22689-2 | 115.3 | |
| | 22689-3 | 148.5 | 61.1 |
| | 22689-4 | 149.5 | |
| | 22698-5 | 133.8 | 60.3 |

These results indicate that there is a substantial increase in tryptophan when soybean plant tissues are transformed with the C28 maize AS gene.

The high trp levels shown in Table G correlate with the presence of the AS protein and with increased specific activity (2.5 fold higher than in nontransgenic controls) for the transgenic enzyme (Table H). As shown in Table H—and as predicted by the biochemical properties of the C28 maize AS enzyme—the specific activity of transgenic events is tryptophan-resistant.

Example 4

Rational Design of *Agrobacterium tumefaciens* Anthranilate Synthase Tryptophan Feedback Insensitive Mutants This example describes vectors containing mutant *Agrobacterium tumefaciens* anthranilate synthase enzymes that have various degrees of sensitivity or insensitivity to feedback inhibition by tryptophan or tryptophan analogs.

Generation of *Agrobacterium tumefaciens* Mutant Anthranilate Synthase Genes

Using protein structural information from *Solfolobus solfataricus* anthranilate synthase as a guide (Knochel et al., 1999) several *Agrobacterium tumefaciens* anthranilate synthase mutants were rationally designed utilizing protein informatics to confidently assign several residues involved in tryptophan binding. This was accomplished by alignment of the *Agrobacterium tumefaciens* anthranilate synthase gene with the anthranilate synthase amino acid sequence from *Sulfolobus solfataricus* (FIG. 3). The putative tryptophan binding and catalysis regions of the *Agrobacterium tumefaciens* were assigned by combining the knowledge of the structural information with the sequence homology. Residues in the binding pocket were identified as potential candidates for altering to provide resistance to feedback inhibition by tryptophan.

Based on the structural analysis of the *Sulfolobus solfataricus* anthranilate synthase enzyme, it suggested that amino acids E30, S31, I32, S42, V43, N204, P205, M209, F210, G221, and A373 were involved in tryptophan binding. Based on the pairwise alignment, $N_{204}$, P205, and F210 of *Sulfolobus solfataricus* were also conserved in the monomeric *Agrobacterium tumefaciens* anthranilate synthase as residues N292, P293, and F298 respectively.

However, due to multiple insertions and deletions, the N-terminal regions of the *Sulfolobus solfataricus* and *Agrobacterium tumefaciens* enzymes were highly divergent. For this reason, it was necessary to manually assign residues at the N-terminal region of the *Agrobacterium tumefaciens* anthranilate synthase involved in tryptophan regulation (FIG.

3). Structural analysis indicated that the motif "LLES" formed a β sheet in the tryptophan-binding pocket. This structure appeared to be highly conserved among the heterotetrameric enzymes. The known monomeric enzymes were then manually aligned to the *Sulfolobus solfataricus* sequence using the "LLES" motif as a landmark (FIG. 7). Based on this protein informatics analysis, amino acid residues V48, S50, S51, and N52 in *Agrobacterium tumefaciens* AS were also likely to be involved in tryptophan binding.

With the putative tryptophan binding residues assigned in the *Agrobacterium tumefaciens* monomeric enzyme, several distinct strategies were rationalized for reducing the sensitivity of the enzyme to tryptophan inhibition. These substitutions included for example, enlarging the tryptophan-binding pocket (F298A), narrowing the binding pocket (V48F, V48Y, S51F, S51C, N52F, F298W), increasing the polarity of the binding pocket (S50K), or distorting the shape of the binding pocket by changing the protein main chain conformation (P293A, P29G).

*A. tumefaciens* AS Site-Directed Mutagenesis

Site directed mutagenesis was used to generate ten single amino acid substitutions six sites. The mutations were introduced into the *Agrobacterium tumefaciens* AS in pMON34705 using the QuikChange™ Site-Directed Mutagenesis Kit (Stratagene, Cedar Creek, Tex.). The primers used for site directed mutagenesis were SEQ ID NOs: 9-42 (FIG. 4; F=forward, R=reverse). Each primer sequence is specific for alteration of the nucleic acid at a specific location in the sequence and thus changing the encoded codon to code for a new amino acid. For example, S51C designates a change from serine to cysteine at amino acid position 51 in the *Agrobacterium tumefaciens* AS peptide sequence.

Following mutagenesis the sequence of the entire gene was reconfirmed and the variants expressed and purified from *E. coli* as described below for the wild type enzyme. The resultant plasmids comprising mutant *Agrobacterium tumefaciens* AS are suitably cloned into a plasmid for overproduction of protein using the T7 expression system as described in Example 1.

*Agrobacterium tumefaciens* AS Protein Expression and Purification

*Agrobacterium tumefaciens* AS wild type and mutant enzymes were expressed in *E. coli* as described in Example 1. The purification of all the *Agrobacterium tumefaciens* AS enzymes, including wild type and mutants thereof, was performed at 4° C. The cells (approximate wet weight of 1 g) were suspended in 20 ml of purification buffer (50 mM potassium phosphate, pH 7.3, 10 mM MgCl₂, 10 mM 2-mercaptoethanol, 10% glycerol) and lysed by ultrasonication (Branson sonifier Cell Disruptor, W185). Supernatant was collected after centrifugation of the homogenate at 20,000×g for 15 min. The supernatant was subjected to ammonium sulfate fractionation (30 to 65% saturation). The precipitate was collected after centrifugation at 20,000×g for 15 min and dissolved in 3 ml of the purification buffer and then loaded as a whole on an Econo-Pac 10DG desalting column, pre-equilibrated with the same buffer. Fractions containing the enzyme were detected by the developed assay and pooled. The pooled enzyme (4.3 mls) was loaded on a 10 ml DEAE Sephacel (Pharmacia Biotech) column (1.5×7.5 cm) equilibrated with the same buffer. The column was washed with 30 ml of the purification buffer and the enzyme was eluted with 30 ml of 50 mM NaCl in the same buffer. Fractions containing high AS activity were pooled and precipitated by 65% ammonium sulfate saturation and isolated and desalted as above. Fractions containing the enzyme were pooled and stored at −80° C.

Anthranilate Synthase Enzyme Assay and Kinetic Analysis

The standard assay for *Agrobacterium tumefaciens* AS was performed at 25° C. in an assay buffer containing 100 mM potassium phosphate, pH 7.0, 10 mM MgCl₂, 1 mM dithiothreitol, 200 µM chorismate and 10 mM L-glutamine. The reaction was started by adding 30 µl of enzyme to the reaction mixture and mixing. The formation of anthranilate was directly monitored by the absorbance increase at 320 m for 3 minutes. Initial rate of reaction was calculated as unit absorbance increase per second based on the slope of the absorbance change over the reaction time. $K_m$ for chorismate ($K_m^{Cho}$) was determined in the total volume of 1 ml assay buffer containing 100 mM potassium phosphate, pH 7.0, 10 mM MgCl₂, 1 mM dithiothreitol with 10 mM L-glutamine and varying the concentration of chorismate between 2.5-100 µM chorismate. The $K_m$ for glutamine ($K_m^{Gln}$) was determined in the total volume of 1 ml assay buffer containing 100 mM potassium phosphate, pH 7.0, 10 mM MgCl₂, 1 mM dithiothreitol with 200 µM chorismate and varying the concentration of L-glutamine between 0.1-2 mM L-glutamine. $IC_{50}$ for tryptophan ($IC_{50}^{Trp}$) was determined with in the total volume of 1 ml assay buffer containing 100 mM potassium phosphate, pH 7.0, 10 mM MgCl₂, 1 mM dithiothreitol, 10 mM L-glutamine, 200 µM chorismate and varying the concentration of L-tryptophan between 0.1-10 mM L-tryptophan. Kinetic parameters and $IC_{50}$ of AS were calculated after fitting the data to a non-linear regression program (GraFit; Erithacus Software: Surrey, UK).

Several mutants demonstrated reduced sensitivity to tryptophan inhibition while still maintaining enzymatic activity comparable to the wild type enzyme (Table I). These results demonstrate that the extent of sensitivity to tryptophan inhibition can be decreased, for example, by mutating amino acids in the tryptophan-binding pocket of anthranilate synthase and by optimizing of the mutations demonstrating feedback insensitivity.

TABLE I

Anthranilate Synthase Activity and Effect of Tryptophan on *Agrobacterium tumefaciens* AS Mutants

| Mutation | Codon | $K_m^{Cho}$ (µM) | $K_m^{Gln}$ (mM) | $k_{cat}(s^{-1})$ | $k_{cat}/K_m^{Cho}$ (µM⁻¹s⁻¹) | $IC_{50}^{Trp}$ (µM) |
|---|---|---|---|---|---|---|
| WT | | 8.0 | 0.11 | 0.43 | 5.37 × 10⁻² | 5 |
| V48F | TTT | 4.5 | 0.08 | 0.24 | 5.33 × 10⁻² | 150 |
| V48Y | TAT | 4.2 | 0.10 | 0.18 | 4.28 × 10⁻² | 650 |
| S50K | AAG | 13 | 0.01 | 0.13 | 1.00 × 10⁻² | 0.1 |
| S51F | TTC | 10 | 0.06 | 0.08 | 0.80 × 10⁻² | >32,000 |
| S51C | TGC | 2.8 | 0.08 | 0.15 | 5.36 × 10⁻² | 1,500 |
| N52F | TTC | 5.5 | 0.04 | 0.21 | 3.82 × 10⁻² | 41 |
| P293A | GCG | 24 | 0.16 | 0.35 | 1.46 × 10⁻² | 14 |
| P293G | GGG | 33 | 0.07 | 0.48 | 1.45 × 10⁻² | 17 |
| F298A | GCC | 9.2 | 0.10 | 0.46 | 5.00 × 10⁻² | 5.5 |
| F298W | TGG | 18 | 0.14 | 0.44 | 2.44 × 10⁻² | 450 |

Example 5

Random Mutagenesis of *Agrobacterium tumefaciens* AS to Generate Tryptophan Feedback Insensitive Mutants In addition to the rational design approaches described in Example 4, other strategies to generate feedback insensitive mutants of anthranilate synthase include, but are not limited to, random mutagenesis. Random mutagenesis of the *Agrobacterium tumefaciens* AS, can be accomplished, for example, by chemical mutagenesis (isolated DNA or whole organism), error prone PCR, and DNA shuffling. This example describes the use of chemical mutagenesis followed by genetic selection. The genetic selection approach is also useful for selection of desirable mutants derived from other mutagenesis techniques.

Generation of *E. coli* Expression Plasmid Containing *A. tumefaciens* AS

The open reading frame from the *Agrobacterium tumefaciens* AS clone pMON61600 (SEQ ID NO: 1, described in Example 1) was amplified by PCR using primers that contain an Nco 1 site on the 5' end of the forward primer and an XbaI site on the 3' end of the reverse primer:

5'-CATCCCATGGATGGTAACGATCATT CAGGAT-3' (SEQ ID NO: 55); and

5'-GATGTCTAGAGACACTATAGAATACTCAAGC-3' (SEQ ID NO: 56).

The resulting PCR product was ligated into pMON25997, which had the bktB open reading frame (Slater et al., 1998) removed by digestion with BspH1 and Xba1 resulting in plasmid pMON62000. pMON62000 is the base plasmid used for mutagenesis and complementation of the tryptophan auxotroph (EMG2ΔtrpE).

Generation of an *E. coli* Tryptophan Auxotroph EMG2ΔtrpE

*E. coli* strain Ec-8 (EMG2ΔtrpE) was constructed using the suicide vector pKO3 to delete 1,383 base pairs from the chromosomal trpE gene of *E. coli* strain EMG2(K-12 wt F+) (*E. coli* Genetic Stock Center). Two amplicons from *E. coli* genomic DNA were PCR amplified. The first amplicon was approximately 1.5 kb and contained the first 30 bp of the trpE ORF at the 3' end. This amplicon contains a BamH1 site at the 5' end and an EcoR1 site at the 3' end. The second amplicon was approximately 1 kb and contained the last 150 bp of the trpE ORF at the 5' end. This amplicon contains an EcoR1 site at the 5' end and a Sal1 site at the 3' end. The two amplicons were digested with the appropriate enzymes and ligated together at the EcoR1 site to create an in-frame deletion of trpE. FIG. 10 shows the resulting sequence of the truncated gene (SEQ ID NO: 46). The trpE deletion amplicon was ligated into pKO3 at the BamH1 and Sal1 sites. Gene disruption was performed as described in Link et al. (1997).

Complementation of *E. coli* Tryptophan Auxotroph EMG2ΔtrpE with pMON62000

*E. coli* strain Ec-8 (EMG2ΔtrpE) was transformed with pMON62000 and plated on M9 minimal medium to determine if the deletion was complemented by the addition of pMON62000. A plasmid control (minus the *Agrobacterium tumefaciens* AS insert) and a strain control Ec-8 were also plated onto M9 minimal medium and onto M9 minimal medium with 40 μg/ml tryptophan. Growth of strain Ec-8 transformed with pMON62000 was observed on M9 without tryptophan, no growth of either of the controls was observed, indicating complementation of the trpE deletion in strain Ec-8 by pMON62000.

Hydroxylamine Mutagenesis of pMON62000 and Genetic Selection of Mutants

To generate mutants of anthranilate synthase, pMON62000 was mutated with the chemical mutagen hydroxylamine. The following ingredients were combined in an eppendorf tube: 20 μg pMON62000 plasmid DNA and 40 μl 2.5 M hydroxylamine, pH 6.0. The volume was brought to a volume of 200 μl with 0.1M $NaH_2PO_4$, pH6.0+5 mM EDTA, pH 6.0. The tube was incubated at 70° C. After 1.5 hours, 100%1 of reaction mixture was dialyzed on a nitrocellulose filter that was floating on approximately 500 ml $H_2O$. After 15 minutes, the DNA was concentrated using Qiagen PCR Purification Kit. After 3 hours, the remaining 100 μl of the reaction mixture was removed and purified in the same manner.

*E. coli* strain Ec-8 was then transformed by electroporation with 100 ng of pMON62000 that had been mutagenized for either 1.5 or 3 hours with hydroxylamine. Two transformation procedures were performed for each time point. Transformed cells were allowed to recover for 4 or 6 hours in SOC medium (20 g/L Bacto-Tryptone, 5 g/L Bacto Yeast Extract, 10 ml/L 1M NaCl, 2.5 ml/L 1M KCl, 18 g glucose).

Two 245 mm square bioassay plates were prepared containing M9 minimal medium, plus 2% agar, and 50 μg/ml 5-methyl-DL-tryptophan (5-MT). An aliquot of 900 μl of the 1.5 hour mutagenized transformation mixture was plated onto one 50 μg/ml 5-MT plate. The remaining 100 μl was plated onto the M9 control plate. The same procedure was performed for the transformation mixture containing the 3.0 hour mutagenized plasmid.

The plates were then incubated at 37° C. for approx. 2.5 days. Resistant colonies were isolated from the 5-MT plates and were streaked onto LB-kanamycin (50 μg/ml) plates to confirm the presence of the plasmid. All of the selected colonies grew on these plates. Individual colonies from each of the resistant clones were prepped in duplicate to isolate the plasmid. Restriction digests and PCR were performed and confirmed that all the clones contained the desired *Agrobacterium tumefaciens* AS insert.

The rescued plasmids were then transformed back into strain Ec-8. One colony from each transformation was purified by streaking onto new LB-Kanamycin plates. To confirm resistance to 5-MT, individual purified colonies were streaked onto plates containing M9 plus 50 μg/ml 5-MT and 2% agar, and then grown at 37° C. for 3 days. Resistance was confirmed for most of the clones. To determine if resistant mutants would remain resistant at an even higher concentration of 5-MT, they were plated onto M9 plus 300 μg/ml 5-MT and 2% Agar. Most clones demonstrated resistance at this high concentration also.

The plasmids from all of the resistant clones were isolated and sequenced on both strands. Some of the mutations from this experiment are diagrammed in Table J.

TABLE J

| | *A. tumefaciens* trpEG Sequence Variations in 5-MT Resistant Clones. | | | |
|---|---|---|---|---|
| Database Clone # | Original Clone # | Determined Sequence Variations | $K_m^{cho}$ (μM) | $IC_{50}^{trp}$ (μM) |
| Wt | | | 8.0 | 5.0 |
| Ec-12 | 1 | G4A Val2Ile | | |
| Ec-18 | 8 | C35T Thr12Ile | 15 | 2.5 |
| Ec-19 | 9 | C2068T Pro690Ser | 5.0 | 3.4 |
| Ec-20 | 11 | G1066A Glu356Lys & C1779T Ile593Ile | | |

As indicated by the data in Table J, several mutants had little effect on the $K_m^{cho}$ and $IC_{50}^{trp}$ of the mutant enzyme, indicating that these mutations are likely not the source of resistance to tryptophan feedback inhibition. For example, the mutation of C to T at nucleotide 35, which changes a threonine residue to isoleucine at amino acid position 12 (Thr12Ile), gives rise to a minor change in $K_m^{cho}$ and $IC_{50}^{trp}$ values. Similarly, a change of C to T at nucleotide position 2068, which changes a proline to a serine also gives rise to a minor change in $K_m^{cho}$ and $IC_{50}^{trp}$ values. These mutations may therefore, may be "silent" mutations that give rise to variant gene products having enzymatic properties like those of wild type.

Example 6

High Tryptophan Transgenic Soybean Plants

This example sets forth preparation of transgenic soybean plants having elevated tryptophan levels resulting from transformation with tryptophan feedback insensitive mutants of anthranilate synthase from *Agrobacterium tumefaciens*.

Vector Construction

Plasmid pMON34711, which harbors the anthranilate synthase clone from *Agrobacterium tumefaciens* containing the F298W mutation described in Example 4, was digested with restriction enzyme NotI. The ends of the resulting fragment were blunted and then digested with NcoI. The plasmid pMON13773 was then digested with restriction enzyme EcoRI, the ends blunted and then digested with NcoI. The resulting fragments were ligated resulting in plasmid pMON58044, which contained the AS gene under the control of the 7S promoter and NOS 3' UTR.

Plasmid pMON58044 was then cut with restriction enzymes BglII and NcoI and ligated with a fragment that was generated by digesting pMON53084 with BglII and NcoI. The resulting fragment was named pMON58045 and contained the sequence for the *Arabidopsis* SSU1A transit peptide.

Figure 5:
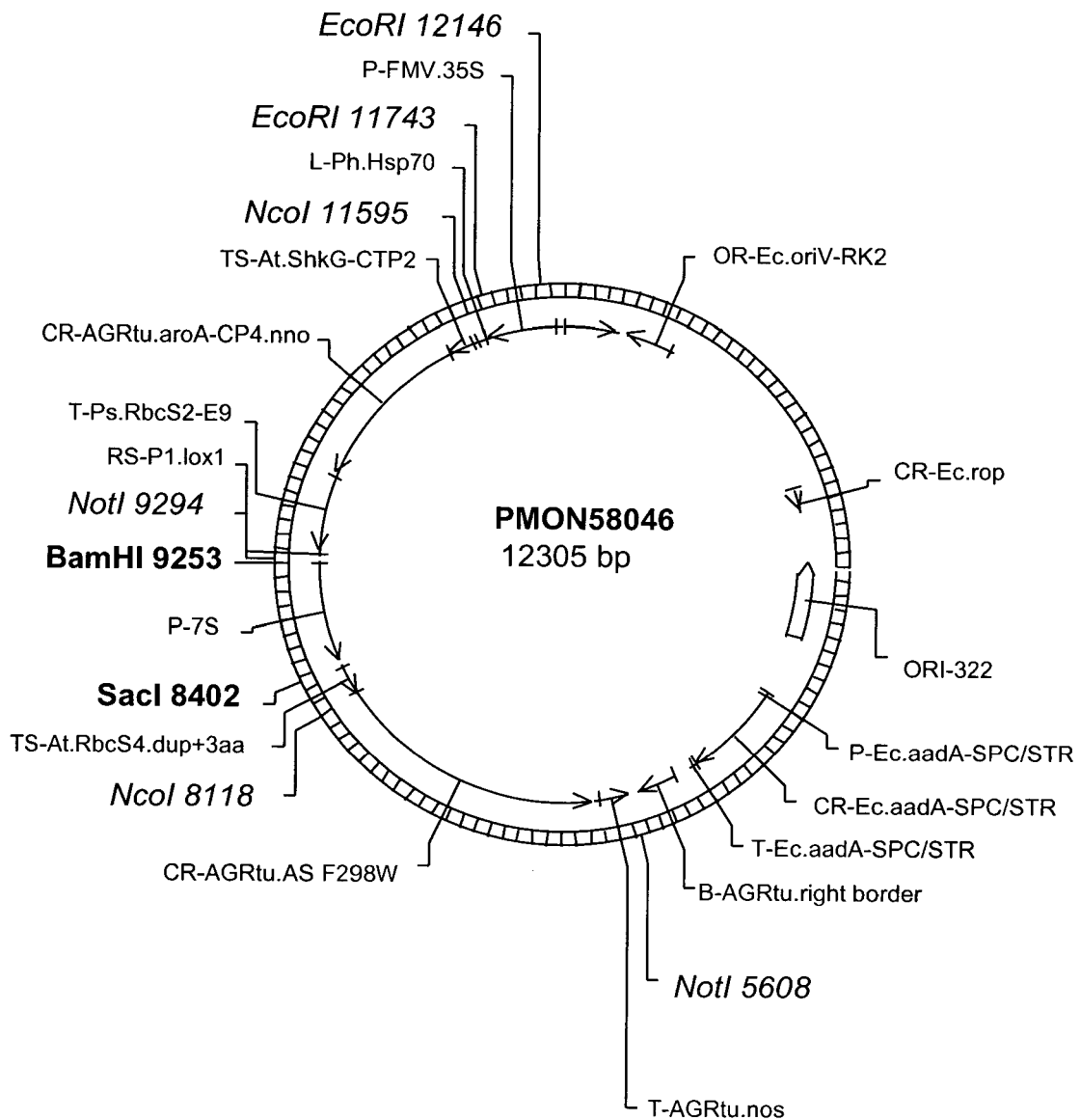
FIG. 5 depicts a restriction map of plasmid pMON58046.
Figure 6:
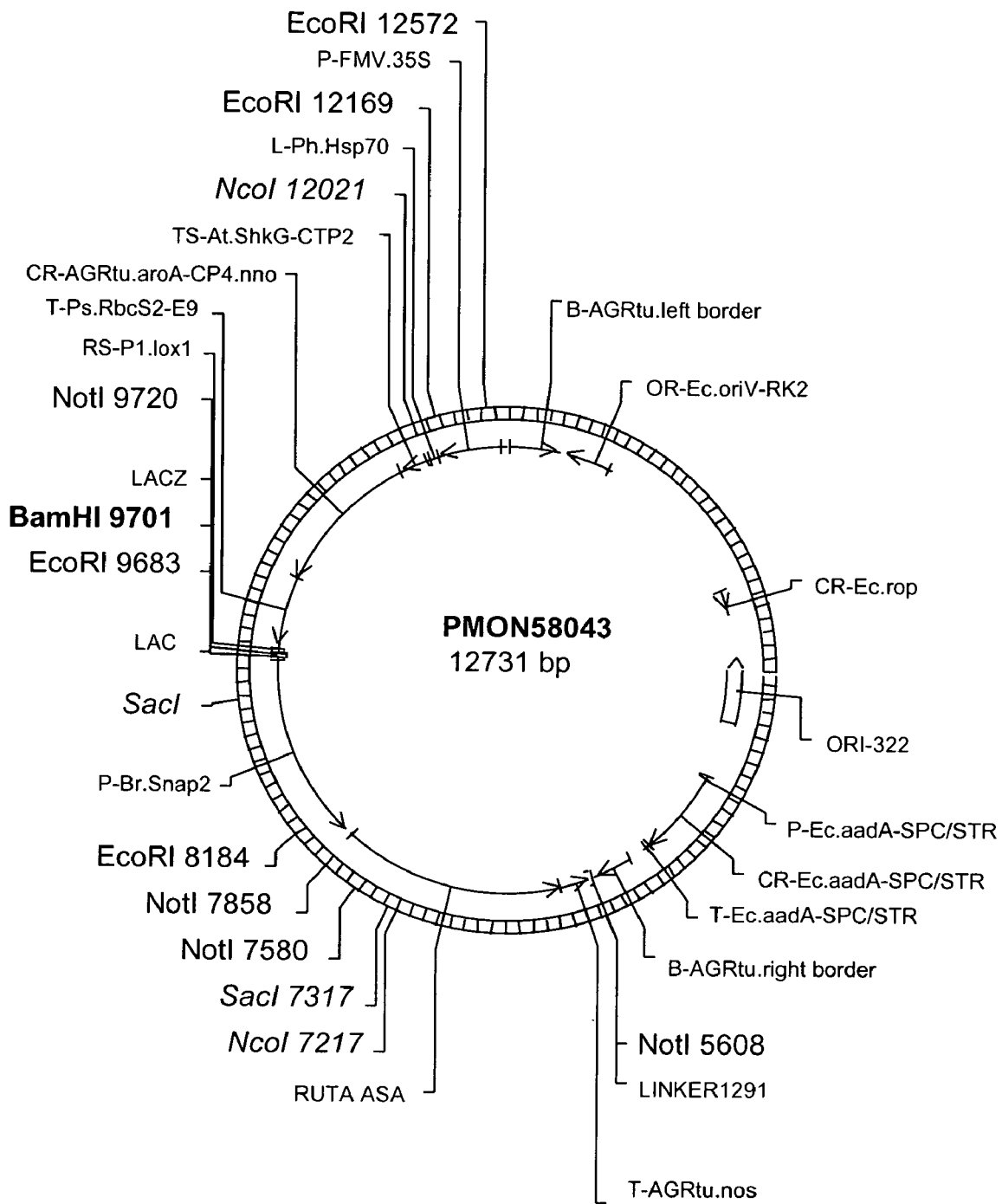
FIG. 6 depicts a restriction map of plasmid pMON58043.

Finally, plasmid pMON58046 (FIG. 5) was constructed by ligating the fragments generated by digesting pMON58045 and pMON38207 with restriction enzyme NotI. This resulted in the pMON58046 vector (FIG. 5) that was used for soybean transformation.

Soybean Transformation By Microprojectile Bombardment

For the particle bombardment transformation method, commercially available soybean seeds (i.e., Asgrow A3244, A4922) were germinated overnight for approximately 18-24 hours and the meristem explants were excised. The primary leaves were removed to expose the meristems and the explants were placed in targeting media with the meristems positioned perpendicular to the direction of the particle delivery.

The pMON58046 transformation vector described above was precipitated onto microscopic gold particles with $CaCl_2$ and spermidine and subsequently resuspended in ethanol. The suspension was coated onto a Mylar sheet that was then placed onto the electric discharge device. The particles were accelerated into the plant tissue by electric discharge at approximately 60% capacitance.

Following bombardment, the explants were placed in selection media (WPM+0.075 mM glyphosate) (WPM=Woody Plant Medium (McCown & Lloyd, 1981) minus BAP)) for 5-7 weeks to allow for selection and growth of transgenic shoots. Phenotype positive shoots were harvested approximately 5-7 weeks post-bombardment and placed into selective rooting media (BRM+0.025 mM glyphosate) (see, below for BRM recipe) for 2-3 weeks. Shoots producing roots were transferred to the greenhouse and potted in soil. Shoots that remained healthy on selection, but did not produce roots were transferred to non-selective rooting media (BRM without glyphosate) for an additional 2 weeks. The roots from any shoots that produced roots off the selection were tested for expression of the plant selectable marker before transferring to the greenhouse and potting in soil. Plants were maintained under standard greenhouse conditions until R1 seed harvest.

The recipe used for Bean Rooting Medium (BRM) is provided in Table K below.

TABLE K

Recipe for Bean Rooting Medium.

| Compound | Quantity for 4 L |
|---|---|
| MS Salts*** | 8.6 g |
| Myo-inositol(cell culture grade) | 0.40 g |
| SBRM Vitamin Stock** | 8.0 ml |
| L-Cysteine (10 mg/ml) | 40.0 ml |
| Sucrose (ultra pure) | 120 g |
| Adjust pH to 5.8 | |
| Washed Agar | 32 g |
| Additions after autoclaving: | |
| SBRM/TSG Hormone Stock* | 20.0 ml |

*SBRM/TSG Hormone Stock (per 1 L of BRM): 3.0 ml IAA (0.033 mg/ml), 2.0 ml sterile distilled water. Store stock in dark at 4° C..
**SBRM Vitamin Stock (per 1 L of stock): Glycine (1.0 g), Nicotinic Acid (0.25 g), Pyridoxine HCl (0.25 g), Thiamine HCl (0.25 g).
***3× MInor MS Salts (per 1 L stock): $H_2BO_3$ (1.86 g), $MnSO_4$ (5.07 g), $ZnSO_4$—$H_2O$ (2.58 g), KI (0.249 g), 7.5 ul NaMoO—$2H_2O$ (1.0 mg/ml), 7.5 ul $CoSO_4$—$5H_2O$ (1.0 mg/ml), 7.5 ul $CoCl_2$—$6H_2O$ (1.0 mg/ml).

One ingredient at a time was added and dissolved, the volume was brought to one liter with sterile distilled water, and the solution was stored in a foil-covered bottle in the refrigerator for no longer than one month.

Soybean Transformation Using *Agrobacterium tumefaciens*

For the *Agrobacterium* transformation method, commercially available soybean seeds (Asgrow A3244, A4922) were germinated overnight (approximately 10-12 hours) and the meristem explants were excised. The primary leaves may or may not have been removed to expose the meristems and the explants were placed in a wounding vessel.

*Agrobacterium* strain ABI containing the plasmid of interest was grown to log phase. Cells were harvested by centrifugation and resuspended in inoculation media containing inducers. Soybean explants and the induced *Agrobacterium* culture were mixed no later than 14 hours from the time of initiation of seed germination and wounded using sonication.

Following wounding, explants were incubated in *Agrobacterium* for a period of approximately one hour. Following this inoculation step, the *Agrobacterium* was removed by pipetting and the explants were placed in co-culture for 2-4 days. At this point, they were transferred to selection media (WPM+0.075 mM glyphosate+antibiotics to control *Agrobacterium* overgrowth) for 5-7 weeks to allow selection and growth of transgenic shoots.

Phenotype positive shoots were harvested approximately 5-7 weeks post-bombardment and placed into selective rooting media (BRM+0.025 mM glyphosate) for 2-3 weeks. Shoots producing roots were transferred to the greenhouse and potted in soil. Shoots that remained healthy on selection, but did not produce roots were transferred to non-selective rooting media (BRM without glyphosate) for an additional 2 weeks. The roots from any shoots that produced roots off the selection were tested for expression of the plant selectable marker glyphosate resistance before transferring to the greenhouse and potting in soil. Plants were maintained under standard greenhouse conditions until R1 seed harvest.

Analysis of Amino Acid Content of R1 Seed

Mature R1 seed is produced and analyzed for free amino acid content using fluorescence detection as described in Agilent Technologies Technical Bulletin REV14. Five seeds are chosen for single seed analysis from each event. Soy seeds expressing AgroAS F298W, AgroAS S51F, AgroAS V48F, AgroAS V48Y or AgroAS S51C mutant proteins generate very high amounts of tryptophan. The highest levels of tryptophan have a negative impact on germination. Results are shown in Tables, L, M and N.

TABLE L

Protein expression in Seeds Transformed with pMON58046

| Pedigree | Trp average (ppm) | Protein present? |
|---|---|---|
| Control | 96 | no |
| 22817 | 9922 | yes |
| 22891 | 12955 | yes |
| 23026 | 7968 | yes |

TABLE M

AS Protein expression Correlated with pMON58123 Transformation

| Pedigree | Trp average (ppm) | Protein present? |
|---|---|---|
| Control | 96 | No |
| 23562 | 88 | No |
| 23590 | 8795 | Yes |
| 23911 | 388 | No |

TABLE N

Average and max trp levels in soybeans carrying one of the following AgroAS alleles: V48F (pMON66877), V48Y (pMON66878) and S51C (pMON66879).

| PMON number | Description | Event number | Average of trp (ppm) | Max of trp (ppm) |
|---|---|---|---|---|
| 66877 | 7Salpha-V48F AgroAS | 26640 | 12,283 | 28,762 |
| 66877 | 7Salpha-V48F AgroAS | 26641 | 5,588 | 14,579 |
| 66877 | 7Salpha-V48F AgroAS | 26642 | 11,833 | 18,712 |
| 66878 | 7Salpha-V48Y AgroAS | 26872 | 6,015 | 11,902 |
| 66878 | 7Salpha-V48Y AgroAS | 26875 | 12,361 | 17,181 |
| 66878 | 7Salpha-V48Y AgroAS | 27010 | 13,962 | 19,323 |
| 66879 | 7Salpha-S51C AgroAS | 27105 | 12,614 | 31,827 |
| 66879 | 7Salpha-S51C AgroAS | 27300 | 16,711 | 34,263 |
| 66879 | 7Salpha-S51C AgroAS | 27568 | 10,135 | 20,237 |

AS Enzyme Activity in R1 Seed Transformed with AgroAS

Mature R1 seed is produced and analyzed for anthranilate synthase activity. Anthranilate synthase enzymatic activity was determined in R1 soy seeds carrying the AgroAS F298W (SEQ ID NOs: 65 or 91) or the AgroAS S51F (SEQ ID NOs: 60 or 86) mutant alleles. Very high levels of tryptophan-resistant anthranilate synthase activity was observed, consistent with the high amounts of tryptophan generated by these seeds. Results are shown in Tables O and P.

TABLE O

Specific activity of AS in R1 Seeds Transformed with pMON58046

| Event | Seed number | Specific activity (pmoles/mg/min) | Specific activity (pmoles/mg/min) (+25 micromolar Trp) |
|---|---|---|---|
| Control | | 77.6 | |
| 23076 | 23076-1 | 100.5 | 1.04 |

TABLE O-continued

Specific activity of AS in R1 Seeds Transformed with pMON58046

| Event | Seed number | Specific activity (pmoles/mg/min) | Specific activity (pmoles/mg/min) (+25 micromolar Trp) |
|---|---|---|---|
| | 23076-2 | 4512.8 | |
| | 23076-3 | 9737.4 | 9290.4 |
| | 23076-4 | 136.12 | |
| | 23076-5 | 8992.5 | 9749.9 |

TABLE P

Specific activity of AS in R1 Seeds Transformed with pMON58123

| Event | Seed number | Specific activity (pmoles/mg/min) | Specific activity (pmoles/mg/min) (+25 micromolar Trp) |
|---|---|---|---|
| Control | | 83.7 | 32.7 |
| 23590 | 23590-1 | 891 | 692.3 |
| | 23590-2 | 466.2 | 186.5 |
| | 23590-3 | 71.7 | 38.3 |
| | 23590-4 | 320.5 | 316.2 |

Example 7

Preparation of Transformation Vector Comprising *Ruta graveolens* Anthranilate Synthase α-Subunit The anthranilate synthase α gene from *Ruta graveolens* (Genbank Accession No. GI 960291) provides another anthranilate synthase domain useful in the present invention (Bohlmann, 1996). One isoenzyme of anthranilate synthase present in the genome of *Ruta graveolens* demonstrates less susceptibility to feedback inhibition by L-tryptophan. This allele may also be useful in the present invention to elevate the levels of free L-tryptophan in transgenic plants. The vector pMON58030 contains the *Ruta graveolens* anthranilate synthase α-subunit that is less sensitive to tryptophan inhibition. The *Ruta graveolens* anthranilate synthase a gene was PCR amplified from pMON58030 to provide a BamHI site at the 5' end and a BglII site at the 3' end of the *Ruta graveolens* anthranilate synthase a gene fragment by utilizing PCR primers that contained these two restriction enzyme sites:

```
5'-CAAAAGCTGGATCCCCACC-3';         (SEQ ID NO: 53)
and

5'-CCTATCCGAGATCTCTCAACTCC-3'.     (SEQ ID NO: 54)
```

The PCR fragment was purified, digested with the respective restriction enzymes, to form pMON58041, which contains the transcriptional fusion of the *Ruta graveolens* ASα to the napin promoter. The *Agrobacterium* mediated plant transformation plasmid, pMON58043, was created comprising the napin promoter, *Ruta graveolens* AS, NOS terminator, glyphosate resistance (CP4) selectable marker and borders suitable for proper chromosomal integration of the cassette as described. The resulting plant transformation vector was used to transform plants using standard plant transformation techniques as described in Examples 2, 3, and 6.

Example 8

Transforming Multi-Polypeptide Anthranilate Synthases into Monomeric Single Polypeptide Anthranilate Synthases Generation of a monomeric anthranilate synthase by fusion of selected multi-subunit enzymes is desirable, for example, to maximize the catalytic efficiency, to stabilize the enzyme, to achieve coordinated expression, for example, of subunits comprising activities of TrpE and TrpG and for effective communication between the two subunits. In some instances, it may be useful to employ TrpE or α-subunits from either plant or microbial source that are deregulated with respect to feedback inhibition by standard mutagenesis techniques or by rational design as described in the foregoing Examples, e.g. in Example 4. In other instances, wild type TrpE or α-subunits from either plant or microbial source are employed.

The C-terminus of the selected TrpE or α-subunit is linked to the N-terminus of the TrpG subunit or β-subunit, preferably with a peptide linker. A linker can be rationally designed to provide suitable spacing and flexibility for both subunits to properly align. Alternatively a linker can be identified by sequence alignment of monomeric and heterotetrameric anthranilate synthases. Examples of sequence alignments of monomeric and heterotetrameric anthranilate synthase forms are shown in FIGS. 7 and 15. It is also envisioned that it may be necessary to generate monomeric anthranilate synthases comprising heterologous subunit in order to maximize the benefits. For example, an α-subunit may be obtained from a bacterial source, for example, *E. coli* and fused to a β-subunit from a plant source, for example, *Arabidopsis*.

The novel protein produced can be introduced into plants, for example, as described in Examples 2, 3, or 6. The present invention is not limited to the exact details shown and described, for it should be understood that many variations and modifications may be made while remaining within the spirit and scope of the present invention defined by the claims.

Example 9

Identification of Anthranilate Synthases from Genomic Sequence Databases

Monomeric anthranilate synthases as well as α and β domains useful in the invention can be identified by bioinformatics analysis by searching for example, genbank and/or swissprot databases using BLAST (www.ncbi.nlm.nih.gov/blast/). Useful query sequences to identify monomeric anthranilate synthase include, for example, domains of anthranilate synthase such as the α-domain (GI 1004323) or β-domain (GI 1004324) from *Sulfolobus solfataricus*, or monomeric anthranilate synthase such as *Agrobacterium tumefaciens* AS (GI 15889565). Putative monomeric anthranilate synthase will have between 50% and 100% homology with the query sequence and should minimally contain 700 amino acids. If the AS-α-domain is used to query the genomic database, in addition to identifying putative anthranilate synthase genes it is also likely to identify genes involved in PABA synthesis for example 4-amino-4-deoxychorismate (ADC) synthase. The monomeric ADC synthase genes can be easily identified away from putative monomeric AS genes based on the observation that the amidotransferase domain (β-domain) of ADC synthase resides at the N-terminus of the protein whereas the amidotransferase domain (β-domain) of AS resides at the C-terminus. Monomeric anthranilate synthases useful in the present invention identified by bioinformatics analysis include, but are not limited to, for example, *Rhizobium meliloti* (GI 95177), *Mesorhizobium loti* (GI 13472468), *Brucella melitensis* (GI 17982357), *Nostoc* sp. PCC7120 (GI 17227910, GI 17230725), *Azospirillum brasilense* (GI 1174156), *Rhodopseudomonas palustris, Anabaena* M22983 (GI 152445). FIG. 7 is an example of a sequence alignment of 2 monomeric anthranilate synthases (*Agrobacterium tumefaciens* and *Rhizobium meliloti*) with 2 heterotetrameric anthranilate synthases (*Sulfolobus solfataricus* and *Arabidopsis thaliana*) useful in the present invention. FIG. 15 is an example of a sequence alignment of several monomeric anthranilate synthases with the *Rhodopseudomonas palustris* heterotetrameric anthranilate synthase.

Example 10

Optimized Codon Usage

This example sets forth a method of providing an increased level of free tryptophan in the seed of a plant by improving the expression of an anthranilate synthase gene by optimization of the codon usage.

The AgroAS S51F mutant allele described in Example 4 was used to generate a codon-optimized AgroAS S51C mutant allele according to the following procedure:

1. The amino acid sequence of the AgroAS S51F allele (SEQ ID NO: 60) was scanned using a monocot high codon usage table (Table P) along with some of the additional criteria described below to generate an optimized DNA sequence.
2. Codons were optimized by selecting codons 1-50 from the most abundant codons from the monocot high usage table (Table Q) and selecting codons 51-729 randomly from the table.
3. Undesirable sequences such as insert stops in the wrong frames were not used, even if it meant changing the codon usage.
4. Codon repeats were not used.
5. Rare codons in the first 50 positions were not used; and codons were randomized in other positions.
6. A+T-rich regions or those which may contain cryptic mRNA processing sites were avoided. Table R lists the sites which were avoided.
7. The output sequence was manually edited according to the monocot high codon usage table (Table Q) to increase the GC content from 56% to 59.86%, which is similar to the GC content of the native AgroAS wild type alleles (60.3%).
8. The resultant sequence was again scanned according to the method described in Flasinski, S., WO 2004/009761A2, using the SeqLab FINDPATTERNS program to eliminate any unwanted restriction sites or cryptic polyadenylation signals present in the coding region (Table R). Regions which were identified by this process were manually edited to eliminate such sites.
9. The final optimized DNA sequence (SEQ ID NO: 144; FIG. 22A-B) was assembled and analyzed for integrity by translation to the corresponding amino acid sequence (FIG. 26) and by comparing the nucleotide and amino acid sequences with the unmodified AgroAS S51F mutant allele (FIGS. 23A-C and 24A-B). The nucleotide and amino acid sequences have 82.9% and 100% identity to the nucleotide and amino acid sequences of the non-optimized AgroAS S51F mutant allele.

10. The codon-optimized AgroAS S51F DNA sequence was modified at codon 51 from TTC to TGC (nucleotides 151-153) to generate the AgroAS S51C codon-optimized mutant allele as described in U.S. patent application Ser. No. 10/430,011.

11. The DNA sequence of the codon-optimized AgroAS S51C allele (FIG. 25A-B; SEQ ID NO: 145) was synthesized (BlueHeron Biotechnology, Bothell, Wash.).

TABLE Q

Monocot high codon usage table.
Codon Usage Frequencies of Monocot_High

| | | | |
|---|---|---|---|
| G GGG 0.19 | A GCC 0.36 | T ACT 0.25 | S TCA 0.11 |
| G GGA 0.16 | R AGG 0.27 | T ACC 0.42 | S TCT 0.18 |
| G GGT 0.23 | R AGA 0.11 | W TGG 1.00 | S TCC 0.28 |
| G GGC 0.42 | S AGT 0.09 | * TGA 0.54 | R CGG 0.14 |
| E GAG 0.77 | S AGC 0.22 | C TGT 0.23 | R CGA 0.05 |
| E GAA 0.23 | K AAG 0.84 | C TGC 0.77 | R CGT 0.14 |
| D GAT 0.41 | K AAA 0.16 | * TAG 0.30 | R CGC 0.30 |
| D GAC 0.59 | N AAT 0.30 | * TAA 0.16 | Q CAG 0.78 |
| V GTG 0.36 | N AAC 0.70 | Y TAT 0.28 | Q CAA 0.22 |
| V GTA 0.05 | M ATG 1.00 | Y TAC 0.72 | H CAT 0.32 |
| V GTT 0.24 | I ATA 0.10 | L TTG 0.10 | H CAC 0.68 |
| V GTC 0.34 | I ATT 0.29 | L TTA 0.02 | L CTG 0.30 |
| A GCG 0.20 | I ATC 0.61 | F TTT 0.28 | L CTA 0.05 |
| A GCA 0.15 | T ACG 0.18 | F TTC 0.72 | L CTT 0.20 |
| A GCT 0.28 | T ACA 0.15 | S TCG 0.12 | L CTC 0.33 |
| | | | P CCG 0.24 |
| | | | P CCA 0.22 |
| | | | P CCT 0.26 |
| | | | P CCC 0.28 |

The numbers in Table Q are the probabilities of having a particular codon used to code a particular amino acid, which are based on observed frequencies of each codon for any particular amino acid. This means that if there are four codons that encode a given amino acid, and if all of the codons are represented equally in that sequence, then each codon will get a value of 0.25. The higher the value, the higher is the frequency with which a particular amino acid is encoded by a corresponding codon.

The use of codon high usage tables in the process of codon optimization is well known in the art. Due to the rate at which genomic information is becoming available on a daily basis, construction of such tables is a dynamic process. As such, the information contained in such tables regarding the frequency of usage of each codon will change with the currently prevailing knowledge for each particular species. With this in mind, the present invention contemplates the dynamic alteration in rates of usage of each codon in the monocot high codon usage table (Table P) which was used to design the artificial polynucleotide molecules encompassed herein.

TABLE R

List of unwanted restriction sites/mRNA splicing sites to be avoided when possible in the AgroAS (S51F) allele during the final scanning process using the SeqLab FINDPATTERN program. An example of a pattern data file for the program FINDPATTERNS in SeqLab.

| Name | Offset | Pattern |
|---|---|---|
| 1 | 1 | AATAAA |
| 2 | 1 | AACCAA |
| 3 | 1 | ATATAA |
| 4 | 1 | AATCAA |
| 5 | 1 | ATACTA |
| 6 | 1 | ATAAAA |
| 7 | 1 | ATGAAA |
| 8 | 1 | AAGCAT |

TABLE R-continued

List of unwanted restriction sites/mRNA splicing sites to be avoided when possible in the AgroAS (S51F) allele during the final scanning process using the SeqLab FINDPATTERN program. An example of a pattern data file for the program FINDPATTERNS in SeqLab.

| Name | Offset | Pattern |
|---|---|---|
| 9 | 1 | ATACAT |
| 10 | 1 | AAAATA |
| 11 | 1 | ATTAAA |
| 12 | 1 | AATTAA |
| 13 | 1 | AATACA |
| 14 | 1 | CATAAA |
| 15 | 1 | ATTAAT |
| 16 | 1 | ATTTA |
| 17 | 1 | GGATCC |
| 18 | 1 | TGATCA |
| 19 | 1 | AGATCT |
| 20 | 1 | CATTT |
| 21 | 1 | CATTTTGTAT |
| 22 | 1 | ATCGAT |
| 23 | 1 | ATAGATT |
| 24 | 1 | CTGAAG |
| 25 | 1 | GAATTC |
| 26 | 1 | GATATC |
| 27 | 1 | GGCGCC |
| 28 | 1 | TGCGCA |
| 29 | 1 | AAGCTT |
| 30 | 1 | GTTAAC |
| 31 | 1 | GGTACC |
| 31 | 1 | ACGCGT |
| 32 | 1 | CCATGG |
| 33 | 1 | CATATG |
| 34 | 1 | GCCGGC |
| 35 | 1 | GCTAGC |
| 36 | 1 | GCGGCCGC |
| 37 | 1 | TCGCGA |
| 38 | 1 | ATGCAT |
| 39 | 1 | TTAATTAA |
| 40 | 1 | TGTAT |
| 41 | 1 | ACATGT |
| 42 | 1 | CCANNNNNTGG |
| 43 | 1 | AATAAT |
| 44 | 1 | AACCAA |
| 45 | 1 | CTGCAG |
| 46 | 1 | CGATCG |
| 47 | 1 | CAGCTG |
| 48 | 1 | GAGCTC |
| 49 | 1 | CCGCGG |
| 50 | 1 | GTCGAC |
| 51 | 1 | AGTACT |
| 52 | 1 | CCCGGG |
| 53 | 1 | TACGTA |
| 54 | 1 | ACTAGT |
| 55 | 1 | GCATGC |
| 56 | 1 | AGGTAA |
| 57 | 1 | AGGTA |
| 58 | 1 | GGTAA |
| 59 | 1 | GCAGGT |
| 60 | 1 | GCAGG |
| 61 | 1 | CAGGT |
| 62 | 1 | AATATT |
| 63 | 1 | AGGCCT |
| 64 | 1 | TGGGTA |
| 65 | 1 | GACNNNGTC |
| 66 | 1 | ATTAAT |
| 67 | 1 | TCTAGA |
| 68 | 1 | CTCGAG |
| 69 | 1 | TTTTT |
| 70 | 1 | CCCC |
| 71 | 1 | GGGG |
| 72 | 1 | AAAAA |
| 73 | 1 | CCCCC |
| 74 | 1 | GGGGG |

Construction of Agro AS-S51C (pMON69770 & pMON68065) and Agro AS-S51C-nno (Non-Native Optimized Gene; pMON68066

Figure 20:
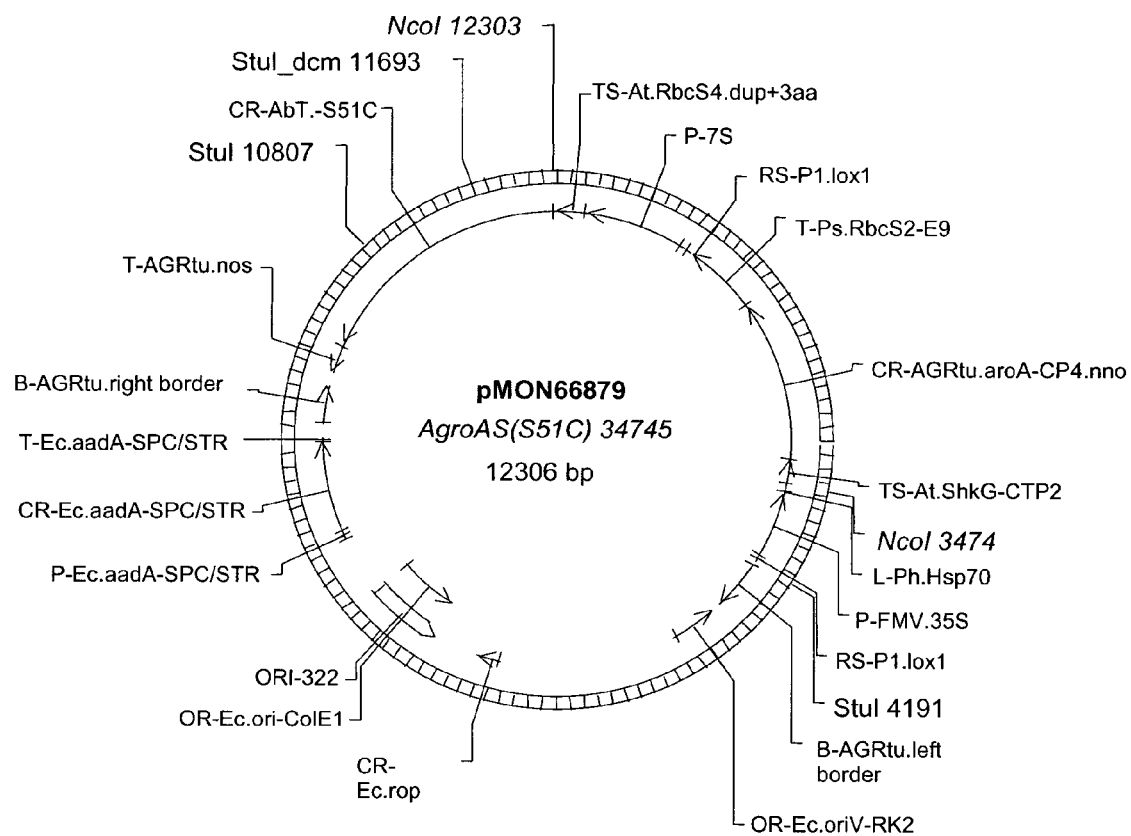
FIG. 20 is a restriction map of plasmid pMON66879.

A base vector, pMON66879 (FIG. 20), was constructed comprising two transcription units between the right and left borders from *Agrobacterium tumefaciens*. One transcription unit for a marker comprised:
  (a) DNA of FMV.35S promoter (promoter for the 35S RNA from Figwort mosaic virus)
  (b) DNA of L-Ph.Hsp70 (5'-untranslated region from *Petunia hybrida* heat shock protein 70 gene)
  (c) DNA of At.ShkF-CTP2 (targeting peptide of *Arabidopsis* EPSP (5-enol pyruvulshikimate-3-phosphate) synthase)
  (d) DNA of AGRtu.aroA-CP4 (coding region for non-naturally occurring aroA-CP4)

The other transcription unit for the *Agrobacterium tumefaciens* anthranilate synthase S51C (AgroAS-S51C)mutant allele comprised:
  (a) DNA of 7S promoter (7S alpha' promoter from soybean)
  (b) DNA of ATSSU1AMAT (*Arabidopsis thaliana* Ribulose bisphosphate carboxylase oxygenase (RUBISCO) small subunit chloroplast targeting peptide plus parts of the N-terminal region of mature protein)
  (c) DNA of AgroAS (S51C) mutant allele; and
  (d) DNA of *Agrobacterium tumefaciens* nopaline synthase (nos) terminator.

SEQ ID NO: 149 is the polynucleotide sequence of a transformation vector comprising the above-described marker and mutant allele transcription elements. See Table S below for a description of the elements of the transformation vector contained within SEQ ID NO: 149.

TABLE S

Elements in a Transformation Vector

| Bases of SEQ ID NO: 149 | Description of DNA segment |
| --- | --- |
| 1-474 | *A. tumefaciens* left border |
| 516-1067 | DNA of FMV.35S promoter |
| 1071-1166 | DNA of L-Ph.Hsp70 |
| 1176-1403 | DNA of At.ShkF-CTP2 |
| 1404-2771 | DNA of AGRtu.aroA-CP4 |
| 3524-4363 | DNA of 7S promoter |
| 4389-4652 | DNA of ATSSU1AMAT |
| 4653-6846 | DNA of *Agrobacterium tumefaciens* anthranilate synthase S51C mutant allele |
| 7233-7561 | *A. tumefaciens* right border |

Figure 27:
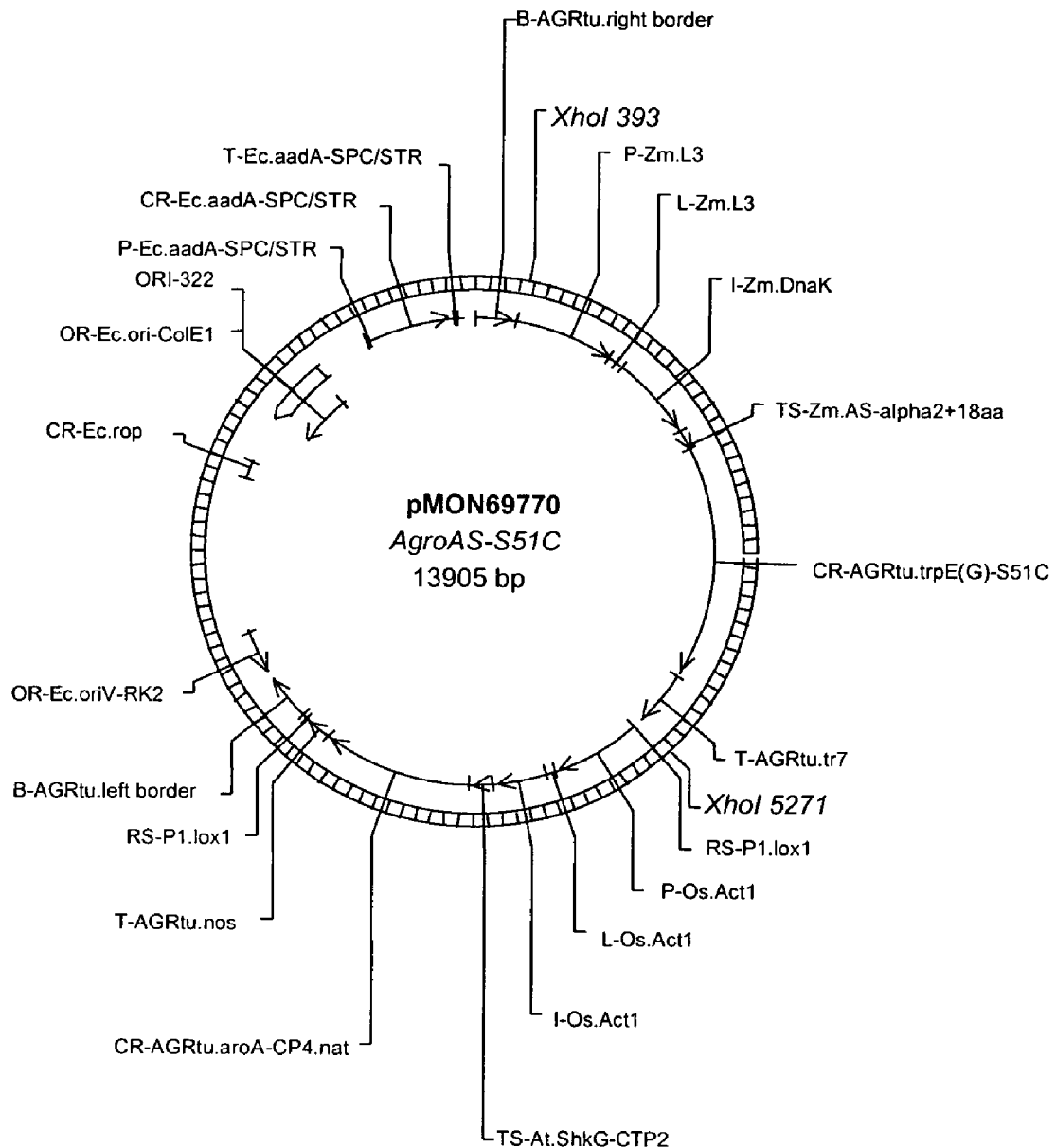
FIG. 27 is a restriction map of plasmid pMON69770.

The DNA of a vector with the elements listed in Table S, pMON66879 (FIG. 20), was digested with NcoI and StuI restriction enzymes, separated on 1 percent agarose gel, and the 1499 bp DNA fragment that represents part of the *Agrobacterium* anthranilate synthase S51C mutant allele (from nucleotide 1 to nucleotide 1498 of Seq ID 87) was cut out from the gel. The DNA fragment was purified using QIAGEN gel extraction kit (QIAGEN Inc.). pMON69754 was also cut with NcoI and StuI restriction enzymes and separated on 1 percent agarose gel. The 6286 bp fragment was cut out from the gel and the DNA fragment was purified using a QIAGEN gel extraction kit (QIAGEN Inc.). Ligation reactions were carried out by mixing the 6286 bp DNA fragment corresponding to pMON69754 DNA, and the 1499 bp DNA fragment corresponding to pMON66879 (FIG. 20), to generate pMON69769. The DNA of pMON69769 was digested with XhoI restriction enzyme, and the isolated 4893 bp fragment containing the *Zea mays* (Zm) oleosin promoter fused to the Zmhsp70 (heat shock protein 70; Zm.DNAK) intron, the AgroAS-S51C allele and the Tr7-3'UTR was cloned into the XhoI site of pMON78808 to make the final transformation vector pMON69770 (FIG. 27).

Construction of pMON68065

The DNA of pMON69769 was subjected to partial digestion by XhoI and BamHI restriction enzymes, separated on 1 percent agarose gel, and the 7238 bp DNA fragment comprising all of the genetic elements of pMON69769, except the Tr7-3'-untranslated region (3'-UTR) was isolated according to the procedures recited above.

The rice glutelin 1 (Os-gt1) 3'-UTR was amplified from pMON47901 DNA by PCR using the following primers:

```
5' primer (ACGCGGATCCGTTGGCAATGCGGATAAAGAATAAC;
          SEQ ID NO 150)

3' primer (TACGCTCGAGCCATAAGATAAGGGAGGGTTGTCC;
          SEQ ID NO:151)
```

Figure 28:
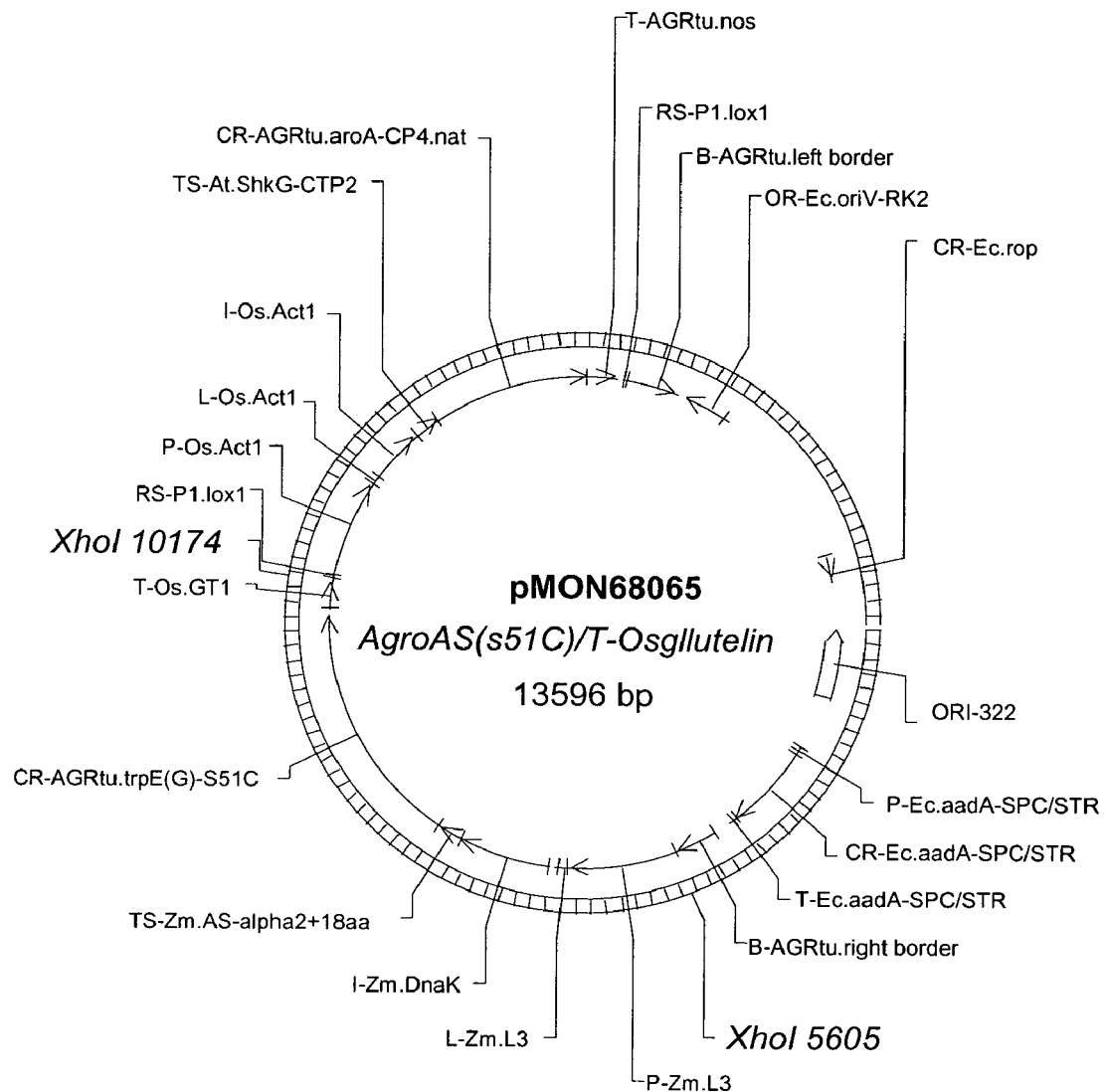
FIG. 28 is a restriction map of plasmid pMON68065.

The amplified DNA fragment was cut with XhoI and BamHI restriction enzymes, and was ligated with the 7238 bp fragment of pMON69769, to generate pMON68063.

pMON68063 was then digested with XhoI restriction enzyme, separated on 1 percent agarose gel, and the 4569 bp DNA fragment that corresponds to the *Zea mays* Oleosin promoter fused to the Zmhsp70 (Zm.DNAK) intron, the AgroAS-S51C allele and the Os-gt1-3'UTR was isolated from the gel.

pMON78808 DNA was also cut with XhoI restriction enzyme, dephosphorylated using alkaline phosphatase enzyme (New England BioLabs Inc.), and the DNA was purified using a QIAGEN PCR purification kit (QIAGEN Inc.). The XhoI-digested DNA of pMON78808 and the 4569 bp XhoI-digested DNA fragment of pMON68063 were ligated together to generate pMON68065 (FIG. 28).

Construction of pMON68066

Figure 29:
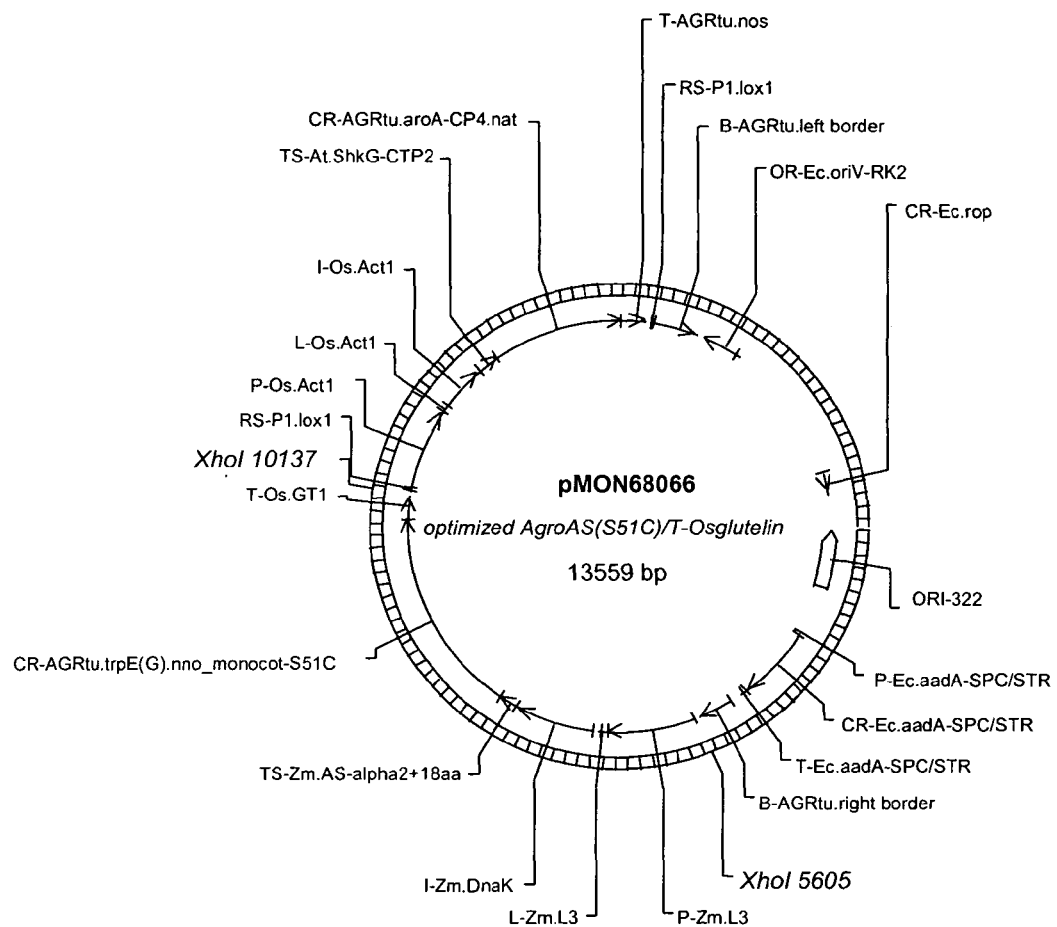
FIG. 29 is a restriction map of plasmid pMON68066.

Codon optimization of the AgroAS-S51C mutant allele was carried out as described above. Codon-optimized AgroAS-S51C-nno DNA was synthesized (Blue Heron Biotechnology Group, Bothell, Wash., USA). The synthetic DNA was then digested with NcoI and BamHI restriction enzymes, separated on 1 percent agarose gel, and the 2193 bp DNA fragment corresponding to AgroAS-S51C-nno was cut out from the gel and purified as described above. The DNA of pMON68063 was also cut with NcoI and BamHI restriction enzymes and separated on 1 percent agarose gel. The isolated 5244 bp NcoI/BamHI-digested DNA fragment contains all the genetic elements described in pMON68063 except the AgroAS-S51C mutant allele. Ligation reactions were carried out by mixing the DNA of the NcoI/BamHI-digested AgroAS-S51C-nno DNA (2193 bp fragment) and pMON68063 (5244 bp DNA fragment), to generate pMON68064. pMON68064 was then cut with XhoI restriction enzyme, separated on 1 percent agarose gel, and the 4532 bp DNA fragment that contains the *Zea mays* oleosin promoter fused to the hsp70 (Zm.DNAK) intron, the AgroAS-S51C-nno and the Os-gt1-3'UTR was purified as described above. The DNA of pMON78808 DNA was also cut with XhoI restriction enzyme, dephosphorylated using alkaline phosphatase enzyme (New England BioLabs Inc.), and purified using a QIAGEN PCR purification kit (QIAGEN Inc.). Ligation reactions were carried out by mixing the dephosphorylated XhoI-cut pMON78808 DNA and the 4532 bp DNA fragment of pMON68064, to generate pMON68066 (FIG. 29).

Transformation of Maize

PMON69770, pMON68065, and pMON68066 were transformed into an elite corn inbred (LH244) (Corn States Hybrid Serv., LLC, Des Moines, Iowa) essentially as described in U.S. Patent Application Publication 20050005327, which is herein incorporated in its entirety by reference. Briefly, ears containing immature embryos are harvested approximately 10 days after pollination and kept refrigerated at 4° C. until use (up to 5 days post-harvest). The preferred embryo size for this method of transformation is ~1.5-2.0 mm. This size is usually achieved 10 days after pollination inside the greenhouse with the growth conditions of an average temperature of 87° F., day length of 14 hours with supplemental lighting supplied by GE 1000 Watt High Pressure Sodium lamps.

Immature embryos are isolated from surface sterilized ears and directly dropped into the prepared Agrobacterium cell suspension in a 1.5-mL microcentrifuge tube. The isolation lasts continuously for approximately 5 to 60 minutes. Alternately, embryos are excised directly into inoculation medium (without Agrobacterium or acetosyringone) for 5-60 minutes and subsequently inoculated for 5-30 minutes with Agrobacterium cell suspension. After the Agrobacterium cell suspension is removed using a fine tipped sterile transfer pipette, the immature embryos are transferred onto a crn398 co-culture medium (Table T). The embryos are then placed on the medium with the scutellum side facing up. The embryos are cultured in a dark incubator (23° C.) for approximately 14-48 hours.

The embryos are then transferred onto a callus induction medium (crn336, Table T) which contains 0.1 mM glyphosate and 500 mg/L carbenicillin to inhibit Agrobacterium in Petri dishes (100 mm×25 mm). The cultures are incubated in a dark culture room/incubator at 30° C. for 2 weeks followed by an additional week in a dark culture room/incubator at 27° C. All the callus pieces are then transferred individually onto the first regeneration medium (crn335, Table T) which contains 0.1 mM glyphosate and 250 mg/L carbenicillin. The cultures are grown on this medium in a 27° C. culture room with 16 hours light/8 hours dark photoperiod for 7 to 10 days. They are then transferred onto the second regeneration medium (crn333, Table T) in Petri dishes (100 mm×25 mm) at 27° C. with 16 hours of light for approximately 2 to 3 weeks. All the callus pieces with regenerating shoots and living tissue are then transferred onto either fresh crn333 plates or crn334 phytatrays (Table T) or directly transferred to sundae cups containing a rooting medium (crn366, Table T) to grow further prior to being transferred to soil (approximately 1 to 3 weeks). The regeneration media (crn335, crn333 and crn334) all contain 250 mg/L carbenicillin and 0.1 mM glyphosate.

Plantlets are then transferred to soil, hardened off in a growth chamber at 27° C., 80% humidity, and low light intensity for approximately 1 to 2 weeks, and then transferred to a greenhouse and grown under standard greenhouse conditions. The resulting kernels are collected and analyzed as described below.

TABLE T

Composition of media used in corn transformation (per Liter).

| Component | Co-culture media (crn398) | Callus induction media (crn336) | First regeneration media (crn335) | Second regeneration media (crn333 (plates)/ crn334 (phytatrays)) | Rooting media (crn366) |
|---|---|---|---|---|---|
| MS salts | 2.17 g | 4.33 g | 4.33 g | 4.33 g | 2.17 g |
| Sucrose | 20 g | 30 g | 30 g | | 20 g |
| Maltose | | | | 20 g | |
| Glucose | 10 g | | | 10 g | |
| 1-Proline | 115 mg | 1.38 g | 1.38 g | | |
| Casamino Acids | | 0.5 g | 0.05 g | | |
| IBA (1 mg/mL stock) | | | | | 0.75 mL |
| 1-Asparagine | | | | 0.15 g | |
| Myo-inositol | | | | 0.1 g | |
| NAA (1 mg/mL stock) | | | | | 0.5 mL |
| Thiamine-HCl (0.5 mg/mL stock) | 1.0 mL | 1.0 mL | | | |
| 2,4-D (1 mg/mL stock) | 3.0 mL | 0.5 mL | | | |
| Silver Nitrate (2 mg/mL stock) | 1.7 mL | 1.7 mL | | | |
| MS Vitamins 100× | 10 mL | 10 mL | | | 5.0 mL |
| MS Fromm 1000× | | | 1.0 mL | 1.0 mL | |
| Carbenecillin (250 mg/mL) | | 2.0 mL | 1.0 mL | 1.0 mL | |
| Glyphosate (0.5 M stock) | | 0.2 mL | 0.2 mL | 0.2 mL | 0.2 mL |
| Phytagel | | 3.0 g | 3.0 g | 3.0 g | 3.0 g |
| BAP (0.5 mg/mL stock) | | 0.02 mL | 7.0 mL | | |
| Acetosyringone (1.0 M) | 0.2 mL | | | | |
| Agarose Low EEO | 5.5 g | | | | |

Analysis of Amino Acid Content of R1 Seed

Maize events transformed with the codon-optimized AgroAS constructs listed above as well as non-transgenic control events were analyzed to quantify free tryptophan levels in the kernels. Twelve mature kernels from each event were ground separately into powder and analyzed for free tryptophan (Trp) content.

To extract the amino acid fraction, 30 mg of crushed kernels are placed in a centrifuge vial. One milliliter of 5% trichloroacetic acid is added to each sample. The samples are mixed by vortex, and placed, with agitation, at room temperature for 15 minutes. The samples are then spun in a microcentrifuge for 15 minutes at 14,000 rpm. Some of the supernatant is then removed, placed in an HPLC vial and sealed. Samples are kept at 4° C. prior to analysis.

The amino acid analysis is performed as described in the Agilent Technical Publication, 2000. The separation is done using an Agilent 1100 series HPLC system (Agilent, Palo Alto, Calif.) with an Eclipse XDB-C18 5 μm, 4.6×150 mm column, and a flow rate of 1.2 ml/minute. Amino acid concentrations are measured using fluorescence: excitation at 340 nm, emission at 450 nm. Elution is accomplished with a gradient of HPLC Buffers A and B according to Table U, where HPLC Buffer A is 40 mM $Na_2HPO_4$, pH 7.8 and HPLC Buffer B is 9:9:2::Methanol:Acetonitrile:Water.

TABLE U

Amino Acid Elution

| | Time | | | | |
|---|---|---|---|---|---|
| | 0 | 20 | 21 | 26 | 27 |
| % Buffer A | 95 | 35 | 0 | 0 | 0 |
| % Buffer B | 5 | 65 | 100 | 100 | 100 |

Amino acid standards are prepared or purchased in concentrations ranging from 0 to 100 μg/ml. Proline analysis requires an additional derivatization step using 9-fluorenyl-methyl-chloroformate (FMOC). Results, as shown in Table V, are reported in ppm.

Figure 30:
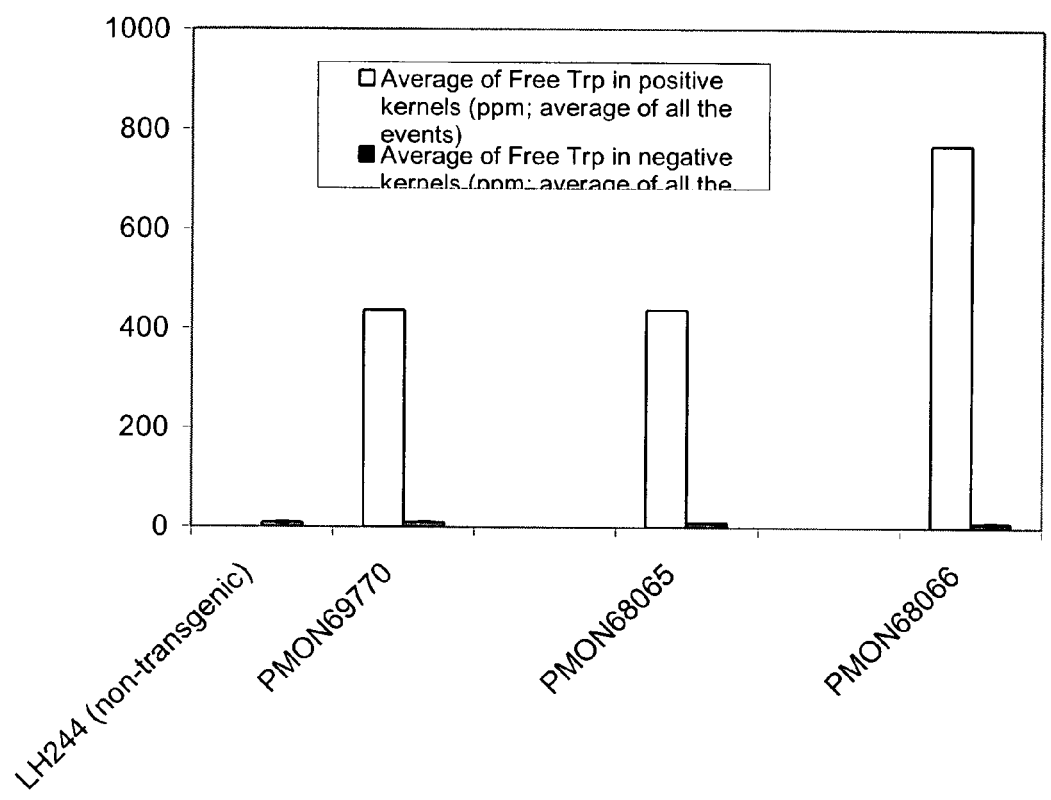
FIG. 30 is a graphic comparison of free tryptophan levels in kernels from non-transgenic corn plants vs. transgenic corn plants containing the plasmids pMON69770, pMON68065 and pMON68066.
Figure 31:
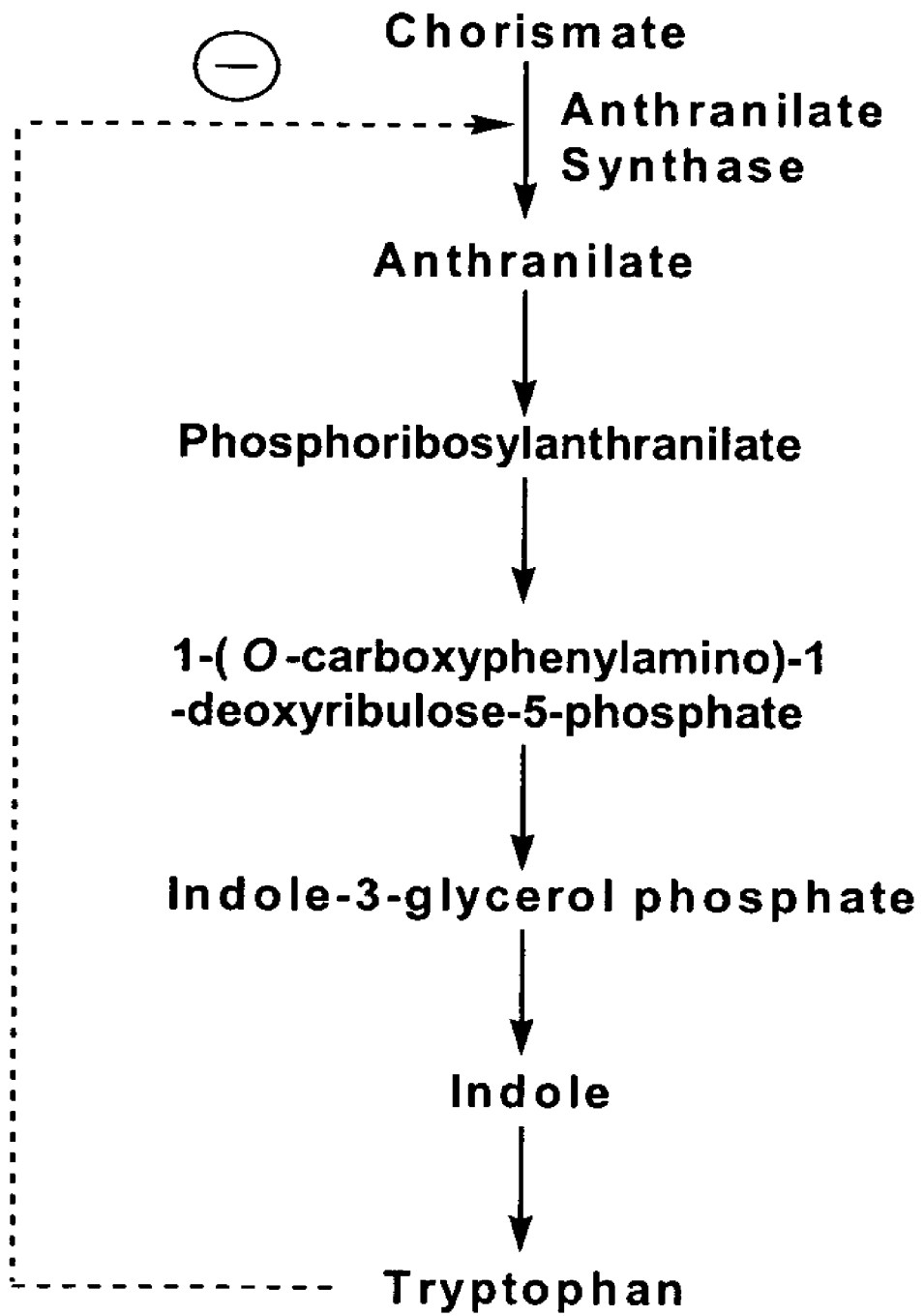
FIG. 31 shows tryptophan synthetic pathway.

Kernels that had free tryptophan at or below 25 ppm were grouped as negative kernels and were used to calculate the average free tryptophan in negative kernels in each event (Table V) or in the construct (Table W and FIG. 30). Kernels that had free tryptophan >25 ppm were grouped as positive kernels and the data was used to calculate the average free tryptophan in positive kernels in each event (Table V) or in the construct (Table W and FIG. 30). Mature kernels from non-transgenic events (LH244) were also analyzed for free tryptophan content. The data is presented as the average of the free tryptophan in negative kernels.

In general, transgenic events expressing the non-optimized AgroAS-S51C allele (pMON69770, and pMON68065) demonstrated an average free tryptophan level of 437 ppm. This is significantly higher than the free tryptophan levels seen in non-transgenic LH244 kernels, for which the average is 8.8 ppm. In contrast, expression of the codon-optimized AgroAS-S51C allele (pMON68066; AgroAS_S51C_nno), results in an enhanced average free tryptophan content of 768 ppm, with one event as high as 1435 ppm. Enhanced levels of free tryptophan due to expression of the codon-optimized AgroAS-S51C allele is clearly demonstrated in many transgenic events derived from pMON68066 (Tables V and W; FIG. 30).

TABLE V

| Construct | Event | Average of Free Trp in positive kernels (ppm) | Standard deviation | Average of Free Trp in negative kernels (ppm) | Standard deviation |
|---|---|---|---|---|---|
| LH244 (non-transgenic) | LH244 | | | 8.8 | 1.4 |
| pMON69770 | ZM_S102609 | 481.3 | 5.5 | 9.9 | 1.7 |
| | ZM_S102614 | 441.7 | 135.5 | 9.0 | 1.0 |
| | ZM_S102630 | 593.7 | 42.6 | 12.2 | 4.0 |
| | ZM_S102637 | 343.8 | 27.1 | 9.3 | 1.0 |
| | ZM_S103183 | 412.4 | 40.4 | 8.6 | 1.0 |
| | ZM_S103189 | 433.0 | 61.2 | 9.3 | 0.5 |
| | ZM_S103202 | 417.2 | 48.1 | 10.0 | 1.4 |
| | ZM_S103233 | 353.5 | 102.0 | 11.8 | 1.3 |
| | ZM_S103234 | 515.2 | 61.9 | 10.3 | 2.7 |
| | ZM_S103245 | 537.8 | 38.8 | 10.9 | 1.4 |
| | ZM_S103257 | 386.4 | 24.8 | 8.1 | 0.9 |
| | ZM_S103261 | 413.9 | 46.4 | 10.3 | 1.0 |
| | ZM_S103276 | 371.0 | 61.9 | 8.8 | 0.5 |
| | ZM_S103277 | 417.8 | 40.4 | 7.9 | 1.1 |

TABLE V-continued

| Construct | Event | Average of Free Trp in positive kernels (ppm) | Standard deviation | Average of Free Trp in negative kernels (ppm) | Standard deviation |
|---|---|---|---|---|---|
| pMON68065 | ZM_S134462 | 550.8 | 102.3 | 11.7 | 1.7 |
| | ZM_S137274 | 218.2 | 32.5 | 9.2 | 1.6 |
| | ZM_S138234 | 197.1 | 2.1 | 8.6 | 0.8 |
| | ZM_S139813 | 584.8 | 92.1 | 9.8 | 0.5 |
| | ZM_S139815 | 571.5 | 37.2 | 7.4 | 0.7 |
| | ZM_S139816 | 535.3 | 58.8 | 10.0 | 1.4 |
| | ZM_S139817 | 416.5 | 58.3 | 11.0 | 0.7 |
| | ZM_S142728 | 525.3 | 97.3 | 10.3 | 2.5 |
| | ZM_S142738 | 404.7 | 25.5 | 9.2 | 0.7 |
| | ZM_S142742 | 384.6 | 39.9 | 7.5 | 0.8 |
| | ZM_S142747 | 423.9 | 39.7 | 8.3 | 0.6 |
| pMON68066 | ZM_S133073 | 824.0 | 71.3 | 8.0 | 1.1 |
| | ZM_S133076 | 672.4 | 52.0 | 8.3 | 1.0 |
| | ZM_S133078 | 524.7 | 66.7 | 8.4 | 0.5 |
| | ZM_S133080 | 670.6 | 40.8 | 9.6 | 1.1 |
| | ZM_S133082 | 588.0 | 38.0 | 8.6 | 1.3 |
| | ZM_S133083 | 731.0 | 81.6 | 7.6 | 0.8 |
| | ZM_S133089 | 800.3 | 87.9 | 10.4 | 1.3 |
| | ZM_S133092 | 603.5 | 89.0 | 10.3 | 2.1 |
| | ZM_S133093 | 1011.3 | 263.4 | 9.3 | 4.9 |
| | ZM_S133097 | 592.3 | 225.3 | 12.0 | 1.7 |
| | ZM_S133098 | 727.5 | 81.1 | 8.0 | 1.3 |
| | ZM_S133099 | 759.3 | 74.7 | 8.5 | 0.7 |
| | ZM_S133421 | 1435.2 | 43.7 | 13.1 | 2.5 |
| | ZM_S133431 | 692.6 | 41.8 | 8.3 | 0.8 |
| | ZM_S133433 | 697.0 | 48.1 | 9.2 | 1.9 |
| | ZM_S133434 | 966.3 | 126.9 | 9.8 | 4.2 |

TABLE W

| Construct | Average of Free Trp in positive kernels (ppm; average of all the events) | Standard deviation | Average of Free Trp in negative kernels (ppm; average of all the events) | Standard deviation |
|---|---|---|---|---|
| LH244 (non-transgenic) | | | 8.8 | 1.4 |
| PMON69770 | 437.0 | 52.6 | 9.7 | 1.4 |
| PMON68065 | 437.5 | 53.2 | 9.4 | 1.1 |
| PMON68066 | 768.5 | 89.5 | 9.3 | 1.7 |

Example 11

Preparation of a Transformation Vector Comprising Monomeric *Rhizobium meliloti* Anthranilate Synthase Cloning of *Rhizobium meliloti* AS gene A stab culture of *Rhizobium meliloti* 1021 obtained from ATCC was used to streak a YM media (10 g mannitol, 0.5 g $K_2HPO_4$, 0.2 g $MgSO_4$·$7H_2O$, 1.0 g yeast extract, 0.2 g NaCl, 88 mg $FeCl_3$-$6H_2O$, 15 g agar per 1 L) plate. This plate was grown for two days at 30° C. A single colony was used to inoculate 1 liter of YM media. This culture was grown overnight at 30° C. The cell pellet was spun down at 5,000×g for 10 minute and frozen at −20° C. The Qiagen Genomic-tip DNA kit (Qiagen Inc., Valencia, Calif.) was used to extract genomic DNA according to the August 1999 Qiagen Genomic DNA Handbook (p. 42).

A PCR reaction was used to amplify the gene. The primers used were Rhizo F2: ATGGCAGCGGTAATTCTGGAAG (SEQ ID NO: 138) and Rhizo R8: TCAGGCTGCCTTG-GTCTTC (SEQ ID NO: 139). The resulting PCR fragment was cloned into the pGEM (Promega Corp., Madison, Wis.) vector.

Finally, the PCR product in pGEM was amplified using PCR with the following primers: Rhizo NcoI ACTGACTC-CATGGCAGCGGTAATTCTGGAA (SEQ ID NO: 140) and RhizoSpeI: CTGACTAGTTCAGGCTGCTT (SEQ ID NO: 141) and the product was cloned into TOPO 2.1 PCR vector (Invitrogen Corp., Grand Island, N.Y.).

Vector Construction

Figure 21:
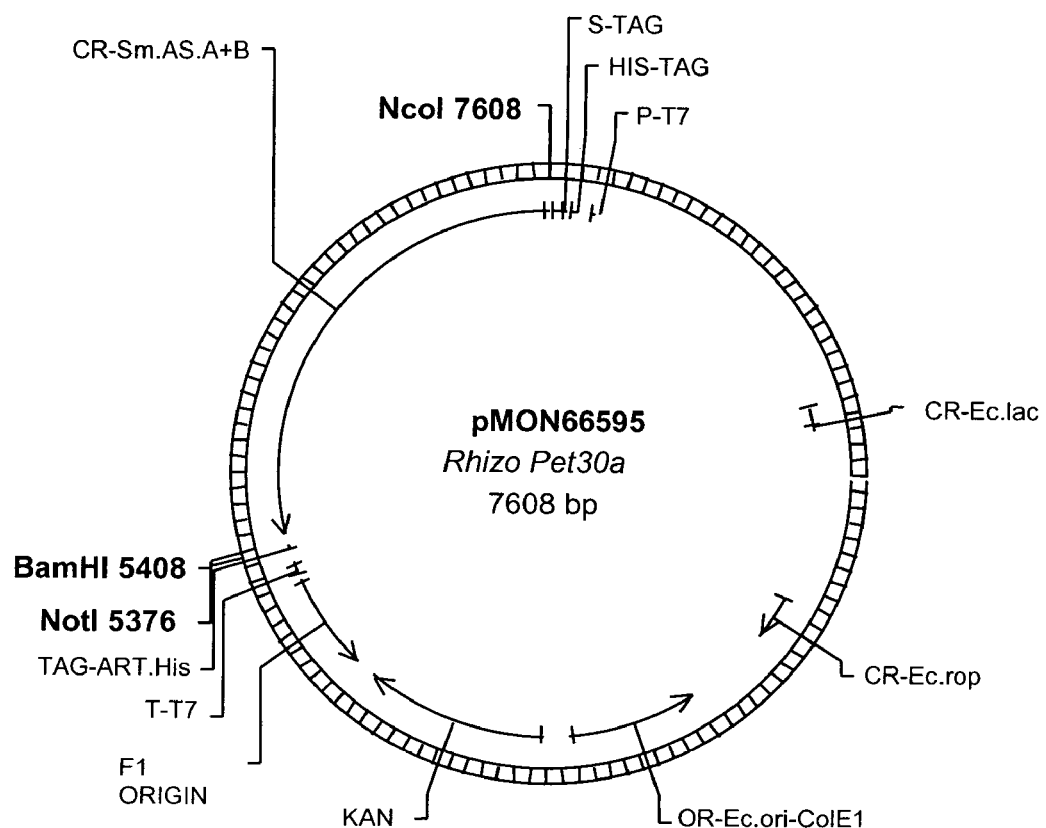
FIG. 21 is a restriction map of plasmid pMON66595.

The vector containing the *Rhizobium* gene in the TOPO 2.1 vector was digested with SpeI and a Klenow reaction was performed to blunt the site. The DNA was PCR purified (Qiagen PCR purification kit and MinElute Handbook, 2001) and then digested with NcoI. This fragment was cloned into pET30a at the EcoRV and NcoI site creating pMON66595 (FIG. 21).

The *Arabidopsis* transformation vector was created in several steps by first digesting pMON13773 with NcoI/EcoRI to generate a backbone piece. pMON66595 was digested with NcoI and EcoRI and the larger portion of the *Rhizobium* AS gene (approximately 2000 base pairs) was removed. The two pieces were then ligated together. A positive clone was digested with EcoRI and treated with calf intestinal phosphatase (CIP). The second fragment of the *Rhizobium* gene was removed by digesting pMON66595 with EcoRI and keeping the approximately 200 base pair piece. The two fragments were ligated together and the resultant clones were sequenced to check for correct orientation of the small *Rhizobium* fragment.

One of the above clones, having correct sequence and orientation, was digested with BglII and NcoI. Then pMON58046 (FIG. 5) was digested with BglII and NcoI and the CTP2 transit peptide fragment removed. These fragments were ligated together to complete the cassette.

The ligated fragments were digested with NotI to remove the cassette. They were then ligated into pMON36524 at the CIP treated NotI site. These clones were digested to find a cassette inserted in the same orientation as the NPTII gene creating pMON66599.

The vector pMON66599 was then transformed into *Agrobacterium* and used to transform *Arabidopsis*. The control construct in this experiment was pMON66598, which is the same cassette insert as described for pMON66599, except containing the *Agrobacterium* AS wild type gene.

Complementation Assay

The *Rhizobium* AS gene from pMON66595 was excised with BamHI and NcoI and cloned into the corresponding sites of the pSE280 vector (Invitrogen), creating pMON66596. pMON66596 was then transformed into a mutant *E. coli* strain, EMG2 ΔtrpE (created from the EMG strain WT K12, F+, which was obtained from ATCC) showing that the homomeric gene complements the genome of the trp-strain.

Activity Assay pMON66596 was transformed into BL-21 cells and induced with IPTG to express protein. The crude cell extract was assayed by HPLC and found to have activity and an $IC_{50}$ around 10 µM trp (Poulson, 1991).

Protein Expression and Purification

His-tagged protein was expressed by inducing pMON66595 with IPTG. Protein purification was completed using native conditions outlined in the QIAexpressionist 2002 Handbook and nickel resin (Ni-NTA Spin Handbook, 2000). Rabbit sera show recognition of purified protein.

Plants are transformed with the vector containing the *Rhizobium* anthranilate synthase gene, as in Examples 2, 3, and 6, and show elevated levels of tryptophan in the seed.

Example 12

Corn Transformation with a Vector Containing a Maize Anthranilate Synthase α-Subunit Gene and a Maize Anthranilate Synthase β-Subunit Gene To create a shuttle vector containing the coding sequence for maize anthranilate synthase α-subunit, pMON65150, was digested with both EcoRI and SacII. The resulting 6195 base pair fragment was gel purified and then dephosphorylated. The plasmid pMON66604 was digested with both EcoRI and SacII, to generate a 1077 base pair fragment that was gel purified. The 1077 base pair fragment was then ligated in the sticky-ended 6195 base pair fragment containing the maize ASα coding sequence to generate pMON67149, a maize L3 (oleosin) promoter-maize hsp70 intron-maizeASα-Tr7 3' UTR expression vector. This vector, was subsequently digested with XhoI, resulting in a 4364 base pair DNA fragment containing the maize oleosin promoter, maize heat shock protein 70 intron, maize anthranilate α-subunit coding sequence, and the Tr7 3' UTR.

The plasmid pMON30167 was digested with XhoI resulting in an 8.89 Kb DNA fragment. This fragment was then ligated to the 4964 base pair fragment to create pMON79951, a transformation vector containing L3 promoter-zmhsp70 intron-maizeASα-Tr7 3' UTR.

The coding sequence for a maize anthranilate synthase β-subunit was isolated by PCR from a Monsanto proprietary cDNA library, using the following primers:

5' primer 5'TGCTGACCATGGCCTGCTCCCA-CATCGTCG3' (SEQ ID NO: 142), which contains the NcoI restriction site (shown in bold), and 3' primer 5'CAGTGAATTCCTACGAACGCTGCT-TCTCCAGTTC3' (SEQ ID NO: 143), which contains the EcoRI restriction site (shown in bold).

The PCR parameters used were 2°/second to 95°; 95° for 5 minutes; 95° for 30 seconds; 2°/second to 55°; 55° for 45 sec; 2°/second to 72°; 72° for 55 seconds; cycle 25 times starting at the third step; 2°/second to 72°; 72° for 10 minutes; 2°/second to 4° forever (all temperatures shown are in ° C., unless otherwise noted). The PCR mix contained: 1 µl of miniprep (Qiagen method) DNA from pMON79952, 1.5 µl of each primer (10 µM stock) 5 µl of Roche 10×PCR buffer with magnesium chloride, 2 µl 10 mM dNTP mix, 1 µl Hi-Fi Taq mix (Roche Expand High Fidelity PCR System # 1732650) and water to a total volume of 50 µl. The resulting PCR product was ligated into the pGEM-T vector (Promega pGEM-T Vector System I #A3600). Sequencing the above-described fragment revealed that it was missing restriction sites. The PCR was performed again using the pGEM clone as a template and the product cloned into the TOPO2.1 PCR Vector (Invitrogen TOPO TA Cloning Kit pCR 2.1-TOPO vector #45-0641). This clone was confirmed by sequencing. The resulting vector, containing maize ASβ, was named pMON66592. This vector was then digested with both NcoI and EcoRI, to generate an 850 bp fragment. After isolation, the ends of the 850 bp fragment were made blunt and dephosphorylated. The plasmid pMON79953 was digested with BamHI and SmaI, to generate a 5353 bp fragment. After isolation, the ends of the 5353 bp fragment were made blunt. The 850 bp fragment containing the ASβ gene was then ligated into the blunt-ended 5353 bp pMON79953 fragment to generate pMON79954, a maize L3 promoter-maize hsp70 intron-maizeASβ-Tr7 3' UTR vector.

The vector pMON79954, was subsequently digested with XhoI to generate a 2907 base pair DNA fragment containing the maize oleosin promoter, maize hsp70 intron, maize ASβ coding sequence, and the Tr7 3' UTR. The plasmid pMON30167 was digested with XhoI to generate an 8.89 Kb fragment. The two fragments were ligated together to generate pMON79955, a transformation vector containing L3 promoter-zmhsp70 intron-maizeASβ-Tr7 3' UTR.

To create the maize ASα and ASβ stacking vector, pMON79955 was digested with HindIII, to generate a 16.57 Kb fragment. The fragment was made blunt and dephosphorylated. The plasmid pMON67149 was digested with XhoI, to generate a 4364 base pair DNA fragment, which was subsequently blunt ended. The two fragments were ligated together to create pMON79956), a final transformation vector containing maize L3 promoter-maize hsp70 intron-maizeASα-Tr7 3' UTR stacked with maize L3 promoter-maize hsp70 intron-maizeASβ-Tr7 3' UTR.

Maize Transformation Using *Agrobacterium tumefaciens*

Maize plants (inbred line LH198/Hi11) are grown in a greenhouse under standard practices. The ears of the plants are harvested when the embryos are 1.5 to 2.0 mm in length, usually 10-15 days after pollination. The ears are surface sterilized by spraying or soaking in 80% ethanol.

The immature embryos are isolated from individual kernels using methods known to those of skill in the art. Immature embryos are cultured on medium 211 (N6 salts, 2% sucrose, 1 mg/L 2,4-dichlorphenyoxyacetic acid (2,4-D), 0.5 mg/L niacin, 1.0 mg/L thiamine-HCl, 0.91 g/L L-asparagine, 100 mg/L: myo-inositol, 0.5 g/L MES, 100 mg/L casein hydrolysate, 1.6 g/L MgCl2, 0.69 g/L L-proline, 2 g/L GELGRO™, pH 5.8) containing 16.9 mg/L AgNO3 (designated medium 2112V) for 3-6 days prior to transformation.

Methods of *Agrobacterium* mediated transformation of maize cells and other monocots are known (U.S. Pat. Nos. 5,591,616 and 5,981,840; and EP 0 672 752). The *Agrobacterium* strain ABI, and an *Agrobacterium tumefaciens* binary vector system are used for the transformations.

Prior to co-culture with the maize embryo cells, *Agrobacterium* cells are grown at 28° C. in LB (DIFCO) liquid medium containing approximately 50 μg/ml kanamycin and 100 μg/ml spectinomycin to select for maintenance of the modified Ti plasmid and binary vector. Prior to inoculation of maize cells the *Agrobacterium* cells are grown overnight at room temperature in AB medium (Chilton et al., (1974) comprising appropriate antibiotics for plasmid maintenance and 200 μM acetosyringone. Immediately prior to inoculation the *Agrobacterium* cells are pelleted by centrifugation, washed in ½ MSVI medium (2.2 g/L GIBCO MS (Murashige and Skoog, 1962) basal salts, 2 mg/L glycine, 0.5 g/L niacin, 0.5 g/L L-pyridoxin-HCl, 0.1 mg/L thiamine, 115 g/L L-proline, 10 g/L D-glucose, and 10 g/L sucrose, pH 5.4) containing 200 μM acetosyringone.

The immature maize embryos are excised, immersed in an *Agrobacterium* suspension in ½ MSPL medium and incubated at room temperature with *Agrobacterium* for approximately 5 minutes.

Following *Agrobacterium* infection and co-culture, the embryos are transferred to type II delay medium for 5 to 7 days and cultured at 27° C. in the dark. The delay medium consists of MS basal salts containing 2.0 mg/L 2,4-D (GIBCO), 100 mg/L-casamino acids, 12 mM proline, 500 mg/L carbenicillin and 20 μM silver thiosulfate. All media chemicals were tissue culture grade. Once signs of type II callus initiation from immature embryos are observed, as defined by Selman et al (1994), the coleoptiles are removed from the embryos. The embryos are then transferred to MS medium containing 2.0 mg/L 2,4-D, 12 mM proline, 20 μM silver thiosulfate, 500 mg/L carbenicillin and 0.5 mM glyphosate (Monsanto Company, St. Louis, Mo.) and incubated at 27° C. in the dark for 2 weeks.

Embryos forming callus are transferred to the MS medium described above, but additionally containing 1.0 mM glyphosate. The cultures are then incubated for 2 weeks in the dark at 27° C. The embryos still having callus are then transferred to MS medium containing 3.0 mM glyphosate for an additional 2 weeks.

Plant regeneration is achieved by transferring the callus to MS medium containing 0.1 mg/L 2,4-D and 0.1 μM abscisic acid (ABA) for 2 weeks and then to MS medium containing 6% sucrose and no 2,4-D for another 2 weeks. Both incubations are done in the dark at 27° C. to permit somatic embryo maturation and conversion in the regeneration process.

Somatic embryos that are ready to germinate are transferred to hormone-free MS medium, and incubated in the light until shoots with attached roots are produced. After approximately 2 to 3 weeks, plantlets are produced.

Plantlets are then transferred to the greenhouse and grown under standard greenhouse conditions.

Analysis of Amino Acid Content of R1 Seed

Several transgenic corn lines were established for each vector and propagated through the number of generations. These lines are grown and self-pollinated to generate homozygous lines. At each generation, expression of the transgenes are determined using western blot analysis on immature seed and mature R1 seed is produced and analyzed for free amino acid content using fluorescence detection as described in Agilent Technologies Technical Bulletin REV14. Maize seeds expressing ASα protein generate elevated amounts of tryptophan relative to baseline levels (corresponding to negative isolines and nontransgenic controls). Baseline free tryptophan levels for corn range from about 5 to about 25 ppm.

Example 13

Production of Meal and Feed Products Containing Codon-Optimized AgroAS

Any of the plants or parts thereof of the present invention may be processed to produce a feed, meal, protein, or oil preparation, including feed, meal, protein and oil preparations high in total tryptophan content. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748; 5,100,679; 5,219, 596; 5,936,069; 6,005,076; 6,146,669; and 6,156,227. In a preferred embodiment, the feed, meal, protein or oil preparation is a high tryptophan preparation. Such a high tryptophan preparation preferably has a tryptophan content of greater than about 200 to 400 ppm, more preferably 400 to 600 ppm, and even more preferably 600 to 800 ppm.

Example 14

Detection of Unique Polynucleotide Sequences in Meal, Feed, Protein and Oil Products This example describes methods that can be used to detect the presence of unique fragments of an artificial polynucleotide sequence of the present invention in meal, feed, protein and oil products. Methods for comparing a known sequence to other known sequences in order to determine which parts of the known sequence are unique (e.g. less than 100% identical) to other known sequences are well known to those of skill in the art. It has been determined by using a BLAST search of all known corn DNA sequences that the polynucleotides of the present invention are unique to at least the 21 mer level. That is to say that the polynucleotides of the present invention contain no segments of consecutive nucleotides greater than 20 nucleotide bases that are a 100% identical match to any other known corn DNA sequence. Additionally, a comparison of the polynucleotides of the present invention with all known anthranilate synthase sequences using a BLAST search revealed that there are no other anthranilate synthase sequences that match 100% to the claimed polynucleotide sequences for more than 32 consecutive nucleotides. That is to say that the polynucleotides of the present invention, when compared to all known corn DNA sequences and all known anthranilate synthase sequences, are unique to at least the 33 mer level. Sequences that are unique to the claimed invention may be measured by methods well-known to those of skill in the art including, but not limited to hybridization by the Southern blot method.

Isolation of Genomic DNA

Genomic DNA from test and control samples can be extracted using standard extraction protocols for nucleic acids. Briefly, 200 to 500 mg of corn meal or seed powder is transferred to 10 ml conical tubes; approximately 10 ml of CTAB extraction buffer (1.5% (w/v) CTAB, 75 mM Tris-HCl pH 8.0, 100 mM EDTA pH 8.0, 1.05 M NaCl, and 0.75% (w/v) PVP (MW 40,000)) is added to the tube. The samples are incubated at 65° to 70° C. for 60 minutes with intermittent mixing. Approximately 12 ml of chloroform is added to the samples. The suspensions are inverted for 5 minutes by hand, and then the samples are aliquotted into 10 ml polypropylene tubes (3/sample). The samples are centrifuged at ~10,000×g for 5 to 10 minutes at room temperature. The aqueous (upper) layer is transferred to a clean 10 ml polypropylene tube and the chloroform extraction as above is repeated with 1 volume of chloroform. The aqueous layers from same event samples are combined in a single 50 ml conical tube and an equal volume of 95% EtOH is added. The precipitated DNA is pooled into a 10 ml polypropylene tube containing 5 ml 70% ethanol, and centrifuged at ~10,000 rpm for 2-3 minutes to pellet the DNA. The pellet is transferred to a microfuge tube containing 1 ml 70% EtOH and spun at 14,000 rpm in a microcentrifuge for 1 minute. The DNA is dissolved in $H_2O$, and the DNA is quantified using Sigma's DNA Quantitation kit (catalog #DNA-QF) (or equivalent) and a Hoefer DyNA Quant 200 Fluorometer (or equivalent).

Restriction Enzyme Digestion of Genomic DNA

Approximately 10 µg of genomic DNA from a test substance and ~10 µg of genomic DNA from a control substance can be used in independent restriction enzyme digestions. Overnight digests are carried out at 37° C. (60° C. for BstEII) in a total volume of 300-500 µl using 100 units of the appropriate restriction enzyme(s) and 50 ng DNase-free RNase (Roche or equivalent). After digestion, DNA is precipitated from the samples by adding 2-2.5 volumes of 100% ethanol followed by incubation in a −20° C. freezer for at least 1 hour and centrifugation for 20 minutes in a microcentrifuge. The DNA is redissolved in water.

DNA Probe Preparation for Southern Blot Analysis

Probe template DNA containing sequences of plasmid pMON68066 is prepared by standard PCR amplification. Approximately 25 ng of each probe template can be used to label with $^{32}$P-dCTP (~6000 Ci/mmol) by a random priming method (RadPrime DNA Labeling System, Life Technologies, Gaithersburg, Md.). The labeled probes are purified with Roche G-50 columns per the manufacturer's protocol. One microliter of each labeled probe is counted, and $1.0\text{-}1.5\times10^6$ cpm/ml hybridization buffer can be used per blot.

Southern Blot Analysis of Genomic DNA

Separation of the samples of DNA digested with restriction enzymes is based on size using 0.8% (w/v) agarose gel electrophoresis in 1×TBE buffer. The gels are depurinated in a 0.25 M HCL solution for 20 minutes, denatured for 30 minutes in 0.4 N NaOH, 0.6 M NaCl and neutralized in 1.5 M NaCl, 0.5 M Tris Base pH 7.0 for 30 minutes. Treated gels are transferred to pretreated GeneScreen Plus® membranes for 4-20 hrs in 10×SSC using a Turbo Blotter. The membranes are crosslinked in a UV Stratalinker® 2400 (Stratagene, La Jolla, Calif. at 120 mjoules. The membranes are prehybridized in 10% Dextran Sulfate solution (10% Dextran Sulfate, 1% SDS, 1 M $NaCl_2$, 100 µg/ml denatured, single stranded fish sperm DNA) for 1 hr at 65° C. The prehybridization solution is replaced with a hybridization solution containing $1.0\text{-}1.5\times10^6$ cpm/ml denatured probe in a 10% Dextran Sulfate solution. Hybridization is performed at 65° C. for 15 to 20 hrs. The blots are washed at 68° C. in varying concentrations of SSC, SDS solutions, and exposed to Kodak BIOMAX MS film (Kodak, Rochester, N.Y.) in conjunction with one Kodak BIOMAX MS intensifying screen in a −80° C. freezer.

All publications and patents are incorporated by reference herein, as though individually incorporated by reference. The invention is not limited to the exact details shown and described, for it should be understood that many variations and modifications may be made while remaining within the spirit and scope of the invention defined by the claims.

REFERENCES

U.S. Patents

U.S. Pat. No. 5,500,365; U.S. Pat. No. 4,581,847; U.S. Pat. No. 4,940,838; U.S. Pat. No. 4,957,748; U.S. Pat. No. 5,100,679; U.S. Pat. No. 5,219,596; U.S. Pat. No. 5,258,300; U.S. Pat. No. 5,290,924; U.S. Pat. No. 5,302,523; U.S. Pat. No. 5,384,253; U.S. Pat. No. 5,489,520; U.S. Pat. No. 5,550,318; U.S. Pat. No. 5,591,616; U.S. Pat. No. 5,936,069; U.S. Pat. No. 5,981,840; U.S. Pat. No. 5,990,390; U.S. Pat. No. 5,990,390; U.S. Pat. No. 6,005,076; U.S. Pat. No. 6,069,289; U.S. Pat. No. 6,118,047; U.S. Pat. No. 6,146,669; U.S. Pat. No. 6,156,227; U.S. Pat. No. 6,160,208; U.S. Pat. No. 6,268,550; U.S. Pat. No. 6,281,411; U.S. Pat. No. 6,303,364; U.S. Pat. No. 6,320,100; U.S. Pat. No. 6,329,574; U.S. Pat. No. 6,331,655; U.S. Pat. No. 6,331,880; U.S. Pat. No. 6,433,252

U.S. patent application Ser. No. 10/430,011
U.S. Patent Publn. 20050005327
Adang et al., *Gene*, 36:289, 1985.
Agilent Technical Publication, "Amino Acid Analysis Using Zorbax Eclipse-AAA Columns and the Agilent 1100 HPLC", Mar. 17, 2000
Altschul et al., *Nucleic Acid Res.*, 25:3389-3402, 1997.
An, *Methods in Enzymology*, 153:292, 1987.
Bae et al., *J. Bacteriol.*, 171:3471-3478, 1989.
Barnes et al, *Adv. Exp. Med. Biol.*, 401:87, 1996.
Beachy et al., *EMBO J*, 4:3047, 1985.
Berg et al., *Biotechnology*, 1:417, 1983.
Bevan et al., *Nucl. Acid Res.*, 11:369, 1983.
Bock., *J. Mol. Biol.*, 312:425-438, 2001.
Bohlmann, et al., *Plant Phys.*, 111:507-514, 1996.
Bouchez et al., *EMBO J*, 8:4197, 1989.
Bowler et al., *Ann. Rev. Plant Physiol.*, 43:83, 1992.
Broadbent et al., *Curr. Med. Chem.*, 5:469, 1998.
Caligiuri and Bauerle, *J. Biol. Chem.*, 266:8328-8335, 1991.
Callis et al., *Genes Develop.*, 1:1183, 1987.
Campbell, W. C., Ed., Ivermectin and Abamectin. Springer Verlag, New York, N.Y., 1989.
Chandler et al., *The Plant Cell*, 1:1175, 1989.
Chilton et al., *Proc. Nat. Acad. Sci. USA*, 71:3672-3676, 1974.
Conkling et al., *Plant Physiol.*, 93:1203, 1990.
Cutler et al., *J. Plant Physiol.*, 135:351, 1989.
Czapla and Lang, *J. Econ. Entomol.*, 83:2480, 1990.
Daniell et al., *Trends in Plant Science*, 7:84-91, 2002.
Dayhoff, In: *Atlas of Protein Sequence and Structure*, Natl. Biomed. Res. Found., 5:101-110; 5(2):1-10, 1972.
De Troch et al., *Curr. Microbiol.*, 34:27-32, 1997.
Dean et al., *Nucleic Acids Res.*, 14:2229-2240, 1986.
Dellaporta et al., In: *Chromosome Structure and Function: Impact of New Concepts*, 18th Stadler Genetics Symposium, 11:263-282, 1988.
D'Halluin et al., *The Plant Cell*, 4:1495, 1992.
Dure et al., *Plant Molecular Biology*, 12:475, 1989.
Ebert et al., *Proc. Nat. Acad. Sci. USA*, 84:5745, 1987.
Ellis et al., *EMBO J.*, 6:3203, 1987.
EP 0 672 752
EP 154 204
Frey et al., *Proc. Natl. Acad. Sci. USA*, 97:14801, 2000.
Fromm et al., *Bio/Technology*, 8:833, 1990.
Fromm et al., *The Plant Cell*, 1:977, 1989.
Gatehouse et al., *J. Sci. Food Agric.*, 35:373, 1984.
Geiser et al., *Gene*, 48:109, 1986.
Goodall and Filipowich, *Cell*, 58:473-483, 1989.
Goodner et al. *Science*, 294:2323-2328, 2001.
Gordon-Kamm et al., *Plant Cell*, 2:603, 1990.
Gupta et al., *Proc. Natl. Acad. Sci. USA*, 90:1629, 1993.
Hajdukiewicz et al., *EMBO J*, 16:4041-4048, 1997.
Hammock et al., *Nature*, 344:458, 1990.
Hankins et al., *Plant Physiol.*, 57:101, 1976.
Heifetz, *Biochimie*, 82:655-666, 2000.
Heijne et al., *Eur. J. Biochem.*, 180:535, 1989.
Hilder et al., *Nature*, 330:160, 1987.
Hinchee et al., *Biotech.*, 6:915, 1988.
Hofte et al., *Microbiol. Rev.*, 53:242, 1989.
Hudspeth et al., *Plant Mol. Biol.*, 12:579, 1989.
Ikeda et al., *J. Bacteriol.*, 169:5615, 1987.
Ikuta et al., *Biotech.*, 8:241, 1990.
Jones et al., *Analyst*, 106:968, 1981.
Joshi, *Nucl. Acid Res.*, 15:6643, 1987.
Kaasen et al., *J. Bacteriology*, 174:889, 1992.
Katz et al., *J. Gen. Microbiol.*, 129:2703, 1983.
Keegstra et al., *Ann. Rev. Plant Physiol. Plant Mol. Biol.*, 40:471, 1989.
Knochel et al., *Proc. Natl. Acad. Sci. USA*, 96:9479-9484, 1999.
Laursen et al., *Plant Mol. Biol.*, 24:51, 1994.
Lawton et al., *Plant Mol. Biol.*, 9:31F, 1987.
Lee and Saier, *J. Bacteriol.*, 258:10761, 1982.
Levings, *Science*, 250:942-947, 1990.
Li and Last, *Plant Physiol.*, 110:51-59, 1996.
Link et al. *J. Bacteriol.*, 179:6228, 1997.
Loomis et al, *J. Expt. Zoology*, 252:9, 1989.
Maliga, *Current Opinion in Plant Biology*, 5:164-172, 2002.
Mantegani et al., *Farmaco*, 54:288, 1999.
Mash et al., *Ann. NY Acad. Sci.*, 844:274, 1998.
McCown & Lloyd, Proc. *International Plant Propagation Soc.*, 30:421, 1981.
Melanson et al., *Proc. Natl. Acad. Sci. USA*, 94:13345, 1997.
Mitra et al., *Molec. Gen. Genetic.*, 215:294, 1989.
Muller et al., *Biol. Chem.*, 381:679, 2000.
Murakami et al., *Mol. Gen. Genet.*, 205:42, 1986.
Murashige and Skoog, *Physiol Plant*, 15:473-497, 1962.
Murdock et al., *Phytochemistry*, 29 85, 1990.
Murray et al., *Nucl. Acids Res.*, 17:477, 1989.
Niedz et al., *Plant Cell Reports*, 14:403, 1995.
Niyogi and Fink, *Plant Cell*, 4:721, 1992.
Niyogi et al., *Plant Cell*, 5:1011, 1993.
Odell et al., *Nature*, 313:810, 1985.
Ow et al., *Science*, 234:856, 1986.
Paulsen, *J. Chromatogr.*, 547:155-160, 1991.
PCT Appln. PCT/CA99/00219
PCT Appln. WO 2004/009761A2
Perlak et al., *Proc. Natl. Acad. Sci. USA*, 88:3324-3328, 1991.
Potrykus et al., *Mol. Gen. Genet.*, 199:183, 1985.
Poulson, *J. Chromatogr.*, 547:155-160, 1991.
Prasher et al., *Biochem. Biophys. Res. Comm.*, 126:1259 (1985)
Ranch et al., *Plant Physiol.*, 71:136, 1983.
Sambrook and Russell, Molecular Cloning: A Laboratory Manual, $3^{rd}$ Edition, 2001.
Sambrook et al., Molecular Cloning: A Laboratory Manual, $2^{nd}$ Edition, 1989.
Selman et al. In: *The Maize Handbook*, Freeling and Walbot (Eds.), Springer Verlag, 672, 1994.
Siehl, D., pp 171-204 In: *Plant Amino Acids: Biochemistry and Biotechnology*, BK Singh (Ed.), Marcel Dekker, 1999.
Slater et al., *J. Bact.*, 180:1979-1987, 1998.
Smith and Waterman, *Adv. in Appl. Math.*, 2:482-489, 1981.
Smith et al., *Nucl. Acids Res.* 11:2205-2220, 1983.
Stalker et al., *Science*, 242:419, 1988.
Stark et al., *Science*, 258:287, 1992.
Sullivan et al., *Mol. Gen. Genet.*, 215:431, 1989.
Sutcliffe, *Proc. Nat. Acad. Sci. USA*, 75:3737, 1978.
Thillet et al., *J. Biol. Chem.*, 263:12500, 1988.
Twell et al., *Plant Physiol.*, 91:1270, 1989.
Umbarger, *Ann. Rev. Biochem.*, 47:555, 1978.
Vasil et al., *Plant Physiol.*, 91:5175, 1989.
Walker et al., *Proc. Nat. Acad. Sci. USA*, 84:6624, 1987.
Walters et al., *Plant Molecular Biology*, 18:189, 1992.
Wang et al., *Mol. Cell. Biol.*, 12:3399, 1992.
Whitely et al., *Ann. Rev. Microbiol.*, 40:549, 1986.
Widholm, *Biochim. Biophys. Acta*, 320:217, 1973.
Widholm, *Biochimica et Biophysica Acta*, 279:48, 1972.
Wolter et al., *The EMBO J.*, 11:4685, 1992.
Yang et al., *Proc. Nat. Acad. Sci. USA*, 87:4144, 1990.
Zeligs, *J. Med. Food*, 1:67, 1998.
Zukowsky et al., *Proc. Nat. Acad. Sci. USA*, 80:1101, 1983.

What is claimed:

1. A polynucleotide molecule comprising a nucleotide sequence at least 84% identical to SEQ ID NO:145, wherein said polynucleotide molecule encodes a tryptophan feedback insensitive anthranilate synthase polypeptide comprising one or more amino acid substitutions at positions corresponding to position 48, 51, 52, 293, or 298 in wild-type *Agrobacterium tumefaciens* anthranilate synthase depicted in SEQ ID NO:4.

2. The polynucleotide molecule of claim 1, wherein the nucleotide sequence comprises SEQ ID NO:145.

3. The polynucleotide molecule of claim 1, wherein the tryptophan feedback insensitive anthranilate synthase polypeptide comprises the polypeptide sequence of SEQ ID NO:61.

4. A DNA construct comprising the polynucleotide molecule of claim 1 operably linked to a promoter that functions in plants.

5. A transgenic cell transformed with the construct of claim 4.

6. The cell of claim 5, further defined as a plant cell.

7. The transgenic cell of claim 6, wherein the plant cell is from a plant selected from the group consisting of corn, rice, wheat, barley, millet, oat, and sorghum.

8. The transgenic cell of claim 7, wherein the cell is a corn cell.

9. The transgenic cell of claim 5, wherein the polynucleotide molecule is expressed in the cell and confers an increased level of tryptophan to the cell relative to an isogenic cell lacking said molecule.

10. A transgenic plant comprising the construct of claim 4.

11. A transgenic plant produced from the cell of claim 5.

12. The transgenic plant of claim 10, wherein the polynucleotide molecule is expressed in seeds of said plant and confers a nutritionally enhanced phenotype compared to isogenic plant seeds lacking said molecule.

13. The transgenic plant of claim 12, wherein the nutritionally enhanced phenotype is selected from the group consisting of increased tryptophan, increased isoleucine, increased valine, increased arginine, increased lysine, increased methionine, and increased threonine.

14. The transgenic plant of claim 12, wherein the transgenic plant is a plant selected from the group consisting of corn, rice, wheat, barley, millet, oat, and sorghum.

15. The transgenic plant of claim 14, wherein the plant is a corn plant.

16. Seed or silage comprising the plant cell of claim 6.

17. A method of producing a nutritionally enhanced feed product, comprising processing the transgenic plant of claim 12 or a part thereof into meal, animal feed, protein or oil.

18. A feed product produced by the method of claim 17, wherein the feed product comprises a detectable nucleic acid sequence comprising the polynucleotide molecule of claim 1 or a complement thereof.

19. The feed product of claim 18, wherein the feed product is an animal feed or human food.

20. A method of providing an increased level of tryptophan in the seed of a plant comprising:
    a) obtaining a DNA construct according to claim 4;
    b) introducing the DNA construct into a plant cell;
    c) regenerating said plant cell into a fertile transgenic plant; and
    d) obtaining at least one seed from the fertile transgenic plant or progeny thereof that comprises the DNA construct and exhibits increased tryptophan compared to a plant seed lacking said construct, wherein said increased tryptophan is a result of the expression of the DNA construct in the seed.

21. A method of providing seed with an increased level of tryptophan comprising:
    a) introducing into a plant the construct of claim 4; and
    b) allowing the plant to produce seed expressing the construct; wherein said seed comprise an increased level of tryptophan compared to seed lacking said construct.

22. A progeny plant produced from the seed of claim 21, wherein the progeny plant comprises said construct.

23. A seed produced from the progeny plant of claim 22, wherein said seed comprises said construct.

24. The method of claim 21, wherein the plant is selected from the group consisting of corn, rice, wheat, barley, millet, oat, and sorghum.

25. The polynucleotide molecule of claim 1, wherein the tryptophan feedback insensitive anthranilate synthase polypeptide comprises an amino acid substitution at position 51.

26. The polynucleotide molecule of claim 25, wherein the tryptophan feedback insensitive anthranilate synthase polypeptide comprises a Phe or Cys substitution at position 51.

27. The polynucleotide sequence of claim 26, wherein the tryptophan feedback insensitive anthranilate synthase polypeptide comprises a Cys substitution at position 51.

28. The polynucleotide molecule of claim 1, wherein the one or more amino acid substitution(s) are selected from the group consisting of: Phe or Tyr at position 48; Phe or Cys at position 51; Phe at position 52; Ala or Gly at position 293; and Trp at position 298.

29. The transgenic plant of claim 10, wherein the tryptophan feedback insensitive anthranilate synthase polypeptide comprises the polypeptide sequence of SEQ ID NO:58; SEQ ID NO:59; SEQ ID NO:60; SEQ ID NO:61; SEQ ID NO:62; SEQ ID NO:63; SEQ TD NO:64; or SEQ ID NO:65.

30. The polynucleotide molecule of claim 1, wherein the tryptophan feedback insensitive anthranilate synthase polypeptide comprises an amino acid substitution at a position corresponding to position 48 in wild-type Agrobacterium tumefaciens anthranilate synthase depicted in SEQ ID NO:4.

31. The polynucleotide molecule of claim 1, wherein the tryptophan feedback insensitive anthranilate synthase polypeptide comprises an amino acid substitution at a position corresponding to position 51 in wild-type Agrobacterium tumefaciens anthranilate synthase depicted in SEQ ID NO:4.

32. The polynucleotide molecule of claim 1, wherein the tryptophan feedback insensitive anthranilate synthase polypeptide comprises an amino acid substitution at a position corresponding to position 52 in wild-type Agrobacterium tumefaciens anthranilate synthase depicted in SEQ ID NO:4.

33. The polynucleotide molecule of claim 1, wherein the tryptophan feedback insensitive anthranilate synthase polypeptide comprises an amino acid substitution at a position corresponding to position 293 in wild-type Agrobacterium tumefaciens anthranilate synthase depicted in SEQ ID NO:4.

34. The polynucleotide molecule of claim 1, wherein the tryptophan feedback insensitive anthranilate synthase polypeptide comprises an amino acid substitution at a position corresponding to position 298 in wild-type Agrobacterium tumefaciens anthranilate synthase depicted in SEQ ID NO:4.

* * * * *

UNITED STATES PATENT AND TRADEMARK OFFICE
CERTIFICATE OF CORRECTION

PATENT NO. : 7,714,189 B2  Page 1 of 1
APPLICATION NO. : 11/503532
DATED : May 11, 2010
INVENTOR(S) : Manjunath et al.

It is certified that error appears in the above-identified patent and that said Letters Patent is hereby corrected as shown below:

In claim 19, column 321 line 38, delete "or human" and insert --or a human--.

In claim 29, column 322 line 28, delete "TD NO:64" and insert --ID NO:64--.

Signed and Sealed this

Fifth Day of October, 2010

David J. Kappos
*Director of the United States Patent and Trademark Office*